US009006234B2

(12) United States Patent
Jain et al.

(10) Patent No.: US 9,006,234 B2
(45) Date of Patent: Apr. 14, 2015

(54) BRIDGED HETEROCYCLIC COMPOUNDS AND METHODS OF USE

(75) Inventors: Rajendra Parasmal Jain, Pune (IN); Sarvajit Chakravarty, Mountain View, CA (US)

(73) Assignee: Medivation Technologies, Inc., San Francisco, CA (US)

( * ) Notice: Subject to any disclaimer, the term of this patent is extended or adjusted under 35 U.S.C. 154(b) by 16 days.

(21) Appl. No.: 13/540,472

(22) Filed: Jul. 2, 2012
(Under 37 CFR 1.47)

(65) Prior Publication Data

US 2013/0172366 A1 Jul. 4, 2013

Related U.S. Application Data

(63) Continuation of application No. 13/498,097, filed as application No. PCT/US2010/050081 on Sep. 23, 2010, now abandoned.

(60) Provisional application No. 61/245,151, filed on Sep. 23, 2009.

(51) Int. Cl.
*A61K 31/54* (2006.01)
*C07D 487/08* (2006.01)
*C07D 471/08* (2006.01)
*C07D 471/18* (2006.01)

(52) U.S. Cl.
CPC ............ *C07D 487/08* (2013.01); *C07D 471/08* (2013.01); *C07D 471/18* (2013.01)

(58) Field of Classification Search
None
See application file for complete search history.

(56) References Cited

U.S. PATENT DOCUMENTS

| 4,360,673 | A  | 11/1982 | Berger et al. |
| 5,250,537 | A  | 10/1993 | Mewshaw et al. |
| 5,620,988 | A  | 4/1997  | Glase et al. |
| 6,187,785 | B1 | 2/2001  | Zefirov et al. |
| 6,251,893 | B1 | 6/2001  | Maddaford et al. |
| 7,071,206 | B2 | 7/2006  | Zefirov et al. |
| 8,338,408 | B2 | 12/2012 | Hung et al. |
| 8,338,447 | B2 | 12/2012 | Hung et al. |
| 8,362,277 | B2 | 1/2013  | McKnight et al. |
| 8,541,437 | B2 | 9/2013  | Ivashchenko et al. |
| 8,546,381 | B2 | 10/2013 | Hung et al. |
| 8,569,287 | B2 | 10/2013 | Hung et al. |
| 8,604,074 | B2 | 12/2013 | McKnight et al. |
| 8,735,440 | B2 | 5/2014  | McKnight et al. |
| 8,741,919 | B2 | 6/2014  | Jain et al. |
| 8,791,132 | B2 | 7/2014  | Protter et al. |
| 8,815,843 | B2 | 8/2014  | Protter et al. |
| 8,859,561 | B2 | 10/2014 | Jain et al. |
| 8,877,797 | B2 | 11/2014 | McKnight et al. |
| 8,906,925 | B2 | 12/2014 | Hung et al. |
| 8,907,097 | B2 | 12/2014 | Hung et al. |
| 2001/0020028 | A1 | 9/2001  | Zefirov et al. |
| 2002/0115682 | A1 | 8/2002  | Zefirov et al. |
| 2004/0044022 | A1 | 3/2004  | Zefirov, Jr. et al. |
| 2006/0140866 | A1 | 6/2006  | Zefirov et al. |
| 2007/0117834 | A1 | 5/2007  | Hung |
| 2007/0117835 | A1 | 5/2007  | Hung |
| 2007/0179174 | A1 | 8/2007  | Bachurin et al. |
| 2007/0225316 | A1 | 9/2007  | Bachurin et al. |
| 2008/0234310 | A1 | 9/2008  | Bachurin et al. |
| 2009/0247561 | A1 | 10/2009 | Zemoka et al. |
| 2010/0022580 | A1 | 1/2010  | Hung et al. |
| 2010/0029706 | A1 | 2/2010  | Miller et al. |
| 2010/0087471 | A1 | 4/2010  | Schrimpf et al. |
| 2010/0099700 | A1 | 4/2010  | Hung |
| 2010/0152108 | A1 | 6/2010  | Hung et al. |
| 2010/0152225 | A1 | 6/2010  | Hung |
| 2010/0178277 | A1 | 7/2010  | Hung et al. |
| 2010/0216814 | A1 | 8/2010  | Hung et al. |
| 2010/0249105 | A1 | 9/2010  | Schrimpf et al. |
| 2010/0286188 | A1 | 11/2010 | Bachurin et al. |
| 2011/0046368 | A1 | 2/2011  | Ivashchenko et al. |
| 2011/0112132 | A1 | 5/2011  | Bachurin et al. |
| 2011/0237582 | A1 | 9/2011  | Jain et al. |

(Continued)

FOREIGN PATENT DOCUMENTS

EP 0 876 818 A2 11/1998
EP 2 236 511 A2 10/2010

(Continued)

OTHER PUBLICATIONS

Bartolini, L. et al. (1996). "Aniracetam Restores Object Recognition Impaired by Age, Scopolamine, and Nucleus Basalis Lesions," *Pharmacology Biochemistry Behavior* 53(2):277-283.
Berge, S.M. et al. (Jan. 1977). "Pharmaceutical Salts," *J. Pharm. Sci.* 66(1):1-19.
Boess, F.G. et al. (1997). "Analysis of the Ligand Binding Site of the $5-HT_3$ Receptor Using Site Directed Mutagenesis: Importance of Glutamate 106," *Neuropharmacology* 36(4/5):637-647.
Bonhaus, D.W. et al. (1995). "The Pharmacology and Distribution of Human 5-Hydroxytryptamine$_{2B}$ ($5-HT_{2B}$) Receptor Gene Products: Comparison with $5-HT_{2A}$ and $5-HT_{2C}$ Receptors," *British Journal of Pharmacology* 115:622-628.
Brown, C.M. et al. (1990). "$\beta_2$-Adrenoceptor Subtypes and Imidazoline-Like Binding Sites in the Rat Brain," *Br. J. Pharmacol.* 99:803-809.

(Continued)

*Primary Examiner* — Jeffrey S Lundgren
*Assistant Examiner* — Michael Schmitt
(74) *Attorney, Agent, or Firm* — Morrison & Foerster LLP

(57) ABSTRACT

This disclosure relates to new compounds that may be used to modulate a histamine receptor in an individual. Novel compounds are described, including new bridged heterocyclic[4,3-b]indole compounds. Pharmaceutical compositions are also provided. Pharmaceutical compositions comprising the compounds are also provided, as are methods of using the compounds in a variety of therapeutic applications, including the treatment of a cognitive disorder, psychotic disorder, neurotransmitter-mediated disorder and/or a neuronal disorder.

16 Claims, No Drawings

(56) References Cited

U.S. PATENT DOCUMENTS

| | | |
|---|---|---|
| 2011/0245272 A1 | 10/2011 | Jain et al. |
| 2011/0269777 A1 | 11/2011 | Bachurin et al. |
| 2012/0022096 A1 | 1/2012 | McKnight et al. |
| 2012/0101121 A1 | 4/2012 | Bachurin et al. |
| 2012/0136008 A1 | 5/2012 | Jain et al. |
| 2013/0040977 A1 | 2/2013 | McKnight et al. |
| 2013/0053367 A1 | 2/2013 | Protter et al. |
| 2013/0079352 A1 | 3/2013 | Hung et al. |
| 2013/0123277 A1 | 5/2013 | Jain et al. |
| 2013/0131054 A1 | 5/2013 | Hung et al. |
| 2013/0131077 A1 | 5/2013 | Hung et al. |
| 2013/0137705 A1 | 5/2013 | Jain et al. |
| 2013/0172320 A1 | 7/2013 | Chakravarty et al. |
| 2013/0184269 A1 | 7/2013 | Hung et al. |
| 2013/0184303 A1 | 7/2013 | Jain et al. |
| 2013/0184304 A1 | 7/2013 | Jain et al. |
| 2013/0184306 A1 | 7/2013 | Hung et al. |
| 2013/0190293 A1 | 7/2013 | Chakravarty et al. |
| 2013/0190294 A1 | 7/2013 | Protter et al. |
| 2013/0190295 A1 | 7/2013 | Hung et al. |
| 2013/0190303 A1 | 7/2013 | Hung et al. |
| 2013/0190304 A1 | 7/2013 | Hung et al. |
| 2013/0190308 A1 | 7/2013 | Jain et al. |
| 2013/0190322 A1 | 7/2013 | Hung et al. |
| 2013/0190323 A1 | 7/2013 | Hung et al. |
| 2013/0190328 A1 | 7/2013 | Jain et al. |
| 2013/0190331 A1 | 7/2013 | Jain et al. |
| 2013/0190344 A1 | 7/2013 | Jain et al. |
| 2013/0190347 A1 | 7/2013 | Hung et al. |
| 2013/0190348 A1 | 7/2013 | Hung et al. |
| 2013/0190359 A1 | 7/2013 | Jain et al. |
| 2013/0203746 A1 | 8/2013 | Hung et al. |
| 2013/0210803 A1 | 8/2013 | Chakravarty et al. |
| 2013/0217675 A1 | 8/2013 | Chakravarty et al. |
| 2013/0225558 A1 | 8/2013 | Chakravarty et al. |
| 2014/0024643 A1 | 1/2014 | Hung et al. |
| 2014/0088086 A1 | 3/2014 | Protter et al. |
| 2014/0088087 A1 | 3/2014 | Hung et al. |
| 2014/0155384 A1 | 6/2014 | Protter et al. |
| 2014/0194414 A1 | 7/2014 | Hung et al. |
| 2014/0206711 A1 | 7/2014 | Chakravarty et al. |
| 2014/0213577 A1 | 7/2014 | Hung et al. |
| 2014/0228353 A1 | 8/2014 | Protter et al. |
| 2014/0296209 A1 | 10/2014 | Protter et al. |
| 2014/0303144 A1 | 10/2014 | Protter et al. |

FOREIGN PATENT DOCUMENTS

| | | |
|---|---|---|
| WO | WO-2005/005951 A2 | 6/2005 |
| WO | WO-2005/005951 A3 | 6/2005 |
| WO | WO-2007/022502 A2 | 2/2007 |
| WO | WO-2007/022502 A3 | 2/2007 |
| WO | WO-2007/041697 A2 | 4/2007 |
| WO | WO-2007/041697 A3 | 4/2007 |
| WO | WO-2007/087425 A1 | 8/2007 |
| WO | WO-2008/036400 A2 | 3/2008 |
| WO | WO-2008/036400 A3 | 3/2008 |
| WO | WO-2008/036410 A2 | 3/2008 |
| WO | WO-2008/036410 A3 | 3/2008 |
| WO | WO-2008/051599 A2 | 5/2008 |
| WO | WO-2008/051599 A3 | 5/2008 |
| WO | WO-2008/060190 A2 | 5/2008 |
| WO | WO-2008/060190 A3 | 5/2008 |
| WO | WO-2008/069963 A1 | 6/2008 |
| WO | WO-2008/073231 A1 | 6/2008 |
| WO | WO-2008/115098 A2 | 9/2008 |
| WO | WO-2008/115098 A3 | 9/2008 |
| WO | WO-2008/123796 A2 | 10/2008 |
| WO | WO-2008/123796 A3 | 10/2008 |
| WO | WO-2008/123800 A2 | 10/2008 |
| WO | WO-2008/123800 A3 | 10/2008 |
| WO | WO-2008/147551 A1 | 12/2008 |
| WO | WO-2009/005771 A1 | 1/2009 |
| WO | WO-2009/017836 A1 | 2/2009 |
| WO | WO-2009/039420 A1 | 3/2009 |
| WO | WO-2009/039420 A9 | 3/2009 |
| WO | WO-2009/055828 A1 | 4/2009 |
| WO | WO-2009/082268 A2 | 7/2009 |
| WO | WO-2009/082268 A3 | 7/2009 |
| WO | WO-2009/094668 A1 | 7/2009 |
| WO | WO-2009/094668 A8 | 7/2009 |
| WO | WO-2009/094668 C1 | 7/2009 |
| WO | WO-2009/111540 A1 | 9/2009 |
| WO | WO-2009/120717 A2 | 10/2009 |
| WO | WO-2009/120717 A3 | 10/2009 |
| WO | WO 2009120720 A1 * | 10/2009 |
| WO | WO-2009/135091 A1 | 11/2009 |
| WO | WO-2010/036998 A2 | 4/2010 |
| WO | WO-2010/036998 A3 | 4/2010 |
| WO | WO-2010/051501 A1 | 5/2010 |
| WO | WO-2010/051503 A1 | 5/2010 |
| WO | WO-2010/081115 A1 | 7/2010 |
| WO | WO-2010/127177 A1 | 11/2010 |
| WO | WO-2011/008312 A2 | 1/2011 |
| WO | WO-2011/008312 A3 | 1/2011 |
| WO | WO-2011/014098 A1 | 2/2011 |
| WO | WO-2011/014695 A1 | 2/2011 |
| WO | WO-2011/019417 A1 | 2/2011 |
| WO | WO-2011/038161 A1 | 3/2011 |
| WO | WO-2011/038162 A1 | 3/2011 |
| WO | WO-2011/038163 A1 | 3/2011 |
| WO | WO-2011/038164 A1 | 3/2011 |
| WO | WO-2011/103430 A1 | 8/2011 |
| WO | WO-2011/103433 A1 | 8/2011 |
| WO | WO-2011/103448 A1 | 8/2011 |
| WO | WO-2011/103460 A1 | 8/2011 |
| WO | WO-2011/103485 A1 | 8/2011 |
| WO | WO-2011/103487 A1 | 8/2011 |
| WO | WO-2012/006419 A2 | 1/2012 |
| WO | WO-2012/006419 A3 | 1/2012 |
| WO | WO-2012/112961 A1 | 8/2012 |
| WO | WO-2012/112962 A1 | 8/2012 |
| WO | WO-2012/112963 A1 | 8/2012 |
| WO | WO-2012/112964 A2 | 8/2012 |
| WO | WO-2012/112964 A3 | 8/2012 |
| WO | WO-2012/112965 A1 | 8/2012 |
| WO | WO-2012/112966 A1 | 8/2012 |
| WO | WO-2012/154261 A1 | 11/2012 |
| WO | WO-2014/031125 A1 | 2/2014 |
| WO | WO-2014/031165 A1 | 2/2014 |
| WO | WO-2014/031167 A1 | 2/2014 |
| WO | WO-2014/031170 A1 | 2/2014 |

OTHER PUBLICATIONS

Bubber, P. et al. (May 2005, e-published Apr. 25, 2005). "Mitochondrial Abnormalities in Alzheimer Brain: Mechanistic Implications," *Ann Neurol.* 57(5):695-703.

Cava, M.P. et al. (Nov. 1965). "A New Isoquinuclidine Synthesis. A New Route to *dl*-Dioscorone," *J. Org. Chem.* 30:3772-3775.

Cordero, F.M. et al. (1995). "Intramolecular Cycloadditions and Thermal Rearrangement of Cyclopropylidene Nitrones. Straightforward Access to Bicyclic Tetrahydropyridones," *Tetrahedron Lett.* 36(8):1343-1346.

Cordonnier, G. et al. (1994). "Synthesis of Uncommon Heterocyclic Systems: Pyrano- and [1]Benzopyrano[3,2-f]indolizines,"*Tetrahedron Lett.* 35(46):8617-8618.

De Backer, M.D. et al. (Dec. 30, 1993). "Genomic Cloning, Heterologous Expression and Pharmacological Characterization of a Human Histamine H1 Receptor," *Biochemical and Biophysical Research Communications* 197(3):1601-1608.

Ennaceur, A. et al. (1988). "A New One-Trial Test for Neurobiological Studies of Memory in Rats. 1: Behavioral Data," *Behav. Brain. Res.* 31:47-59.

Extended European Search Report mailed on Feb. 5, 2013 for EP Application No. 10819490.3 filed on Sep. 23, 2010, 24 pages.

Extended European Search Report mailed Feb. 6, 2013 for EP Application No. 10819493.7, filed on Sep. 23, 2010, 7 pages.

Final Office Action mailed on Dec. 2, 2011, for U.S. Appl. No. 12/360,061, filed Jan. 26, 2009, 13 pages.

(56) References Cited

OTHER PUBLICATIONS

Final Office Action mailed on Jul. 19, 2012, for U.S. Appl. No. 12/410,425, filed Mar. 24, 2009, 10 pages.
Final Office Action mailed on Jul. 25, 2013, for U.S. Appl. No. 12/610,217, filed Oct. 30, 2009, 11 pages.
Final Office Action mailed on Jul. 1, 2014, for U.S. Appl. No. 13/789,606, filed Mar. 7, 2013, 17 pages.
García-Sáinz, J.A. et al. (Jul. 31, 1992). "Species Heterogeneity of Hepatic $\alpha_1$-Adrenoceptors: $\alpha_{1A}$-, $\alpha_{1C}$-Subtypes," *Biochemical and Biophysical Research Communications* 186(2):760-767.
Gilliland, S.L. et al. (2000, e-pub. Feb. 29, 2000). "Characterization of Dopaminergic Compounds at $hD_{2short}$, $hD_{4.2}$ and $h_{D4.7}$ Receptors in Agonist-Stimulated [$^{35}$S]GTPγS Binding Assays," *Naunyn-Schmiedeberg's Archives of Pharmacology* 361:498-504.
Grandy, D.K. et al. (Dec. 1989). "Cloning of the cDNA and Gene for a Human $D_2$ Dopamine Receptor," *Proc. Natl. Acad. Sci. USA* 86:9762-9766.
Grossman, C.J. et al. (1993). "Development of a Radioligand Binding Assay for 5-$HT_4$ Receptors in Guinea-Pig and Rat Brain," *Br. J. Pharmacol.* 109:618-624.
Hardy, J. (1996). "New Insights Into the Genetics of Alzheimer's Disease," *Annals of Medicine* 28:255-258.
Hardy, J. (1997). "Amyloid, the Presenilins and Alzheimer's Disease," *Trends Neurosci.* 20(4):154-159.
Hayes, G. et al. (1992). "Structural Subtypes of the Dopamine D2 Receptor are Functionally Distinct: Expression of the Cloned $D2_A$ and $D2_B$ Subtypes in a Heterologous Cell Line," *Mol. Endocrinol.* 6(6):920-926.
Howard, A.S. et al. (1980). "Vinylogous Urethanes in Alkaloid Synthesis: Formal Syntheses of Elaeocarpus Alkaloids," *Tetrahedron Lett.* 21(14):1373-1374.
Hoyer, D. et al. (1985). "Characterization of the 5-$HT_{1B}$ Recognition Site in Rat Brain: Binding Studies with (-)[$^{125}$I]Iodocyanopindolol," *European Journal of Pharmacology* 118:1-12.
International Search Report mailed on Jun. 15, 2009 for PCT Patent Application No. PCT/US2009/038142, filed on Mar. 24, 2009, 2 pages.
International Search Report mailed on Nov. 10, 2010, for PCT Application No. PCT/US2010/050078, filed on Sep. 23, 2010, 2 pages.
International Search Report mailed on Nov. 10, 2010, for PCT Application No. PCT/US2010/50081, filed on Sep. 23, 2010, 3 pages.
Jentsch, J.D. et al. (Aug. 15, 1997). "Enduring Cognitive Deficits and Cortical Dopamine Dysfunction in Monkeys After Long-Term Administration of Phencyclidine," *Science* 277:953-955.
Jerman, J.C. et al. (2001). "Pharmacological Characterisation of Human 5-$HT_2$ Receptor Subtypes," *European Journal of Pharmacology* 414:23-30.
Kenny, B.A. et al. (1995). "Characterization of an $\alpha_{1D}$-Adrenoceptor Mediating the Contractile Response of Rat Aorta to Noradrenaline," *British Journal of Pharmacology* 115:981-986.
King, F.D. (1983). "A Facile Synthesis of Quinolizidines and Indolizidines," *Tetrahedron Lett.* 24(31):3281-3282.
King, F.D. et al. (1993). "Substituted Benzamides With Conformationally Restricted Side Chains. 5. Azabicyclo[x.y.z] Derivatives as 5-HT4 Receptor Agonists and Gastric Motility Stimulants," *J. Med. Chem.* 36(6):683-689.
Kohen, R. et al. (1996). "Cloning, Characterization and Chromosomal Localization of a Human 5-$HT_6$ Serotonin Receptor," *J. Neurochem.* 66(1):47-56.
Lee, J. et al. (2006, e-published Oct. 14, 2005). "The Role of Stimulus Salience in CPT-AX Performance of Schizophrenia Patients," *Schizophr. Res.* 81(2-3):191-197.
Levinoff, E.J. et al. (Jan. 2006). "Cognitive Estimation Impairment in Alzheimer Disease and Mild Cognitive Impairment," *Neuropsychology* 20(1)123-132.
Lohr, J.B. et al. (Aug. 28, 1995). "Motor Asymmetry, a Neurobiologic Abnormality in the Major Psychoses," *Psychiatry Research* 57(3):279-282.
Martin, G.R. (1994). "Receptors for 5-Hydroxytryptamine: Current Perspectives on Classification and Nomenclature," *Neuropharmacology* 33(3/4):261-273.
May, J.A. et al. (2003). "Evaluation of the Ocular Hypotensive Response of Serotonin 5-$HT_{1A}$ and 5-$HT_2$ Receptor Ligands in Conscious Ocular Hypertenisve Cynomolgus Monkeys," *The Journal of Pharmacology and Experimental Therapeutics* 306(1):301-309.
Mewshaw, R.E. et al. (1993). "Bridged γ-carbolines and Derivatives Possessing Selective and Combined Affinity for 5-$HT_2$ and $D_2$ Receptors," *J. Med. Chem.* 36(10):1488-1495.
Mewshaw, R.E. et al. (1993). "Synthesis and in Vitro Evaluation of 5,6,7,8,9,10-Hexahydro-7,10-iminocyclohept[*b*]indoles: High-Affinity Ligands for the N,N'-Di-*o*-tolylguanidine-Labeled σ Binding Site," *J. Med. Chem.* 36(3):343-352.
Michel, A.D. et al. (1989). "Identification of a Single $\alpha_1$-Adrenoceptor Corresponding to the $\alpha_{1A}$-Subtype in Rat Submaxillary Gland," *Br. J. Pharmacol.* 98:883-889.
Miller, K et al. (1992). "Membrane-Bound and Solubilized Brain $5HT_3$ Receptors: Improved Radioligand Binding Assays Using Bovine Area Postrema or Rat Cortex and the Radioligands $^3$H-GR65630, $^3$H-BRL43694, and $^3$H-LY278584," *Synapse* 11:58-66.
Miller, T.R. et al. (1999). "Analysis of Apparent Noncompetitive Responses to Competitive $H_1$-Histamine Receptor Antagonists in Fluorescent Imaging Plate Reader-Based Calcium Assays," *Journal of Biomolecular Screening* 4(5):249-258.
Monsma, F.J. Jr. et al. (1993). "Cloning and Expression of a Novel Serotonin Receptor with High Affinity for Tricyclic Psychotropic Drugs," *Molecular Pharmacology* 43:320-327.
Navarra, R. et al. (2008, e-published Jun. 27, 2007). "Effects of Atomoxetine and Methylphenidate on Attention and Impulsivity in the 5-Choice Serial Reaction Time Test," *Prog. Neuropsychopharmacol. Biol. Psychiatry* 32(1):34-41.
Non-Final Office Action mailed on Jun. 14, 2011, for U.S. Appl. No. 12/360,061, filed Jan. 26, 2009, 22 pages.
Non-Final Office Action mailed on Apr. 16, 2013, for U.S. Appl. No. 12/610,217, filed Oct. 30, 2009, 10 pages.
Non-Final Office Action mailed on Dec. 19, 2013, for U.S. Appl. No. 13/789,606, filed Mar. 7, 2013, 13 pages.
Non-Final Office Action mailed on Feb. 14, 2014, for U.S. Appl. No. 13/498,099, filed Jan. 14, 2013, 20 pages.
Non-Final Office Action mailed on Jul. 11, 2014, for U.S. Appl. No. 14/033,234, filed Sep. 20, 2013, 51 pages.
Non-Final Office Action mailed on Jul. 31, 2014, for U.S. Appl. No. 13/734,873, filed Jan. 4, 2013, 16 pages.
Non-Final Office Action mailed on Aug. 6, 2014, for U.S. Appl. No. 13/791,832, filed Mar. 8, 2013, 9 pages.
Pazos, A. et al. (1985). "Mesulergine, A Selective Serotonin-2 Ligand in the Rat Cortex, Does Not Label these Receptors in Porcine and Human Cortex: Evidence for Species Differences in Brain Serotonin-2 Receptors," *European Journal of Pharmacology* 106:531-538.
Piercey, M.F. et al. (1988). "Dramatic Limbic and Cortical Effects Mediated by High Affinity PCP Receptors," *Life Sciences* 43(4):379-385.
Prichep, L.S. et al. (1994). "Quantitative EEG Correlates of Cognitive Deterioration in the Elderly," *Neurobiology of Aging* 15(1):85-90.
Reddy, P.H. et al. (2005, e-pub. Apr. 19, 2005). "Are Mitochondria Critical in the Pathogenesis of Alzheimer's Disease?" *Brain Res Rev.* 49(3):618-632.
Rees, S. et al. (Oct. 11, 1994). "Cloning and Characterisation of the Human 5-$HT_{5A}$ Serotonin Receptor," *FEBS Letters* 355:242-246.
Reisberg, B. et al. (Sep. 1982). "The Global Deterioration Scale for Assessment of Primary Degenerative Dementia," *Am. J. Psychiatry* 139(9):1136-1139.
Riccio, C.A. et al. (2001). "Effects of Stimulants on the Continuous Performance Test (CPT): Implications for CPT use and Interpretation," *J. Neuropsychiatry Clin. Neurolsci.* 13(3):326-335.
Robbins, T. (Oct. 2002, e-pub. Aug. 9, 2002). "The 5-Choice Serial Reaction Time Task: Behavioural Pharmacology and Functional Neurochemistry," *Psychopharmacology* 163(3-4):362-380.

(56) References Cited

OTHER PUBLICATIONS

Roth, B.L. et al. (1994). "Binding of Typical and Atypical Antipsychotic Agents to 5-Hydroxytryptamine-6 and 5-Hydroxytryptamine-7 Receptors," *J. Pharmacol. Exp. Ther.* 268(3):1403-1410.

Ruat, M. et al. (Mar. 1990). "Reversible and Irreversible Labeling and Autoradiographic Localization of the Cerebral Histamine $H_2$ Receptor Using [$^{125}$I]Iodinated Probes," *Proc. Natl. Acad. Sci. USA* 87(5):1658-1662.

Saucier, C. et al. (1997). "Identification of an Endogenous 5-Hydroxytryptamine$_{2A}$ Receptor in NIH-3T3 Cells: Agonist-Induced Down-Regulation Involves Decreases in Receptor RNA and Number," *Journal of Neurochemistry* 68(5):1998-2011.

Scali, C. et al. (1994). "Nerve Growth Factor Increases Extracellular Acetylcholine Levels in the Parietal Cortex and Hippocampus of Aged Rats and Restores Object Recognition," *Neuroscience Letters* 170:117-120.

Senogles, S.E. et al. (Mar. 15, 1990). "Specificity of Receptor-G Protein Interactions. Discrimination of $G_i$ Subtypes by the $D_2$ Dopamine Receptor in a Reconstituted System," *Journal of Biological Chemistry* 265(8):4507-4514.

Shen, Y. et al. (Aug. 25, 1993). "Molecular Cloning and Expression of a 5-Hydroxytryptamine$_7$ Serotonin Receptor Subtype," *The Journal of Biological Chemistry* 268(24):18200-18204.

Swerdlow, R.H. et al. (2002). "Mitochondria in Alzheimer's Disease," *International Review of Neurobiology* 53:341-385.

Tanzi, R.E. et al. (1996). "The Gene Defects Responsible for Familial Alzheimer's Disease," *Neurobiology of Disease* 3:159-168.

Uhlén, S. et al. (1994). "The Novel *Alpha*-2 Adrenergic RadioLigand [$^3$H]-MK912 is *Alpha*-2C Selective Among Human *Alpha*-2A, *Alpha*-2B and *Alpha*-2C Adrenoceptors," *Journal of Pharmacology and Experimental Therapeutics* 271(3):1558-1565.

Uhlén, S. et al. (1998). "[$^3$H]S79948-197 Binding to Human, Rat, Guinea Pig and Pig $\alpha_{2A}$-, $\alpha_{2B}$- and $\alpha_{2C}$-Adrenoceptors. Comparison with MK912, RX821002, Rauwolscine and Yohimbine," *European Journal of Pharmacology* 343:93-101.

Vippagunta, S.R. et al. (2001). "Crystalline Solids," *Advanced Drug Delivery Reviews* 48:3-26.

Wang, X. et al. (2007, e-pub. Sep. 21, 2007). "Insights Into Amyloid-β-Induced Mitochondrial Dysfunction in Alzheimer Disease," *Free Radical Biology & Medicine* 43:1569-1573.

Williams, D.A. et al. 2002. *Foye's Principles of Medicinal Chemistry*, 5$^{th}$ Edition, pp. 59-63.

Wolf, W.A. et al. (1997). "The Serotonin 5-HT$_{2C}$ Receptor is a Prominent Serotonin Receptor in Basal Ganglia: Evidence from Functional Studies on Serotonin-Mediated Phosphoinositide Hydrolysis," *Journal of Neurochemistry* 69(4):1449-1458.

Written Opinion of the International Searching Authority mailed on Jun. 15, 2009 for PCT Patent Application No. PCT/US2009/038142, filed on Mar. 24, 2009, 8 pages.

Written Opinion mailed on Nov. 10, 2010, for PCT Application No. PCT/US2010/050078, filed on Sep. 23, 2010, 4 pages.

Written Opinion mailed on Nov. 10, 2010, for PCT Application No. PCT/US2010/50081, filed on Sep. 23, 2010, 5 pages.

Yanai, K. et al. (1994). "Binding Characteristics of a Histamine $H_3$-Receptor Antagonist, [$^3$H]S-Methylthioperamide: Comparison with [$^3$H](R)α-Methylhistamine Binding to Rat Tissues," *Jpn. J. Pharmacol.* 65:107-112.

Zhu, Y. et al. (2001). "Cloning, Expression, and Pharmacological Characterization of a Novel Human Histamine Receptor," *Molecular Pharmacology* 59(3):434-441.

U.S. Appl. No. 14/000,171, filed Aug. 16, 2013, by Protter et al.
U.S. Appl. No. 14/000,184, filed Aug. 16, 2013, by Protter et al.
U.S. Appl. No. 14/000,197, filed Aug. 16, 2013, by Protter et al.
U.S. Appl. No. 14/485,238, filed Sep. 12, 2014, by Jain et al.
U.S. Appl. No. 14/531,915, filed Nov. 3, 2014, by Hung et al.

* cited by examiner

BRIDGED HETEROCYCLIC COMPOUNDS AND METHODS OF USE

CROSS-REFERENCE TO RELATED APPLICATIONS

This application is a continuation application claiming the priority benefit of U.S. application Ser. No. 13/498,097, submitted Mar. 23, 2012 under 35 U.S.C. §371 as a U.S. national stage application of International Application No. PCT/US2010/050081, having an International Filing Date of Sep. 23, 2010, and which claims priority to U.S. Provisional Patent Application No. 61/245,151, filed Sep. 23, 2009, the disclosure of which is hereby incorporated herein by reference in its entirety.

STATEMENT OF RIGHTS TO INVENTIONS MADE UNDER FEDERALLY SPONSORED RESEARCH

Not applicable.

BACKGROUND OF THE INVENTION

Neurotransmitters such as histamine, serotonin, dopamine and norepinephrine mediate a large number of processes in the central nervous system (CNS) as well as outside the CNS. Abnormal neurotransmitter levels are associated with a wide variety of diseases and conditions including, but not limited to, Alzheimer's disease, Parkinson's Disease, autism, attention deficit disorder (ADD), attention deficit hyperactivity disorder (ADHD), Guillain-Barré syndrome, mild cognitive impairment, schizophrenia (such as cognitive impairment associated with schizophrenia (CIAS), positive symptoms, disorganized symptoms, and negative symptoms of schizophrenia), anxiety, multiple sclerosis, stroke, traumatic brain injury, spinal cord injury, diabetic neuropathy, fibromyalgia, bipolar disorders, psychosis, depression and a variety of allergic diseases. Compounds that modulate these neurotransmitters may be useful therapeutics.

Histamine receptors belong to the superfamily of G protein-coupled seven transmembrane proteins. G protein-coupled receptors constitute one of the major signal transduction systems in eukaryotic cells. Coding sequences for these receptors, in those regions believed to contribute to the agonist-antagonist binding site, are strongly conserved across mammalian species. Histamine receptors are found in most peripheral tissue and within the central nervous system. Compounds capable of modulating a histamine receptor may find use in therapy, e.g., as antihistamines.

Dimebon is a known anti-histamine drug that has also been characterized as a neuroprotective agent useful to treat, inter alia, neurodegenerative diseases. Dimebon has been shown to inhibit the death of brain cells (neurons) in preclinical models of Alzheimer's disease and Huntington's disease, making it a novel potential treatment for these and other neurodegenerative diseases. In addition, dimebon has been shown to improve the mitochondrial function of cells in the setting of cellular stress with very high potency. For example, dimebon treatment improved mitochondrial function and increased the number of surviving cells after treatment with the cell toxin ionomycin in a dose dependent fashion. Dimebon has also been shown to promote neurite outgrowth and neurogenesis, processes important in the formation of new and/or enhanced neuronal cell connections, and evidence of dimebon's potential for use in additional diseases or conditions. See, e.g., U.S. Pat. Nos. 6,187,785 and 7,071,206 and PCT Patent Application Nos. PCT/US2004/041081, PCT/US2007/020483, PCT/US2006/039077, PCT/US2008/077090, PCT/US2007/020516, PCT/US2007/022645, PCT/US2007/002117, PCT/US2008/006667, PCT/US2007/024626, PCT/US2008/009357, PCT/US2007/024623, PCT/US2008/008121 and PCT/US2009/032065. Hydrogenated pyrido[4,3-b]indoles and uses thereof have been disclosed in PCT Patent Application Nos. PCT/US2008/081390, PCT/US2009/032065 and PCT/US2009/038142. Hydrogenated pyrido[3,4-b]indoles and uses thereof have been described in PCT/US2009/038138. All references disclosed herein and throughout, such as publications, patents, patent applications and published patent applications, are incorporated herein by reference in their entireties.

Although dimebon holds great promise as a drug for the treatment of neurodegenerative diseases and/or diseases in which neurite outgrowth and/or neurogenesis may be implicated in therapy, there remains a need for new and alternative therapies for the treatment of such diseases or conditions. In addition, there remains a need for new and alternative antihistamine drugs, preferably ones in which side-effects such as drowsiness are reduced or eliminated. Compounds that exhibit enhanced and/or more desirable properties than dimebon (e.g., superior safety and efficacy) may find particular use in the treatment of at least those indications for which dimebon is believed to be advantageous. Further, compounds that exhibit a different therapeutic profile than dimebon as determined, e.g. by in vitro and/or in vivo assays, may find use in additional diseases and conditions.

BRIEF SUMMARY OF THE INVENTION

Hydrogenated pyrido[4,3-b]indoles are provided Compositions and kits comprising the compounds are also provided, as are methods of using and making the compounds. The compounds provided herein may find use in treating neurodegenerative diseases. Compounds of the invention may also find use in treating diseases and/or conditions in which modulation of aminergic G protein-coupled receptors and/or neurite outgrowth may be implicated in therapy. Compounds disclosed herein may find use in the methods disclosed herein, including use in treating, preventing, delaying the onset and/or delaying the development of a cognitive disorder, psychotic disorder, neurotransmitter-mediated disorder and/or a neuronal disorder in an individual in need thereof, such as humans. For example, compounds of the general formulae herein, such as compounds of the formula (I), (I-1)-(I-5), (I-3a)-(I-3g), A-2, E, F, F-1, F-2, H-5, H-6, (J-1)-(J-11), (K-1)-K-7) and (L-1)-(L-8) are described as new histamine receptor modulators and may also find use in treating neurodegenerative diseases.

Compounds of the formula (E) are detailed herein:

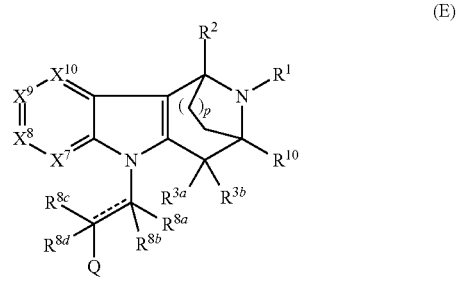

(E)

where:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

$R^2$ is H, hydroxyl, alkoxy or substituted or unsubstituted $C_1$-$C_8$ alkyl;

each $R^{3a}$ and $R^{3b}$ is independently H, substituted or unsubstituted $C_1$-$C_8$ alkyl, halo, cyano, nitro, hydroxyl, alkoxy, substituted or unsubstituted amino, cycloalkyl, aryl, heteroaryl, heterocyclyl, acylamino or acyloxy or $R^{3a}$ and $R^{3b}$ are taken together with the carbon to which they are attached to form a cycloalkyl moiety or a carbonyl moiety;

each $X^7$, $X^8$, $X^9$ and $X^{10}$ is independently N or $CR^4$;

p is 1 or 2;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, carbonylalkoxy, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$ and $R^{8d}$ is independently H, hydroxyl, alkoxy, halo, substituted or unsubstituted $C_1$-$C_8$ alkyl, substituted or unsubstituted $C_3$-$C_8$ cycloalkyl, substituted or unsubstituted $C_2$-$C_8$ alkenyl, $C_1$-$C_8$ perhaloalkyl, carboxyl, carbonylalkoxy, substituted or unsubstituted aryl, substituted or unsubstituted heteroaryl, or is taken together with a geminal $R^{8(a-d)}$ to form a substituted or unsubstituted methylene moiety or a moiety of the formula —OCH$_2$CH$_2$O—, or is taken together with a geminal $R^{8(a-d)}$ and the carbon to which they are attached to form a carbonyl moiety or a cycloalkyl moiety, or is taken together with a vicinal $R^{8(a-d)}$ and the carbon atoms to which they are attached to form a substituted or unsubstituted $C_3$-$C_8$ cycloalkyl, substituted or unsubstituted $C_3$-$C_8$ cycloalkenyl, or substituted or unsubstituted heterocyclyl moiety, or is taken together with a vicinal $R^{8(a-d)}$ to form a bond provided when an $R^{8(a-d)}$ is taken together with a vicinal $R^{8(a-d)}$ to form a bond, the geminal $R^{8(a-d)}$ is other than hydroxyl;

===== represents a single or double bond, provided that when ===== is a double bond, $R^{8a}$ and $R^{8c}$ are absent and $R^{8b}$ and $R^{8d}$ are other than OH;

$R^{10}$ is H, hydroxyl, alkoxy or a substituted or unsubstituted $C_1$-$C_8$ alkyl;

Q is a substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted amino, alkoxy, aminoacyl, acyloxy, carbonylalkoxy, aminocarbonylalkoxy, acylamino, carboxy, alkynyl or cyano;

or a salt or solvate thereof.

In one aspect, compounds are of the formula (E), provided that when $X^7$-$X^{10}$ is $CR^4$, and each $R^2$, $R^{3a}$, $R^{3b}$ and $R^{10}$ is H then at least one of $R^{8(a-d)}$ is hydroxyl or alkoxy. In another variation, compounds are of the formula (E), provided that when $X^7$, $X^8$ and $X^{10}$ are $CR^4$ where $R^4$ is H and $X^9$ is $CR^4$, then (i) at least one of $R^{8(a-d)}$ is hydroxyl, alkyl or alkoxy, and/or (ii) Q is other than a substituted or unsubstituted aryl, substituted or unsubstituted heteroaryl or heterocyclyl.

Compounds of formula (F-1) are also provided:

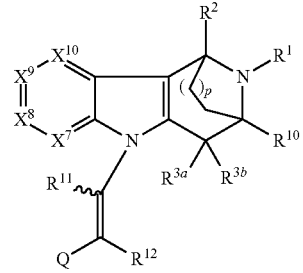

(F-1)

where:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^2$ and $R^{10}$ is independently H, hydroxyl, alkoxy or substituted or unsubstituted $C_1$-$C_8$ alkyl;

each $R^{3a}$ and $R^{3b}$ is independently H, substituted or unsubstituted $C_1$-$C_8$ alkyl, halo, cyano, nitro, hydroxyl, alkoxy, substituted or unsubstituted amino, cycloalkyl, aryl, heteroaryl, heterocyclyl, acylamino or acyloxy or $R^{3a}$ and $R^{3b}$ are taken together with the carbon to which they are attached to form a cycloalkyl or a carbonyl moiety;

p is 1 or 2;

each $X^7$, $X^8$, $X^9$ and $X^{10}$ is independently N or $CR^4$;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, carbonylalkoxy, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{11}$ and $R^{12}$ is independently H, halo, alkoxy, substituted or unsubstituted aryl, substituted or unsubstituted heteroaryl, substituted or unsubstituted $C_1$-$C_8$ alkyl, substituted or unsubstituted $C_2$-$C_8$ alkenyl, substituted or unsubstituted $C_3$-$C_8$ cycloalkyl, carboxy, carbonylalkoxy or $C_1$-$C_8$ perhaloalkyl and the ∿∿∿ bond indicates the presence of either an E or Z double bond configuration, or $R^{11}$ and $R^{12}$ are taken together to form a bond or are taken together with the carbon atoms to which they are attached to form a substituted or unsubstituted $C_{3-8}$ cycloalkenyl or substituted or unsubstituted heterocyclyl moiety;

∿∿∿ indicates the presence of either an E or Z double bond configuration when $R^{11}$ and $R^{12}$ are independently H or $C_1$-$C_8$ alkyl; and Q is a substituted or unsubstituted aryl, substituted or unsubstituted heteroaryl, substituted or unsubstituted cycloalkyl, substituted or unsubstituted cycloalkenyl, substituted or an unsubstituted heterocyclyl, substituted or unsubstituted amino, alkoxy, aminoacyl, acyloxy, carbonylalkoxy, aminocarbonylalkoxy, acylamino, carboxy, alkynyl or cyano;

provided that when $X^7$-$X^{10}$ is $CR^4$, and each $R^2$, $R^{3a}$, $R^{3b}$ and $R^{10}$ is H then at least one of $R^{11}$ or $R^{12}$ is alkoxy;

or a salt thereof.

Also described is a compound of the formula (F-2):

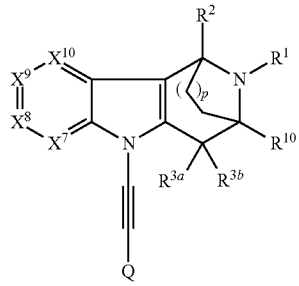

(F-2)

where:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^2$ and $R^{10}$ is independently H, hydroxyl, alkoxy or substituted or unsubstituted $C_1$-$C_8$ alkyl;

each $R^{3a}$ and $R^{3b}$ is independently H, substituted or unsubstituted $C_1$-$C_8$ alkyl, halo, cyano, nitro, hydroxyl, alkoxy, substituted or unsubstituted amino, cycloalkyl, aryl, heteroaryl, heterocyclyl, acylamino or acyloxy or $R^{3a}$ and $R^{3b}$ are taken together with the carbon to which they are attached to form a cycloalkyl or a carbonyl moiety;

p is 1 or 2;

each $X^7$, $X^8$, $X^9$ and $X^{10}$ is independently N or $CR^4$;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, carbonylalkoxy, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl; and Q is a substituted or unsubstituted aryl, substituted or unsubstituted heteroaryl, substituted or unsubstituted cycloalkyl, substituted or unsubstituted cycloalkenyl, substituted or an unsubstituted heterocyclyl, substituted or unsubstituted amino, alkoxy, aminoacyl, acyloxy, carbonylalkoxy, aminocarbonylalkoxy, acylamino, carboxy, alkynyl or cyano;

or a salt thereof.

The invention also includes all salts of compounds referred to herein, such as pharmaceutically acceptable salts. The invention also includes any or all of the stereochemical forms, including any enantiomeric or diastereomeric forms, of the compounds described. Unless stereochemistry is explicitly indicated in a chemical structure or name, the structure or name is intended to embrace all possible stereoisomers of a compound depicted. All forms of the compounds are also embraced by the invention, such as crystalline or non-crystalline forms of the compounds. Compositions comprising a compound of the invention are also intended, such as a composition of substantially pure compound, including a specific stereochemical form thereof. Compositions comprising a mixture of compounds of the invention in any ratio are also embraced by the invention, including mixtures of two or more stereochemical forms of a compound of the invention in any ratio, such that racemic, non-racemic, enantioenriched and scalemic mixtures of a compound are embraced.

The invention is also directed to pharmaceutical compositions comprising a compound of the invention and a pharmaceutically acceptable carrier or excipient. Kits comprising a compound of the invention and instructions for use are also embraced by this invention. Compounds as detailed herein or a pharmaceutically acceptable salt thereof are also provided for the manufacture of a medicament for the treatment of a cognitive disorder, psychotic disorder, neurotransmitter-mediated disorder or a neuronal disorder.

In one aspect, compounds of the invention are used to treat, prevent, delay the onset and/or delay the development of any one or more of the following: cognitive disorders, psychotic disorders, neurotransmitter-mediated disorders and/or neuronal disorders in individuals in need thereof, such as humans. In one variation, compounds of the invention are used to treat, prevent, delay the onset and/or delay the development of diseases or conditions for which the modulation of an aminergic G protein-coupled receptor is believed to be or is beneficial. In one variation, compounds of the invention are used to treat, prevent, delay the onset and/or delay the development of any one or more of diseases or conditions for which neurite outgrowth and/or neurogenesis and/or neurotrophic effects are believed to be or are beneficial. In another variation, compounds of the invention are used to treat, prevent, delay the onset and/or delay the development of diseases or conditions for which the modulation of an aminergic G protein-coupled receptor and neurite outgrowth and/or neurogenesis and/or neurotrophic effects are believed to be or are beneficial. In one variation, the disease or condition is a cognitive disorder, psychotic disorder, neurotransmitter-mediated disorder and/or a neuronal disorder.

In another aspect, compounds of the invention are used to improve cognitive function and/or reduce psychotic effects in an individual, comprising administering to an individual in need thereof an amount of a compound described herein or a pharmaceutically acceptable salt thereof effective to improve cognitive function and/or reduce psychotic effects.

In a further aspect, compounds of the invention are used to stimulate neurite outgrowth and/or promote neurogenesis and/or enhance neurotrophic effects in an individual comprising administering to an individual in need thereof an amount of a compound described herein or a pharmaceutically acceptable salt thereof effective to stimulate neurite outgrowth and/or to promote neurogenesis and/or to enhance neurotrophic effects. Synapse loss is associated with a variety of neurodegenerative diseases and conditions including Alzheimer's disease, schizophrenia, Huntington's disease, Parkinson's disease, amyotrophic lateral sclerosis, stroke, head trauma and spinal cord injury. Compounds of the invention that stimulate neurite outgrowth may have a benefit in these settings.

In another aspect, compounds described herein are used to modulate an aminergic G protein-coupled receptor comprising administering to an individual in need thereof an amount of a compound described herein or a pharmaceutically acceptable salt thereof effective to modulate an aminergic G protein-coupled receptor. In one variation, a compound of the invention modulates at least one of the following receptors: adrenergic receptor (e.g., $a_{1D}$, $a_{2A}$ and/or $a_{2B}$), serotonin receptor (e.g., 5-$HT_{2A}$, 5-$HT_{2C}$, 5-$HT_6$ and/or 5-$HT_7$), dopamine receptor (e.g., $D_{2L}$) and histamine receptor (e.g., $H_1$, $H_2$ and/or $H_3$). In another variation, at least two of the following receptors are modulated: adrenergic receptor (e.g., $a_{1D}$, $a_{2A}$ and/or $a_{2B}$), serotonin receptor (e.g., 5-$HT_{2A}$, 5-$HT_{2C}$, 5-$HT_6$ and/or 5-$HT_7$), dopamine receptor (e.g., $D_{2L}$) and histamine receptor (e.g., $H_1$, $H_2$ and/or $H_3$). In another variation, at least three of the following receptors are modulated: adrenergic receptor (e.g., $a_{1D}$, $a_{2A}$ and/or $a_{2B}$), serotonin receptor (e.g., 5-$HT_{2A}$, 5-$HT_{2C}$, 5-$HT_6$ and/or 5-$HT_7$), dopamine receptor (e.g., $D_{2L}$) and histamine receptor (e.g., $H_1$, $H_2$ and/or $H_3$). In another variation, each of the following receptors is modulated: adrenergic receptor (e.g., $a_{1D}$, $a_{2A}$ and/or $a_{2B}$), serotonin receptor (e.g., 5-$HT_{2A}$, 5-$HT_{2C}$, 5-$HT_6$ and/or 5-$HT_7$), dopamine receptor (e.g., $D_{2L}$) and histamine receptor (e.g., $H_1$, $H_2$ and/or $H_3$). In another variation, at least one of the following receptors is modulated: $a_{1D}$, $a_{2A}$, $a_{2B}$, 5-$HT_{2A}$, 5-$HT_{2C}$, 5-$HT_6$, 5-$HT_7$, $D_{2L}$, $H_1$, $H_2$ and $H_3$. In another variation, at least two or three or four or five or six or seven or eight or nine or ten or eleven of the following receptors are modulated: $a_{1D}$, $a_{2A}$, $a_{2B}$, 5-$HT_{2A}$, 5-$HT_{2C}$, 5-$HT_6$, 5-$HT_7$, $D_{2L}$, $H_1$, $H_2$ and $H_3$. In a particular variation, at least dopamine receptor $D_{2L}$ is modulated. In another particular variation, at least dopamine receptor $D_{2L}$ and serotonin receptor 5-$HT_{2A}$ are modulated. In a further particular variation, at least adrenergic receptors $a_{1D}$, $a_{2A}$, $a_{2B}$ and serotonin receptor 5-$HT_6$ are modulated. In another particular variation, at least adrenergic receptors $a_{1D}$, $a_{2A}$, $a_{2B}$, serotonin receptor 5-$HT_6$ and one or more of serotonin receptor 5-$HT_7$, 5-$HT_{2A}$, 5-$HT_{2C}$ and histamine receptor $H_1$ and $H_2$ are modulated. In a further particular variation, histamine receptor $H_1$ is modulated. In another variation, compounds of the invention exhibit any receptor modulation activity detailed herein and further stimulate neurite outgrowth and/or neurogenesis and/or enhance neurotrophic effects.

The invention is also directed to pharmaceutical compositions comprising a compound of the invention and a pharmaceutically acceptable carrier or excipient. Kits comprising a compound of the invention and instructions for use are also embraced by this invention.

DETAILED DESCRIPTION OF THE INVENTION

Definitions

For use herein, unless clearly indicated otherwise, use of the terms "a", "an" and the like refers to one or more.

Reference to "about" a value or parameter herein includes (and describes) embodiments that are directed to that value or parameter per se. For example, description referring to "about X" includes description of "X".

As used herein, the term "aminergic G protein-coupled receptors" refers to a family of transmembrane proteins involved in cellular communication. Aminergic G protein coupled receptors are activated by biogenic amines and represent a subclass of the superfamily of G protein coupled receptors, which are structurally characterized by seven transmembrane helices. Aminergic G protein-coupled receptors include but are not limited to adrenergic receptors, serotonin receptors, dopamine receptors, histamine receptors and imidazoline receptors.

As used herein, the term "adrenergic receptor modulator" intends and encompasses a compound that binds to or inhibits binding of a ligand to an adrenergic receptor or reduces or eliminates or increases or enhances or mimics an activity of an adrenergic receptor. As such, an "adrenergic receptor modulator" encompasses both an adrenergic receptor antagonist and an adrenergic receptor agonist. In some aspects, the adrenergic receptor modulator binds to or inhibits binding to a ligand to an $\alpha_1$-adrenergic receptor (e.g., $\alpha_{1A}$, $\alpha_{1B}$ and/or $\alpha_{1D}$) and/or a $\alpha_2$-adrenergic receptor (e.g., $\alpha_{2A}$, $\alpha_{2B}$ and/or $\alpha_{2C}$) and/or reduces or eliminates or increases or enhances or mimics an activity of a $\alpha_1$-adrenergic receptor (e.g., $\alpha_{1A}$, $\alpha_{1B}$ and/or $\alpha_{1D}$) and/or a $\alpha_2$-adrenergic receptor (e.g., $\alpha_{2A}$, $\alpha_{2B}$ and/or $\alpha_{2C}$) in a reversible or irreversible manner. In some aspects, the adrenergic receptor modulator inhibits binding of a ligand by at least about or about any one of 10%, 20%, 30%, 40%, 50%, 60%, 70%, 80%, 90%, 95% or 100% as determined in the assays described herein. In some aspects, the adrenergic receptor modulator reduces an activity of an adrenergic receptor by at least or about any of 10%, 20%, 30%, 40%, 50%, 60%, 70%, 80%, 90%, 95% or 100% as compared to the corresponding activity in the same subject prior to treatment with the adrenergic receptor modulator or compared to the corresponding activity in other subjects not receiving the adrenergic receptor modulator. In some aspects, the adrenergic receptor modulator enhances an activity of an adrenergic receptor by at least about or about any of 10%, 20%, 30%, 40%, 50%, 60%, 70%, 80%, 90%, 95% or 100 or 200% or 300% or 400% or 500% or more as compared to the corresponding activity in the same subject prior to treatment with the adrenergic receptor modulator or compared to the corresponding activity in other subjects not receiving the adrenergic receptor modulator. In some aspects, the adrenergic receptor modulator is capable of binding to the active site of an adrenergic receptor (e.g., a binding site for a ligand). In some embodiments, the adrenergic receptor modulator is capable of binding to an allosteric site of an adrenergic receptor.

As used herein, the term "dopamine receptor modulator" intends and encompasses a compound that binds to or inhibits binding of a ligand to a dopamine receptor or reduces or eliminates or increases or enhances or mimics an activity of a dopamine receptor. As such, a "dopamine receptor modulator" encompasses both a dopamine receptor antagonist and a dopamine receptor agonist. In some aspects, the dopamine receptor modulator binds to or inhibits binding of a ligand to a dopamine-1 ($D_1$) and/or a dopamine-2 ($D_2$) receptor or reduces or eliminates or increases or enhances or mimics an activity of a dopamine-1 ($D_1$) and/or a dopamine-2 ($D_2$) receptor in a reversible or irreversible manner. Dopamine $D_2$ receptors are divided into two categories, $D_{2L}$ and $D_{2S}$, which are formed from a single gene by differential splicing. $D_{2L}$ receptors have a longer intracellular domain than $D_{2S}$. In some embodiments, the dopamine receptor modulator inhibits binding of a ligand by at least about or about any one of 10%, 20%, 30%, 40%, 50%, 60%, 70%, 80%, 90%, 95% or 100% as determined in the assays described herein. In some embodiments, the dopamine receptor modulator reduces an activity of a dopamine receptor by at least about or about any of 10%, 20%, 30%, 40%, 50%, 60%, 70%, 80%, 90%, 95% or 100% as compared to the corresponding activity in the same subject prior to treatment with the dopamine receptor modulator or compared to the corresponding activity in other subjects not receiving the dopamine receptor modulator. In some embodiments, the dopamine receptor modulator enhances an activity of a dopamine receptor by at least about or about any of 10%, 20%, 30%, 40%, 50%, 60%, 70%, 80%, 90%, 95% or 100 or 200% or 300% or 400% or 500% or more as compared to the corresponding activity in the same subject prior to treatment with the dopamine receptor modulator or compared to the corresponding activity in other subjects not receiving the dopamine receptor modulator. In some embodiments, the dopamine receptor modulator is capable of binding to the active site of a dopamine receptor (e.g., a binding site for a ligand). In some embodiments, the dopamine receptor modulator is capable of binding to an allosteric site of a dopamine receptor.

As used herein, the term "serotonin receptor modulator" intends and encompasses a compound that binds to or inhibits binding of a ligand to a serotonin receptor or reduces or eliminates or increases or enhances or mimics an activity of a serotonin receptor. As such, a "serotonin receptor modulator" encompasses both a serotonin receptor antagonist and a serotonin receptor agonist. In some embodiments, the serotonin receptor modulator binds to or inhibits binding of a ligand to a $5-HT_{1A}$ and/or a $5-HT_{1B}$ and/or a $5-HT_{2A}$ and/or a $5-HT_{2B}$ and/or a $5-HT_{2C}$ and/or a $5-HT_3$ and/or a $5-HT_4$ and/or a $5-HT_6$ and/or a $5-HT_7$ receptor or reduces or eliminates or increases or enhances or mimics an activity of a $5-HT_{1A}$ and/or a $5-HT_{1B}$ and/or a $5-HT_{2A}$ and/or a $5-HT_{2B}$ and/or a $5-HT_{2C}$ and/or a $5-HT_3$ and/or a $5-HT_4$ and/or a $5-HT_6$ and/or a $5-HT_7$ receptor in a reversible or irreversible manner. In some embodiments, the serotonin receptor modulator inhibits binding of a ligand by at least about or about any one of 10%, 20%, 30%, 40%, 50%, 60%, 70%, 80%, 90%, 95% or 100% as determined in the assays described herein. In some embodiments, the serotonin receptor modulator reduces an activity of a serotonin receptor by at least about or about any of 10%, 20%, 30%, 40%, 50%, 60%, 70%, 80%, 90%, 95% or 100% as compared to the corresponding activity in the same subject prior to treatment with the serotonin receptor modulator or compared to the corresponding activity in other subjects not receiving the serotonin receptor modulator. In some embodiments, the serotonin receptor modulator enhances an activity of a serotonin receptor by at least about or about any of 10%, 20%, 30%, 40%, 50%, 60%, 70%, 80%, 90%, 95% or 100 or 200% or 300% or 400% or 500% or more as compared to the corresponding activity in the same subject prior to treatment with the serotonin receptor modulator or compared to the corresponding activity in other subjects not receiving the serotonin receptor modulator. In some embodiments, the serotonin receptor modulator is capable of binding to the active site of a serotonin receptor (e.g., a binding site for a ligand). In some embodiments, the serotonin receptor modulator is capable of binding to an allosteric site of a serotonin receptor.

As used herein, the term "histamine receptor modulator" intends and encompasses a compound that binds to or inhibits binding of a ligand to a histamine receptor or reduces or eliminates or increases or enhances or mimics an activity of a histamine receptor. As such, a "histamine receptor modulator" encompasses both a histamine receptor antagonist and a histamine receptor agonist. In some embodiments, the histamine receptor modulator binds to or inhibits binding of a ligand to a histamine $H_1$ and/or $H_2$ and/or $H_3$ receptor or reduces or eliminates or increases or enhances or mimics an activity of a histamine $H_1$ and/or $H_2$ and/or $H_3$ receptor in a reversible or irreversible manner. In some embodiments, the histamine receptor modulator inhibits binding of a ligand by at least about or about any one of 10%, 20%, 30%, 40%, 50%, 60%, 70%, 80%, 90%, 95% or 100% as determined in the assays described herein. In some embodiments, the histamine receptor modulator reduces an activity of a histamine receptor by at least about or about any of 10%, 20%, 30%, 40%, 50%, 60%, 70%, 80%, 90%, 95% or 100% as compared to the corresponding activity in the same individual prior to treatment with the histamine receptor modulator or compared to the corresponding activity in like individuals not receiving the histamine receptor modulator. In some embodiments, the histamine receptor modulator enhances an activity of a histamine receptor by at least about or about any of 10%, 20%, 30%, 40%, 50%, 60%, 70%, 80%, 90%, 95% or 100 or 200% or 300% or 400% or 500% or more as compared to the corresponding activity in the same individual prior to treatment with the histamine receptor modulator or compared to the corresponding activity in like individuals not receiving the histamine receptor modulator. In some embodiments, the histamine receptor modulator is capable of binding to the active site of a histamine receptor (e.g., a binding site for a ligand). In some embodiments, the histamine receptor modulator is capable of binding to an allosteric site of a histamine receptor.

Unless clearly indicated otherwise, "an individual" as used herein intends a mammal, including but not limited to a human. An individual includes but is not limited to human, bovine, primate, equine, canine, feline, porcine, and ovine animals. Thus, the invention finds use in both human medicine and in the veterinary context, including use in agricultural animals and domestic pets. The individual may be a human who has been diagnosed with or is suspected of having a cognitive disorder, a psychotic disorder, a neurotransmitter-mediated disorder and/or a neuronal disorder. The individual may be a human who exhibits one or more symptoms associated with a cognitive disorder, a psychotic disorder, a neurotransmitter-mediated disorder and/or a neuronal disorder. The individual may be a human who has a mutated or abnormal gene associated with a cognitive disorder, a psychotic disorder, a neurotransmitter-mediated disorder and/or a neuronal disorder. The individual may be a human who is genetically or otherwise predisposed to developing a cognitive disorder, a psychotic disorder, a neurotransmitter-mediated disorder and/or a neuronal disorder.

As used herein, "treatment" or "treating" is an approach for obtaining a beneficial or desired result, such as a clinical result. For purposes of this invention, beneficial or desired clinical results include, but are not limited to, alleviation of a symptom and/or diminishment of the extent of a symptom and/or preventing a worsening of a symptom associated with a disease or condition. In one variation, beneficial or desired clinical results include, but are not limited to, alleviation of a symptom and/or diminishment of the extent of a symptom and/or preventing a worsening of a symptom associated with a cognitive disorder, a psychotic disorder, a neurotransmitter-mediated disorder and/or a neuronal disorder. Preferably, treatment of a disease or condition with a compound of the invention or a pharmaceutically acceptable salt thereof is accompanied by no or fewer side effects than are associated with currently available therapies for the disease or condition and/or improves the quality of life of the individual.

As used herein, "delaying" development of a disease or condition means to defer, hinder, slow, retard, stabilize and/or postpone development of the disease or condition. This delay can be of varying lengths of time, depending on the history of the disease and/or individual being treated. As is evident to one skilled in the art, a sufficient or significant delay can, in effect, encompass prevention, in that the individual does not develop the disease or condition. For example, a method that "delays" development of Alzheimer's disease is a method that reduces probability of disease development in a given time frame and/or reduces extent of the disease in a given time frame, when compared to not using the method. Such comparisons are typically based on clinical studies, using a statistically significant number of subjects. For example, Alzheimer's disease development can be detected using standard clinical techniques, such as routine neurological examination, patient interview, neuroimaging, detecting alterations of levels of specific proteins in the serum or cerebrospinal fluid (e.g., amyloid peptides and Tau), computerized tomography (CT) or magnetic resonance imaging (MRI). Similar techniques are known in the art for other diseases and conditions. Development may also refer to disease progression that may be initially undetectable and includes occurrence, recurrence and onset.

As used herein, an "at risk" individual is an individual who is at risk of developing a cognitive disorder, a psychotic disorder, a neurotransmitter-mediated disorder and/or a neuronal disorder that can be treated with a compound of the invention. An individual "at risk" may or may not have a detectable disease or condition, and may or may not have displayed detectable disease prior to the treatment methods described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s). These risk factors include, but are not limited to, age, sex, race, diet, history of previous disease, presence of precursor disease, genetic (i.e., hereditary) considerations, and environmental exposure. For example, individuals at risk for Alzheimer's disease include, e.g., those having relatives who have experienced this disease and those whose risk is determined by analysis of genetic or biochemical markers. Genetic markers of risk for Alzheimer's disease include mutations in the APP gene, particularly mutations at position 717 and positions 670 and 671 referred to as the Hardy and Swedish mutations, respectively (Hardy, *Trends Neurosci.*, 20:154-9, 1997). Other markers of risk are mutations in the presenilin genes (e.g., PS1 or PS2), ApoE4 alleles, family history of Alzheimer's disease, hypercholesterolemia and/or atherosclerosis. Other such factors are known in the art for other diseases and conditions.

As used herein, the term "pro-cognitive" includes but is not limited to an improvement of one or more mental processes such as memory, attention, perception and/or thinking, which may be assessed by methods known in the art.

As used herein, the term "neurotrophic" effects includes but is not limited to effects that enhance neuron function such as growth, survival and/or neurotransmitter synthesis.

As used herein, the term "cognitive disorders" refers to and intends diseases and conditions that are believed to involve or be associated with or do involve or are associated with progressive loss of structure and/or function of neurons, including death of neurons, and where a central feature of the disorder may be the impairment of cognition (e.g., memory, attention, perception and/or thinking). These disorders include pathogen-induced cognitive dysfunction, e.g. HIV associated cognitive dysfunction and Lyme disease associated cognitive dysfunction. Examples of cognitive disorders include Alzheimer's Disease, Huntington's Disease, Parkinson's Disease, schizophrenia, amyotrophic lateral sclerosis (ALS), autism, ADD, ADHD, mild cognitive impairment (MCI), stroke, traumatic brain injury (TBI) and age-associated memory impairment (AAMI).

As used herein, the term "psychotic disorders" refers to and intends mental diseases or conditions that are believed to cause or do cause abnormal thinking and perceptions. Psychotic disorders are characterized by a loss of reality which may be accompanied by delusions, hallucinations (perceptions in a conscious and awake state in the absence of external stimuli which have qualities of real perception, in that they are vivid, substantial, and located in external objective space), personality changes and/or disorganized thinking. Other common symptoms include unusual or bizarre behavior, as well as difficulty with social interaction and impairment in carrying out the activities of daily living. Exemplary psychotic disorders are schizophrenia, bipolar disorders, psychosis, anxiety and depression.

As used herein, the term "neurotransmitter-mediated disorders" refers to and intends diseases or conditions that are believed to involve or be associated with or do involve or are associated with abnormal levels of neurotransmitters such as histamine, serotonin, dopamine, norepinephrine or impaired function of aminergic G protein-coupled receptors. Exemplary neurotransmitter-mediated disorders include spinal cord injury, diabetic neuropathy, allergic diseases and diseases involving geroprotective activity such as age-associated hair loss (alopecia), age-associated weight loss and age-associated vision disturbances (cataracts). Abnormal neurotransmitter levels are associated with a wide variety of diseases and conditions including, but not limited, to Alzheimer's disease, Parkinson's Disease, autism, ADD, ADHD, Guillain-Barré syndrome, mild cognitive impairment, schizophrenia, anxiety, multiple sclerosis, stroke, traumatic brain injury, spinal cord injury, diabetic neuropathy, fibromyalgia, bipolar disorders, psychosis, depression and a variety of allergic diseases.

As used herein, the term "neuronal disorders" refers to and intends diseases or conditions that are believed to involve, or be associated with, or do involve or are associated with neuronal cell death and/or impaired neuronal function or decreased neuronal function. Exemplary neuronal indications include neurodegenerative diseases and disorders such as Alzheimer's disease, Huntington's disease, amyotrophic lateral sclerosis (ALS), Parkinson's disease, canine cognitive dysfunction syndrome (CCDS), Lewy body disease, Menkes disease, Wilson disease, Creutzfeldt-Jakob disease, Fahr disease, an acute or chronic disorder involving cerebral circulation, such as ischemic or hemorrhagic stroke or other cerebral hemorrhagic insult, age-associated memory impairment (AAMI), mild cognitive impairment (MCI), injury-related mild cognitive impairment (MCI), post-concussion syndrome, post-traumatic stress disorder, adjuvant chemotherapy, traumatic brain injury (TBI), neuronal death mediated ocular disorder, macular degeneration, age-related macular degeneration, autism, including autism spectrum disorder, ADD, ADHD, Asperger syndrome, and Rett syndrome, an avulsion injury, a spinal cord injury, myasthenia gravis, Guillain-Barré syndrome, multiple sclerosis, diabetic neuropathy, fibromyalgia, neuropathy associated with spinal cord injury, schizophrenia, bipolar disorder, psychosis, anxiety or depression.

As used herein, the term "neuron" represents a cell of ectodermal embryonic origin derived from any part of the nervous system of an animal. Neurons express well-characterized neuron-specific markers, including neurofilament proteins, NeuN (Neuronal Nuclei marker), MAP2, and class III tubulin. Included as neurons are, for example, hippocampal, cortical, midbrain dopaminergic, spinal motor, sensory, sympathetic, septal cholinergic and cerebellar neurons.

As used herein, the term "neurite outgrowth" or "neurite activation" refers to the extension of existing neuronal processes (e.g., axons and dendrites) and the growth or sprouting of new neuronal processes (e.g., axons and dendrites). Neurite outgrowth or neurite activation may alter neural connectivity, resulting in the establishment of new synapses or the remodeling of existing synapses.

As used herein, the term "neurogenesis" refers to the generation of new nerve cells from undifferentiated neuronal progenitor cells, also known as multipotential neuronal stem cells. Neurogenesis actively produces new neurons, astrocytes, glia, Schwann cells, oligodendrocytes and/or other neural lineages. Much neurogenesis occurs early in human development, though it continues later in life, particularly in certain localized regions of the adult brain.

As used herein, the term "neural connectivity" refers to the number, type, and quality of connections ("synapses") between neurons in an organism. Synapses form between neurons, between neurons and muscles (a "neuromuscular junction"), and between neurons and other biological structures, including internal organs, endocrine glands, and the like. Synapses are specialized structures by which neurons transmit chemical or electrical signals to each other and to non-neuronal cells, muscles, tissues, and organs. Compounds that affect neural connectivity may do so by establishing new synapses (e.g., by neurite outgrowth or neurite activation) or by altering or remodeling existing synapses. Synaptic remodeling refers to changes in the quality, intensity or type of signal transmitted at particular synapses.

As used herein, the term "neuropathy" refers to a disorder characterized by altered function and/or structure of motor, sensory, and autonomic neurons of the nervous system, initiated or caused by a primary lesion or other dysfunction of the nervous system. Patterns of peripheral neuropathy include polyneuropathy, mononeuropathy, mononeuritis multiplex and autonomic neuropathy. The most common form is (symmetrical) peripheral polyneuropathy, which mainly affects the feet and legs. A radiculopathy involves spinal nerve roots, but if peripheral nerves are also involved the term radiculoneuropathy is used. The form of neuropathy may be further broken down by cause, or the size of predominant fiber involvement, e.g. large fiber or small fiber peripheral neuropathy. Central neuropathic pain can occur in spinal cord injury, multiple sclerosis, and some strokes, as well as fibromyalgia. Neuropathy may be associated with varying combinations of weakness, autonomic changes and sensory changes. Loss of muscle bulk or fasciculations, a particular fine twitching of muscle may also be seen. Sensory symptoms encompass loss of sensation and "positive" phenomena including pain. Neuropathies are associated with a variety of disorders, including diabetes (e.g., diabetic neuropathy), fibromyalgia, multiple sclerosis, and herpes zoster infection, as well as with spinal cord injury and other types of nerve damage.

As used herein, the term "Alzheimer's disease" refers to a degenerative brain disorder characterized clinically by progressive memory deficits, confusion, behavioral problems, inability to care for oneself, gradual physical deterioration and, ultimately, death. Histologically, the disease is characterized by neuritic plaques, found primarily in the association cortex, limbic system and basal ganglia. The major constituent of these plaques is amyloid beta peptide (Aβ), which is the cleavage product of beta amyloid precursor protein (βAPP or APP). APP is a type I transmembrane glycoprotein that contains a large ectopic N-terminal domain, a transmembrane domain and a small cytoplasmic C-terminal tail. Alternative splicing of the transcript of the single APP gene on chromosome 21 results in several isoforms that differ in the number of amino acids. Aβ appears to have a central role in the neuropathology of Alzheimer's disease. Familial forms of the disease have been linked to mutations in APP and the presenilin genes (Tanzi et al., 1996, *Neurobiol. Dis.*, 3:159-168; Hardy, 1996, *Ann. Med.*, 28:255-258). Diseased-linked mutations in these genes result in increased production of the 42-amino acid form of Aβ, the predominant form found in amyloid plaques. Mitochondrial dysfunction has also been reported to be an important component of Alzheimer's disease (Bubber et al., Mitochondrial abnormalities in Alzheimer brain: Mechanistic Implications, *Ann Neurol.*, 2005, 57(5), 695-703; Wang et al., Insights into amyloid-β-induced mitochondrial dysfunction in Alzheimer disease, *Free Radical Biology & Medicine*, 2007, 43, 1569-1573; Swerdlow et al., Mitochondria in Alzheimer's disease, *Int. Rev. Neurobiol.*, 2002, 53, 341-385; and Reddy et al., Are mitochondria critical in the pathogenesis of Alzheimer's disease?, *Brain Res Rev.* 2005, 49(3), 618-32). It has been proposed that mitochondrial dysfunction has a causal relationship with neuronal function (including neurotransmitter synthesis and secretion) and viability. Compounds which stabilize mitochondria may therefore have a beneficial impact on Alzheimer's patients.

As used herein, the term "Huntington's disease" refers to a fatal neurological disorder characterized clinically by symptoms such as involuntary movements, cognition impairment or loss of cognitive function and a wide spectrum of behavioral disorders. Common motor symptoms associated with Huntington's disease include chorea (involuntary writhing and spasming), clumsiness, and progressive loss of the abilities to walk, speak (e.g., exhibiting slurred speech) and swallow. Other symptoms of Huntington's disease can include cognitive symptoms such as loss of intellectual speed, attention and short-term memory and/or behavioral symptoms that can span the range of changes in personality, depression, irritability, emotional outbursts and apathy. Clinical symptoms typically appear in the fourth or fifth decade of life. Huntington's disease is a devastating and often protracted illness, with death usually occurring approximately 10-20 years after the onset of symptoms. Huntington's disease is inherited through a mutated or abnormal gene encoding an abnormal protein called the mutant huntingtin protein; the mutated huntingtin protein produces neuronal degeneration in many different regions of the brain. The degeneration focuses on neurons located in the basal ganglia, structures deep within the brain that control many important functions including coordinating movement, and on neurons on the outer surface of the brain or cortex, which controls thought, perception and memory.

"Amyotrophic lateral sclerosis" or "ALS" is used herein to denote a progressive neurodegenerative disease that affects upper motor neurons (motor neurons in the brain) and/or lower motor neurons (motor neurons in the spinal cord) and results in motor neuron death. As used herein, the term "ALS" includes all of the classifications of ALS known in the art, including, but not limited to classical ALS (typically affecting both lower and upper motor neurons), Primary Lateral Sclerosis (PLS, typically affecting only the upper motor neurons), Progressive Bulbar Palsy (PBP or Bulbar Onset, a version of ALS that typically begins with difficulties swallowing, chewing and speaking), Progressive Muscular Atrophy (PMA, typically affecting only the lower motor neurons) and familial ALS (a genetic version of ALS).

The term "Parkinson's disease" as used herein refers to any medical condition wherein an individual experiences one or more symptoms associated with Parkinson's disease, such as without limitation one or more of the following symptoms: rest tremor, cogwheel rigidity, bradykinesia, postural reflex impairment, symptoms having good response to 1-dopa treatment, the absence of prominent oculomotor palsy, cerebellar or pyramidal signs, amyotrophy, dyspraxia and/or dysphasia. In a specific embodiment, the present invention is utilized for the treatment of a dopaminergic dysfunction-related disorder. In a specific embodiment, the individual with Parkinson's disease has a mutation or polymorphism in a synuclein, parkin or NURR1 nucleic acid that is associated with Parkinson's disease. In one embodiment, the individual with Parkinson's disease has defective or decreased expression of a nucleic acid or a mutation in a nucleic acid that regulates the development and/or survival of dopaminergic neurons.

As used herein, the term "canine cognitive dysfunction syndrome," or "CCDS" refers to an age-related deterioration of mental function typified by multiple cognitive impairments that affect an afflicted canine's ability to function normally. The decline in cognitive ability that is associated with CCDS cannot be completely attributed to a general medical condition such as neoplasia, infection, sensory impairment, or organ failure. Diagnosis of CCDS in canines, such as dogs, is generally a diagnosis of exclusion, based on thorough behavior and medical histories and the presence of clinical symptoms of CCDS that are unrelated to other disease processes. Owner observation of age-related changes in behavior is a practical means used to detect the possible onset of CCDS in aging domestic dogs. A number of laboratory cognitive tasks may be used to help diagnose CCDS, while blood counts, chemistry panels and urinalysis can be used to rule out other underlying diseases that could mimic the clinical symptoms of CCDS. Symptoms of CCDS include memory loss, which in domestic dogs may be manifested by disorientation and/or confusion, decreased or altered interaction with family members and/or greeting behavior, changes in sleep-wake cycle, decreased activity level, and loss of house training or frequent, inappropriate elimination. A canine suffering from CCDS may exhibit one or more of the following clinical or behavioral symptoms: decreased appetite, decreased awareness of surroundings, decreased ability to recognize familiar places, people or other animals, decreased hearing, decreased ability to climb up and down stairs, decreased tolerance to being alone, development of compulsive behavior or repetitive behaviors or habits, circling, tremors or shaking, disorientation, decreased activity level, abnormal sleep wake cycles, loss of house training, decreased or altered responsiveness to family members, and decreased or altered greeting behavior. CCDS can dramatically affect the health and well-being of an afflicted canine. Moreover, the companionship offered by a pet with CCDS can become less rewarding as the severity of the disease increases and its symptoms become more severe.

As used herein, the term "age-associated memory impairment" or "AAMI" refers to a condition that may be identified as GDS stage 2 on the global deterioration scale (GDS) (Reisberg, et al. (1982) Am. J. Psychiatry 139: 1136-1139) which differentiates the aging process and progressive degenerative dementia in seven major stages. The first stage of the GDS is one in which individuals at any age have neither subjective complaints of cognitive impairment nor objective evidence of impairment. These GDS stage 1 individuals are considered normal. The second stage of the GDS applies to those generally elderly persons who complain of memory and cognitive functioning difficulties such as not recalling names as well as they could five or ten years previously or not recalling where they have placed things as well as they could five or ten years previously. These subjective complaints appear to be very common in otherwise normal elderly individuals. AAMI refers to persons in GDS stage 2, who may differ neurophysiologically from elderly persons who are normal and free of subjective complaints, i.e., GDS stage 1. For example, AAMI subjects have been found to have more electrophysiologic slowing on a computer analyzed EEG than GDS stage 1 elderly persons (Prichep, John, Ferris, Reisberg, et al. (1994) Neurobiol. Aging 15: 85-90).

As used herein, the term "mild cognitive impairment" or "MCI" refers to a type of cognitive disorder characterized by a more pronounced deterioration in cognitive functions than is typical for normal age-related decline. As a result, elderly or aged patients with MCI have greater than normal difficulty performing complex daily tasks and learning, but without the inability to perform normal social, everyday, and/or professional functions typical of patients with Alzheimer's disease, or other similar neurodegenerative disorders eventually resulting in dementia. MCI is characterized by subtle, clinically manifest deficits in cognition, memory, and functioning, amongst other impairments, which are not of sufficient magnitude to fulfill criteria for diagnosis of Alzheimer's disease or other dementia. MCI also encompasses injury-related MCI, defined herein as cognitive impairment resulting from certain types of injury, such as nerve injury (i.e., battlefield injuries, including post-concussion syndrome, and the like), neurotoxic treatment (i.e., adjuvant chemotherapy resulting in "chemo brain" and the like), and tissue damage resulting from physical injury or other neurodegeneration, which is separate and distinct from mild cognitive impairment resulting from stroke, ischemia, hemorrhagic insult, blunt force trauma, and the like.

As used herein, the term "traumatic brain injury" or "TBI" refers to a brain injury caused by a sudden trauma, such as a blow or jolt or a penetrating head injury, which disrupts the function or damages the brain. Symptoms of TBI can range from mild, moderate to severe and can significantly affect many cognitive (deficits of language and communication, information processing, memory, and perceptual skills), physical (ambulation, balance, coordination, fine motor skills, strength, and endurance), and psychological skills.

"Neuronal death mediated ocular disease" intends an ocular disease in which death of the neuron is implicated in whole or in part. The disease may involve death of photoreceptors. The disease may involve retinal cell death. The disease may involve ocular nerve death by apoptosis. Particular neuronal death mediated ocular diseases include but are not limited to macular degeneration, glaucoma, retinitis pigmentosa, congenital stationary night blindness (Oguchi disease), childhood onset severe retinal dystrophy, Leber congenital amaurosis, Bardet-Biedle syndrome, Usher syndrome, blindness from an optic neuropathy, Leber's hereditary optic neuropathy, color blindness and Hansen-Larson-Berg syndrome.

As used herein, the term "macular degeneration" includes all forms and classifications of macular degeneration known in the art, including, but not limited to diseases that are characterized by a progressive loss of central vision associated with abnormalities of Bruch's membrane, the choroid, the neural retina and/or the retinal pigment epithelium. The term thus encompasses disorders such as age-related macular degeneration (ARMD) as well as rarer, earlier-onset dystrophies that in some cases can be detected in the first decade of life. Other maculopathies include North Carolina macular dystrophy, Sorsby's fundus dystrophy, Stargardt's disease, pattern dystrophy, Best disease, and Malattia Leventinese.

As used herein, the term "autism" refers to a brain development disorder that impairs social interaction and communication and causes restricted and repetitive behavior, typically appearing during infancy or early childhood. The cognitive and behavioral defects are thought to result in part from altered neural connectivity. Autism encompasses related disorders sometimes referred to as "autism spectrum disorder," as well as Asperger syndrome and Rett syndrome.

As used herein, the term "nerve injury" or "nerve damage" refers to physical damage to nerves, such as avulsion injury (i.e., where a nerve or nerves have been torn or ripped) or spinal cord injury (i.e., damage to white matter or myelinated fiber tracts that carry sensation and motor signals to and from the brain). Spinal cord injury can occur from many causes, including physical trauma (i.e., car accidents, sports injuries, and the like), tumors impinging on the spinal column, developmental disorders, such as spina bifida, and the like.

As used herein, the term "myasthenia gravis" or "MG" refers to a non-cognitive neuromuscular disorder caused by immune-mediated loss of acetylcholine receptors at neuromuscular junctions of skeletal muscle. Clinically, MG typically appears first as occasional muscle weakness in approximately two-thirds of patients, most commonly in the extraocular muscles. These initial symptoms eventually worsen, producing drooping eyelids (ptosis) and/or double vision (diplopia), often causing the patient to seek medical attention. Eventually, many patients develop general muscular weakness that may fluctuate weekly, daily, or even more frequently. Generalized MG often affects muscles that control facial expression, chewing, talking, swallowing, and breathing; before recent advances in treatment, respiratory failure was the most common cause of death.

As used herein, the term "Guillain-Barré syndrome" refers to a non-cognitive disorder in which the body's immune system attacks part of the peripheral nervous system. The first symptoms of this disorder include varying degrees of weakness or tingling sensations in the legs. In many instances the weakness and abnormal sensations spread to the arms and upper body. These symptoms can increase in intensity until certain muscles cannot be used at all and, when severe, the patient is almost totally paralyzed. In these cases the disorder is life threatening—potentially interfering with breathing and, at times, with blood pressure or heart rate—and is considered a medical emergency. Most patients, however, recover from even the most severe cases of Guillain-Barré syndrome, although some continue to have a certain degree of weakness.

As used herein, the term "multiple sclerosis" or "MS" refers to an autoimmune condition in which the immune system attacks the central nervous system (CNS), leading to demyelination of neurons. It may cause numerous symptoms, many of which are non-cognitive, and often progresses to physical disability. MS affects the areas of the brain and spinal cord known as the white matter. White matter cells carry signals between the grey matter areas, where the processing is done, and the rest of the body. More specifically, MS destroys oligodendrocytes which are the cells responsible for creating and maintaining a fatty layer, known as the myelin sheath, which helps the neurons carry electrical signals. MS results in a thinning or complete loss of myelin and, less frequently, the cutting (transection) of the neuron's extensions or axons. When the myelin is lost, the neurons can no longer effectively conduct their electrical signals. Almost any neurological symptom can accompany the disease. MS takes several forms, with new symptoms occurring either in discrete attacks (relapsing forms) or slowly accumulating over time (progressive forms). Most people are first diagnosed with relapsing-remitting MS but develop secondary-progressive MS (SPMS) after a number of years. Between attacks, symptoms may go away completely, but permanent neurological problems often persist, especially as the disease advances.

As used herein, the term "schizophrenia" refers to a chronic, mental disorder characterized by one or more positive symptoms (e.g., delusions and hallucinations) and/or negative symptoms (e.g., blunted emotions and lack of interest) and/or disorganized symptoms (e.g., disorganized thinking and speech or disorganized perception and behavior). Schizophrenia as used herein includes all forms and classifications of schizophrenia known in the art, including, but not limited to catatonic type, hebephrenic type, disorganized type, paranoid type, residual type or undifferentiated type schizophrenia and deficit syndrome and/or those described in American Psychiatric Association: *Diagnostic and Statistical Manual of Mental Disorders*, Fourth Edition, Washington D.C., 2000 or in International Statistical Classification of Diseases and Related Health Problems, or otherwise known to those of skill in the art.

"Cognitive impairment associated with schizophrenia" or "CIAS" includes neuropsychological deficits in attention, working memory, verbal learning, and problem solving. These deficits are believed to be linked to impairment in functional status (e.g., social behavior, work performance, and activities of daily living).

As used herein "geroprotective activity" or "geroprotector" means a biological activity that slows down ageing and/or prolongs life and/or increases or improves the quality of life via a decrease in the amount and/or the level of intensity of pathologies or conditions that are not life-threatening but are associated with the aging process and which are typical for elderly people. Pathologies or conditions that are not life-threatening but are associated with the aging process include such pathologies or conditions as loss of sight (cataract), deterioration of the dermatohairy integument (alopecia), and an age-associated decrease in weight due to the death of muscular and/or fatty cells.

As used herein, attention-deficit hyperactivity disorder (ADHD) is the most common child neuropsychiatric condition present in school-aged children, affecting about 5-8% of this population. ADHD refers to a chronic disorder that initially manifests in childhood and is characterized by hyperactivity, impulsivity, and/or inattention. ADHD is characterized by persistent patterns of inattention and/or impulsivity-hyperactivity that are much more extreme than is observed in individuals at the same developmental level or stage. There is considerable evidence, from family and twin studies, that ADHD has a significant genetic component. This disorder is thought to be due to an interaction of environmental and genetic factors. ADHD includes all known types of ADHD. For example, *Diagnostic & Statistical Manual for Mental Disorders* (DSM-IV) identifies three subtypes of ADHD: (1) ADHD, Combined Type which is characterized by both inattention and hyperactivity-impulsivity symptoms; (2) ADHD, Predominantly Inattentive Type which is characterized by inattention but not hyperactivity-impulsivity symptoms; and (3) ADHD, Predominantly Hyperactive-Impulsive Type which is characterized by Hyperactivity-impulsivity but not inattention symptoms.

As used herein, attention-deficit disorder (ADD) refers to a disorder in processing neural stimuli that is characterized by distractibility and impulsivity that can result in inability to control behavior and can impair an individual's social, academic, or occupational function and development. ADD may be diagnosed by known methods, which may include observing behavior and diagnostic interview techniques.

As used herein "allergic disease" refers to a disorder of the immune system which is characterized by excessive activation of mast cells and basophils and production of IgE immunoglobulins, resulting in an extreme inflammatory response. It represents a form of hypersensitivity to an environmental substance known as allergen and is an acquired disease. Common allergic reactions include eczema, hives, hay fever, asthma, food allergies, and reactions to the venom of stinging insects such as wasps and bees. Allergic reactions are accompanied by an excessive release of histamines, and can thus be treated with antihistaminic agents.

As used herein, by "combination therapy" is meant a therapy that includes two or more different compounds. Thus, in one aspect, a combination therapy comprising a compound detailed herein and anther compound is provided. In some variations, the combination therapy optionally includes one or more pharmaceutically acceptable carriers or excipients, non-pharmaceutically active compounds, and/or inert substances. In various embodiments, treatment with a combination therapy may result in an additive or even synergistic (e.g., greater than additive) result compared to administration of a single compound of the invention alone. In some embodiments, a lower amount of each compound is used as part of a combination therapy compared to the amount generally used for individual therapy. Preferably, the same or greater therapeutic benefit is achieved using a combination therapy than by using any of the individual compounds alone. In some embodiments, the same or greater therapeutic benefit is achieved using a smaller amount (e.g., a lower dose or a less frequent dosing schedule) of a compound in a combination therapy than the amount generally used for individual compound or therapy. Preferably, the use of a small amount of compound results in a reduction in the number, severity, frequency, and/or duration of one or more side-effects associated with the compound.

As used herein, the term "effective amount" intends such amount of a compound of the invention which in combination with its parameters of efficacy and toxicity, as well as based on the knowledge of the practicing specialist should be effective in a given therapeutic form. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any of the co-administered compounds may optionally be lowered due to the combined action (e.g., additive or synergistic effects) of the compounds.

As used herein, "unit dosage form" refers to physically discrete units, suitable as unit dosages, each unit containing a predetermined quantity of active ingredient calculated to produce the desired therapeutic effect in association with the required pharmaceutical carrier. Unit dosage forms may contain a single or a combination therapy.

As used herein, the term "controlled release" refers to a drug-containing formulation or fraction thereof in which release of the drug is not immediate, i.e., with a "controlled release" formulation, administration does not result in immediate release of the drug into an absorption pool. The term encompasses depot formulations designed to gradually release the drug compound over an extended period of time. Controlled release formulations can include a wide variety of drug delivery systems, generally involving mixing the drug compound with carriers, polymers or other compounds having the desired release characteristics (e.g., pH-dependent or non-pH-dependent solubility, different degrees of water solubility, and the like) and formulating the mixture according to the desired route of delivery (e.g., coated capsules, implantable reservoirs, injectable solutions containing biodegradable capsules, and the like).

As used herein, by "pharmaceutically acceptable" or "pharmacologically acceptable" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

"Pharmaceutically acceptable salts" are those salts which retain at least some of the biological activity of the free (non-salt) compound and which can be administered as drugs or pharmaceuticals to an individual. A pharmaceutically acceptable salt intends ionic interactions and not a covalent bond. As such, an N-oxide is not considered a salt. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine and the like. Acceptable inorganic bases include aluminum hydroxide, calcium hydroxide, potassium hydroxide, sodium carbonate, sodium hydroxide, and the like. Further examples of pharmaceutically acceptable salts include those listed in Berge et al., Pharmaceutical Salts, *J. Pharm. Sci.* (1977), 66(1):1-19. Pharmaceutically acceptable salts can be prepared in situ in the manufacturing process, or by separately reacting a purified compound of the invention in its free acid or base form with a suitable organic or inorganic base or acid, respectively, and isolating the salt thus formed during subsequent purification. It should be understood that a reference to a pharmaceutically acceptable salt includes the solvent addition forms or crystal forms thereof, particularly solvates or polymorphs. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The term "excipient" as used herein means an inert or inactive substance that may be used in the production of a drug or pharmaceutical, such as a tablet containing a compound of the invention as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

"Alkyl" refers to and includes saturated linear, branched, or cyclic univalent hydrocarbon structures and combinations thereof. Particular alkyl groups are those having 1 to 20 carbon atoms (a "$C_1$-$C_{20}$ alkyl"). More particular alkyl groups are those having 1 to 8 carbon atoms (a "$C_1$-$C_8$ alkyl"). When an alkyl residue having a specific number of carbons is named, all geometric isomers having that number of carbons are intended to be encompassed and described; thus, for example, "butyl" is meant to include n-butyl, sec-butyl, iso-butyl, tert-butyl and cyclobutyl; "propyl" includes n-propyl, iso-propyl and cyclopropyl. This term is exemplified by groups such as methyl, t-butyl, n-heptyl, octyl, cyclohexylmethyl, cyclopropyl and the like. Cycloalkyl is a subset of alkyl and can consist of one ring, such as cyclohexyl, or multiple rings, such as adamantyl. A cycloalkyl comprising more than one ring may be fused, spiro or bridged, or combinations thereof. A preferred cycloalkyl is a saturated cyclic hydrocarbon having from 3 to 13 annular carbon atoms. A more preferred cycloalkyl is a saturated cyclic hydrocarbon having from 3 to 8 annular carbon atoms (a "$C_3$-$C_8$ cycloalkyl"). Examples of cycloalkyl groups include adamantyl, decahydronaphthalenyl, cyclopropyl, cyclobutyl, cyclopentyl, cyclohexyl and the like.

"Alkylene" refers to the same residues as alkyl, but having bivalency. Examples of alkylene include methylene (—$CH_2$—), ethylene (—$CH_2CH_2$—), propylene (—$CH_2CH_2CH_2$—), butylene (—$CH_2CH_2CH_2CH_2$—) and the like.

"Alkenyl" refers to an unsaturated hydrocarbon group having at least one site of olefinic unsaturation (i.e., having at least one moiety of the formula C=C) and preferably having from 2 to 10 carbon atoms and more preferably 2 to 8 carbon atoms. Examples of alkenyl include but are not limited to —$CH_2$—CH=CH—$CH_3$ and —$CH_2$—$CH_2$-cyclohexenyl, where the ethyl group of the latter example can be attached to the cyclohexenyl moiety at any available position on the ring. Cycloalkenyl is a subset of alkenyl and can consist of one ring, such as cyclohexyl, or multiple rings, such as norbornenyl. A more preferred cycloalkenyl is an unsaturated cyclic hydrocarbon having from 3 to 8 annular carbon atoms (a "$C_3$-$C_8$ cycloalkenyl"). Examples of cycloalkenyl groups include cyclopropenyl, cyclobutenyl, cyclopentenyl, cyclohexenyl and the like.

"Alkynyl" refers to an unsaturated hydrocarbon group having at least one site of acetylenic unsaturation (i.e., having at least one moiety of the formula C≡C) and preferably having from 2 to 10 carbon atoms and more preferably 3 to 8 carbon atoms.

"Substituted alkyl" refers to an alkyl group having from 1 to 5 substituents including, but not limited to, substituents such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkenyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Substituted alkenyl" refers to alkenyl group having from 1 to 5 substituents s including, but not limited to, substituents such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Substituted alkynyl" refers to alkynyl groups having from 1 to 5 substituents including, but not limited to, groups such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted heterocyclyl, substituted or unsubstituted aralkyl, aminosulfonyl, sulfonylamino, sulfonyl, oxo, carbonylalkylenealkoxy and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups H—C(O)O—, alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, heteroaryl-C(O)O—, substituted heteroaryl-C(O)O—, heterocyclic-C(O)O—, and substituted heterocyclic-C(O)O—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Heterocycle", "heterocyclic" or "heterocyclyl" refers to a saturated or an unsaturated non-aromatic group having a single ring or multiple condensed rings, and having from 1 to 10 annular carbon atoms and from 1 to 4 annular heteroatoms, such as nitrogen, sulfur or oxygen. A heterocycle comprising more than one ring may be fused, spiro or bridged, or any combination thereof. In fused ring systems, one or more of the rings can be aryl or heteroaryl. A heterocycle having more than one ring where at least one ring is aromatic may be connected to the parent structure at either a non-aromatic ring position or at an aromatic ring position. In one variation, a heterocycle having more than one ring where at least one ring is aromatic is connected to the parent structure at a non-aromatic ring position.

"Substituted heterocyclic" or "substituted heterocyclyl" refers to a heterocycle group which is substituted with from 1 to 3 substituents including, but not limited to, substituents such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted alkynyl, substituted or unsubstituted aralkyl, aminosulfonyl, sulfonylamino, sulfonyl, oxo, carbonylalkylenealkoxy and the like. In one variation, a substituted heterocycle is a heterocycle substituted with an additional ring, wherein the additional ring may be aromatic or non-aromatic.

"Aryl" or "Ar" refers to an unsaturated aromatic carbocyclic group having a single ring (e.g., phenyl) or multiple condensed rings (e.g., naphthyl or anthryl) which condensed rings may or may not be aromatic. In one variation, the aryl group contains from 6 to 14 annular carbon atoms. An aryl group having more than one ring where at least one ring is non-aromatic may be connected to the parent structure at either an aromatic ring position or at a non-aromatic ring position. In one variation, an aryl group having more than one ring where at least one ring is non-aromatic is connected to the parent structure at an aromatic ring position.

"Heteroaryl" or "HetAr" refers to an unsaturated aromatic carbocyclic group having from 2 to 10 annular carbon atoms and at least one annular heteroatom, including but not limited to heteroatoms such as nitrogen, oxygen and sulfur. A heteroaryl group may have a single ring (e.g., pyridyl, furyl) or multiple condensed rings (e.g., indolizinyl, benzothienyl) which condensed rings may or may not be aromatic. A heteroaryl group having more than one ring where at least one ring is non-aromatic may be connected to the parent structure at either an aromatic ring position or at a non-aromatic ring position. In one variation, a heteroaryl group having more than one ring where at least one ring is non-aromatic is connected to the parent structure at an aromatic ring position.

"Substituted aryl" refers to an aryl group having 1 to 5 substituents including, but not limited to, groups such as alkoxy, substituted alkoxy, acyl, acyloxy, carbonylalkoxy, acylamino, substituted or unsubstituted amino, aminoacyl, aminocarbonylamino, aminocarbonyloxy, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Substituted heteroaryl" refers to a heteroaryl group having 1 to 5 substituents including, but not limited to, groups such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Aralkyl" refers to a residue in which an aryl moiety is attached to an alkyl residue and wherein the aralkyl group may be attached to the parent structure at either the aryl or the alkyl residue. Preferably, an aralkyl is connected to the parent structure via the alkyl moiety. A "substituted aralkyl" refers to a residue in which an aryl moiety is attached to a substituted alkyl residue and wherein the aralkyl group may be attached to the parent structure at either the aryl or the alkyl residue. When an aralkyl is connected to the parent structure via the alkyl moiety, it may also be referred to as an "alkaryl". More particular alkaryl groups are those having 1 to 3 carbon atoms in the alkyl moiety (a "$C_1$-$C_3$ alkaryl").

"Alkoxy" refers to the group alkyl-O—, which includes, by way of example, methoxy, ethoxy, n-propoxy, iso-propoxy, n-butoxy, tert-butoxy, sec-butoxy, n-pentoxy, n-hexoxy, 1,2-dimethylbutoxy, and the like. Similarly, alkenyloxy refers to the group "alkenyl-O—" and alkynyloxy refers to the group "alkynyl-O—". "Substituted alkoxy" refers to the group substituted alkyl-O.

"Unsubstituted amino" refers to the group —$NH_2$.

"Substituted amino" refers to the group —$NR_aR_b$, where either (a) each $R_a$ and $R_b$ group is independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, provided that both $R_a$ and $R_b$ groups are not H; or (b) $R_a$ and $R_b$ are joined together with the nitrogen atom to form a heterocyclic or substituted heterocyclic ring.

"Acylamino" refers to the group —C(O)$NR_aR_b$ where $R_a$ and $R_b$ are independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic, substituted heterocyclic or $R_a$ and $R_b$ groups can be joined together with the nitrogen atom to form a heterocyclic or substituted heterocyclic ring.

"Aminocarbonylalkoxy" refers to the group —$NR_aC(O)OR_b$ where each $R_a$ and $R_b$ group is independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic and substituted heterocyclyl.

"Aminoacyl" refers to the group —$NR_aC(O)R_b$ where each $R_a$ and $R_b$ group is independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic or substituted heterocyclic. Preferably, $R_a$ is H or alkyl.

"Aminosulfonyl" refers to the groups —$NRSO_2$-alkyl, —$NRSO_2$ substituted alkyl, —$NRSO_2$-alkenyl, —$NRSO_2$-substituted alkenyl, —$NRSO_2$-alkynyl, —$NRSO_2$-substituted alkynyl, —$NRSO_2$-aryl, —$NRSO_2$— substituted aryl, —$NRSO_2$-heteroaryl, —$NRSO_2$-substituted heteroaryl, —$NRSO_2$-heterocyclic, and —$NRSO_2$-substituted heterocyclic, where R is H or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Sulfonylamino" refers to the groups —$SO_2NH_2$, —$SO_2$NR-alkyl, —$SO_2$NR-substituted alkyl, —$SO_2$NR-alkenyl, —$SO_2$NR-substituted alkenyl, —$SO_2$NR-alkynyl, —$SO_2$NR-substituted alkynyl, —$SO_2$NR-aryl, —$SO_2$NR-substituted aryl, —$SO_2$NR-heteroaryl, —$SO_2$NR-substituted heteroaryl, —$SO_2$NR-heterocyclic, and —$SO_2$NR-substituted heterocyclic, where R is H or alkyl, or —$SO_2NR_2$, where the two R groups are taken together and with the nitrogen atom to which they are attached to form a heterocyclic or substituted heterocyclic ring.

"Sulfonyl" refers to the groups —$SO_2$-alkyl, —$SO_2$-substituted alkyl, —$SO_2$-alkenyl, —$SO_2$-substituted alkenyl, —$SO_2$-alkynyl, —$SO_2$-substituted alkynyl, —$SO_2$-aryl, —$SO_2$-substituted aryl, —$SO_2$-heteroaryl, —$SO_2$-substituted heteroaryl, —$SO_2$-heterocyclic, and —$SO_2$-substituted heterocyclic.

"Carbonylalkylenealkoxy" refers to the group —C(=O)—(CH$_2$)$_a$—OR where R is a substituted or unsubstituted alkyl and n is an integer from 1 to 100, more preferably n is an integer from 1 to 10 or 1 to 5.

"Halo" or "halogen" refers to elements of the Group 17 series having atomic number 9 to 85. Preferred halo groups include the radicals of fluorine, chlorine, bromine and iodine. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halogen; thus 4-chloro-3-fluorophenyl is within the scope of dihaloaryl. An alkyl group in which each H is replaced with a halo group is referred to as a "perhaloalkyl." A preferred perhaloalkyl group is trifluoroalkyl (—CF$_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy (—OCF$_3$).

"Carbonyl" refers to the group C=O.

"Cyano" refers to the group —CN.

"Oxo" refers to the moiety =O.

"Nitro" refers to the group —NO$_2$.

"Thioalkyl" refers to the groups —S-alkyl.

"Alkylsulfonylamino" refers to the groups —R$^1$SO$_2$NR$_a$R$_b$ where R$_a$ and R$_b$ are independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, or the R$_a$ and R$_b$ groups can be joined together with the nitrogen atom to form a heterocyclic or substituted heterocyclic ring and R$^1$ is an alkyl group.

"Carbonylalkoxy" refers to as used herein refers to the groups —C(O)O-alkyl, —C(O)O-substituted alkyl, —C(O)O-aryl, —C(O)O-substituted aryl, —C(O)O-alkenyl, —C(O)O-substituted alkenyl, —C(O)O-alkynyl, —C(O)O-substituted alkynyl, —C(O)O-heteroaryl, —C(O)O-substituted heteroaryl, —C(O)O-heterocyclic or —C(O)O-substituted heterocyclic.

"Geminal" refers to the relationship between two moieties that are attached to the same atom. For example, in the residue —CH$_2$—CHR$^1$R$^2$, R$^1$ and R$^2$ are geminal and R$^1$ may be referred to as a geminal R group to R$^2$.

"Vicinal" refers to the relationship between two moieties that are attached to adjacent atoms. For example, in the residue —CHR$^1$—CH$_2$R$^2$, R$^1$ and R$^2$ are vicinal and R$^1$ may be referred to as a vicinal R group to R$^2$.

A composition of "substantially pure" compound means that the composition contains no more than 15% or preferably no more than 10% or more preferably no more than 5% or even more preferably no more than 3% and most preferably no more than 1% impurity, which impurity may be the compound in a different stereochemical form. For instance, a composition of substantially pure S compound means that the composition contains no more than 15% or no more than 10% or no more than 5% or no more than 3% or no more than 1% of the R form of the compound.

Compounds of the Invention

Compounds are detailed herein, including in the Brief Summary of the Invention and the appended claims. The invention includes the use of all of the compounds described herein, including any and all stereoisomers, salts and solvates of the compounds described as histamine receptor modulators.

The invention embraces compounds of the formula (I):

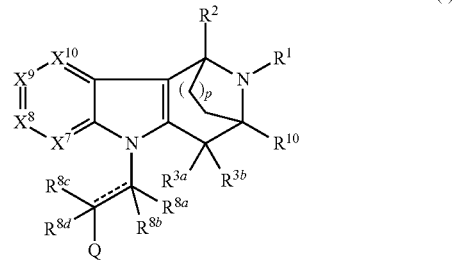

(I)

where:

R$^1$ is H, hydroxyl, nitro, cyano, halo, substituted or unsubstituted C$_1$-C$_8$ alkyl, substituted or unsubstituted C$_2$-C$_8$ alkenyl, substituted or unsubstituted C$_2$-C$_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, C$_1$-C$_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

R$^2$ is H, substituted or unsubstituted C$_1$-C$_8$ alkyl, halo, hydroxyl, alkoxy, cyano, nitro;

each R$^{3a}$ and R$^{3b}$ is independently H, substituted or unsubstituted C$_1$-C$_8$ alkyl, halo, cyano, nitro, hydroxyl, alkoxy, substituted or unsubstituted amino, cycloalkyl, aryl, heteroaryl, heterocyclyl, acylamino or acyloxy or R$^{3a}$ and R$^{3b}$ are taken together with the carbon to which they are attached to form a cycloalkyl moiety or a carbonyl moiety;

each X$^7$, X$^8$, X$^9$ and X$^{10}$ is independently N or CR$^4$;

p is 1 or 2;

each R$^4$ is independently H, hydroxyl, nitro, cyano, halo, C$_1$-C$_8$ perhaloalkyl, substituted or unsubstituted C$_1$-C$_8$ alkyl, substituted or unsubstituted C$_2$-C$_8$ alkenyl, substituted or unsubstituted C$_2$-C$_8$ alkynyl, substituted or unsubstituted aryl, substituted or unsubstituted heteroaryl, C$_1$-C$_8$ perhaloalkoxy, C$_1$-C$_8$ alkoxy, aryloxy, carboxyl, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each R$^{8a}$, R$^{8b}$, R$^{8c}$ and R$^{8d}$ is independently H, hydroxyl, alkoxy, halo, substituted or unsubstituted C$_1$-C$_8$ alkyl, substituted or unsubstituted C$_3$-C$_8$ cycloalkyl, substituted or unsubstituted C$_2$-C$_8$ alkenyl, C$_1$-C$_8$ perhaloalkyl, carboxyl, carbonylalkoxy, substituted or unsubstituted aryl, substituted or unsubstituted heteroaryl, or is taken together with a geminal R$^{8(a-d)}$ to form a substituted or unsubstituted methylene moiety or a moiety of the formula —OCH$_2$CH$_2$O—, or is taken together with a geminal R$^{8(a-d)}$ and the carbon to which they are attached to form a carbonyl moiety or a cycloalkyl moiety, or is taken together with a vicinal R$^{8(a-d)}$ and the carbon atoms to which they are attached to form a substituted or unsubstituted C$_3$-C$_8$ cycloalkyl, substituted or unsubstituted C$_3$-C$_8$ cycloalkenyl, or substituted or unsubstituted heterocyclyl moiety, or is taken together with a vicinal R$^{8(a-d)}$ to form a bond provided when an R$^{8(a-d)}$ is taken together with a vicinal R$^{8(a-d)}$ to form a bond, the geminal R$^{8(a-d)}$ is other than hydroxyl;

==== represents a single or double bond, provided that when ==== is a double bond, R$^{8a}$ and R$^{8c}$ are absent and R$^{8b}$ and R$^{8d}$ are other than OH;

R$^{10}$ is H, halo, a substituted or unsubstituted C$_1$-C$_8$ alkyl, hydroxyl or alkoxy;

Q is substituted or unsubstituted aryl, substituted or unsubstituted heteroaryl, substituted or unsubstituted $C_3$-$C_8$ cycloalkyl, substituted or unsubstituted $C_3$-$C_8$ cycloalkenyl, substituted or unsubstituted heterocyclyl, substituted or unsubstituted amino, alkoxy, aminoacyl, acyloxy, carboxyl, carbonylalkoxy, cyano, alkynyl, aminocarbonylalkoxy or acylamino, or a pharmaceutically acceptable salt thereof.

In one variation, compounds of the formula (I) are provided, provided that when $X^7$-$X^{10}$ is $CR^4$, and each $R^2$, $R^{3a}$, $R^{3b}$ and $R^{10}$ is H then at least one of $R^{8(a-d)}$ is hydroxyl or alkoxy.

In one variation, compounds of the formula (I) have one or more of the following structural features: (1) at least one of $X^7$, $X^8$, $X^9$ and $X^{10}$ is N; (2) at least one of the $R^8$ moieties present is other than H (such as when at least one of the $R^8$ moieties is an alkyl, alkoxy or hydroxyl group); (3) and (3) $R^1$ is a substituted or unsubstituted $C_1$-$C_8$ alkyl (such as methyl) or acyl.

In one variation, compounds of the formula (I) are provided, provided that provided that when $X^7$, $X^8$ and $X^{10}$ are $CR^4$ where $R^4$ is H and $X^9$ is $CR^4$ and each $R^2$, $R^{3a}$, $R^{3b}$ and $R^{10}$ is H then at least one of $R^{8(a-d)}$ is hydroxyl or alkoxy and/or Q is other than a substituted or unsubstituted aryl, substituted or unsubstituted heteroaryl or heterocyclyl moiety.

In one variation, compounds of the formula (I) are provided where at least one of $R^{8a-d}$ is a substituted $C_1$-$C_8$ alkyl where the $C_1$-$C_8$ alkyl is substituted with a carbonylalkoxy, carboxyl or acylamino moiety.

In another variation of formula (I), at least one $R^{3a}$ and $R^{3b}$ is aryl. In a particular variation of formula (I), at least one of $R^{3a}$ and $R^{3b}$ is phenyl.

Compounds of the general formula (I) are described as new histamine receptor modulators. Compounds of the invention may also find use in treating neurodegenerative diseases.

In one variation, the compound is of the formula (I) wherein $R^4$ is other than a substituted or unsubstituted aryl, substituted or unsubstituted heteroaryl, an aryloxy or an aralkyl. In one variation the compound is of the formula (I) wherein $R^4$ is other than a substituted or unsubstituted aryl. In one aspect of formula (I), $R^4$ is halo or an unsubstituted $C_1$-$C_8$alkyl.

In one variation, a compound of the invention is of the formula (I) where: $R^1$ is a substituted or unsubstituted $C_1$-$C_8$ alkyl, acyl, acyloxy, carbonylalkoxy, substituted or unsubstituted heterocyclyl or substituted or unsubstituted aryl; $R^2$ is H, methyl or fluoro; each $R^{3a}$ and $R^{3b}$ is independently H or fluoro; and $R^{10}$ is H, halo, hydroxyl or methyl. In one such variation, the compound is further defined by $X^7$, $X^8$, $X^9$ and $X^{10}$ each being $CR^4$.

In a particular embodiment, the compound is of the formula (I) where $X^7$, $X^8$, $X^9$ and $X^{10}$ are each $CR^4$. In another embodiment, the compound is of the formula (I) where at least one of $X^7$, $X^8$, $X^9$ and $X^{10}$ is N. Another variation provides a compound of the formula (I) where at least two of $X^7$, $X^8$, $X^9$ and $X^{10}$ are N. A further variation provides a compound of the formula (I) where two of $X^7$, $X^8$, $X^9$ and $X^{10}$ are N and two of $X^7$, $X^8$, $X^9$ and $X^{10}$ are $CR^4$. A compound of the formula (I) where one of $X^7$, $X^8$, $X^9$ and $X^{10}$ is N and three of $X^7$, $X^8$, $X^9$ and $X^{10}$ are $CR^4$ is also embraced by this invention.

It is understood that variations and aspects that are described herein for one formula, but which are applicable to another formula, apply equally to the other formula the same as if each and every variation and aspect were specifically and individually listed. For example, where a particular description of moiety Q is provided for one formula, it is understood that the same description for Q may be applied to the other formulae provide herein, where applicable (e.g., where the other formulae allow for such Q moieties). For example, all variations referring to formulae (I), where applicable, may apply equally to any formulae provided herein, such as any of formulae (I-1)-(I-5), (I-3a)-(I-3g), A-2, E, F, F-1, F-2, H-5 and H-6 the same as if each and every variation were specifically and individually listed. In addition, any proviso or provision that is described for one formula may also be applied to another formula, where applicable.

In another variation, compounds of the formula (I-1), (I-2), (I-3), (I-4) and (I-5) are provided:

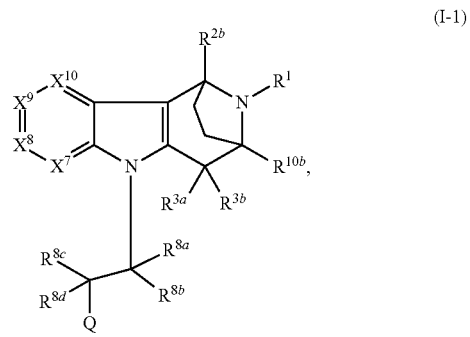

(I-1)

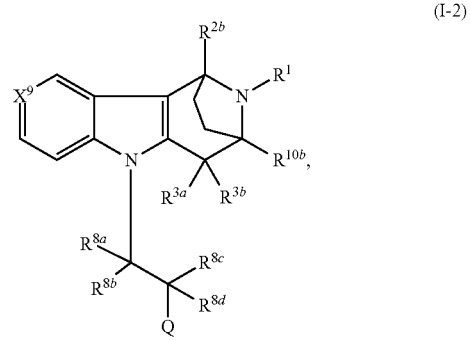

(I-2)

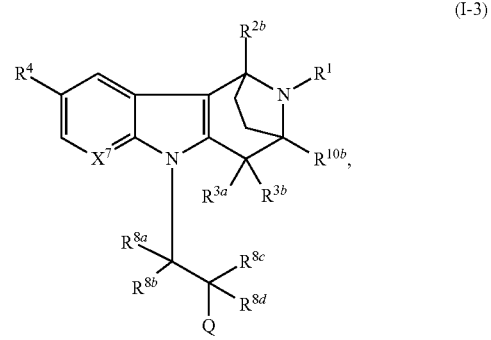

(I-3)

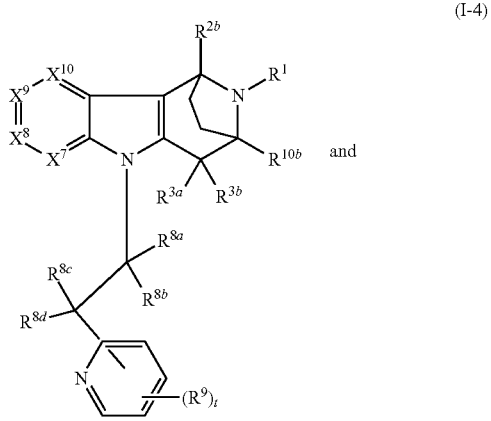

(I-4)

and

-continued (I-5)

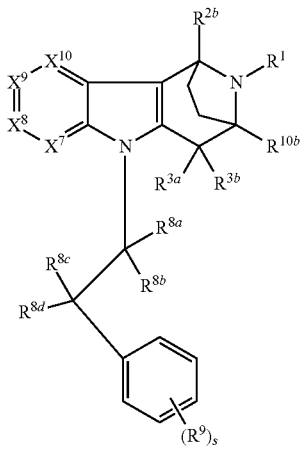

wherein Q, $X^7$, $X^8$, $X^9$, $X^{10}$, $R^4$, $R^1$, $R^{2b}$, $R^{3a}$, $R^{3b}$, $R^{10b}$, $R^{8a}$, $R^{8b}$, $R^{8c}$ and $R^{8d}$, where applicable, are as defined for formula (I) or (E) or any variations thereof;

each $R^9$ is independently halo, cyano, nitro, perhaloalkyl, perhaloalkoxy, substituted or unsubstituted $C_1$-$C_8$ alkyl, substituted or unsubstituted $C_2$-$C_8$ alkenyl, substituted or unsubstituted $C_2$-$C_8$ alkynyl, acyl, acyloxy, carbonylalkoxy, thioalkyl, substituted or unsubstituted heterocyclyl, alkoxy, substituted or unsubstituted amino, acylamino, sulfonylamino, sulfonyl, carbonyl, aminoacyl or aminocarbonylamino moiety;

s is an integer from 0 to 5; and t is an integer from 0 to 4, or a pharmaceutically acceptable salt thereof.

In one aspect, the invention embraces compounds of the formula (I-1) wherein each $X^7$, $X^8$ and $X^{10}$ is $CR^4$ where $R^4$ is H. In another aspect, the invention embraces compounds of the formula (I-1) wherein each $X^7$, $X^8$ and $X^{10}$ is $CR^4$ where $R^4$ is H, $X^9$ is $CR^4$ where $R^4$ is as defined for formula (I), and Q is substituted or unsubstituted aryl or heteroaryl. In another aspect, the invention embraces compounds of the formula (I-1) wherein each $X^7$, $X^8$ and $X^{10}$ is $CR^4$ where $R^4$ is H, $X^9$ is $CR^4$ where $R^4$ is halo (e.g., chloro) or alkyl (e.g., $CH_3$, ethyl, i-propyl or t-butyl), $R^{8a}$ is OH, $R^{8b}$ is H or $CH_3$, each $R^{8c}$ and $R^{8d}$ is H, and Q is substituted or unsubstituted aryl or heteroaryl. In a further aspect, In another aspect, the invention embraces compounds of the formula (I-1) wherein each $X^7$, $X^8$ and $X^{10}$ is $CR^4$ where $R^4$ is H, $X^9$ is $CR^4$ where $R^4$ is halo (e.g., chloro) or alkyl (e.g., $CH_3$, ethyl, i-propyl or t-butyl), $R^{8a}$ is OH, $R^{8b}$ is H or $CH_3$, each $R^{8c}$ and $R^{8d}$ is H, and Q is substituted or unsubstituted pyridyl. In one variation of any of formulae (I-1), (I-2), (I-3), (I-4) and (I-5), $R^1$ is H or a substituted or unsubstituted $C_1$-$C_8$ alkyl (such as methyl).

In one aspect, the invention embraces compounds of the formula (I-1) wherein each $X^8$ and $X^{10}$ is $CR^4$ where $R^4$ is H, $X^9$ is $CR^4$ and Q is substituted or unsubstituted aryl or heteroaryl. In another aspect, the invention embraces compounds of the formula (I-1) wherein $X^7$ is as defined for formula (I) or (E) or any variations thereof, each $X^8$ and $X^{10}$ is $CR^4$ where $R^4$ is H, $X^9$ is $CR^4$ where $R^4$ is halo (e.g., chloro) or alkyl (e.g., $CH_3$, ethyl, i-propyl or t-butyl), $R^{8a}$ and $R^{8b}$ are independently H, OH or $CH_3$, each $R^{8c}$ and $R^{8d}$ is H, and Q is substituted or unsubstituted aryl or heteroaryl; provided that: (i) when $X^7$ is N, $R^{8a}$ and $R^{8b}$ are H; and (ii) when $X^7$ is $CR^4$ where $R^4$ is H, $R^{8a}$ is OH and $R^{8b}$ is H or $CH_3$. In one embodiment, Q is substituted or unsubstituted pyridyl.

In one variation, this invention embraces compounds of formula (I-3a):

(I-3a)

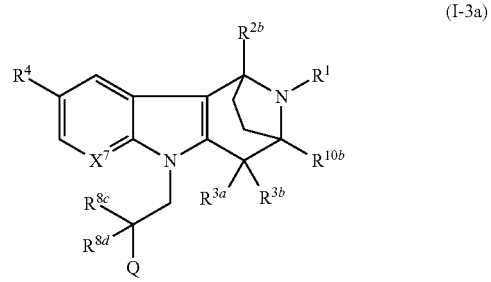

wherein:

$X^7$, $R^1$, $R^{2b}$, $R^{3a}$, $R^{3b}$ and $R^{10b}$ are as defined for formula (I) or (E) or any variations thereof;

$R^4$ is halo (e.g., chloro) or alkyl (e.g., $CH_3$, ethyl, i-propyl or t-butyl);

$R^{8c}$ and $R^{8d}$ are independently H, OH or $CH_3$; and

Q is substituted or unsubstituted aryl or heteroaryl;

provided that: (i) when $X^7$ is N, $R^{8c}$ and $R^{8d}$ are H; and (ii) when $X^7$ is CH, $R^{8c}$ is OH and $R^{8d}$ is H or $CH_3$. In one embodiment, Q is substituted or unsubstituted pyridyl. In a further variation, $R^1$ is H or a substituted or unsubstituted $C_1$-$C_8$ alkyl.

In one variation, this invention embraces compounds of formula (I-3b), (I-3c), (I-3d), (I-3e), (I-3f) and (I-3g):

(I-3b)

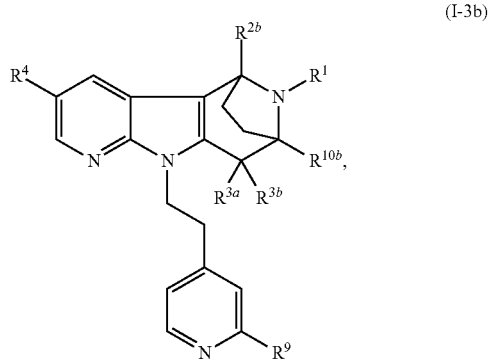

(I-3c)

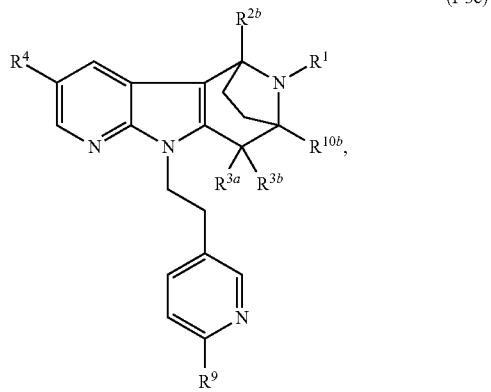

-continued

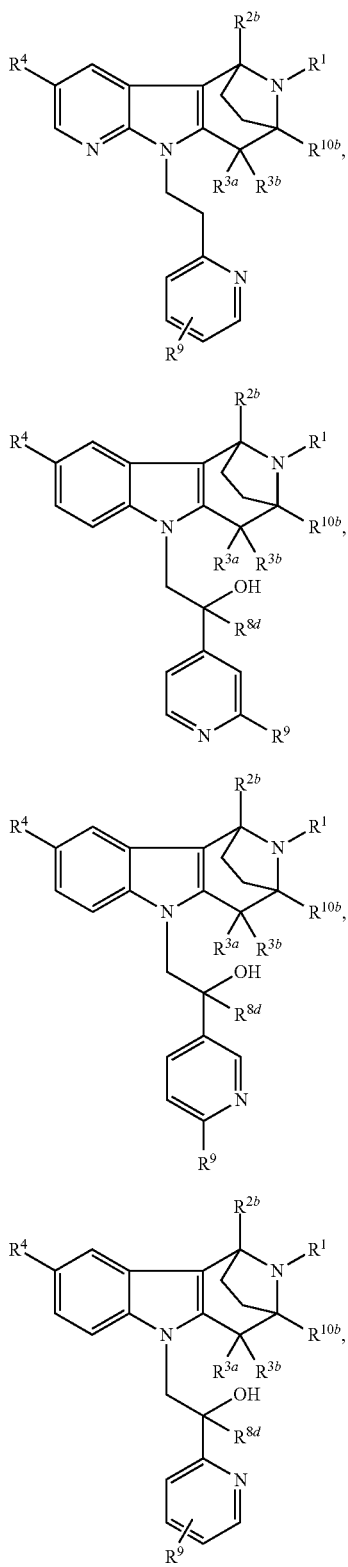

wherein $R^1$, $R^{2b}$, $R^{3a}$, $R^{3b}$ and $R^{10b}$ are as defined for formula (I) or (E) or any variations thereof;
$R^4$ is halo (e.g., chloro) or alkyl (e.g., $CH_3$, ethyl, i-propyl or t-butyl);
$R^9$ is H or $CH_3$; and
$R^{8d}$ is H or $CH_3$.

Although $R^9$ of formulae (I-3b), (I-3c), (I-3e) and (I-3f) is attached to a specific position of the pyridyl group, in other embodiments, analogous structures are provided wherein $R^9$ is attached to the pyridyl ring at any available carbon atom. Likewise, although $R^9$ of formulae (I-3d) and (I-3g) may be attached at any available position of the pyridyl ring, in another embodiment, analogous independent structures are provided where $R^9$ is individually attached to each such available position.

In one variation of any of formulae (I-3b), (I-3c), (I-3e) and (I-3f), $R^1$ is H or a substituted or unsubstituted $C_1$-$C_8$ alkyl (such as methyl).

In one variation, the compound is of the formula (A-2):

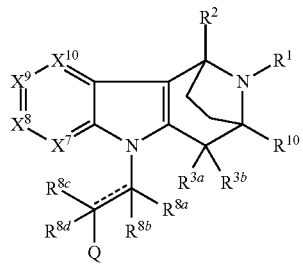

wherein:
Q is substituted or unsubstituted aryl, substituted or unsubstituted heteroaryl, substituted or unsubstituted $C_3$-$C_8$ cycloalkyl, substituted or unsubstituted $C_3$-$C_8$ cycloalkenyl, substituted or unsubstituted heterocyclyl, substituted or unsubstituted amino, alkoxy, aminoacyl, acyloxy, carboxyl, carbonylalkoxy, cyano, alkynyl, aminocarbonylalkoxy or acylamino; and
$R^1$, $X^7$, $X^8$, $X^9$, $X^{10}$, $R^2$, $R^{10}$, $R^{3a}$, $R^{3b}$, $R^{8a}$, $R^{8b}$, $R^{8c}$ and $R^{8d}$ are as defined for formula (I) in one variation and as defined for formula (E) in another variation.

In one variation, compounds of the formula (A-2) are provided where at least one of $R^{8a-d}$ is a substituted $C_1$-$C_8$ alkyl where the $C_1$-$C_8$ alkyl is substituted with a carbonylalkoxy, carboxyl or acylamino moiety.

In another variation of formula (A-2), at least one $R^{3a}$ and $R^{3b}$ is aryl. In a particular variation of formula (A-2), at least one of $R^{3a}$ and $R^{3b}$ is phenyl.

In another variation, the compound is of the formula (A-2) where at least one of $X^7$, $X^8$, $X^9$ and $X^{10}$ is N. In yet another variation, the compound is of the formula (A-2) where two of $X^7$, $X^8$, $X^9$ and $X^{10}$ are N. In one variation, the compound is of the formula (A-2) where $X^9$ is N. In another variation, the compound is of the formula (A-2) where each $X^7$ and $X^{10}$ is N. In one variation, the compound is of the formula (A-2) where each $X^8$ and $X^9$ is independently $CR^4$ where $R^4$ is H, halo or methyl. In one such variation, each $X^7$ and $X^{10}$ is CH. In another such variation, $R^1$ is methyl.

In one variation, the compound is of the formula (A-2), where Q is substituted or unsubstituted heterocyclyl. In another variation, the compound is of the formula (A-2) where Q is aminoacyl. In one variation, the compound is of the formula (A-2), where Q is a substituted or unsubstituted aryl or a substituted or unsubstituted heteroaryl. In one variation, ==== is a single bond and $R^{8a}$ and $R^{8b}$ are both H. In another variation, ==== is a double bond, $R^{8b}$ is H and $R^{8d}$ is methyl. In another such variation, $R^1$ is methyl.

In another variation, the compound is of the formula (A-2) where Q is a substituted phenyl or a substituted or unsubstituted heteroaryl comprising at least one nitrogen atom in the ring. In one such variation, Q is a substituted or unsubstituted heteroaryl comprising two nitrogen atoms in the ring. In another such variation, Q is a substituted phenyl substituted with one or more of halo, methyl and methoxy. In another such variation, Q is unsubstituted pyridyl, substituted pyridyl or substituted pyrimidyl.

In one variation, the compound is of the formula (A-2), where Q is selected from the group consisting of:

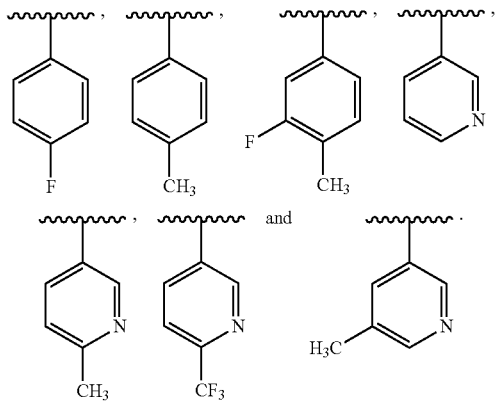

In another variation, the compound is of the formula (A-2) where each $X^8$ and $X^9$ is independently $CR^4$ where $R^4$ is H, halo or methyl, each $X^7$ and $X^{10}$ is CH, $R^1$ is methyl, each $R^{8a}$ and $R^{8b}$ is H when present, each $R^{8c}$ and $R^{8d}$ is H, each $R^{8e}$ and $R^{8f}$ is independently H, hydroxy or methyl and Q is a substituted phenyl or a substituted or unsubstituted heteroaryl. In one such variation, Q is selected from the group consisting of:

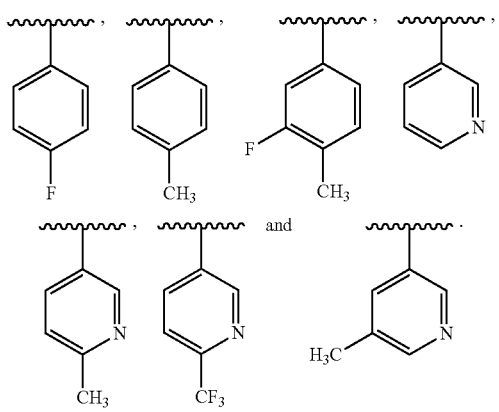

In any one of the variations of compounds of the formulae herein, where applicable, all stereo isomers are intended. For example, the ring bearing the $R^1$ group of the compound in the formula (A-2) can be either

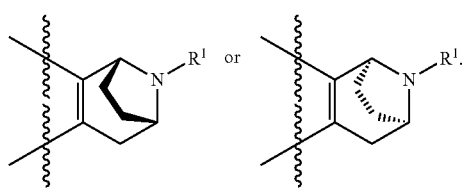

Mixtures of more than one stereo isomers are also intended, such as racemic mixtures.

In one variation, the compound is of the formula (E):

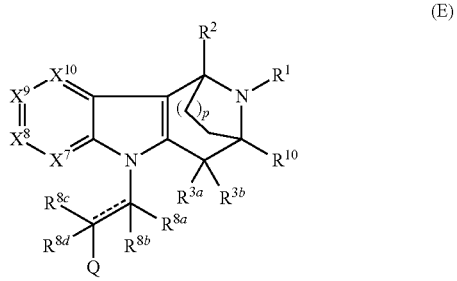

(E)

where:

$R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

$R^2$ is H, substituted or unsubstituted $C_1$-$C_8$ alkyl, halo, cyano, hydroxyl, alkoxy or nitro;

each $R^{3a}$ and $R^{3b}$ is independently H, substituted or unsubstituted $C_1$-$C_8$ alkyl, halo, cyano, nitro, hydroxyl, alkoxy, substituted or unsubstituted amino, cycloalkyl, aryl, heteroaryl, heterocyclyl, acylamino or acyloxy or $R^{3a}$ and $R^{3b}$ are taken together to form a cycloalkyl moiety or a carbonyl moiety;

each $X^7$, $X^8$, $X^9$ and $X^{10}$ is independently N or $CR^4$;

p is 1 or 2;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, carbonylalkoxy, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$ and $R^{8d}$ is independently H, hydroxyl, alkoxy, halo, substituted or unsubstituted $C_1$-$C_8$ alkyl, substituted or unsubstituted $C_3$-$C_8$ cycloalkyl, substituted or unsubstituted $C_2$-$C_8$ alkenyl, $C_1$-$C_8$ perhaloalkyl, carboxyl, carbonylalkoxy, substituted or unsubstituted aryl, substituted or unsubstituted heteroaryl, or is taken together with a geminal $R^{8(a-d)}$ to form a substituted or unsubstituted methylene moiety or a moiety of the formula —OCH$_2$CH$_2$O—, or is taken together with a geminal $R^{8(a-d)}$ and the carbon to which they are attached to form a carbonyl moiety or a cycloalkyl moiety, or is taken together with a vicinal $R^{8(a-d)}$ and the carbon atoms to which they are attached to form a substituted or unsubstituted $C_3$-$C_8$ cycloalkyl, substituted or unsubstituted $C_3$-$C_8$ cycloalkenyl, or substituted or unsubstituted heterocyclyl moiety, or is taken together with a vicinal $R^{8(a-d)}$ to form a bond provided when an $R^{8(a-d)}$ is taken together with a vicinal $R^{8(a-d)}$ to form a bond, the geminal $R^{8(a-d)}$ is other than hydroxyl;

represents a single or double bond, provided that when ═══ is a double bond, $R^{8a}$ and $R^8$ are absent and $R^{8b}$ and $R^{8d}$ are other than OH;

$R^{10}$ is H, halo, a substituted or unsubstituted $C_1$-$C_8$ alkyl, hydroxyl, alkoxy, cyano or nitro;

Q is a substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted amino, alkoxy, aminoacyl, acyloxy, carbonylalkoxy, aminocarbonylalkoxy, acylamino, carboxy, alkynyl or cyano.

or a salt thereof. In one aspect, the salt is a pharmaceutically acceptable salt.

In one variation, compounds of the formula (E) are provided, provided that when $X^7$, $X^8$ and $X^{10}$ is $CR^4$ where R is H and $X^9$ is $CR^4$, and each $R^2$, $R^{3a}$, $R^{3b}$ and $R^{10}$ is H then at least one of $R^{8(a-d)}$ is hydroxyl or alkoxy. In another variation, compounds of the formula (E) are provided wherein Q is other than a substituted or unsubstituted aryl, substituted or unsubstituted heteroaryl or heterocyclic moiety. In one variation of formula (E), at least one of $X^7$, $X^8$, $X^9$ and $X^{10}$ is N. In a particular variation of formula (E), at least one of $X^7$, $X^8$, $X^9$ and $X^{10}$ is N and at least one of $R^{8a}$-$R^{8d}$ is other than H (e.g., methyl or hydroxyl).

In one variation, compounds of the formula (E) are provided where at least one of $R^{8a-d}$ is a substituted $C_1$-$C_8$ alkyl where the $C_1$-$C_8$ alkyl is substituted with a carbonylalkoxy, carboxyl or acylamino moiety.

In another variation of formula (E), at least one $R^{3a}$ and $R^{3b}$ is aryl. In a particular variation of formula (E), at least one of $R^{3a}$ and $R^{3b}$ is phenyl.

In one variation of formula (E), each $R^2$ and $R^{10}$ is independently H, halo, hydroxyl, alkoxy or substituted or unsubstituted $C_1$-$C_8$ alkyl and $R^1$, $R^{3a}$, $R^{3b}$, p, $R^{8a}$, $R^{8b}$, $R^{8c}$, $R^{8d}$, $X^7$, $X^8$, $X^9$, $X^{10}$ and Q are as defined for formula (E). In one such variation, each $R^2$ and $R^{10}$ is independently H, hydroxyl, alkoxy or substituted or unsubstituted $C_1$-$C_8$ alkyl. In one such variation, each $R^2$ and $R^{10}$ is independently H, halo or substituted or unsubstituted $C_1$-$C_8$ alkyl. In one such variation, each $R^2$ and $R^{10}$ is independently H or substituted or unsubstituted $C_1$-$C_8$ alkyl. In another such variation, each $R^2$ and $R^{10}$ is H. Where applicable, any variation of formula (E) detailed herein may in additional variations be further defined by the $R^2$ and $R^{10}$ moieties provided, e.g., as detailed in this paragraph.

In another variation of formula (E), $R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy. In one such variation, $R^1$ is H, hydroxyl, unsubstituted $C_1$-$C_8$ alkyl, substituted $C_1$-$C_8$ alkyl other than alkyl substituted with phenyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy. In another such variation, $R^1$ is H, unsubstituted $C_1$-$C_8$ alkyl, substituted $C_1$-$C_8$ alkyl other than alkyl substituted with phenyl, substituted or unsubstituted $C_2$-$C_8$ alkenyl, substituted or unsubstituted $C_2$-$C_8$ alkynyl, perhaloalkyl, acyl, carbonylalkoxy, substituted or unsubstituted heterocyclyl, substituted or unsubstituted aryl, substituted or unsubstituted heteroaryl, substituted or unsubstituted aralkyl, acylamino, sulfonylamino, sulfonyl or carbonylalkylenealkoxy. In another such variation, $R^1$ is H, hydroxyl, unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy. In another such variation, $R^1$ is H, unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, carbonylalkoxy, substituted or unsubstituted heterocyclyl, substituted or unsubstituted aryl, substituted or unsubstituted heteroaryl, substituted or unsubstituted aralkyl, acylamino or carbonylalkylenealkoxy. In another such variation, $R^1$ is H, acyl, unsubstituted $C_1$-$C_8$ alkyl or substituted $C_1$-$C_8$ alkyl other than alkyl substituted with phenyl. In yet another such variation, $R^1$ is unsubstituted $C_1$-$C_8$ alkyl or acyl. In a particular such variation, $R^1$ is unsubstituted $C_1$-$C_8$ alkyl (e.g. methyl). Where applicable, any variation of formula (E) detailed herein may in additional variations be further defined by the $R^1$ moieties of this paragraph.

In yet another variation of formula (E), $R^1$ is H, hydroxyl, unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy, each $R^2$ and $R^{10}$ is independently H, hydroxyl, alkoxy or substituted or unsubstituted $C_1$-$C_8$ alkyl and $R^{3a}$, $R^{3b}$, p, $R^{8a}$, $R^{8b}$, $R^{8c}$, $R^{8d}$, $X^7$, $X^8$, $X^9$, $X^{10}$ and Q are as defined for formula (E). In one such variation, $R^1$ is H, unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, carbonylalkoxy, substituted or unsubstituted heterocyclyl, substituted or unsubstituted aryl, substituted or unsubstituted heteroaryl, substituted or unsubstituted aralkyl, acylamino, sulfonylamino, sulfonyl or carbonylalkylenealkoxy. In another such variation, $R^1$ is unsubstituted $C_1$-$C_8$ alkyl or acyl. In another such variation, each $R^2$ and $R^{10}$ is independently H or substituted or unsubstituted $C_1$-$C_8$ alkyl.

In another variation of formula (E), Q is a substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted amino, alkoxy, aminoacyl, acyloxy, carbonylalkoxy, aminocarbonylalkoxy, acylamino, carboxy, alkynyl and cyano. In yet another such variation, Q is a substituted aryl, substituted or unsubstituted heteroaryl, substituted or unsubstituted cycloalkyl, substituted or unsubstituted cycloalkenyl, substituted or unsubstituted heterocyclyl, substituted or unsubstituted amino, alkoxy, aminoacyl, acyloxy, carbonylalkoxy, aminocarbonylalkoxy, acylamino, carboxy, alkynyl and cyano. Where applicable, any variation of formula (E) detailed herein may in additional variations be further defined by the Q moieties provided, e.g., the Q moieties detailed in this paragraph.

In one embodiment, compounds of the formulae detailed herein are provided where $X^7$, $X^8$, $X^9$ and $X^{10}$ are $CR^4$. In another embodiment, compounds of the formulae detailed herein are provided where at least one of $X^7$, $X^8$, $X^9$ and $X^{10}$ is N. In one variation, at least two of $X^7$, $X^8$, $X^9$ and $X^{10}$ are N. In another variation, two of $X^7$, $X^8$, $X^9$ and $X^{10}$ are N and two of $X^7$, $X^8$, $X^9$ and $X^{10}$ are $CR^4$. In yet another variation, one of $X^7$, $X^8$, $X^9$ and $X^{10}$ is N and three of $X^7$, $X^8$, $X^9$ and $X^{10}$ are $CR^4$. In a particular variation, $X^9$ is N and $X^7$, $X^8$ and $X^{10}$ are $CR^4$. In another particular variation, $X^7$ and $X^{10}$ are N and $X^8$ and $X^9$ are $CR^4$.

In one variation, the compound is of the formula (F):

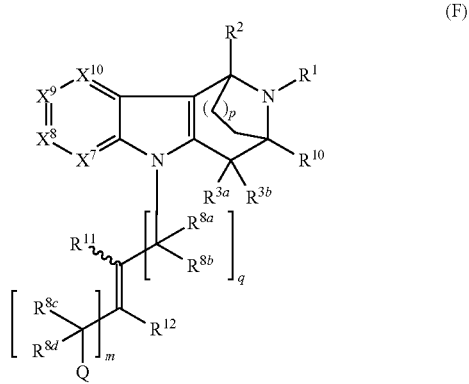

(F)

where:

$R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

$R^2$ is H, substituted or unsubstituted $C_1$-$C_8$ alkyl, halo, cyano, hydroxyl, alkoxy or nitro;

each $R^{3a}$ and $R^{3b}$ is independently H, substituted or unsubstituted $C_1$-$C_8$ alkyl, halo, cyano, nitro, hydroxyl, alkoxy, substituted or unsubstituted amino, cycloalkyl, aryl, heteroaryl, heterocyclyl, acylamino or acyloxy or $R^{3a}$ and $R^{3b}$ are taken together to form a cycloalkyl or a carbonyl moiety;

each $X^7$, $X^8$, $X^9$ and $X^{10}$ is independently N or $CR^4$;

m and q are independently 0 or 1;

p is 1 or 2;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, carbonylalkoxy, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$ and $R^{8d}$ is independently H, hydroxyl, alkoxy, halo, substituted or unsubstituted $C_1$-$C_8$ alkyl, substituted or unsubstituted $C_3$-$C_8$ cycloalkyl, substituted or unsubstituted $C_2$-$C_8$ alkenyl, $C_1$-$C_8$ perhaloalkyl, carboxyl, carbonylalkoxy, substituted or unsubstituted aryl, substituted or unsubstituted heteroaryl, or is taken together with a geminal $R^{8(a-d)}$ to form a substituted or unsubstituted methylene moiety or a moiety of the formula —OCH$_2$CH$_2$O—, or is taken together with a geminal $R^{8(a-d)}$ and the carbon to which they are attached to form a carbonyl moiety or a cycloalkyl moiety;

$R^{10}$ is H, halo, a substituted or unsubstituted $C_1$-$C_8$ alkyl, hydroxyl, alkoxy, cyano or nitro;

each $R^{11}$ and $R^{12}$ is independently H, halo, alkoxy, substituted or unsubstituted aryl, substituted or unsubstituted heteroaryl, substituted or unsubstituted $C_1$-$C_8$ alkyl, substituted or unsubstituted $C_2$-$C_8$ alkenyl, substituted or unsubstituted $C_3$-$C_8$ cycloalkyl, carboxy, carbonylalkoxy or $C_1$-$C_8$ perhaloalkyl and the ∼∼∼ bond indicates the presence of either an E or Z double bond configuration, or $R^{11}$ and $R^{12}$ are taken together to form a bond or are taken together with the carbon atoms to which they are attached to form a substituted or unsubstituted $C_{3-8}$ cycloalkenyl or substituted or unsubstituted heterocyclyl moiety;

Q is a substituted or unsubstituted aryl, substituted or unsubstituted heteroaryl, substituted or unsubstituted cycloalkyl, substituted or unsubstituted cycloalkenyl, substituted or an unsubstituted heterocyclyl, substituted or unsubstituted amino, alkoxy, aminoacyl, acyloxy, carbonylalkoxy, aminocarbonylalkoxy, acylamino, carboxy, alkynyl or cyano, or a pharmaceutically acceptable salt thereof.

In one variation, compounds of the formula (F) are provided, provided that when $X^7$, $X^8$ and $X^{10}$ is $CR^4$ where R is H and $X^9$ is $CR^4$, and each $R^2$, $R^{3a}$, $R^{3b}$ and $R^{10}$ is H then at least one of $R^{11}$ or $R^{12}$ is other than H (e.g., hydroxyl, alkyl or alkoxy) and/or Q is other than a substituted or unsubstituted aryl or a substituted or unsubstituted heteroaryl. In one variation of formula F, at least one of $X^7$, $X^8$, $X^9$ and $X^{10}$ is N.

In one variation, compounds of the formula (F) are provided where at least one of $R^{8a-d}$ is a substituted $C_1$-$C_8$ alkyl where the $C_1$-$C_8$ alkyl is substituted with a carbonylalkoxy, carboxyl or acylamino moiety.

In another variation of formula (F), at least one $R^{3a}$ and $R^{3b}$ is aryl. In a particular variation of formula (F), at least one of $R^{3a}$ and $R^{3b}$ is phenyl.

In still another variation of formula (F), each $R^{11}$ and $R^{12}$ is independently H, halo, alkoxy, substituted or unsubstituted aryl, substituted or unsubstituted heteroaryl, substituted or unsubstituted $C_1$-$C_8$ alkyl, substituted or unsubstituted $C_2$-$C_8$ alkenyl, substituted or unsubstituted $C_3$-$C_8$ cycloalkyl, carboxy, carbonylalkoxy or $C_1$-$C_8$ perhaloalkyl and the ∼∼∼ bond indicates the presence of either an E or Z double bond configuration, or $R^{11}$ and $R^{12}$ are taken together to form a bond.

In one variation of formula (F), $R^{11}$ is H, substituted or unsubstituted $C_1$-$C_8$ alkyl, substituted or unsubstituted $C_3$-$C_8$ cycloalkyl, or substituted or unsubstituted $C_1$-$C_8$ perhaloalkyl and $R^{12}$ is H, substituted or unsubstituted $C_1$-$C_8$ alkyl, substituted or unsubstituted $C_3$-$C_8$ cycloalkyl, or substituted or unsubstituted $C_1$-$C_8$ perhaloalkyl, or is taken together with $R^{11}$ and the carbon atoms to which they are attached to form a substituted or unsubstituted $C_3$-$C_8$ cycloalkenyl moiety.

In one variation of formula (F), $R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy. In another variation of formula (F), $R^1$ is H, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, carbonylalkoxy, substituted or unsubstituted heterocyclyl, substituted or unsubstituted aryl, substituted or unsubstituted heteroaryl, substituted or unsubstituted aralkyl, acylamino or carbonylalkylenealkoxy. In another variation of formula (F), each $R^2$ and $R^{10}$ is independently H or substituted or unsubstituted $C_1$-$C_8$ alkyl. In another variation of formula (F), each $R^2$ and $R^{10}$ is independently H, halo or substituted or unsubstituted $C_1$-$C_8$ alkyl.

In another variation of formula (F), q and n are 0, $R^{11}$ and $R^{12}$ are independently H, $C_1$-$C_8$ alkyl, $C_1$-$C_8$ perhaloalkyl, carboxy or carbonylalkoxy and the compound is of the formula (F-1):

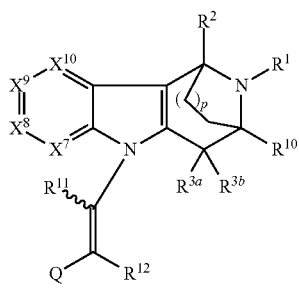

(F-1)

or a salt thereof,
wherein $R^1$, $R^2$, $R^{3a}$, $R^{3b}$, $R^{10}$, p, $X^7$, $X^8$, $X^9$, $X^{10}$ and Q are as defined for formula (F). In one variation of formula (F-1), $R^{11}$ is H, substituted or unsubstituted $C_1$-$C_8$ alkyl, substituted or unsubstituted $C_3$-$C_8$ cycloalkyl, or substituted or unsubstituted $C_1$-$C_8$ perhaloalkyl and $R^{12}$ is H, substituted or unsubstituted $C_1$-$C_8$ alkyl, substituted or unsubstituted $C_3$-$C_8$ cycloalkyl, or substituted or unsubstituted $C_1$-$C_8$ perhaloalkyl, or is taken together with $R^H$ and the carbon atoms to which they are attached to form a substituted or unsubstituted $C_3$-$C_8$ cycloalkenyl moiety.

In a particular variation of formula (F-1), $R^{11}$ is H and Q is a substituted or unsubstituted aryl or heteroaryl e.g., a substituted or unsubstituted phenyl or pyridyl. In a more particular variation of formula (F-1), $R^{11}$ is H, $R^{12}$ is H or methyl and Q is a substituted or unsubstituted aryl or heteroaryl. Examples of substituted or unsubstituted phenyl or pyridyl Q groups include, but are not limited to, 3-pyridyl, 4-pyridyl, 4-methoxyphenyl, 4-chlorophenyl, 4-fluorophenyl, 3-fluoro-4-methoxylphenyl, 3,4-dichlorophenyl, 3,4-difluorophenyl, 4-methyl-3-pyridyl, 4-fluorophenyl and 2-methyl-5-pyrimidyl. In another particular variation, the compound is of the formula (F-1) where $R^1$ is methyl, p is 1, $X^9$ is $CR^4$ where $R^4$ is halo or methyl, $R^{11}$ is H, $R^{12}$ is H or methyl and Q is substituted phenyl. In another particular variation, the compound is of the formula (F-1) where $R^1$ is methyl, each $R^2$, $R^{3a}$, $R^{3b}$ and $R^{10}$ is H, p is 1, $X^9$ is $CR^4$ where $R^4$ is halo or methyl, each $X^7$, $X^8$ and $X^{10}$ is CH, $R^{11}$ is H, $R^{12}$ is methyl and Q is substituted phenyl, e.g. 4-fluorophenyl and 3-fluoro-4-methoxyphenyl.

In another variation of formula (F), q and n are 0, $R^{11}$ and $R^{12}$ are taken together to form a bond and the compound is of the formula (F-2):

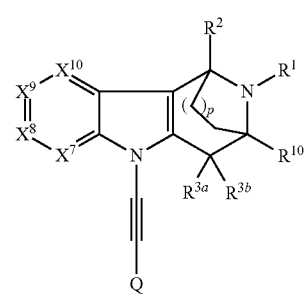

(F-2)

or a salt thereof,
wherein $R^1$, $R^2$, $R^{3a}$, $R^{3b}$, $R^{10}$, p, $X^7$, $X^8$, $X^9$, $X^{10}$ and Q are as defined for formula (F). In one variation of formula (F-2), Q is a substituted or unsubstituted aryl, substituted or unsubstituted heteroaryl, substituted or unsubstituted cycloalkyl, substituted or unsubstituted cycloalkenyl or substituted or unsubstituted heterocyclyl.

In a particular variation of formula (F-2), Q is a substituted or unsubstituted aryl or heteroaryl, e.g., a substituted or unsubstituted phenyl or pyridyl. Examples of Q include, but are not limited to, 4-methoxyphenyl, 4-chlorophenyl, 4-fluorophenyl, 3-fluoro-4-methoxyphenyl, 3,4-dichlorophenyl, 3,4-difluorophenyl, 3-pyridyl, 4-pyridyl, 4-trifluoromethyl-3-pyridyl and 4-methyl-3-pyridyl. In another particular variation, the compound is of the formula (F-2) where $R^1$ is methyl, p is 1, $X^9$ is $CR^4$ where $R^4$ is halo or methyl and Q is substituted or unsubstituted aryl or heteroaryl. In another particular variation, the compound is of the formula (F-2) where $R^1$ is methyl, each $R^2$, $R^{3a}$, $R^{3b}$ and $R^{10}$ is H, p is 1, $X^9$ is $CR^4$ where $R^4$ is halo or methyl, each $X^7$, $X^8$ and $X^{10}$ is CH and Q is substituted pyridyl, e.g. 6-methyl-3-pyridyl.

In another variation, compounds of the formula (H-5) are provided:

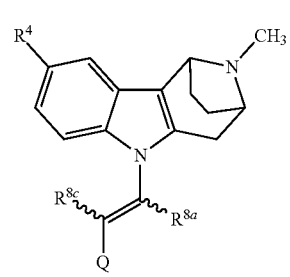

(H-5)

where $R^4$ is as defined for formula (F); $R^{8a}$ is H, hydroxyl, alkoxy, halo, substituted or unsubstituted $C_1$-$C_8$ alkyl, substituted or unsubstituted $C_3$-$C_8$ cycloalkyl, substituted or unsubstituted $C_2$-$C_8$ alkenyl, $C_1$-$C_8$ perhaloalkyl, carboxyl, carbonylalkoxy, substituted or unsubstituted aryl, substituted or unsubstituted heteroaryl and $R^{8c}$ and Q are independently a substituted or unsubstituted aryl or substituted or unsubstituted heteroaryl. In one embodiment of formula (H-5), $R^{8c}$ and Q are the same substituted or unsubstituted aryl or heteroaryl moiety, such as when both $R^{8c}$ and Q are phenyl. In another variation of formula (H-5), $R^4$ is halo, $C_1$-$C_8$alkyl or H. In a further variation of formula (H-5), $R^4$ is halo, $C_1$-$C_8$alkyl or H and $R^{8c}$ and Q are the same substituted or unsubstituted aryl or heteroaryl moiety. In one variation, compounds of the formula (H-5) are provided where at least one of $R^{8a}$ and $R^{8c}$ is a substituted $C_1$-$C_8$ alkyl where the $C_1$-$C_8$ alkyl is substituted with a carbonylalkoxy, carboxyl or acylamino moiety.

In another variation, compounds of the formula (H-6) are provided:

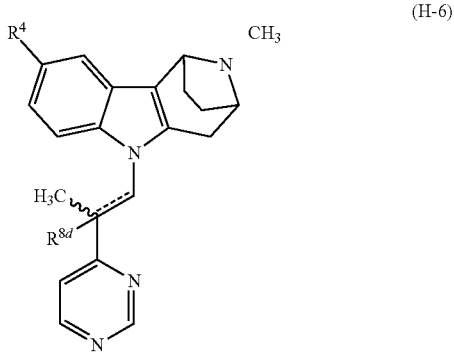

(H-6)

where $R^4$ is as defined for formula (F); ⸺ is a single or a double bond; and $R^{8d}$ is H, OH, substituted or unsubstituted $C_1$-$C_8$ alkyl, halo, substituted or unsubstituted aryl, substituted or unsubstituted heteroaryl, $C_1$-$C_8$ alkyl substituted with a carbonylalkoxy, carboxyl or acylamino moiety, substituted or unsubstituted $C_3$-$C_6$ cycloalkyl when ⸺ is a single bond and $R^{8d}$ is absent when ⸺ is a double bond. In a further variation of formula (H-6), $R^4$ is halo, $C_1$-$C_8$alkyl or H and ⸺ is a double bond. In yet another variation of formula (H-6), $R^4$ is halo, $C_1$-$C_8$alkyl or H and ⸺ is a single bond.

In one variation, the compound is of any formula provided herein, where $R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy. In another variation, the compound is of any formula provided herein, where $R^1$ is substituted or unsubstituted $C_1$-$C_8$ alkyl or acyl. In a further variation, the compound is of any formula provided herein where $R^1$ is unsubstituted $C_1$-$C_8$ alkyl. Where applicable, any variation of a formula detailed herein may in additional variations be further defined by the $R^1$ moieties of this paragraph.

In a particular embodiment, the compound is of any of the foregoing formulae, such as a compound of formula (I), (I-1)-(I-5), (I-3a)-(I-3g), A-2, E, F, F-1, F-2, H-5 and H-6, where, if applicable, $X^7$, $X^8$, $X^9$ and $X^{10}$ are $CR^4$. In another embodiment, compound is of any of the foregoing formulae, where, if applicable, at least one of $X^7$, $X^8$, $X^9$ and $X^{10}$ is N. Another variation provides compounds of any of the foregoing formulae, where, if applicable, at least two of $X^7$, $X^8$, $X^9$ and $X^{10}$ are N. A further variation provides compounds of any of the foregoing formulae, where, if applicable, two of $X^7$, $X^8$, $X^9$ and $X^{10}$ are N and two of $X^7$, $X^8$, $X^9$ and $X^{10}$ are $CR^4$. Compound of any of the foregoing formulae are provided, where, if applicable, one of $X^7$, $X^8$, $X^9$ and $X^{10}$ is N and three of $X^7$, $X^8$, $X^9$ and $X^{10}$ are $CR^4$.

In another variation, compounds of any of the foregoing formulae are provided such as a compound of formula (I), (I-1)-(I-5), (I-3a)-(I-3g), A-2, E, F, F-1, F-2, H-5 and H-6, where, if applicable, $X^7$, $X^8$, $X^9$ and $X^{10}$ are taken together to provide an aromatic moiety selected from the following structures:

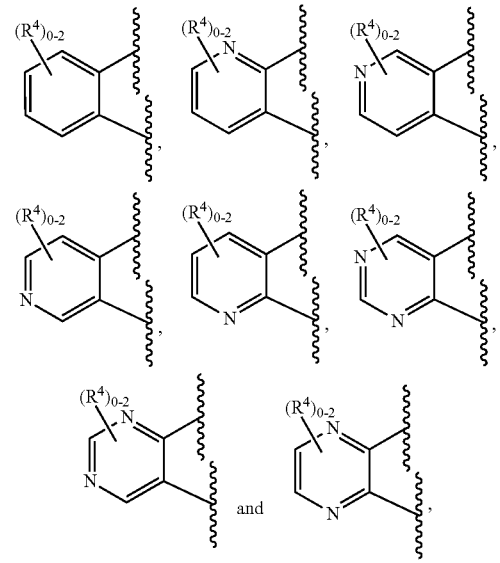

where each $R^4$ is as defined for the formulae; or in a particular variation, where each $R^4$ is independently hydroxyl, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, substituted or unsubstituted heterocyclyl, substituted or unsubstituted aralkyl, thioalkyl, substituted or unsubstituted amino, alkylsulfonylamino or acyl; or in still a further variation, where $R^4$ is independently halo, unsubstituted $C_1$-$C_4$ alkyl or $C_1$-$C_4$ perhaloalkyl. In another variation, each $R^4$ is independently halo or an unsubstituted $C_1$-$C_8$ alkyl. In one embodiment, the foregoing rings are substituted with an $(R^4)_1$ substituent, such that that aromatic moiety is substituted is a single $R^4$ group, which in one variation is halo or unsubstituted $C_1$-$C_8$ alkyl. In a particular variation, $R^4$ is other than H. In one such variation, the foregoing rings have $(R^4)_0$ substituents, such that that aromatic moiety is unsubstituted and contains no $R^4$ groups.

In another variation, compounds of any of the foregoing formulae are provided such as a compound of formula (I), (I-1)-(I-5), (I-3a)-(I-3g), A-2, E, F, F-1, F-2, H-5 and H-6, where, if applicable, $X^7$, $X^8$, $X^9$ and $X^{10}$ are taken together to provide an aromatic moiety selected from the following structures:

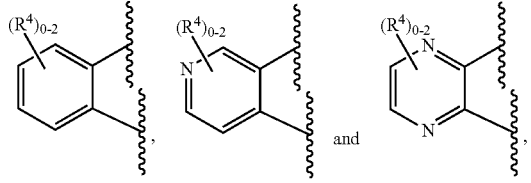

where each $R^4$ is as defined for the formulae; or in a particular variation, where each $R^4$ is independently alkyl, perhaloalkyl or halo or in an even more particular variation, where each $R^4$ is independently methyl, trifluoromethyl, chloro or fluoro. In one embodiment, the foregoing rings are substituted with an $(R^4)_1$ substituent, such that that aromatic moiety is substituted is a single $R^4$ group, which in one variation is halo or unsubstituted $C_1$-$C_8$ alkyl. In a particular variation, $R^4$ is other than H. In one such variation, the foregoing rings have $(R^4)_0$ substituents, such that that aromatic moiety is unsubstituted and contains no $R^4$ groups.

In a further variation, compounds of any of the foregoing formulae are provided such as a compound of formula (I), (I-1)-(I-5), (I-3a)-(I-3g), A-2, E, F, F-1, F-2, H-5 and H-6, where, if applicable, $X^7$, $X^8$, $X^9$ and $X^{10}$ are taken together to provide a structure of the following formulae, where $R^4$ may be as defined in any variation hereinabove:

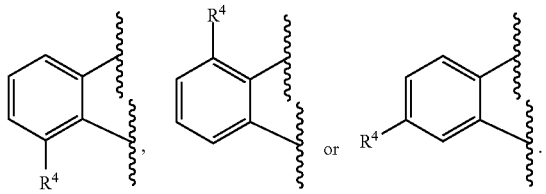

In one such variation, $R^4$ is halo or an unsubstituted $C_1$-$C_8$ alkyl.

In still a further variation, compounds of any of the foregoing formulae are provided, where, if applicable, $X^7$, $X^8$, $X^9$ and $X^{10}$ are taken together provide an aromatic moiety selected from the following structures:

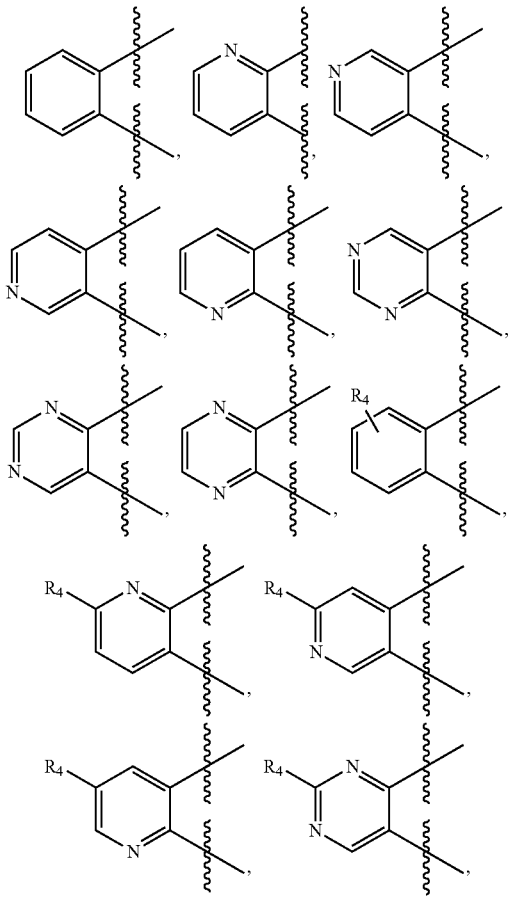

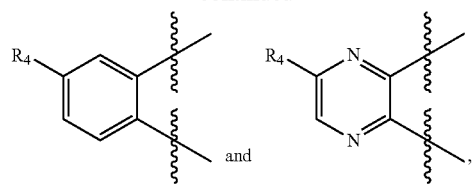

wherein $R^4$ is as defined in the formulae; or in a particular variation, where $R^4$ is hydroxyl, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, substituted or unsubstituted heterocyclyl, substituted or unsubstituted aralkyl, thioalkyl, substituted or unsubstituted amino, alkylsulfonylamino or acyl; or in still a further variation, where each $R^4$ is independently halo, unsubstituted $C_1$-$C_4$ alkyl or $C_1$-$C_4$ perhaloalkyl. In another variation, $R^4$ is halo or unsubstituted $C_1$-$C_8$ alkyl. In yet another variation, compounds of any of the foregoing formulae are provided, where, if applicable, $X^7$, $X^8$, $X^9$ and $X^{10}$ are taken together to provide a structure of the formula:

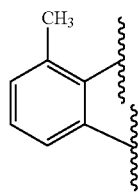

In still a further variation, compounds of any of the foregoing formulae are provided, where, if applicable, $X^7$, $X^8$, $X^9$ and $X^{10}$ are taken together provide an aromatic moiety selected from the following structures:

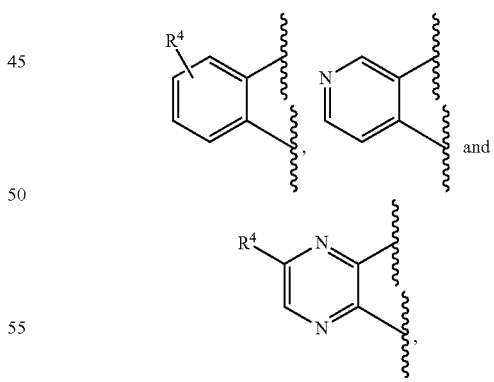

wherein $R^4$ is as defined in the formulae or in any particular variation herein, such as when each $R^4$ is independently alkyl or halo or in an even more particular variation, where each $R^4$ is independently methyl, chloro, iodo or fluoro.

In yet another variation, compounds of any of the foregoing formulae are provided, where, if applicable, $X^7$, $X^8$, $X^9$ and $X^{10}$ are taken together provide an aromatic moiety selected from the following structures:

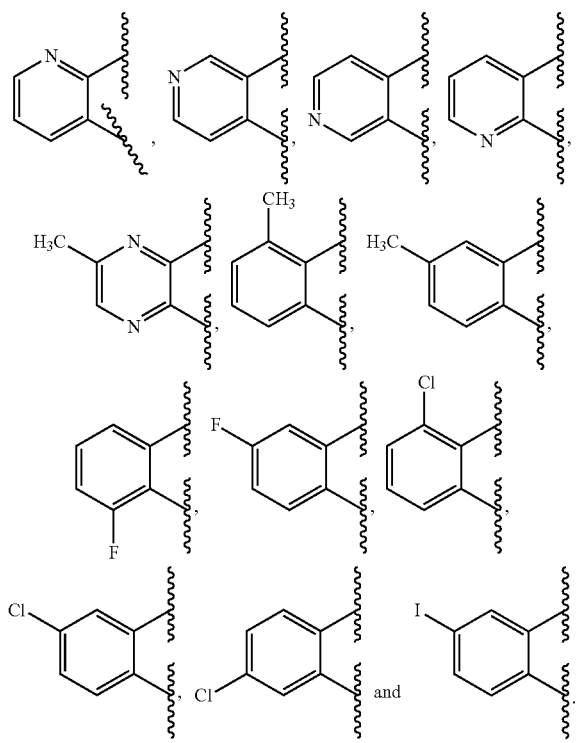

Any formula detailed herein such as a compound of formula (I), (I-1)-(I-5), (I-3a)-(I-3g), A-2, E, F, F-1, F-2, H-5 and H-6, where applicable, may in one variation have $X^7$, $X^8$, $X^9$ and $X^{10}$ taken together to provide an aromatic moiety detailed herein above. It is understood that by "where applicable" it is intended that in one variation such $X^7$, $X^8$, $X^9$ and $X^{10}$ groups are taken together to provide a moiety hereinabove if the formula encompasses such a structure. For example, if a given formula does not encompass structures wherein $X^7$, $X^8$, $X^9$ and $X^{10}$ groups are taken together provide a pyridyl moiety, then a pyridyl moiety as detailed hereinabove is not applicable to that particular formula, but remains applicable to formulae that do encompass structures where $X^7$, $X^8$, $X^9$ and $X^{10}$ groups are taken together provide a pyridyl moiety.

In another embodiment, compounds of the formulae are provided wherein $R^1$ is H, substituted or unsubstituted $C_1$-$C_8$ alkyl, acyl, acyloxy, carbonylalkoxy, substituted or unsubstituted heterocyclyl, substituted or unsubstituted aryl, substituted or unsubstituted heteroaryl, substituted or unsubstituted aralkyl. In a further embodiment, compound of the formulae detailed herein are provided where $R^1$ is a substituted or unsubstituted $C_1$-$C_8$ alkyl, acyl, acyloxy, carbonylalkoxy, substituted or unsubstituted heterocyclyl or substituted or unsubstituted aryl. In a particular variation, compound of the formulae are provided, where, if applicable, $R^1$ is methyl, ethyl, cyclopropyl, propylate, trifluoromethyl, isopropyl, tert-butyl, sec-butyl, 2-methylbutyl, propanal, 1-methyl-2-hydroxyethyl, 2-hydroxyethanal, 2-hydroxyethyl, 2-hydroxypropyl, 2-hydroxy-2-methylpropyl, cyclobutyl, cyclopentyl, cyclohexyl, substituted phenyl, piperidin-4-yl, hydroxycyclopent-3-yl, hydroxycyclopent-2-yl, hydroxycyclopropp-2-yl, 1-hydroxy-1-methylcycloprop-2-yl, or 1-hydroxy-1,2,2-trimethyl-cycloprop-3-yl.

In another variation, compounds of the formulae are provided such as a compound of formula (I), (I-1)-(I-5), (I-3a)-(I-3g), A-2, E, F, F-1, F-2, H-5 and H-6, where, if applicable, $X^7$-$X^{10}$ and $R^1$ are as defined in formula (I) or as detailed in any variation herein, where $R^2$ is H, substituted or unsubstituted $C_1$-$C_8$ alkyl, halo, cyano or nitro and each $R^{3a}$ and $R^{3b}$ is independently H, substituted or unsubstituted $C_1$-$C_8$ alkyl, halo, cyano or nitro. In another variation, compounds are provided, where $X^7$-$X^{10}$ and $R^1$ are as defined in formula (I) or as detailed in any variation herein, where $R^2$ is H, unsubstituted $C_1$-$C_8$ alkyl or halo and each $R^{3a}$ and $R^{3b}$ is independently H, unsubstituted $C_1$-$C_8$ alkyl, halo or $R^{3a}$ and $R^{3b}$ are taken together to form a carbonyl moiety. In still a further variation, compounds of the formula (I) are provided, where $X^7$-$X^{10}$ and $R^1$ are as defined in formula (I) or as detailed in any variation herein, where $R^2$ is H, unsubstituted $C_1$-$C_8$ alkyl or halo; and each $R^{3a}$ and $R^{3b}$ is independently H, unsubstituted $C_1$-$C_8$ alkyl, halo or $R^{3a}$ and $R^{3b}$ are taken together to form a carbonyl moiety. The invention also embraces compounds according to formula (I), where $X^7$-$X^{10}$ and $R^1$ are as defined in formula (I) or as detailed in any variation herein, where $R^2$ is H, methyl or halo and each $R^{3a}$ and $R^{3b}$ is independently H, methyl, halo or $R^{3a}$ and $R^{3b}$ are taken together to form a carbonyl moiety. The invention further embraces compounds of the formula (I), where $X^7$-$X^{10}$ and $R^1$ are as defined in formula (I) or as detailed in any variation herein, where each of $R^2$, $R^{3a}$ and $R^{3b}$ is H. In one variation, compounds of the formula (I) are provided where $X^7$-$X^{10}$ and $R^1$ are as defined in formula (I) or as detailed in any variation herein, where at least one of $R^2$, $R^{3a}$ and $R^{3b}$ is a substituted or unsubstituted $C_1$-$C_8$ alkyl, halo, cyano, nitro or is taken together with a geminal $R^2$ or $R^3$ to form a carbonyl moiety. In another variation, compounds are of the formula (I) where $X^7$-$X^{10}$ and $R^1$ are as defined in formula (I) or as detailed in any variation herein, where at least two of $R^2$, $R^{3a}$ and $R^{3b}$ is a substituted or unsubstituted $C_1$-$C_8$ alkyl, halo, cyano, nitro or is taken together with a geminal $R^2$ or $R^3$ to form a carbonyl moiety. In yet another variation, compounds are of the formula (I) where $X^7$-$X^{10}$ and $R^1$ are as defined in formula (I) or as detailed in any variation herein, where at least one of $R^2$, $R^{3a}$ and $R^{3b}$ is fluoro or methyl or is taken together with a geminal $R^2$ or $R^3$ to form a carbonyl moiety. In still another variation, compounds of the invention are of the formula (I) where $X^7$-$X^{10}$ and $R^1$ are as defined in formula (I) or as detailed in any variation herein, where $R^2$ or either $R^{3a}$ and $R^{3b}$ are each methyl or fluoro (e.g., both $R^{3a}$ and $R^{3b}$ are methyl or one is methyl) or are taken together to form a carbonyl moiety. In another variation, $R^2$ is hydroxyl or alkoxy. In a particular variation, $R^2$ is H, substituted or unsubstituted $C_1$-$C_8$ alkyl, halo, cyano or nitro.

The invention also embraces compounds according to formula (I), where $X^7$-$X^{10}$, $R^1$, $R^2$, $R^{3a}$ and $R^{3b}$ are as defined in formula (I) or as detailed in any variation herein, where $R^{10}$ is H, halo, an unsubstituted $C_1$-$C_8$ alkyl or hydroxyl. Also embraced are compounds according to formula (I), where $X^7$-$X^{10}$, $R^1$, $R^2$, $R^{3a}$ and $R^{3b}$ are as defined in formula (I) or as detailed in any variation herein, where each $R^{10}$ is H, halo, an unsubstituted $C_1$-$C_4$ alkyl or hydroxyl. In another variation, a compound of the invention is of the formula (I), where $X^7$-$X^{10}$, $R^1$, $R^2$, $R^{3a}$ and $R^{3b}$ are as defined in formula (I) or as detailed in any variation herein, where $R^{10}$ is H, bromo, methyl or hydroxyl. In yet another variation, a compound of the invention is of the formula (I), where $X^7$-$X^{10}$, $R^1$, $R^2$, $R^{3a}$ and $R^{3b}$ are as defined in formula (I) or as detailed in any variation herein, where $R^{10}$ is an unsubstituted $C_1$-$C_8$ alkyl, hydroxyl or halo. In still a further variation, a compound of the invention is of the formula (I), where $X^7$-$X^{10}$, $R^1$, $R^2$, $R^{3a}$ and $R^{3b}$ are as defined in formula (I) or as detailed in any variation herein, where $R^{10}$ is methyl, bromo or hydroxyl. In another variation, a compound of the invention is of the formula (I), where $X^7$-$X^{10}$, $R^1$, $R^2$, $R^{3a}$ and $R^{3b}$ are as defined in formula (I) or as detailed in any variation herein, where $R^{10}$ is methyl. In another variation, a compound of the invention is of the formula (I), where $X^7$-$X^{10}$, $R^1$, $R^2$, $R^{3a}$ and $R^{3b}$ are as defined in formula (I). In another variation, a compound of the invention is of the formula (I), where $X^7$-$X^{10}$, $R^1$, $R^2$, $R^{3a}$ and $R^{3b}$ are as defined in formula (I) or as detailed in any variation herein, where $R^{10}$ is H or methyl. In another variation, a compound of the invention is of the formula (I), where $X^7$-$X^{10}$, $R^1$, $R^2$, $R^{3a}$ and $R^{3b}$ are as defined in formula (I) or as detailed in any variation herein, where $R^{10}$ is H or bromo. When the carbon of formula (I) bearing $R^{10}$ is optically active, it may be in the S or R configuration and compositions comprising substantially pure R or S compound or mixtures thereof in any amount are embraced by this invention.

In a particular variation, compounds of any of the foregoing the formulae are provided such as a compound of formula (I), (I-1)-(I-5), (I-3a)-(I-3g), A-2, E, F, F-1, F-2, H-5 and H-6, where, if applicable, $R^2$, $R^{10}$, $R^{3a}$ and $R^{3b}$ are taken together to form a ring selected from the structures:

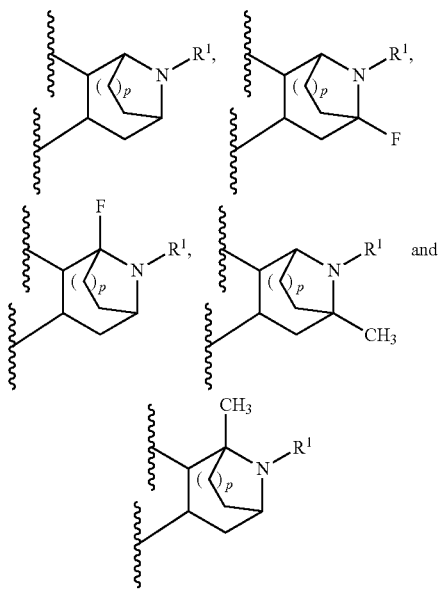

where $R^1$ in the structures above is as defined for formula (I) or any particular variation detailed herein. In one such aspect, p is 1.

In another variation, compounds of the formulae detailed herein are provided and, where applicable, $R^2$, $R^{3a}$ and $R^{3b}$ are taken together to form a ring of the formula:

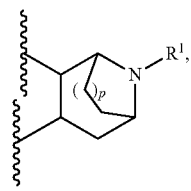

where p is 1 or 2 and $R^1$ is as defined in the formulae. In one such variation, $R^2$, $R^{10}$, $R^{3a}$ and $R^{3b}$ are taken together to form a ring of the formula:

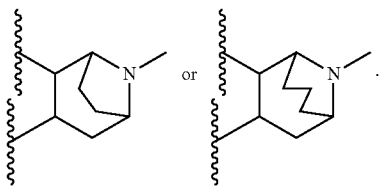

In yet another variation, compounds of the formulae detailed herein are provided and, where applicable, $R^2$, $R^{10}$, $R^{3a}$ and $R^{3b}$ are taken together to form a ring of the formula:

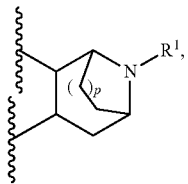

and where $X^7$, $X^8$, $X^9$ and $X^{10}$ are taken together provide an aromatic moiety selected from the following structures:

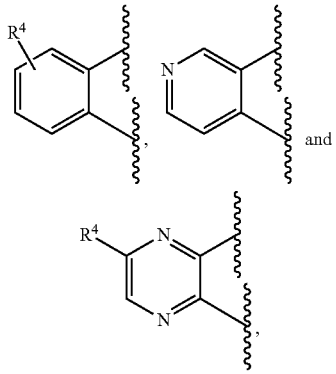

where $R^1$ and $R^4$ are as defined in the formulae and $R^4$ is as defined in formula or in any particular variation herein, such as when each $R^4$ is independently alkyl or halo or in an even more particular variation, where each $R^4$ is independently methyl, chloro, iodo or fluoro or still further, where $R^1$ is methyl and $R^4$ is independently methyl, chloro, iodo or fluoro.

Any formula detailed herein, where applicable, may in one variation have $R^2$, $R^{10}$, $R^{3a}$ and $R^{3b}$ taken together to provide a moiety detailed herein above. It is understood that by "where applicable" or "if applicable," it is intended that in one variation such $R^2$, $R^{10}$, $R^{3a}$ and $R^{3b}$ groups are taken together to provide a moiety hereinabove if the formula encompasses such a structure. For example, if a given formula does not encompass structures wherein $R^2$, $R^{10}$, $R^{3a}$ and $R^{3b}$ are taken together provide a

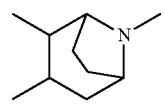

moiety, then a

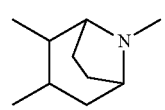

moiety as detailed hereinabove is not applicable to that particular formula, but remains applicable to formulae that do encompass structures where $R^2$, $R^{10}$, $R^{3a}$ and $R^{3b}$ are taken together provide a

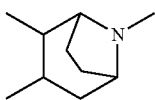

moiety.

In certain embodiments, compounds of formulae detailed herein such as a compound of formula (I), (I-1)-(I-5), (I-3a)-(I-3g), A-2, E, F, F-1, F-2, H-5 and H-6, are provided where $R^1$ is selected from the following moieties:

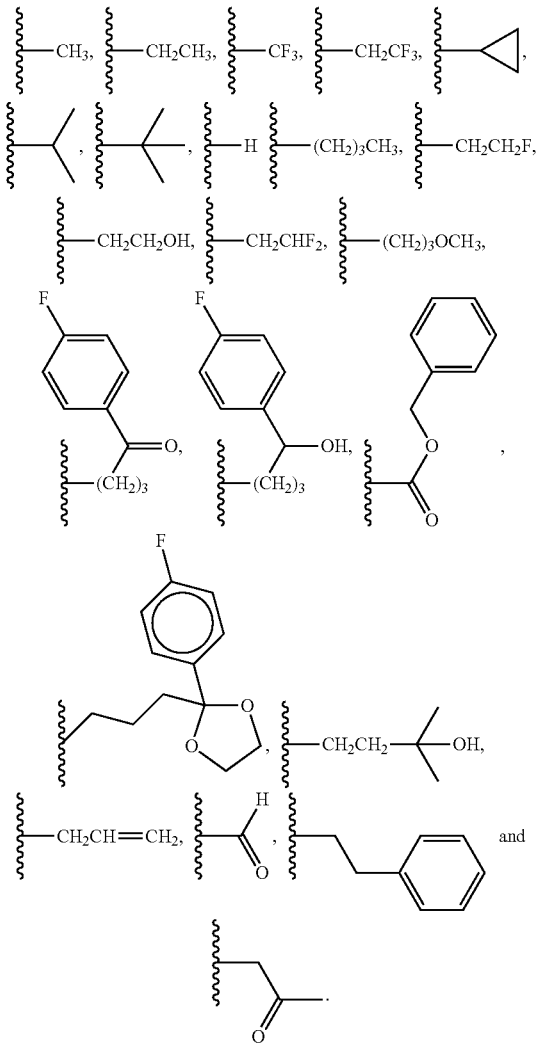

In one variation, compounds of the formulae detailed herein such as a compound of formula (I), (I-1)-(I-5), (I-3a)-(I-3g), A-2, E, F, F-1, F-2, H-5 and H-6, or any variation therein is provided, where each $R^{8a}$, $R^{8b}$, $R^{8c}$, $R^{8d}$, $R^{8e}$ and $R^{8f}$ is independently H, hydroxyl, unsubstituted $C_1$-$C_4$ alkyl or is taken together with the carbon to which it is attached and a geminal $R^8$ to form a cycloalkyl moiety. In one variation, compounds of the formulae herein or any variation thereof are provided, where, if applicable, at least one of $R^{8a}$, $R^{8b}$, $R^{8c}$, $R^{8d}$, $R^{8e}$ and $R^{8f}$ is taken together with the carbon to which it is attached and a geminal $R^8$ to form a carbonyl moiety. In another variation, compounds of the formulae herein or any variation thereof are provided, where, if applicable, each $R^{8a}$, $R^{8b}$, $R^{8c}$, $R^{8d}$, $R^{8e}$ and $R^{8f}$ is independently H, hydroxyl, methyl or is taken together with the carbon to which it is attached and a geminal $R^8$ to form a cyclopropyl moiety. In yet another variation, compounds of the formulae herein or any variation thereof are provided, where, if applicable, q is 0 and m is 1. The invention also embraces compounds where q and m are both 0. The invention further embraces compounds of the formulae herein or any variation thereof are provided, where, if applicable, q, m, $R^{8a}$, $R^{8b}$, $R^{8c}$, $R^{8d}$, $R^{8e}$ and $R^{8f}$ are taken together to form a moiety selected from the group consisting of: —$CH_2$—, —$CH_2CH_2$—, —$CH_2CH_2CH_2$—, —$CH_2$—$C(H)(OH)$—, —$C(H)(OH)$—$CH_2$—, —$CH_2$—$C(OH)(CH_3)$—, —$C(OH)(CH_3)$—$CH_2$—, —$CH_2$—$C(H)(CH_3)$—, —$C(H)(CH_3)$—$CH_2$—, —$CH_2$—$C(CH_3)(CH_3)$—, —$C(CH_2CH_2)$—$CH_2$— and —$CH_2$—$C(CH_2CH_2)$—.

The invention embraces compounds of the formulae herein such as a compound of formula (I), (I-1)-(I-5), (I-3a)-(I-3g), A-2, E, F, F-1, F-2, H-5 and H-6, or any variation thereof are provided, where, if applicable, where each $R^{8a}$, $R^{8b}$, $R^{8c}$, $R^{8d}$, $R^{8e}$ and $R^{8f}$, where present, is independently H, hydroxyl, $C_1$-$C_8$ alkyl, $C_1$-$C_8$ perhaloalkyl, carboxy, carbonylalkoxy, is taken together with the carbon to which it is attached and a geminal $R^8$ to form a cycloalkyl moiety or a carbonyl moiety, is taken together with a geminal $R^8$ to form a methylene or a substituted methylene, is taken together with a vicinal $R^8$ and the carbon atoms to which they are attached to form a substituted or unsubstituted $C_{3-8}$ cycloalkyl, substituted or unsubstituted $C_{3-8}$ cycloalkenyl or substituted or unsubstituted heterocyclyl moiety or is taken together with a vicinal $R^8$ to form a bond, provided that when an $R^8$ is taken together with a vicinal $R^8$ to form a bond, the geminal $R^8$ is other than hydroxyl. In one variation, compounds of the formulae herein or any variation thereof are provided, where, if applicable, where each $R^{8a}$, $R^{8b}$, $R^{8c}$, $R^{8d}$, $R^{8e}$ and $R^{8f}$, where present, is independently H, hydroxyl, unsubstituted $C_1$-$C_4$ alkyl or is taken together with the carbon to which it is attached and a geminal $R^8$ to form a cycloalkyl moiety. In one variation, compounds of the formulae herein or any variation thereof are provided, where, if applicable, at least one of $R^{8a}$, $R^{8b}$, $R^{8c}$, $R^{8d}$, $R^{8e}$ and $R^{8f}$ is taken together with the carbon to which it is attached and a geminal $R^8$ to form a carbonyl moiety. In another variation, compounds of the formulae herein or any variation thereof are provided, where, if applicable, each $R^{8a}$, $R^{8b}$, $R^{8c}$, $R^{8d}$, $R^{8e}$ and $R^{8f}$ is independently H, hydroxyl, methyl or is taken together with the carbon to which it is attached and a geminal $R^8$ to form a cyclopropyl moiety. In one variation, compounds of the formulae herein or any variation thereof are provided, where, if applicable, at least one of $R^{8a}$, $R^{8b}$, $R^{8c}$, $R^{8d}$, $R^{8e}$ and $R^{8f}$ is taken together with a geminal $R^8$ to form a methylene ($CH_2$=) or a substituted methylene such as $CH_3CH$= or the like. In another variation, compounds of the formulae herein or any variation thereof are provided, where, if applicable, at least one of $R^{8a}$, $R^{8b}$, $R^{8c}$, $R^{8d}$, $R^{8e}$ and $R^{8f}$ is taken together with a vicinal $R^8$ to form a bond, where the resultant double bond is in E- or Z-configuration. In one variation, compounds of the formulae herein or any variation thereof are provided, where, if applicable, at least one of $R^{8a}$, $R^{8b}$, $R^{8c}$, $R^{8d}$, $R^{8e}$ and $R^{8f}$ is taken together with a vicinal $R^8$ and the carbons to which they are attached to form a substituted or unsubstituted $C_{3-8}$ cycloalkyl, substituted or unsubstituted $C_{3-8}$ cycloalkenyl or substituted or unsubstituted heterocyclyl moiety. In one variation, compounds of the formulae herein or any variation thereof are provided, where, if applicable, at least one of $R^{8a}$, $R^{8b}$, $R^{8c}$, $R^{8d}$, $R^{8e}$ and $R^{8f}$ is taken together with a vicinal $R^8$ and the carbons to which they are attached to form a $C_{3-8}$ cycloalkyl.

In one variation, compounds of the formulae herein or any variation thereof are provided, where, if applicable, $R^{8c}$, $R^{8d}$ and the carbon to which they are attached are taken together with two other $R^8$ groups that are geminal to each other and the carbon to which they are attached to form a $C_{3-8}$ cycloalkenyl. In yet another variation, compounds of the formulae herein or any variation thereof are provided, where, if applicable, q is 0 and m is 1. The invention also embraces compounds of the formulae herein or any variation thereof are provided, where, if applicable q and m are both 0.

The invention further embraces compounds of the formulae herein such as a compound of formula (I), (I-1)-(I-5), (I-3a)-(I-3g), A-2, E, F, F-1, F-2, H-5 and H-6, or any variation thereof are provided, where, if applicable, q, m, $R^{8a}$, $R^{8b}$, $R^{8c}$, $R^{8d}$, $R^{8e}$ and $R^{8f}$ are taken together to form a moiety selected from the group consisting of the structures:

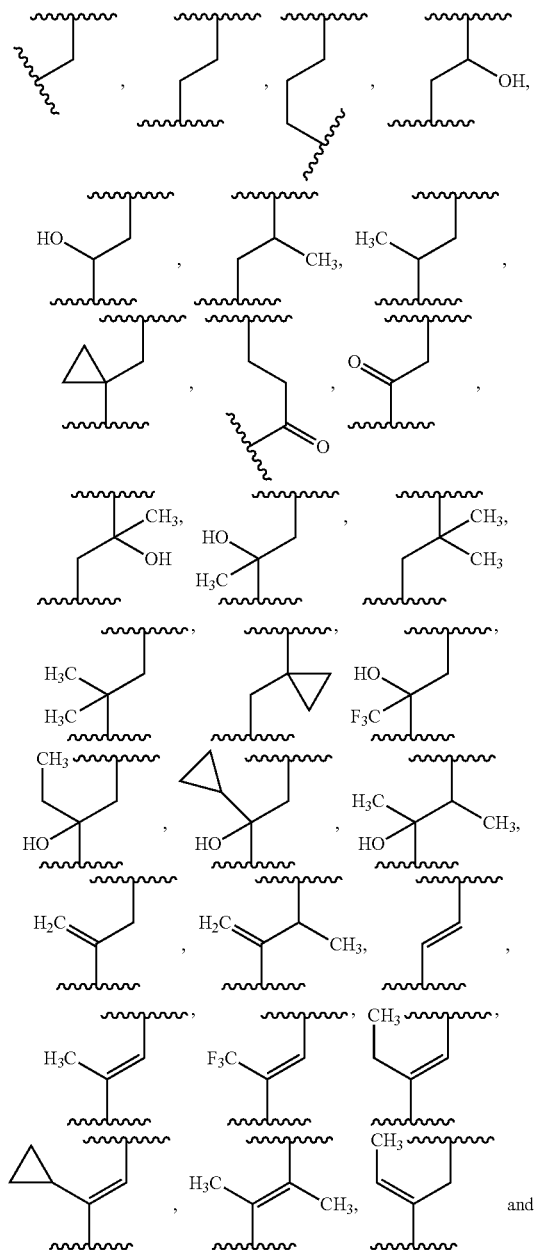

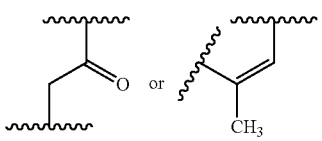

In a further variation and where applicable, compounds of the formulae detailed herein are provided where, if applicable, q, m, $R^{8a}$, $R^{8b}$, $R^{8c}$, $R^{8d}$, $R^{8e}$ and $R^{8f}$ are taken together to form a moiety of the formula:

When the above structures are applied to formula (E) or any variation thereof, it is understood that q, m, n, $R^{8a}$, $R^{8b}$, $R^{8c}$, $R^{8e}$ and $R^{8f}$ where applicable are taken together to form the structures of this paragraph. Likewise, any formula detailed herein, where applicable, may in one variation have q, m, n, $R^{8a}$, $R^{8b}$, $R^{8c}$, $R^{8d}$, $R^{8e}$ and $R^{8f}$ taken together to form a moiety selected from the group consisting of the foregoing structures of this paragraph.

The invention further embraces compounds of the formulae herein or any variation thereof detailed herein, where, if applicable, $R^{8c}$, $R^{8d}$ and the carbon to which they are attached are taken together with $R^{8e}$, $R^{8f}$ and the carbon to which they are attached or $R^{8a}$, $R^{8b}$ and the carbon to which they are attached to form a moiety selected from the group consisting of the structures, each of which may be optionally substituted, where each $R^8$ is independently H, hydroxyl, $C_1$-$C_8$ alkyl, $C_1$-$C_8$ perhaloalkyl, carboxy or carbonylalkoxy:

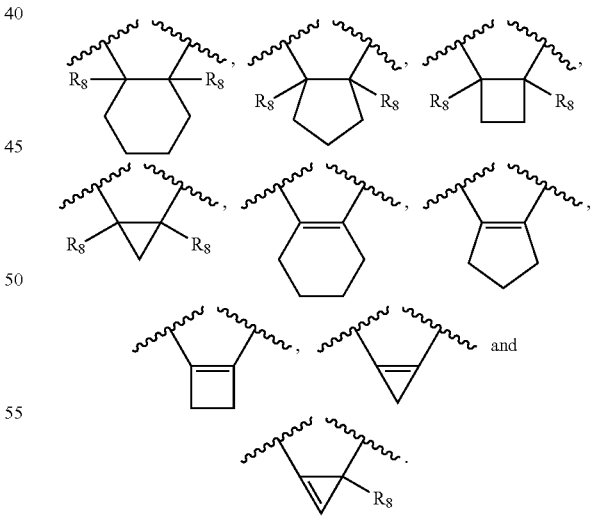

In another variation, compounds of the formulae herein, such as a compound of formula (I), (I-1)-(I-5), (I-3a)-(I-3g), A-2, E, F, F-1, F-2, H-5 and H-6, or any variation thereof are provided, where, if applicable, each $R^4$ is independently H, halo, substituted or unsubstituted $C_1$-$C_8$ alkyl, $C_1$-$C_8$ perhaloalkyl, substituted or unsubstituted heterocyclyl or a substituted or unsubstituted aryl. In yet another variation, compounds of the formulae herein or any variation thereof are provided, where, if applicable, each $R^4$ is independently H or a substituted or unsubstituted $C_1$-$C_8$ alkyl. In still another variation, compounds of the formulae herein or any variation thereof are provided, where, if applicable, each $R^4$ is H. The invention also embraces compounds of the formulae herein or any variation thereof are provided, where, if applicable, each $R^4$ is independently H, halo, unsubstituted $C_1$-$C_4$ alkyl, $C_1$-$C_4$ perhaloalkyl or a substituted or unsubstituted aryl. The invention further embraces compounds of the formulae herein or any variation thereof are provided, where, if applicable, each $R^4$ is independently H, halo, methyl, perfluoromethyl or cyclopropyl.

The invention also embraces c compounds of the formulae herein, such as a compound of formula (I), (I-1)-(I-5), (I-3a)-(I-3g), A-2, E, F, F-1, F-2, H-5 and H-6, or any variation thereof are provided, where, if applicable, Q is a substituted or unsubstituted aryl or a substituted or unsubstituted heteroaryl, which may be but is not limited to a substituted or unsubstituted pyridyl, phenyl, pyrimidinyl, pyrazinyl, imidazolyl, furanyl, pyrrolyl or thiophenyl group. In one variation, compounds of the formulae herein or any variation thereof are provided, where, if applicable, Q is a substituted or unsubstituted phenyl or pyridyl group. In a particular variation, Q is a phenyl or pyridyl group substituted with at least one methyl group. In another variation, compounds of the formulae herein or any variation thereof are provided, where, if applicable, Q is a pyridyl, phenyl, pyrimidinyl, pyrazinyl, imidazolyl, furanyl, pyrrolyl or thiophenyl group substituted with at least one substituted or unsubstituted $C_1$-$C_8$ alkyl, halo or perhaloalkyl moiety. In still another variation, compounds of the formulae herein or any variation thereof are provided, where, if applicable, Q is a substituted or unsubstituted $C_{3-8}$ cycloalkyl or a substituted or unsubstituted heterocyclyl. In yet another variation, compounds of the formulae herein or any variation thereof are provided, where, if applicable, Q is a substituted or unsubstituted pyridyl, phenyl, pyrazinyl, piperazinyl, pyrrolidinyl or thiomorpholinyl group. In a particular variation, Q is a pyridyl, phenyl, pyrazinyl, piperazinyl, pyrrolidinyl or thiomorpholinyl group substituted with at least one methyl or halo group. In one variation, compounds of the formulae herein or any variation thereof are provided, where, if applicable, Q is an unsubstituted $C_{3-8}$ cycloalkyl or an unsubstituted heterocyclyl. In another variation, compounds of the formulae herein or any variation thereof are provided, where, if applicable, Q is a substituted or unsubstituted cyclohexyl, morpholinyl, piperazinyl, thiomorpholinyl, cyclopentyl or pyrrolidinyl moiety. In yet another variation, compounds of the formulae herein or any variation thereof are provided, where, if applicable, Q is a substituted cyclohexyl, morpholinyl, piperazinyl, thiomorpholinyl, cyclopentyl or pyrrolidinyl moiety substituted with at least one carbonyl, hydroxymethyl, methyl or hydroxyl group.

In still another variation, a compound of the invention is of the formulae or any variation of the foregoing detailed herein, where Q is a moiety selected from the structures:

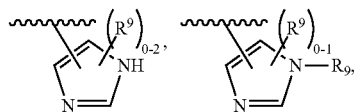

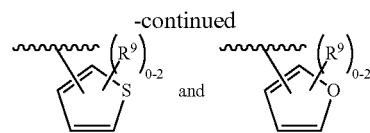

wherein each $R^9$ is independently a halo, cyano, nitro, perhaloalkyl, perhaloalkoxy, substituted or unsubstituted $C_1$-$C_8$ alkyl, substituted or unsubstituted $C_2$-$C_8$ alkenyl, substituted or unsubstituted $C_2$-$C_8$ alkynyl, acyl, acyloxy, carbonylalkoxy, thioalkyl, substituted or unsubstituted heterocyclyl, alkoxy, substituted or unsubstituted amino, acylamino, sulfonylamino, sulfonyl, carbonyl, aminoacyl or aminocarbonylamino. In one variation, Q is substituted with no more than one $R^9$ group. In another variation, Q is substituted with only one $R^9$ group. In one variation, Q is substituted with two $R^9$ groups. In a further variation, Q is selected from the aromatic structures detailed where the residue has the moiety $(R^9)_0$ such that Q either contains no $R^9$ functionality or a moiety of the formula N—$R^9$.

In still another variation, compounds of the formulae herein, such as a compound of formula (I), (I-1)-(I-5), (I-3a)-(I-3g), A-2, E, F, F-1, F-2, H-5 and H-6, or any variation thereof are provided, where, if applicable, Q is a moiety selected from the structures:

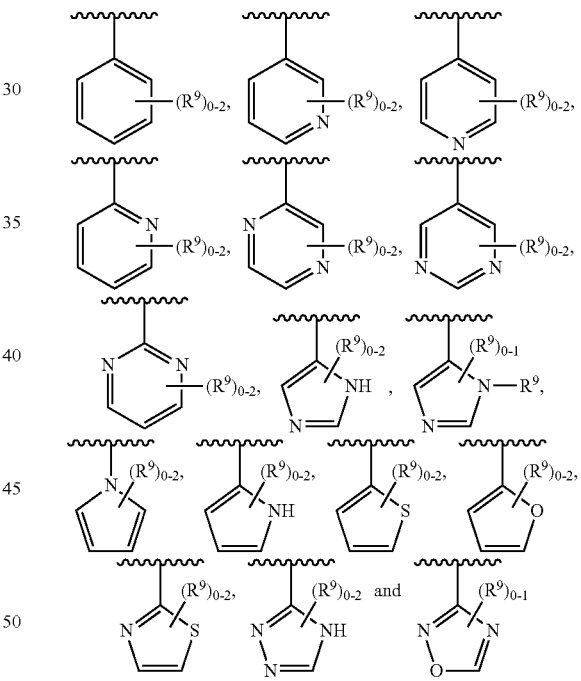

wherein each $R^9$ is independently a halo, cyano, nitro, perhaloalkyl, perhaloalkoxy, substituted or unsubstituted $C_1$-$C_8$ alkyl, substituted or unsubstituted $C_2$-$C_8$ alkenyl, substituted or unsubstituted $C_2$-$C_8$ alkynyl, acyl, acyloxy, carbonylalkoxy, thioalkyl, substituted or unsubstituted heterocyclyl, alkoxy, substituted or unsubstituted amino, acylamino, sulfonylamino, sulfonyl, carbonyl, aminoacyl or aminocarbonylamino. In one variation, Q is substituted with no more than one $R^9$ group. In another variation, Q is substituted with only one $R^9$ group. In one variation, Q is substituted with two $R^9$ groups. In a further variation, Q is selected from the aromatic structures detailed where the residue has the moiety $(R^9)_0$ such that Q either contains no $R^9$ functionality or a moiety of the formula N—$R^9$.

In still another variation, compounds of the formulae herein or any variation thereof are provided, where, if applicable, Q is a moiety selected from the structures:

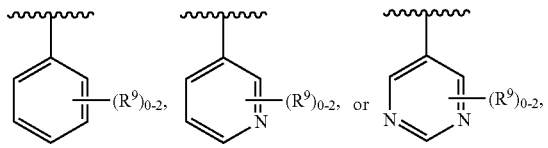

wherein each $R^9$ is independently alkyl, perhaloalkyl or halo.

In another variation, compounds of the formulae herein or any variation thereof are provided, where, if applicable, Q is a moiety selected from the structures:

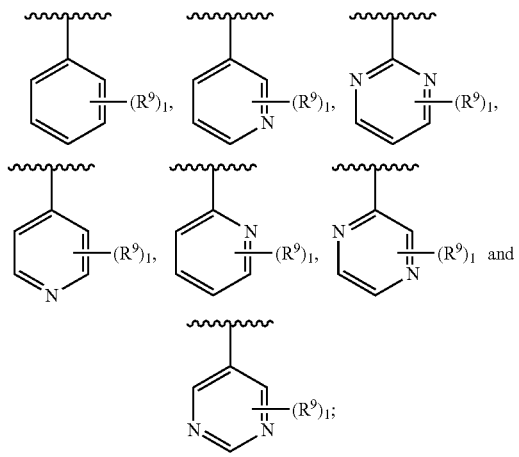

and wherein $R^9$ is connected to Q ortho or para to the position at which Q is connected to the carbon bearing $R^{8e}$ and $R^{8f}$. In a particular variation, Q is a structure of the formula:

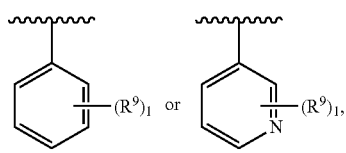

and $R^9$ is connected to Q para to the position at which Q is connected to the carbon bearing $R^{8e}$ and $R^{8f}$. In another particular variation, Q is a structure of the formula

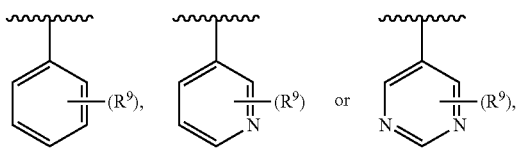

where each $R^9$ is independently alkyl, perhaloalkyl or halo.

In another variation, compounds of the formulae herein or any variation thereof are provided, where, if applicable, Q is a moiety selected from the structures:

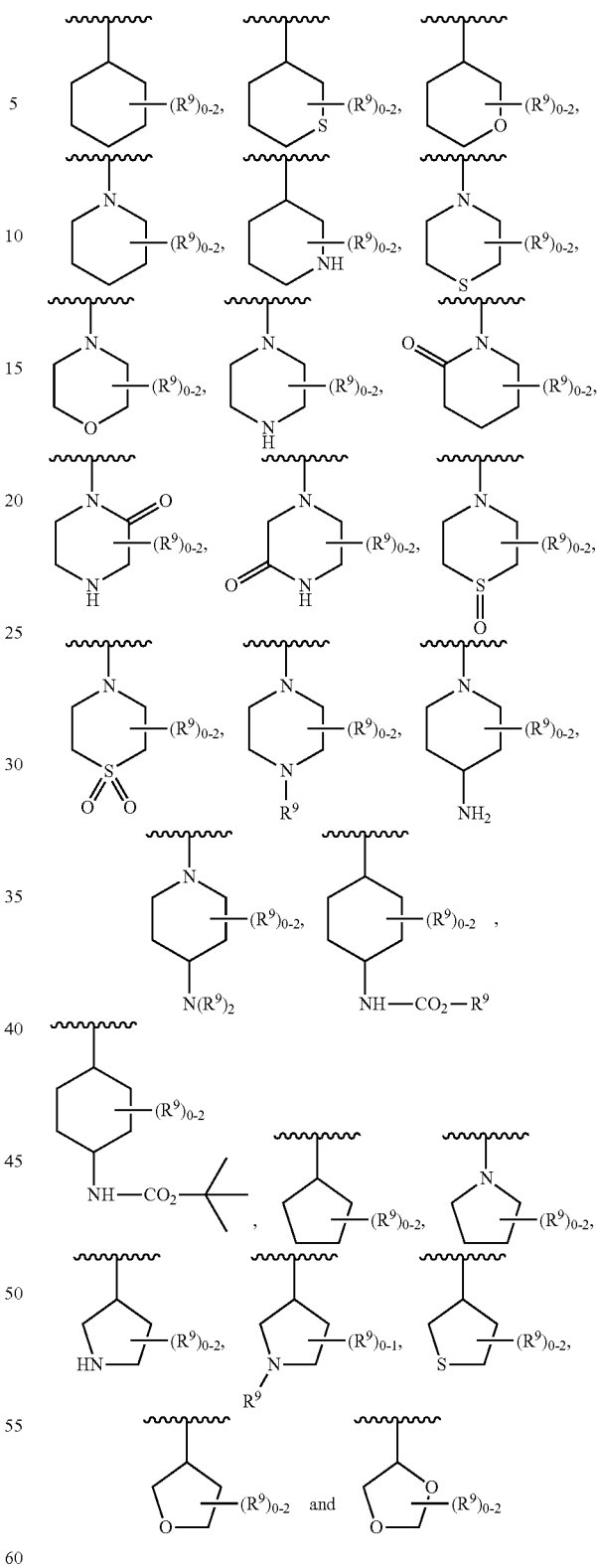

wherein each $R^9$ is independently a halo, cyano, nitro, perhaloalkyl, perhaloalkoxy, substituted or unsubstituted $C_1$-$C_8$ alkyl, substituted or unsubstituted $C_2$-$C_8$ alkenyl, substituted or unsubstituted $C_2$-$C_8$ alkynyl, acyl, acyloxy, carbonylalkoxy, thioalkyl, alkoxy, substituted or unsubstituted amino, acylamino, sulfonylamino, sulfonyl, carbonyl, aminoacyl or aminocarbonylamino. In one variation, Q is substituted with no more than one $R^9$ group. In another variation, Q is substituted with only one $R^9$ group. In yet another variation, Q is substituted with two $R^9$ groups. In a particular variation, Q is selected from the carbocyclic and heterocyclic structures detailed where the residue has the moiety $(R^9)_0$ such that Q either contains no $R^9$ functionality or a moiety of the formula N—$R^9$.

In any structure or variation detailed herein containing an $R^9$ group, in one variation, each $R^9$ is independently a substituted or unsubstituted $C_1$-$C_4$ alkyl, halo, trifluoromethyl or hydroxyl. In another variation, each $R^9$ is independently methyl, —$CH_2OH$, isopropyl, halo, trifluoromethyl or hydroxyl.

In another variation, compounds of the formulae herein, such as a compound of formula (I), (I-1)-(I-5), (I-3a)-(I-3g), A-2, E, F, F-1, F-2, H-5 and H-6, or any variation thereof are provided, where, if applicable, Q is a moiety selected from the structures:

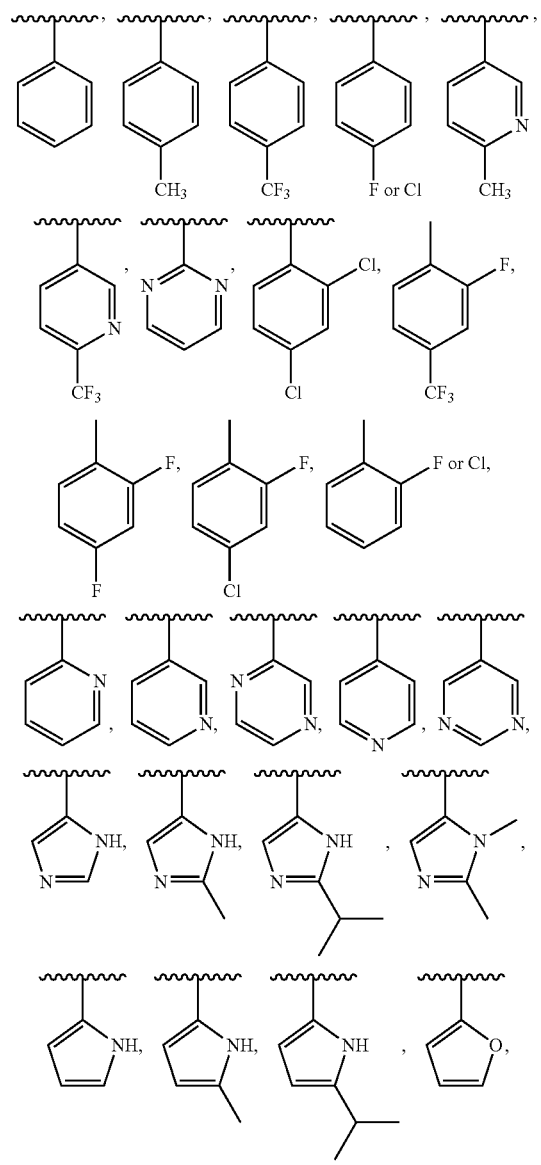

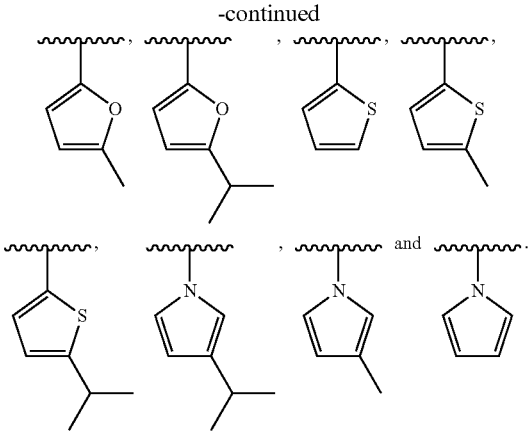

In another variation, compounds of the formulae herein or any variation thereof are provided, where, if applicable, Q is a 6-membered ring heteroaryl or substituted heteroaryl selected from the structures:

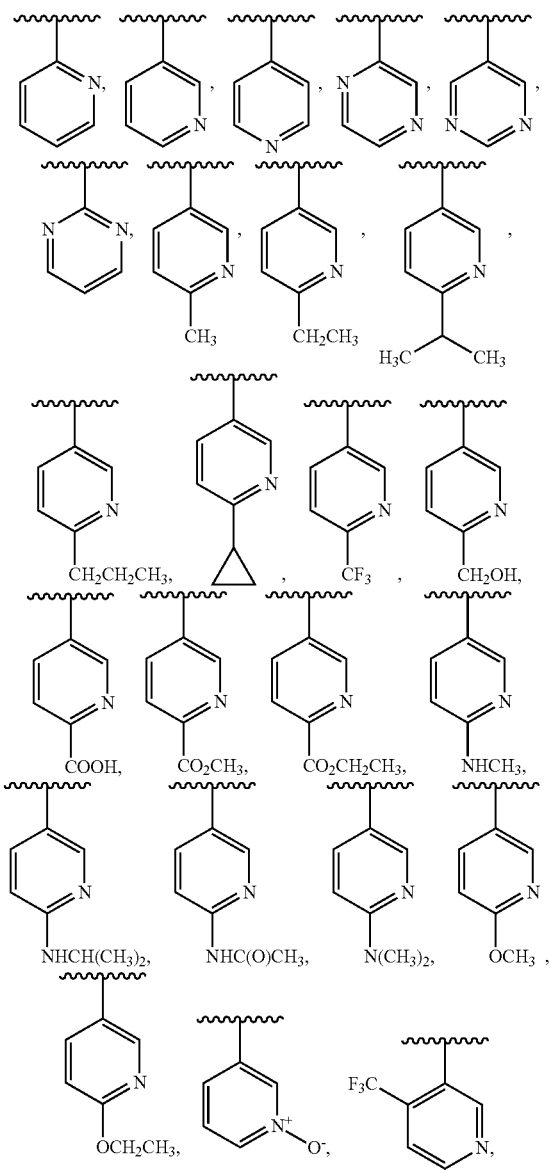

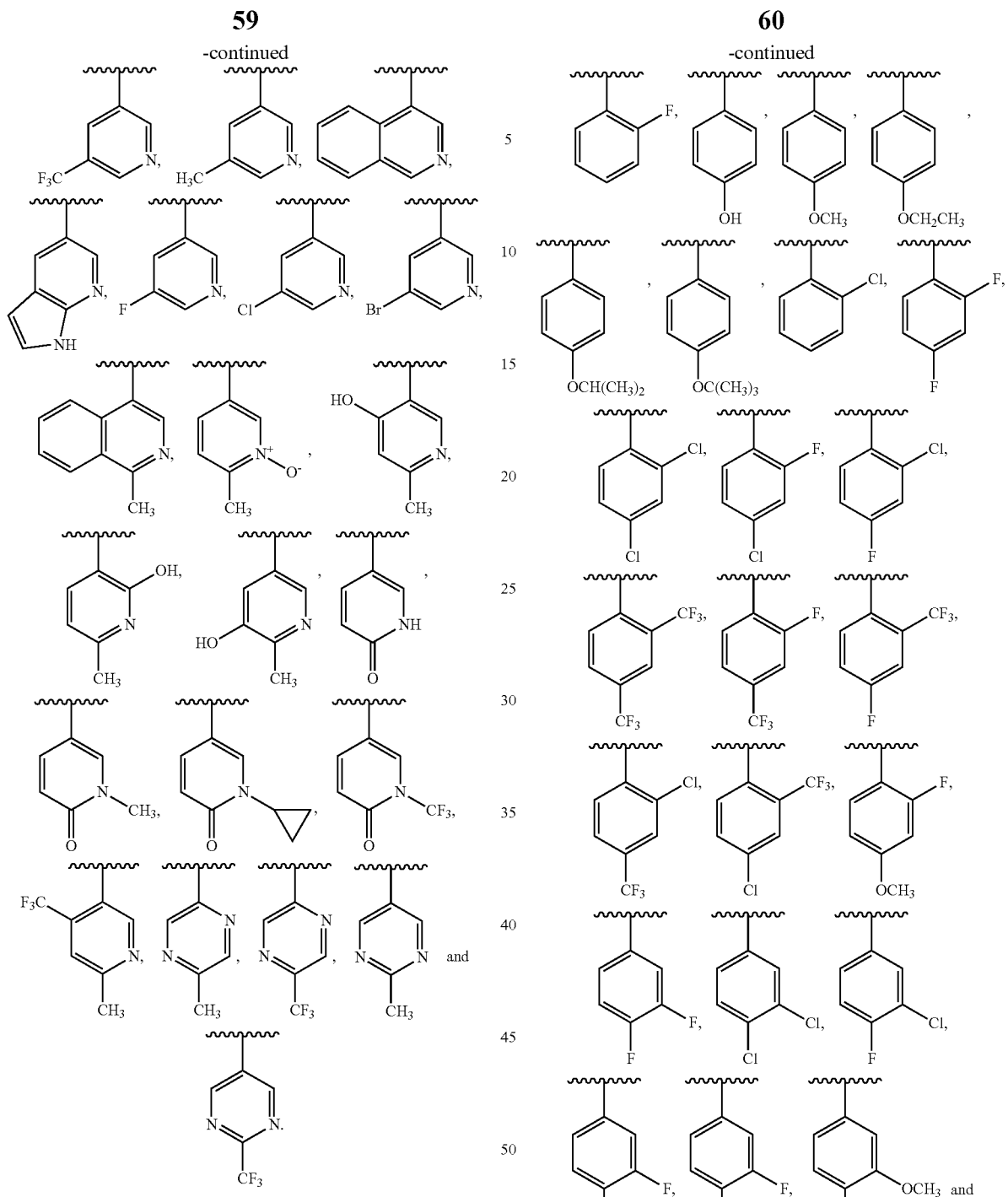

In another variation, compounds of the formulae herein or any variation thereof are provided, where, if applicable, Q is a phenyl or substituted phenyl selected from the structures:

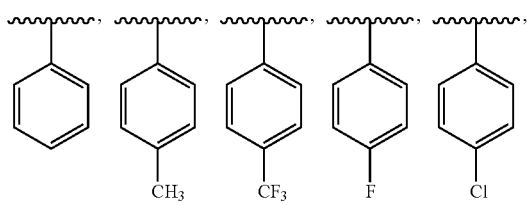

In another variation, compounds of the formulae herein or any variation thereof are provided, where, if applicable, Q is a 5-membered ring heteroaryl or substituted heteroaryl selected from the structures:

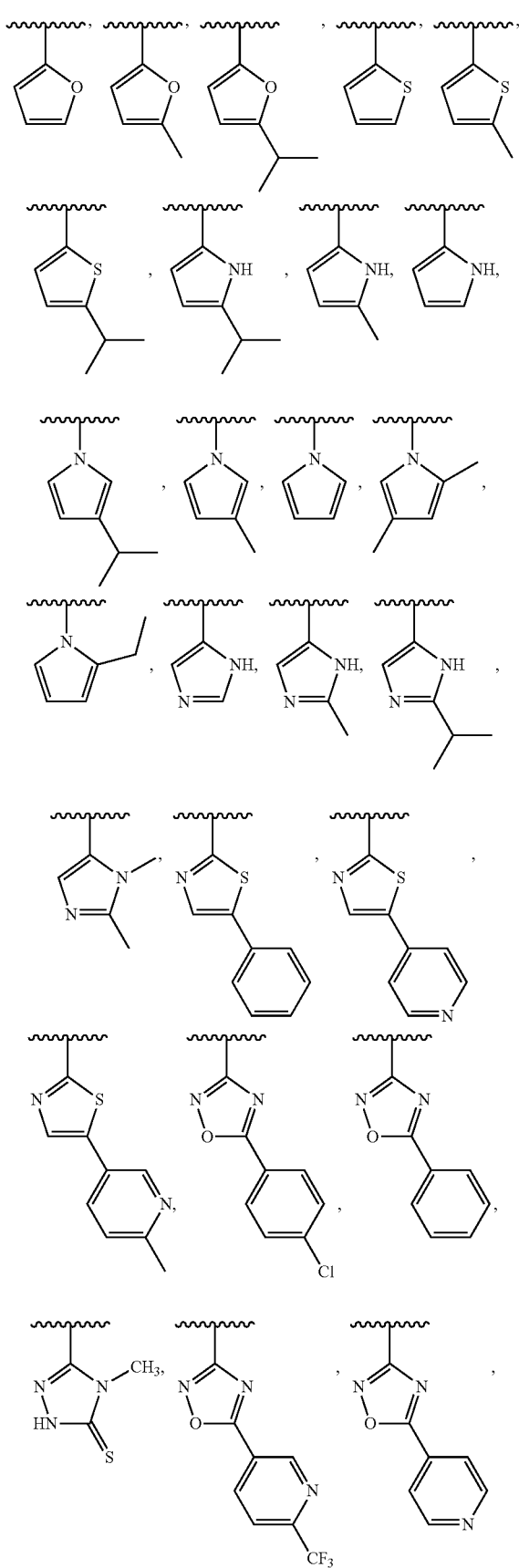

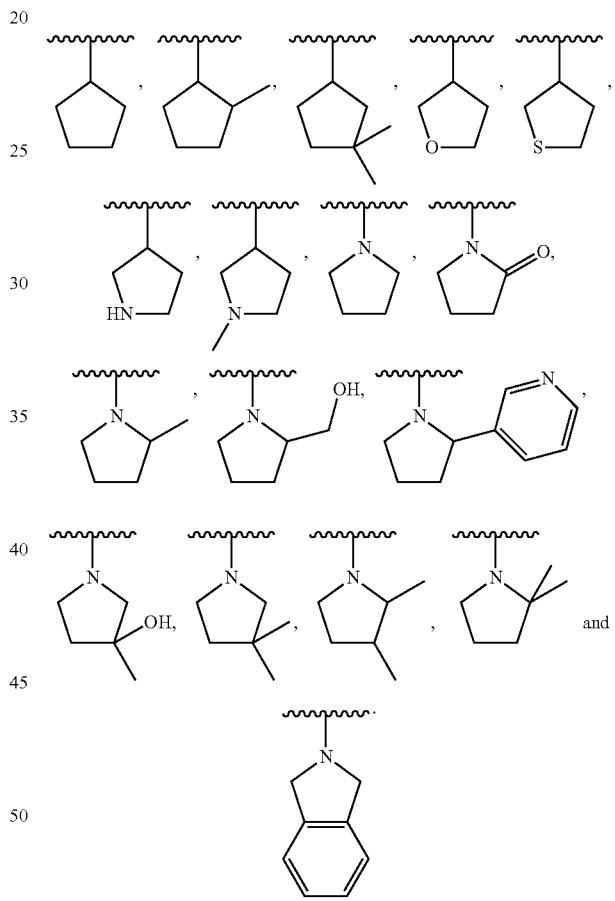

In another variation, compounds of the formulae herein or any variation thereof are provided, where, if applicable, Q is a 5-membered ring substituted or unsubstituted cycloalkyl or heterocyclyl selected from the structures:

In another variation, compounds of the formulae herein or any variation thereof are provided, where, if applicable, Q is a 6-membered ring substituted or unsubstituted cycloalkyl or heterocyclyl selected from the structures:

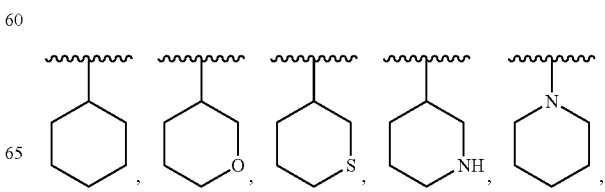

-continued

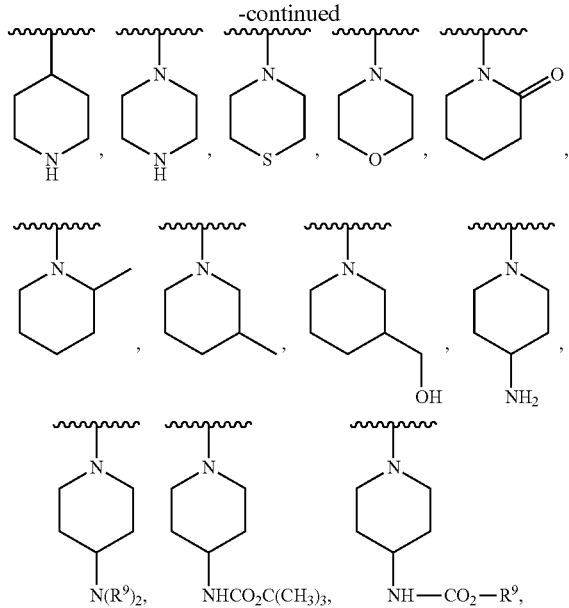

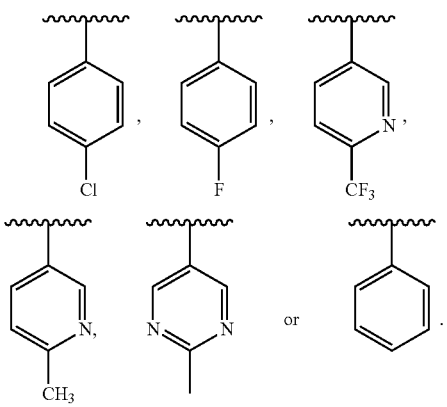

In another variation, compounds of the formulae herein or any variation thereof are provided, where, if applicable, Q is a moiety selected from the structures:

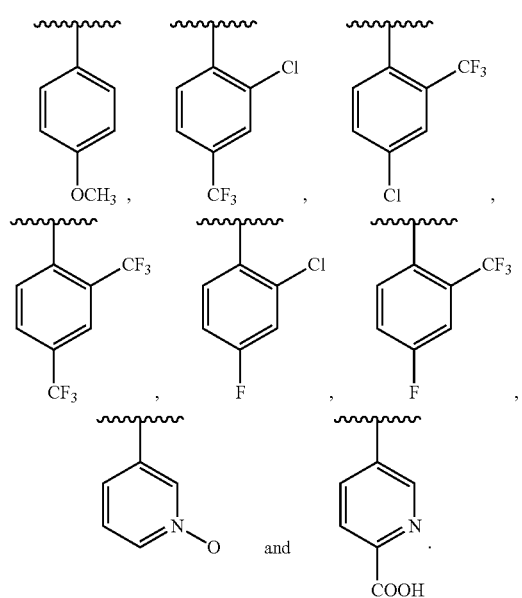

In yet another variation, compounds of the formulae herein or any variation thereof are provided, where, if applicable, Q is a moiety selected from the structures:

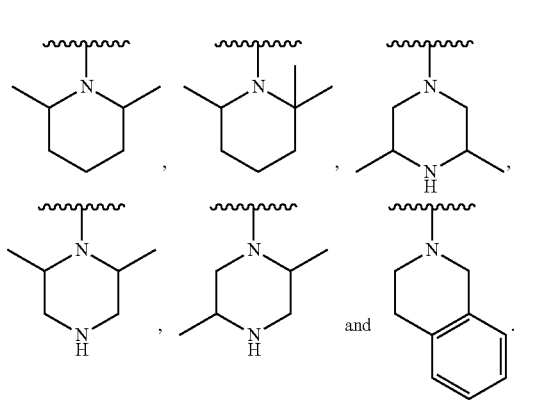

In yet another variation, compounds of the formulae herein or any variation thereof are provided, where, if applicable, Q is a moiety of the structure:

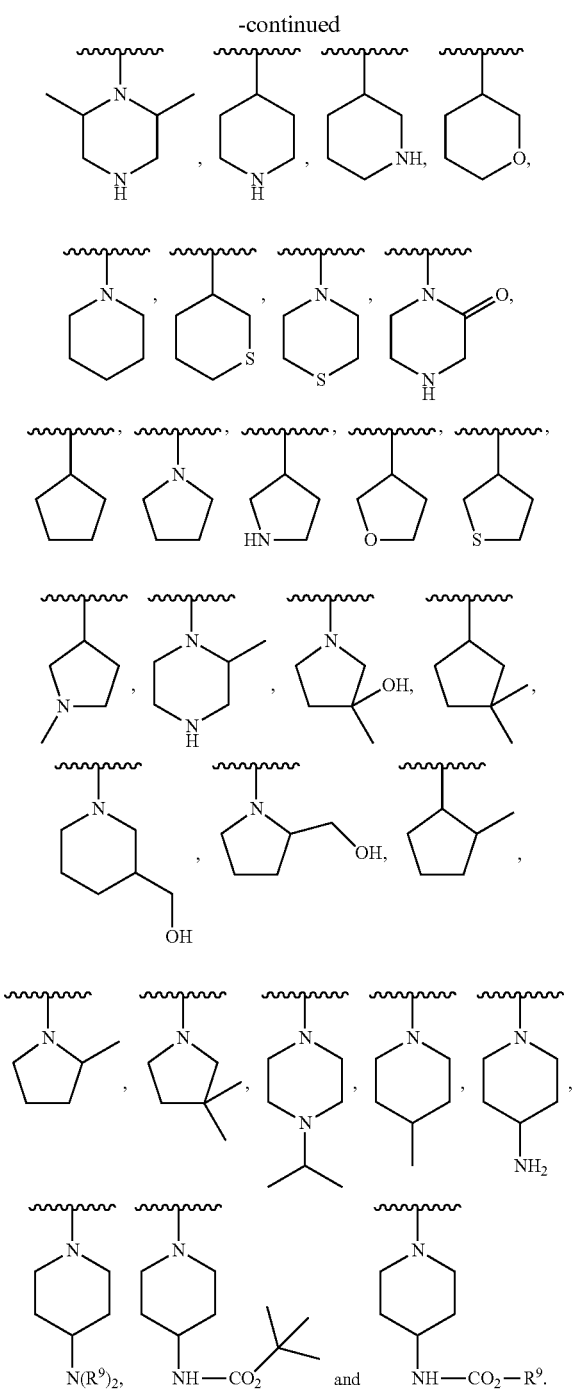

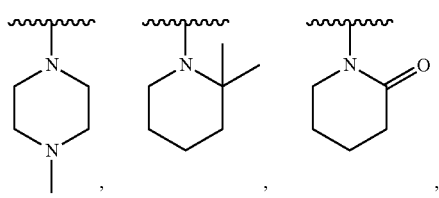

In yet another variation, compounds of the formulae herein or any variation thereof are provided, where, if applicable, Q is a moiety selected from the structures:

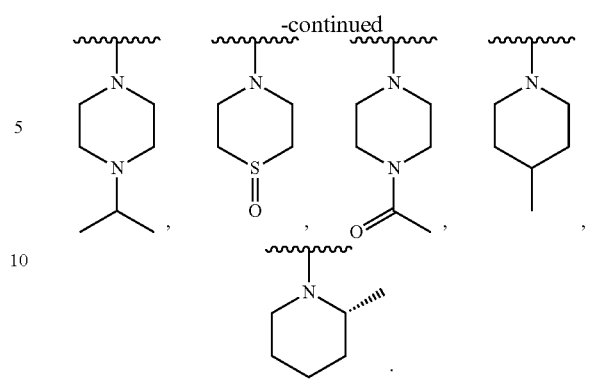

In a further variation of the formulae detailed herein, Q is a moiety of the formula:

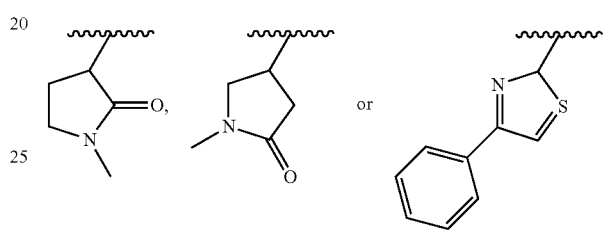

In another variation, compounds of the formulae herein or any variation thereof are provided, where, if applicable, Q is a substituted or unsubstituted amino, alkoxy, aminoacyl, acyloxy, carbonylalkoxy, aminocarbonylalkoxy or acylamino moiety. In a particular variation, Q is an unsubstituted amino. In another variation, Q is substituted amino of the formula —N($C_1$-$C_8$alkyl)$_2$ such as the moiety —N(Me)$_2$, -N(CH$_3$)(CH$_2$CH$_3$). In another variation, Q is a substituted amino of the formula —N(H)(cycloalkyl or substituted cycloalkyl), such as a moiety of the formula:

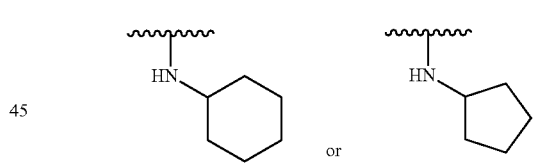

In another variation, Q is a substituted amino of the formula —N(H)(aryl or substituted aryl), such as a moiety of the formula

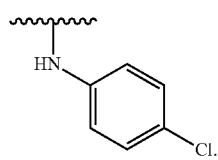

In a particular variation, Q is a substituted or unsubstituted amino and $R^{8e}$ and $R^{8f}$ are taken together to form a carbonyl moiety. In yet another variation, Q is an acylamino moiety. In still another variation, Q is an acylamino moiety and $R^{8e}$ and $R^{8f}$ are both hydrogen.

In another variation, Q is an alkoxy group of the formula —O—$C_1$-$C_8$ alkyl, such as the moiety —O—CH$_2$CH$_3$. In yet another variation, Q is an alkoxy group and $R^{8e}$ and $R^{8f}$ are taken together to form a carbonyl moiety. In still a further variation, Q is a carbonylalkoxy moiety. In yet another variation, Q is a carbonylalkoxy moiety and $R^{8e}$ and $R^{8f}$ are both hydrogen.

In still another variation, Q is an acyloxy, aminocarbonylalkoxy or acylamino moiety. In one variation, Q is an acyloxy, aminocarbonylalkoxy or acylamino moiety and $R^{8e}$ and $R^{8f}$ are both hydrogen.

In one variation, Q is a moiety selected from the structures:

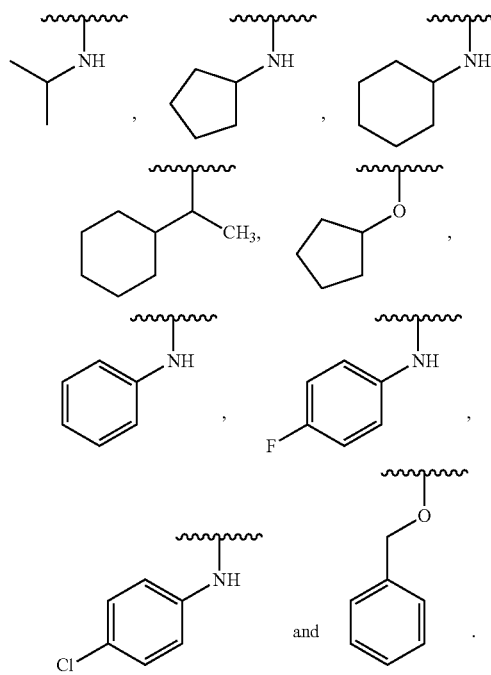

The invention also embraces compounds of the formulae herein or any variation thereof detailed herein, where, if applicable, Q is an aminoacyl moiety. In one variation, Q is an aminoacyl group where at least one of $R_a$ and $R_b$ is H, such as when Q is of the formula —NHC(O)$R_b$. In one variation, Q is an aminoacyl moiety selected from the group consisting of: —NHC(O)-heterocyclyl, —NHC(O)— substituted heterocyclyl, —NHC(O)-alkyl, —NHC(O)-cycloalkyl, —NHC(O)-alkaryl and —NHC(O)-substituted aryl. In another variation, Q is an aminoacyl moiety selected from the group consisting of: —NHC(O)—$C_5$-$C_7$ heterocyclyl, —NHC(O)—$C_1$-$C_6$ alkyl, —NHC(O)—$C_3$-$C_7$cycloalkyl, —NHC(O)—$C_1$-$C_3$ alkaryl and —NHC(O)-substituted phenyl. In a particular variation, Q is a moiety of the formula:

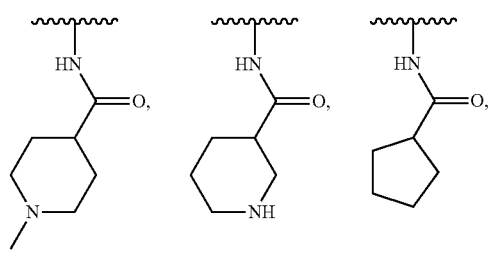

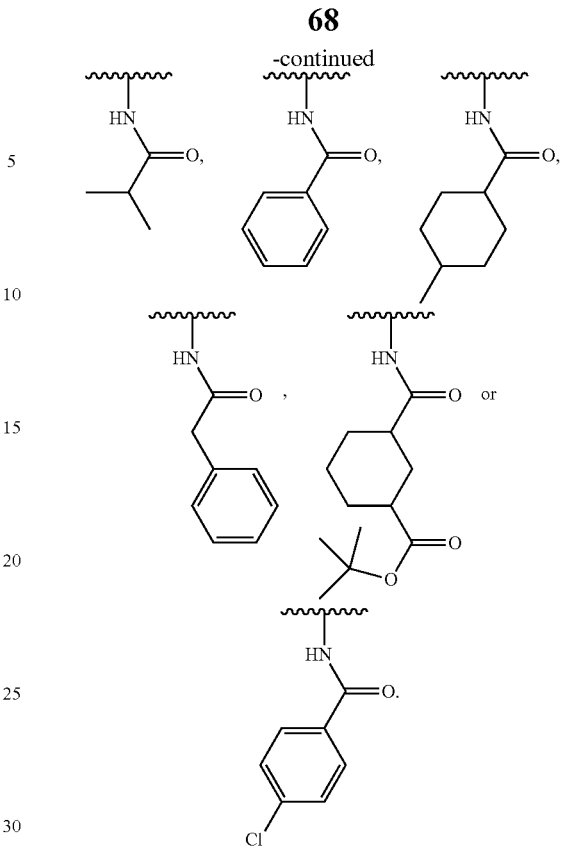

In one variation, compounds of the formulae herein or any variation thereof are provided, where, if applicable, Q is acyloxy.

In one variation, compounds of the formulae herein or any variation thereof are provided, where, if applicable, Q is a carbonylalkoxy moiety. In one variation, Q is a carbonylalkoxy moiety of the formula —C(O)—O—R where R is H, alkyl, substituted alkyl or alkaryl. In one variation, Q is carbonylalkoxy moiety of the formula —C(O)—O—$C_1$-$C_6$ alkyl. In a particular variation, Q is a carbonylalkoxy moiety of the formula —C(O)—O—$C_2H_5$. In one variation, Q is a carbonylalkoxy moiety selected from the group consisting of: —C(O)—O—$C_1$-$C_{10}$ alkyl, —C(O)—O—$C_1$-$C_3$ alkaryl, —C(O)—O—$C_1$-$C_3$ substituted alkyl and —C(O)—OH. In another variation, Q is —C(O)—O—$C_1$-$C_6$ alkyl. In a particular variation, Q is a moiety of the formula:

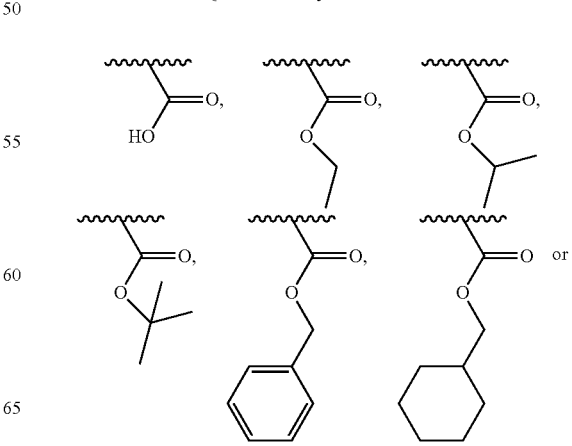

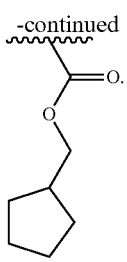

In another variation, compounds of the formulae herein or any variation thereof are provided, where, if applicable, Q is an aminocarbonylalkoxy moiety. In one variation, Q is an aminocarbonylalkoxy moiety of the formula —NHC(O)—O—$R_b$. In another variation, Q is an aminocarbonylalkoxy moiety of the formula —NHC(O)—O—$R_b$ where $R_b$ is a substituted alkyl group. In a particular variation, Q is a moiety of the formula —NH—C(O)—O—$CH_2$—C(Cl)$_3$.

The invention also embraces compounds of the formulae herein or any variation thereof where, if applicable, Q is an acylamino moiety. In one variation, Q is an acylamino group where at least one of $R_a$ and $R_b$ is H, such as when Q is of the formula —C(O)N(H)($R_b$). In another variation, Q is an acylamino group where both $R_a$ and $R_b$ alkyl. In one variation, Q is an acylamino moiety selected from the group consisting of: —C(O)—N(H)(alkyl), —C(O)—N(alkyl)$_2$, —C(O)—N(H)(alkaryl) and —C(O)—N(H)(aryl). In another variation, Q is an acylamino moiety selected from the group consisting of: —C(O)—N(H)$_2$, —C(O)—N(H)($C_1$-$C_8$ alkyl), —C(O)—N($C_1$-$C_6$ alkyl)$_2$ and —C(O)—N(H)($C_1$-$C_3$ alkaryl). In a particular variation, Q is a moiety of the formula:

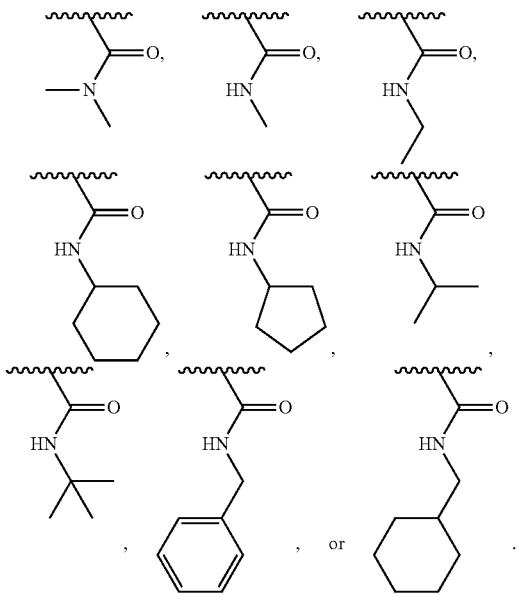

In a further variation of the formulae detailed herein, Q is a moiety of the formula:

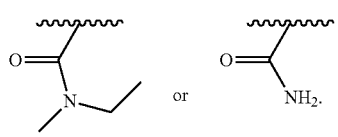

In still a further variation of the formulae detailed herein, Q is a cyano. In one variation of the formula (E) or any variation detailed herein, Q is other than carboxy or alkynyl.

Any formula detailed herein, where applicable, may in one variation have as Q the moieties detailed herein above. It is understood that by "where applicable" it is intended that such Q moieties be a variation if the formula encompasses such a structure. For example, if a given formula does not encompass structures wherein Q is a phenyl moiety, then a phenyl moiety is not applicable to that particular formula, but remains applicable to formulae that do encompass structures where Q is a phenyl moiety.

In a further variation, compounds of the formulae herein or any variation thereof are provided, where, if applicable, $R^1$ is an unsubstituted alkyl, $R^2$, $R^{3a}$, $R^{3b}$, $R^{10}$ is H, each $X^7$, $X^8$, $X^9$ and $X^{10}$ is independently N or CH, each $R^{8a}$, $R^{8b}$, $R^{8c}$, $R^{8d}$, $R^{8e}$ and $R^{8f}$ is independently H or hydroxyl, and Q is a substituted or unsubstituted aryl, substituted or unsubstituted heteroaryl, including but not limited to a substituted or unsubstituted phenyl or pyridyl group. Where Q is a substituted phenyl or pyridyl group, in one variation it is substituted with at least one methyl group.

In yet a further variation, compounds of the formulae herein or any variation thereof are provided, where, if applicable, $R^1$ is a substituted or unsubstituted $C_1$-$C_8$ alkyl, acyl, acyloxy, carbonylalkoxy, substituted or unsubstituted heterocyclyl, substituted or unsubstituted aryl; $R^2$ is H, unsubstituted $C_1$-$C_8$ alkyl or halo; each $R^{3a}$ and $R^{3b}$ is independently H or halo; each $X^7$, $X^8$, $X^9$ and $X^{10}$ is $CR^4$, where $R^4$ is as defined in formula (I) or in a particular variation, $R^4$ is H, halo, pyridyl, methyl or trifluoromethyl; $R^{10}$ is H, and Q is a substituted or unsubstituted aryl, substituted or unsubstituted heteroaryl, including but not limited to a substituted or unsubstituted pyridyl, phenyl, pyrimidinyl, pyrazinyl, imidazolyl, furanyl, pyrrolyl or thiophenyl group. In a particular variation, Q is a pyridyl, phenyl, pyrimidinyl, pyrazinyl, imidazolyl, furanyl, pyrrolyl or thiophenyl group substituted with at least one substituted or unsubstituted $C_1$-$C_8$ alkyl, halo or perhaloalkyl moiety. In one variation, a compound of the variation detailed herein is provided wherein $R^1$ is propylate, methyl, ethyl, cyclopropyl, trifluoromethyl, isopropyl, tert-butyl, sec-butyl, 2-methylbutyl, propanal, 1-methyl-2-hydroxyethyl, 2-hydroxyethanal, 2-hydroxyethyl, 2-hydroxypropyl, 2-hydroxy-2-methylpropyl, cyclobutyl, cyclopentyl, cyclohexyl, substituted phenyl, piperidin-4-yl, hydroxycyclopent-3-yl, hydroxycyclopent-2-yl, hydroxycycloprop-2-yl, 1-hydroxy-1-methylcycloprop-2-yl, or 1-hydroxy-1,2,2-trimethyl-cycloprop-3-yl.

In still a further variation, compounds of the formulae herein, such as a compound of formula (I), (I-1)-(I-5), (I-3a)-(I-3g), A-2, E, F, F-1, F-2, H-5 and H-6, or any variation thereof are provided, where, if applicable, $R^1$ is a substituted or unsubstituted $C_1$-$C_8$ alkyl; each $R^2$, $R^{3a}$ and $R^{3b}$ is independently H or halo; each $R^4$ is independently H, halo, $C_1$-$C_8$ perhaloalkyl, substituted or a unsubstituted $C_1$-$C_8$ alkyl; each $R^{8a}$, $R^{8b}$, $R^{8c}$, $R^{8d}$, $R^{8e}$ and $R^{8f}$ is H; and Q is a substituted or unsubstituted cyclohexyl, morpholinyl, piperazinyl, thiomorpholinyl, cyclopentyl or pyrrolidinyl moiety. The invention also embraces compounds of the formulae herein or any variation thereof are provided, where, if applicable, $R^1$ is a methyl; at least one of $X^7$, $X^8$, $X^9$ and $X^{10}$ is $CR^4$, and each $R^4$ is independently H, halo, methyl or trifluoromethyl. The invention embraces compounds where Q in any variation detailed is substituted with at least one carbonyl, hydroxymethyl, methyl or hydroxyl group.

In a particular variation, compounds of the formulae herein, such as a compound of formula (I), (I-1)-(I-5), (I-3a)-(I-3g), A-2, E, F, F-1, F-2, H-5 and H-6, or any variation thereof are provided, where, if applicable, $R^1$ is a substituted or unsubstituted $C_1$-$C_8$ alkyl; $R^2$ is H, a substituted or unsubstituted $C_1$-$C_8$ alkyl; $R^{3a}$ and $R^{3b}$ are both H; each $R^4$ is independently H, halo or substituted or unsubstituted $C_1$-$C_8$ alkyl; each $R^{8a}$, $R^{8b}$, $R^{8c}$, $R^{8d}$, $R^{8e}$ and $R^{8f}$ is H; $R^{10}$ is H, halo, a substituted or unsubstituted $C_1$-$C_8$ alkyl, hydroxyl, alkoxy. In one aspect of this variation, Q may be a substituted or unsubstituted pyridyl, phenyl, pyrazinyl, piperazinyl, pyrrolidinyl or thiomorpholinyl group. In another aspect of this variation, Q is a pyridyl, phenyl, pyrazinyl, piperazinyl, pyrrolidinyl or thiomorpholinyl group substituted with at least one methyl or halo group. In yet another aspect of this variation, $X^7$, $X^8$, $X^9$ and $X^{10}$ are $CR^4$ and each $R^4$ is independently H, halo or methyl.

In another variation, compounds of the formulae herein or any variation thereof are provided, where, if applicable, q, m, Q and $R^{8a}$-$R^{8f}$ are taken together to form a moiety of the structure:

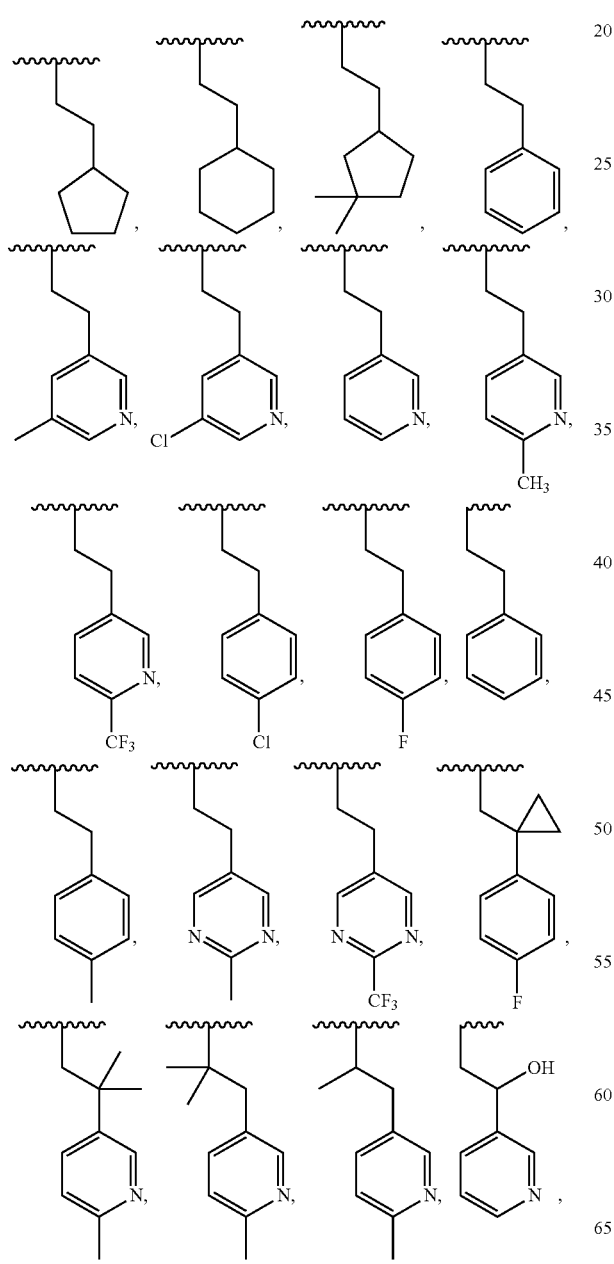
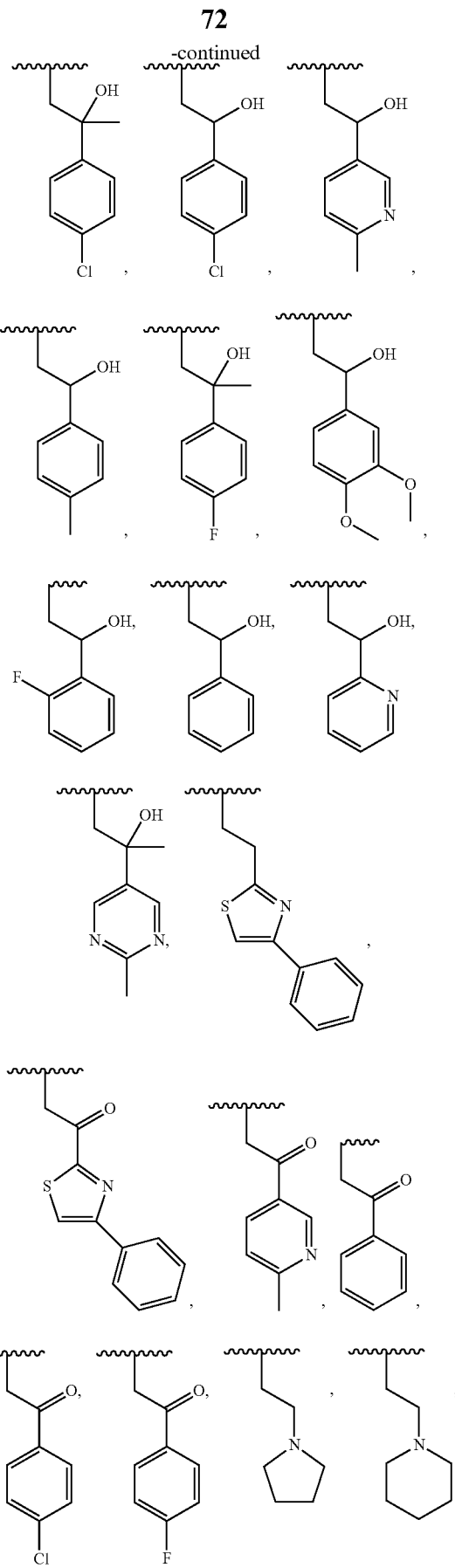

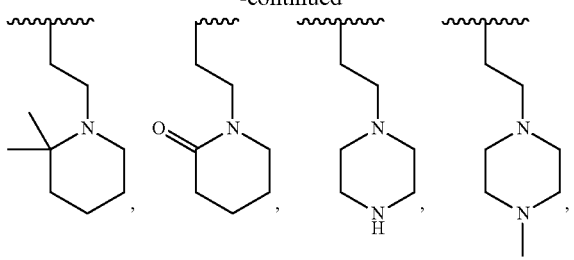
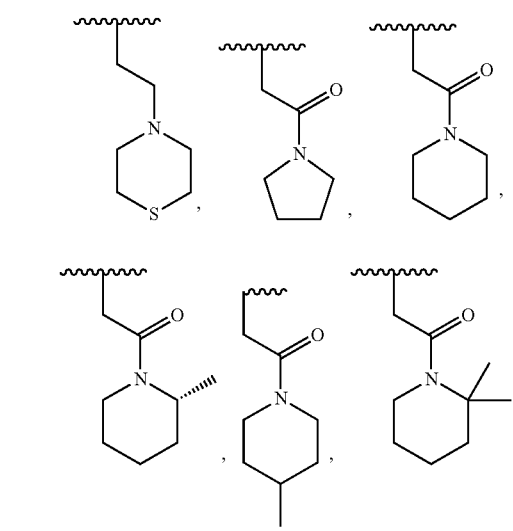
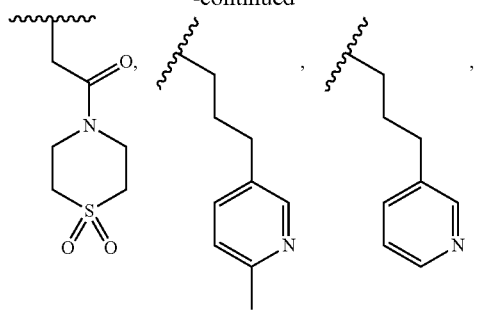
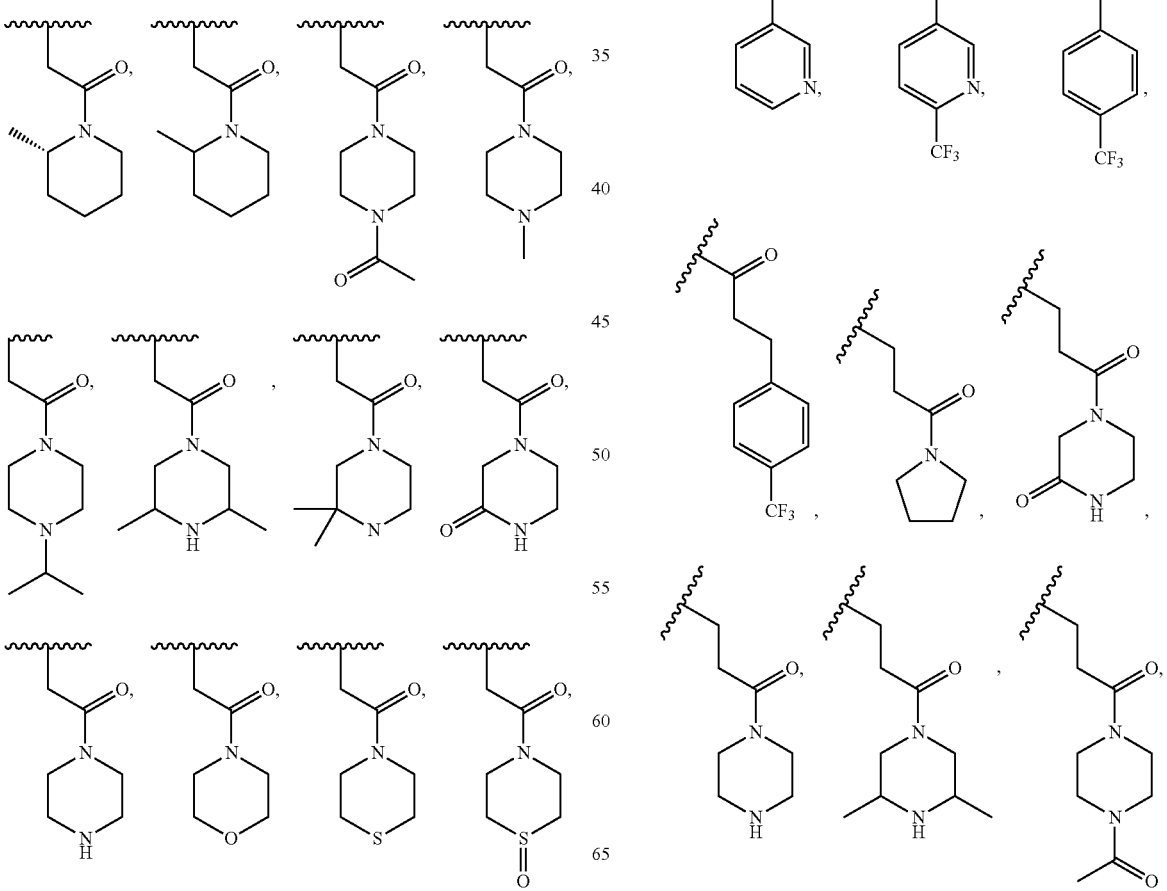

75
-continued
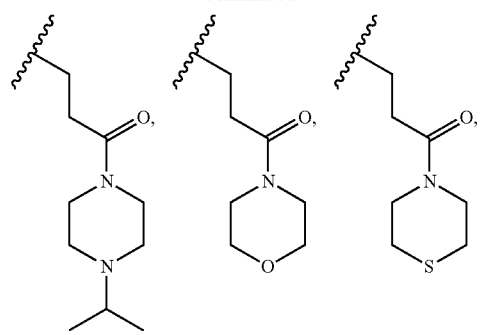
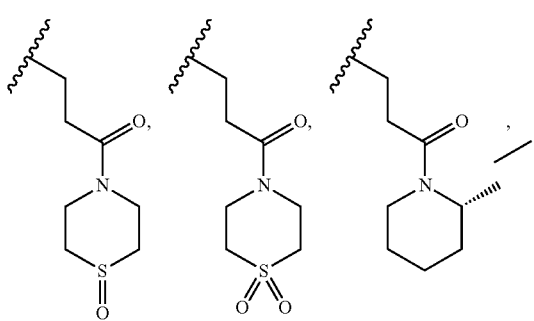
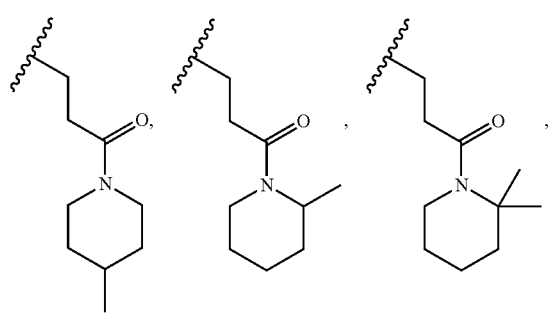
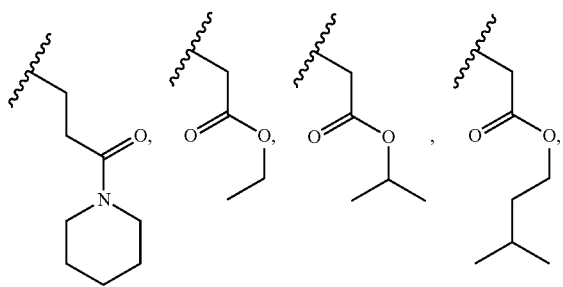
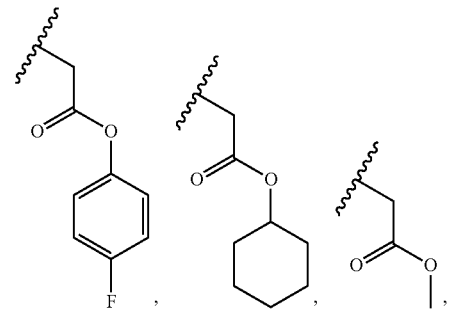
76
-continued
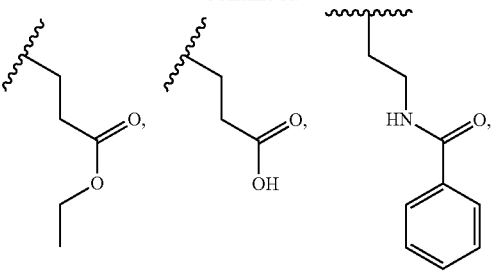
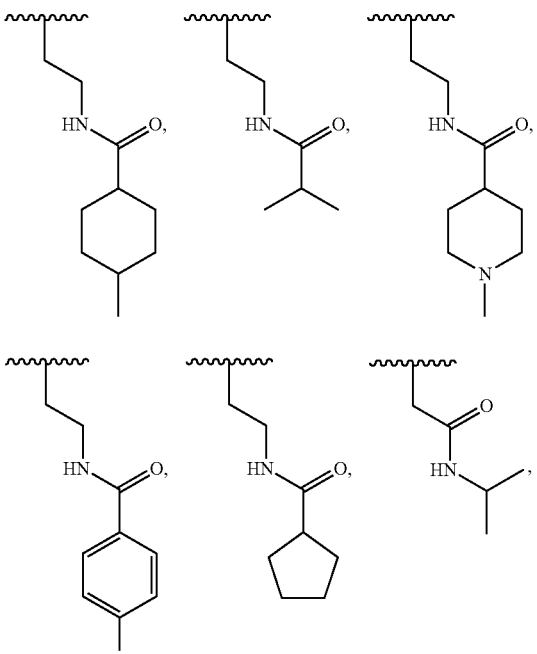
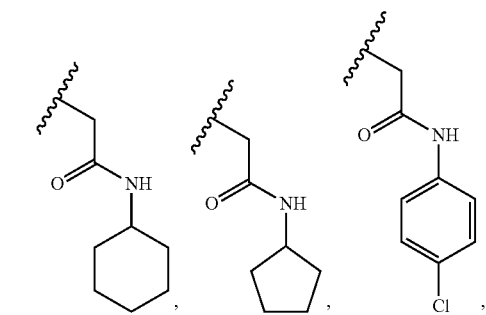
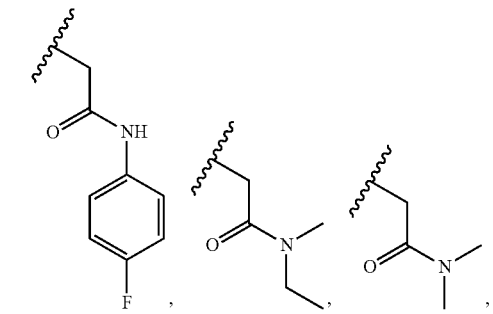

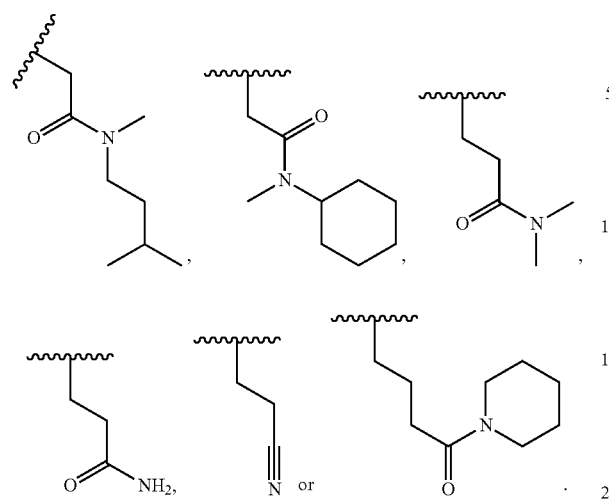

In another variation, compounds of the formulae herein or any variation thereof are provided, where, if applicable, q, m, Q and $R^{8a}$-$R^{8f}$ are taken together to form any of the moieties listed here or a moiety of the structure:

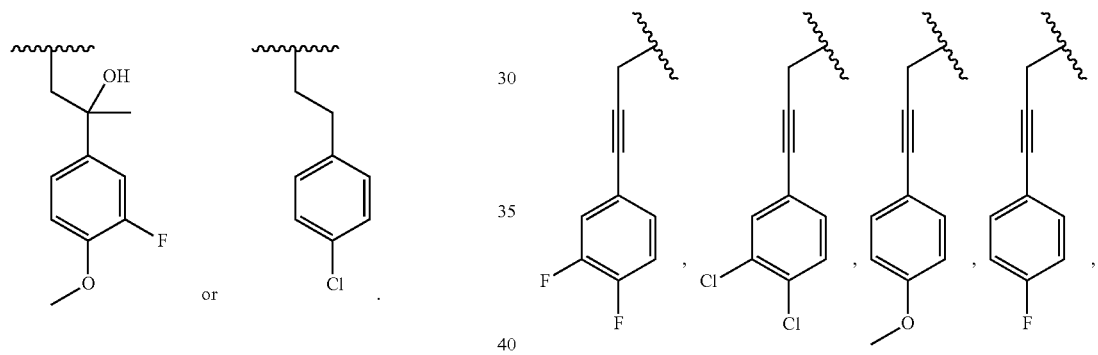

In another variation, compounds of the formulae herein or any variation thereof are provided, where, if applicable, q, m, n, Q, $R^{8a}$-$R^{8f}$, $R^{11}$ and $R^{12}$ where applicable are taken together to form a moiety of the structure:

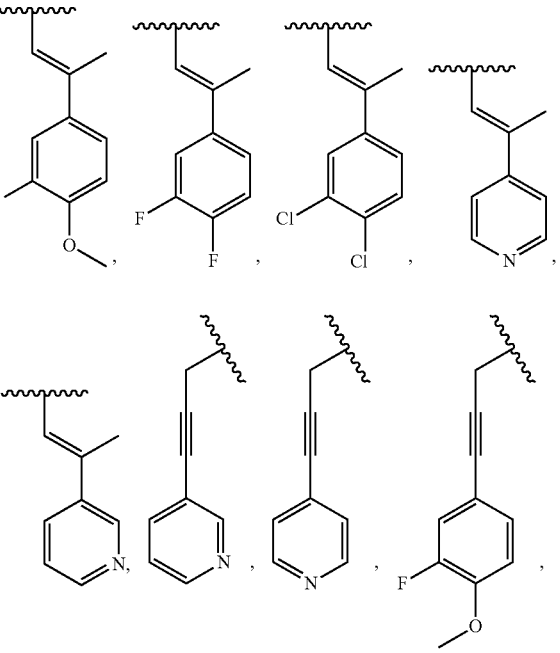

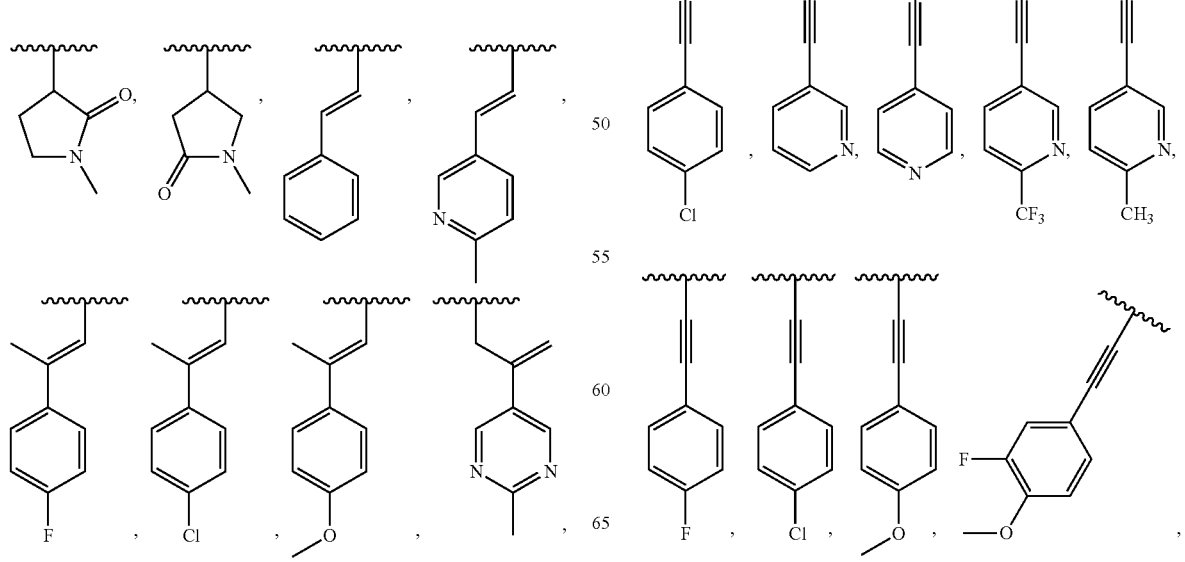

-continued

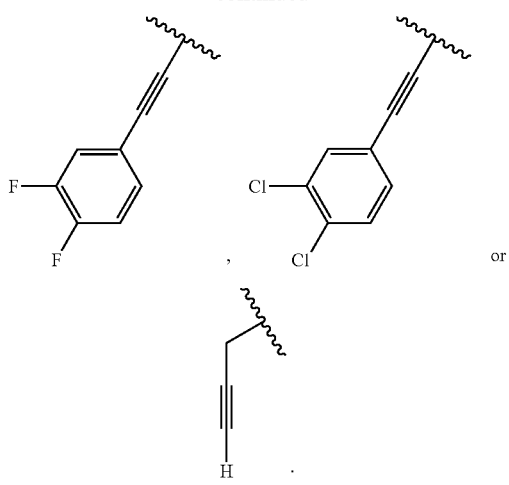

In another variation, compounds of the formulae herein or any variation thereof are provided, where, if applicable, q, m, n, Q, $R^{8a}$-$R^{8f}$, $R^{11}$ and $R^{12}$ where applicable are taken together to form any of the moieties listed here or a moiety of the structure:

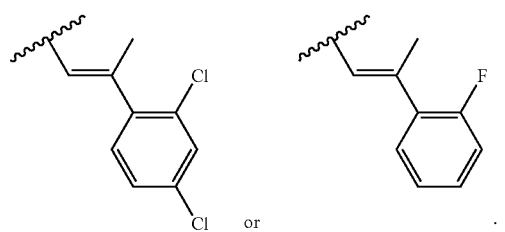 [SMILES: */C=C(\C)c1ccc(Cl)cc1Cl ; "or" ; */C=C(\C)c1ccccc1F ; "."]

Examples of compounds according to the invention are depicted in Table 1. The compounds depicted may be present as salts even if salts are not depicted and it is understood that the invention embraces all salts and solvates of the compounds depicted here, as well as the non-salt and non-solvate form of the compound, as is well understood by the skilled artisan.

TABLE 1

Representative Compounds.

| Comp. # | Structure |
|---|---|
| 1 | 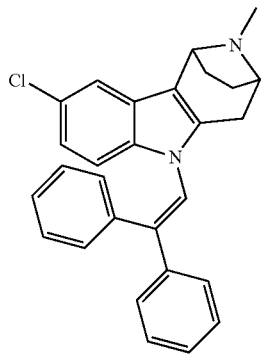 [SMILES: CN1C2CCC1c1c(n(C=C(c3ccccc3)c3ccccc3)c3ccc(Cl)cc13)C2] |

TABLE 1-continued

Representative Compounds.

| Comp. # | Structure |
|---|---|
| 2 | 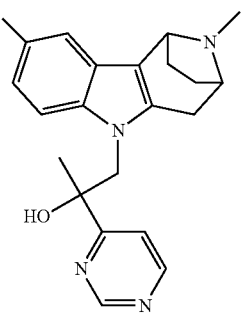 |
| 3 | 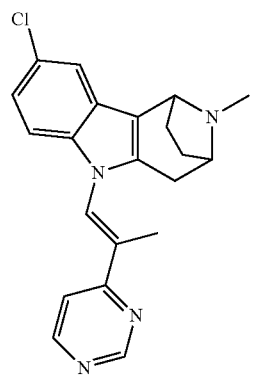 [SMILES: C/C(=C\n1c2c(c3cc(Cl)ccc31)C1CCC(C2)N1C)c1ccncn1] |
| 4 | 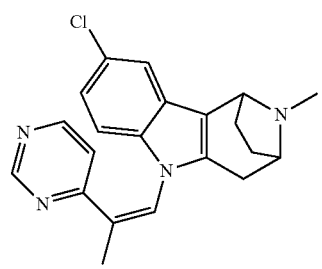 [SMILES: C/C(=C/n1c2c(c3cc(Cl)ccc31)C1CCC(C2)N1C)c1ccncn1] |
| 5 | 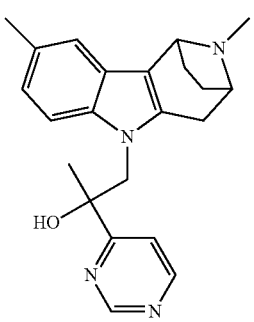 |

TABLE 1-continued

Representative Compounds.

| Comp. # | Structure |
|---|---|
| 6 | 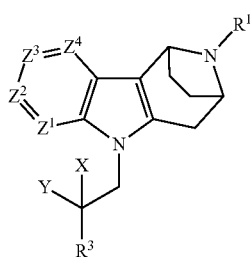 |
| 7 | 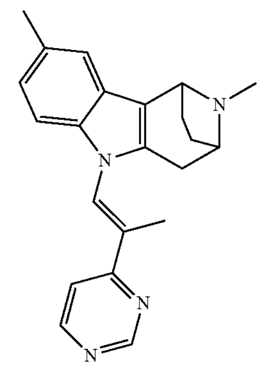 [SMILES: C/C(=C\n1c2c(c3cc(C)ccc31)C1CCC(C2)N1C)c1ccncn1] |

Additional compounds of the invention are provided by formulae (J-1)-(J-11) as detailed below.

Compounds of the formula (J-1) are provided:

(J-1)

wherein:

$R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $Z^1$, $Z^2$, $Z^3$ and $Z^4$ is independently N or $CR^2$;

each $R^2$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

X is H, OH, substituted or unsubstituted $C_1$-$C_8$ alkyl or is taken together with Y to form a moiety of the formula —OCH$_2$CH$_2$O—, or is taken together with Y and the carbon to which they are attached to form a cyclopropyl moiety;

Y is halo, substituted or unsubstituted aryl, substituted or unsubstituted heteroaryl, unsubstituted $C_1$-$C_8$ alkyl, $C_1$-$C_8$ alkyl substituted with a carbonylalkoxy, carboxyl or acylamino moiety, substituted or unsubstituted $C_3$-$C_6$ cycloalkyl, or is taken together with X to form a moiety of the formula —OCH$_2$CH$_2$O—, or is taken together with X and the carbon to which they are attached to form a cyclopropyl moiety; and $R^3$ is acylamino, carbonylalkoxy, acyloxy, aminoacyl or aminocarbonylalkoxy, provided that when $R^3$ is carbonylalkoxy, Y is halo, unsubstituted $C_1$-$C_8$ alkyl, $C_1$-$C_8$ alkyl substituted with a carbonylalkoxy, carboxyl or acylamino moiety, substituted or unsubstituted $C_3$-$C_6$ cycloalkyl, or is taken together with X to form a moiety of the formula —OCH$_2$CH$_2$O—, or is taken together with X and the carbon to which they are attached to form a cyclopropyl moiety;

or a salt or solvate thereof.

In one variation, the salt of formula (J-1) is a pharmaceutically acceptable salt.

In one variation of formula (J-1), $Z^1$, $Z^2$, $Z^3$ and $Z^4$ are each $CR^2$ and the compound is of the formula (J-2):

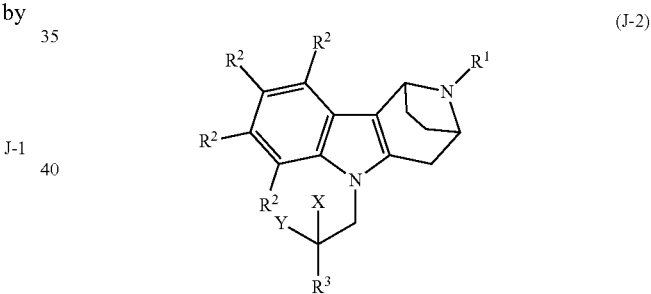

(J-2)

where $R^1$, $R^2$, $R^3$, X and Y are as defined for formula (J-1). In one aspect of formula (J-2), at least one of the $R^2$ moieties is H. In another aspect of formula (J-2), at least two $R^2$ moieties are H. In a further aspect of formula (J-2), at least three $R^2$ moieties are H, such as when (J-2) is of the formula (J-3):

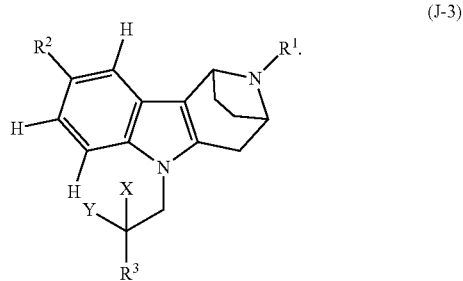

(J-3)

In one variation of formula (J-3), $R^2$ is halo or an unsubstituted $C_1$-$C_8$ alkyl, such as when $R^2$ is chloro or methyl. In one aspect, compounds of the formula (J-3) are provided wherein the compound further has one or more of the following structural features: (i) $R^1$ is a substituted or unsubstituted $C_1$-$C_8$ alkyl; (ii) $R^3$ is an acylamino, carbonylalkoxy or aminoacyl moiety; (iii) X is H, OH, unsubstituted $C_1$-$C_8$ alkyl or is taken together with Y to form a moiety of the formula —OCH$_2$CH$_2$O—, or is taken together with Y and the carbon to which they are attached to form a cyclopropyl moiety, (iv) Y is halo, unsubstituted aryl, unsubstituted $C_1$-$C_8$ alkyl, $C_1$-$C_8$ alkyl substituted with a carbonylalkoxy, carboxyl or acylamino moiety, substituted or unsubstituted $C_3$-$C_6$ cycloalkyl, or is taken together with X to form a moiety of the formula —OCH$_2$CH$_2$O—, or is taken together with X and the carbon to which they are attached to form a cyclopropyl moiety and (v) $R^2$ is halo or an unsubstituted $C_1$-$C_8$ alkyl. In a particular variation, compounds of the formula (J-3) are provided wherein at least two of provisions (i)-(v) apply. In a particular variation, compounds of the formula (J-3) are provided wherein at least three of provisions (i)-(v) apply. In a particular variation of formula (J-3), X and Y are as defined in provisions (iii) and (iv). In a further such variation, X and Y are as defined in provisions (iii) and (iv) and at least one of provisions (i), (ii) and (v) also apply.

Compounds of the formula (J-1) where at least one of $Z^1$, $Z^2$, $Z^3$ and $Z^4$ is N are also embraced. In one aspect, $Z^1$ is N. In another aspect, $Z^2$ is N. In a further aspect, $Z^3$ is N. In yet another aspect, $Z^4$ is N. Where more than one of $Z^1$, $Z^2$, $Z^3$ and $Z^4$ is N, the N atoms may be positioned at any available annular ring position. For example, when $Z^1$ is N, any of $Z^2$, $Z^3$ or $Z^4$ may also be N.

In another variation of formula (J-1), (J-2) or (J-3), $R^1$ is a substituted or unsubstituted $C_1$-$C_8$ alkyl. In a further variation of formula (J-1), (J-2) or (J-3), $R^1$ is an unsubstituted $C_1$-$C_4$ alkyl such as methyl.

In still a further variation of formula (J-1), (J-2) or (J-3), $R^3$ is an acylamino, carbonylalkoxy or aminoacyl moiety. In one aspect of formula (J-1), (J-2) or (J-3), when $R^3$ is an acylamino moiety, $R^3$ is an acyclic acylamino moiety, such as when $R^3$ is an acyclic acylamino moiety of the formula —C(O)NR$_a$R$_b$ where R$_a$ is H or a $C_1$-$C_8$ substituted or unsubstituted alkyl and R$_b$ is H, a $C_1$-$C_8$ substituted or unsubstituted alkyl (e.g., methyl, ethyl, isopropyl or benzyl) or a heterocycle. In another aspect of formula (J-1), (J-2) or (J-3), when $R^3$ is an acylamino moiety, $R^3$ is an acyclic acylamino moiety, such as when $R^3$ is of the formula —C(O)NR$_a$R$_b$ where R$_a$ taken together with R$_b$ and the nitrogen to which they are attached to form a 3-8 membered heterocyclic ring (e.g., —C(O)(1-piperidinyl). In one aspect of formula (J-1), (J-2) or (J-3), when $R^3$ is a carbonylalkoxy moiety, $R^3$ is of the formula —C(O)O-alkyl (e.g., methyl, ethyl, cyclopentyl) or —C(O)O-substituted alkyl and Y is halo, unsubstituted $C_1$-$C_8$ alkyl, $C_1$-$C_8$ alkyl substituted with a carbonylalkoxy, carboxyl or acylamino moiety, substituted or unsubstituted $C_3$-$C_6$ cycloalkyl, or is taken together with X to form a moiety of the formula —OCH$_2$CH$_2$O—, or is taken together with X and the carbon to which they are attached to form a cyclopropyl moiety. For instance, in one variation of formula (J-1), (J-2) or (J-3), $R^3$ is a carbonylalkoxy moiety of the formula —C(O)OR where R is a $C_1$-$C_8$ substituted or unsubstituted alkyl, where in one variation the substitute on the $C_1$-$C_8$ substituted alkyl is one or more halo groups, such as an alkyl substituted with a perhaloalkyl moiety. Compounds of the formula (J-1), (J-2) or (J-3) are provided where $R^3$ is an aminoacyl moiety of the formula —NR$_a$C(O)R$_b$ where R$_a$ is H and R$_b$ is an unsubstituted or substituted alkyl, an unsubstituted or substituted aryl, an unsubstituted or substituted heteroaryl, or a substituted or unsubstituted heterocyclic moi-ety. In one aspect of formula (J-1), (J-2) or (J-3), $R^3$ is an aminoacyl moiety of the formula —NR$_a$C(O)R$_b$ where R$_a$ is H and R$_b$ is a $C_1$-$C_8$ unsubstituted or substituted alkyl; in another such aspect, R$_a$ is H and R$_b$ is an unsubstituted $C_1$-$C_4$ alkyl. In another aspect of formula (J-1), (J-2) or (J-3), $R^3$ is an aminoacyl moiety of the formula —NR$_a$C(O)R$_b$ where R$_a$ is H and R$_b$ is an unsubstituted or substituted single ring aryl moiety, an unsubstituted or substituted single ring heteroaryl moiety, or a substituted or unsubstituted single ring heterocyclic moiety, where the heteroaryl or heterocyclic moieties in one variation bear nitrogen heteroatoms (e.g., pyridinyl, piperidinyl).

Compounds of the formula (J-1), (J-2) or (J-3) are also provided where X is H, OH, unsubstituted $C_1$-$C_8$ alkyl or is taken together with Y to form a moiety of the formula —OCH$_2$CH$_2$O—, or is taken together with Y and the carbon to which they are attached to form a cyclopropyl moiety, and Y is halo, unsubstituted aryl, unsubstituted $C_1$-$C_8$ alkyl, $C_1$-$C_8$ alkyl substituted with a carbonylalkoxy, carboxyl or acylamino moiety, substituted or unsubstituted $C_3$-$C_6$ cycloalkyl, or is taken together with X to form a moiety of the formula —OCH$_2$CH$_2$O—, or is taken together with X and the carbon to which they are attached to form a cyclopropyl moiety. In one variation of formula (J-1), (J-2) or (J-3), X is H, OH or an unsubstituted $C_1$-$C_8$ alkyl (e.g., methyl) and Y is halo, an unsubstituted $C_1$-$C_8$ alkyl (e.g., methyl, isopropyl, n-butyl or cyclobutyl) or an unsubstituted single ring aryl moiety (e.g., phenyl). In one variation of formula (J-1), (J-2) or (J-3), X is OH and Y is an unsubstituted aryl. In one aspect, Y is phenyl. In another variation, X is H and Y is a $C_1$-$C_8$ alkyl substituted with a carbonylalkoxy, carboxyl or acylamino moiety. In one aspect, Y is a methylene substituted with a carbonylalkoxy, carboxyl or acylamino moiety. In a particular aspect, Y is a moiety selected from the following structures

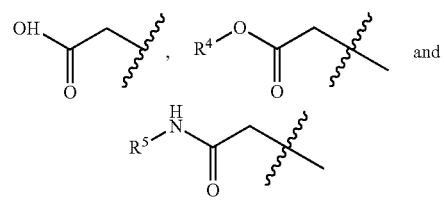

where each $R^4$ and $R^5$ is independently an unsubstituted $C_1$-$C_8$ alkyl. In one variation, Y is a moiety selected from the following structures

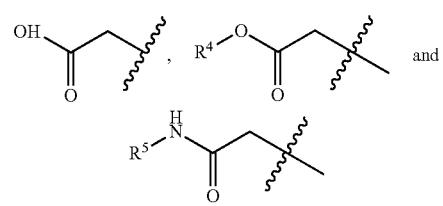

where each $R^4$ and $R^5$ is independently an unsubstituted $C_1$-$C_8$ alkyl and X is H. In another variation, X is an unsubstituted $C_1$-$C_8$ alkyl and Y is halo. In a particular aspect, Y is fluoro.

In a particular variation of formula (J-1), (J-2) or (J-3), $R^1$ is an unsubstituted $C_1$-$C_4$ alkyl; X is H, OH, unsubstituted $C_1$-$C_8$ alkyl or is taken together with Y to form a moiety of the formula —OCH$_2$CH$_2$O—, or is taken together with Y and the carbon to which they are attached to form a cyclopropyl moiety; Y is halo, unsubstituted aryl, unsubstituted $C_1$-$C_8$ alkyl, $C_1$-$C_8$ alkyl substituted with a carbonylalkoxy, carboxyl or acylamino moiety, substituted or unsubstituted $C_3$-$C_6$ cycloalkyl, or is taken together with X to form a moiety of the formula —$OCH_2CH_2O$—, or is taken together with X and the carbon to which they are attached to form a cyclopropyl moiety; and $R^3$ is an acylamino, carbonylalkoxy or aminoacyl moiety, provided that when $R^3$ is carbonylalkoxy, Y is halo, unsubstituted $C_1$-$C_8$ alkyl, $C_1$-$C_8$ alkyl substituted with a carbonylalkoxy, carboxyl or acylamino moiety, substituted or unsubstituted $C_3$-$C_6$ cycloalkyl, or is taken together with X to form a moiety of the formula —$OCH_2CH_2O$—, or is taken together with X and the carbon to which they are attached to form a cyclopropyl moiety. In another variation of formula (J-1), (J-2) or (J-3), $R^1$ is an unsubstituted $C_1$-$C_4$ alkyl; X is H, OH, unsubstituted $C_1$-$C_8$ alkyl or is taken together with Y to form a moiety of the formula —$OCH_2CH_2O$—, or is taken together with Y and the carbon to which they are attached to form a cyclopropyl moiety; Y is halo, unsubstituted aryl, unsubstituted $C_1$-$C_8$ alkyl, $C_1$-$C_8$ alkyl substituted with a carbonylalkoxy, carboxyl or acylamino moiety, substituted or unsubstituted $C_3$-$C_6$ cycloalkyl, or is taken together with X to form a moiety of the formula —$OCH_2CH_2O$—, or is taken together with X and the carbon to which they are attached to form a cyclopropyl moiety; and $R^3$ is an acylamino or aminoacyl moiety. It is understood that when $R^3$ is an acylamino, carbonylalkoxy or aminoacyl moiety, $R^3$ may be any such moiety detailed herein, including but not limited to the moieties provided herein above. As such, it is understood that in one aspect, compounds of the formula (J-1), (J-2) or (J-3) are provided wherein $R^1$ is an unsubstituted $C_1$-$C_4$ alkyl; X is H, OH, unsubstituted $C_1$-$C_8$ alkyl or is taken together with Y to form a moiety of the formula —$OCH_2CH_2O$—, or is taken together with Y and the carbon to which they are attached to form a cyclopropyl moiety; Y is halo, unsubstituted aryl, unsubstituted $C_1$-$C_8$ alkyl, $C_1$-$C_8$ alkyl substituted with a carbonylalkoxy, carboxyl or acylamino moiety, substituted or unsubstituted $C_3$-$C_6$ cycloalkyl, or is taken together with X to form a moiety of the formula —$OCH_2CH_2O$—, or is taken together with X and the carbon to which they are attached to form a cyclopropyl moiety; and $R^3$ is an acyclic or cyclic acylamino as detailed herein or an aminoacyl moiety of the formula —$NR_aC(O)R_b$ where $R_a$ is H and $R_b$ is an unsubstituted or substituted alkyl, an unsubstituted or substituted aryl, an unsubstituted or substituted heteroaryl, or a substituted or unsubstituted heterocyclic moiety.

In one variation of formula (J-3), $R^1$ is unsubstituted $C_1$-$C_8$ alkyl or a $C_1$-$C_8$ alkyl substituted with a perhaloalkyl moiety; and $R^2$ is independently H, halo, unsubstituted $C_1$-$C_8$ alkyl or unsubstituted $C_1$-$C_8$ alkoxy. In one variation of formula (J-3), $R^1$ is unsubstituted $C_1$-$C_8$ alkyl; $R^2$ is unsubstituted $C_1$-$C_8$ alkyl, H or halo, and $R^3$ is acylamino, carbonylalkoxy, acyloxy, aminoacyl or aminocarbonylalkoxy.

In one variation of formula (J-3), X is OH and Y is a substituted or unsubstituted $C_1$-$C_8$ alkyl. In another variation of (J-3), X is OH and the compound is further defined by one or more of the following structural features: (i) Y is a substituted or unsubstituted $C_1$-$C_8$ alkyl (which in one aspect is methyl, butyl or isopropyl); (ii) $R^1$ and $R^2$ are independently an unsubstituted $C_1$-$C_8$ alkyl (in one aspect both $R^1$ and $R^2$ are methyl); (iii) $R^3$ is acylamino, carbonylalkoxy, acyloxy, aminoacyl or aminocarbonylalkoxy. In a particular variation of formula (J-3), X is OH, Y is a substituted or unsubstituted $C_1$-$C_8$ alkyl; $R^1$ and $R^2$ are each methyl and $R^3$ is acylamino, carbonylalkoxy, acyloxy, aminoacyl or aminocarbonylalkoxy.

In one variation of formula (J-3), X is OH and Y is H. In one variation of formula (J-3), X is OH; Y is H; and $R^1$ and $R^2$ are independently an unsubstituted $C_1$-$C_8$ alkyl. In a particular variation of formula (J-3), X is OH; Y is H; $R^1$ and $R^2$ are independently an unsubstituted $C_1$-$C_8$ alkyl; and $R^3$ is acylamino, carbonylalkoxy, acyloxy, aminoacyl or aminocarbonylalkoxy. In one variation of formula (J-3), X is OH; Y and H; $R^1$ and $R^2$ are each methyl; and $R^3$ is acylamino, carbonylalkoxy, acyloxy, aminoacyl or aminocarbonylalkoxy. In a particular variation of formula (J-3), X is OH; Y is H; $R^1$ and $R^2$ are each methyl; and $R^3$ is acylamino, carbonylalkoxy or aminoacyl.

Compounds of the formula (J-4) are detailed herein:

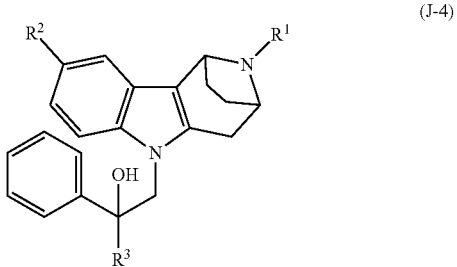

(J-4)

or a salt or solvate thereof, where $R^1$, $R^2$ and $R^3$ are as defined for formula (J-1). In one variation of formula (J-4), $R^1$ and $R^2$ are independently an unsubstituted $C_1$-$C_8$ alkyl. In a particular variation of formula v, $R^1$ and $R^2$ are independently an unsubstituted $C_1$-$C_8$ alkyl and $R^3$ is acylamino, carbonylalkoxy, acyloxy, aminoacyl or aminocarbonylalkoxy. In one variation, $R^1$ and $R^2$ are each methyl and $R^3$ is acylamino, carbonylalkoxy, acyloxy, aminoacyl or aminocarbonylalkoxy. In another variation of formula (J-4), $R^1$ is an unsubstituted $C_1$-$C_8$ alkyl; $R^2$ is halo or an unsubstituted $C_1$-$C_8$ alkyl and $R^3$ is aminoacyl. In one such variation of formula (J-4), $R^1$ is methyl; $R^2$ is halo or a $C_1$-$C_4$ unsubstituted alkyl; and $R^3$ is an aminoacyl of the formula —$NR_aC(O)R_b$ where $R_a$ is H and $R_b$ is an unsubstituted or substituted alkyl, an unsubstituted or substituted aryl, an unsubstituted or substituted heteroaryl, or a substituted or unsubstituted heterocyclic moiety.

Compounds of the formula (J-5) are also detailed herein:

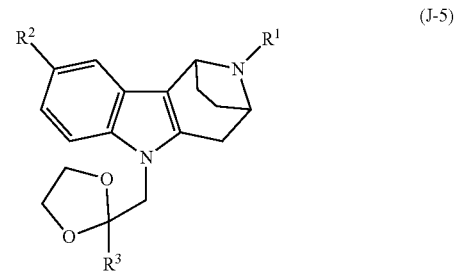

(J-5)

or a salt or solvate thereof, where $R^1$, $R^2$ and $R^3$ are as defined for formula (J-1). In one variation of formula (J-5), $R^1$ is an unsubstituted $C_1$-$C_8$ alkyl (e.g., methyl). In another variation of formula (J-5), $R^2$ is H, an unsubstituted $C_1$-$C_8$ alkyl (e.g., methyl) or halo (e.g., chloro). In one aspect of formula (J-5), $R^1$ is an unsubstituted $C_1$-$C_8$ alkyl and $R^2$ is H, an unsubstituted $C_1$-$C_8$ alkyl or halo. In another variation of formula (J-5), $R_2$ is a halo or an unsubstituted $C_1$-$C_8$ alkyl and $R^1$ is an unsubstituted $C_1$-$C_4$ alkyl. In a particular variation of formula (J-5), $R^1$ is methyl and $R^2$ is H, methyl or chloro. In one variation of formula (J-5), $R^1$ and $R^2$ are independently an unsubstituted $C_1$-$C_8$ alkyl such as methyl. In a further variation of formula (J-5), $R^1$ is an unsubstituted $C_1$-$C_8$ alkyl; $R^2$ is H, an unsubstituted $C_1$-$C_8$ alkyl or halo and $R^3$ is acylamino, carbonylalkoxy, acyloxy, aminoacyl or aminocarbonylalkoxy. In a particular variation, compounds of formula (J-5) are provided where $R^1$ is methyl, $R^2$ is H, methyl or chloro and $R^3$ is acylamino, carbonylalkoxy, acyloxy, aminoacyl or aminocarbonylalkoxy. In a further variation of formula (J-5), $R^1$ is an unsubstituted $C_1$-$C_8$ alkyl; $R^2$ is halo or an unsubstituted $C_1$-$C_8$ alkyl; and $R^3$ is an acylamino of the formula —C(O)NR$_a$R$_b$ where R$_a$ is H and R$_b$ is an unsubstituted $C_1$-$C_8$ alkyl.

Compounds of the formula (J-6) are also detailed herein:

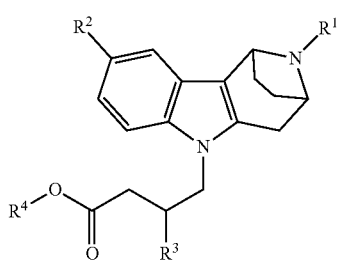

(J-6)

or a salt or solvate thereof, where $R^1$, $R^2$ and $R^3$ are as detailed for formula (J-1) and $R^4$ is an unsubstituted $C_1$-$C_8$ alkyl. In one variation of formula (J-6), $R^1$ is an unsubstituted $C_1$-$C_8$ alkyl. In one variation of formula (J-6), $R^2$ is an unsubstituted $C_1$-$C_8$ alkyl or halo. In one variation of formula (J-6), $R^1$ and $R^2$ are independently an unsubstituted $C_1$-$C_8$ alkyl (e.g., methyl or ethyl). In one variation of formula (J-6), $R^1$ is an unsubstituted $C_1$-$C_8$ alkyl (e.g., methyl or ethyl) and $R^2$ is an unsubstituted $C_1$-$C_8$ alkyl or halo. In a particular variation of formula (J-6), $R^4$ is an unsubstituted $C_1$-$C_4$ alkyl. In a further variation of formula (J-6), $R^4$ is methyl, ethyl, propyl or butyl. In one aspect, $R^4$ is iso-propyl. In another aspect, $R^4$ is tert-butyl. In a particular variation of formula (J-6), $R^1$ is an unsubstituted $C_1$-$C_8$ alkyl; $R^2$ is an unsubstituted $C_1$-$C_8$ alkyl or halo and $R^4$ is an unsubstituted $C_1$-$C_4$ alkyl. In a further variation of formula (J-6), $R^1$ is an unsubstituted $C_1$-$C_8$ alkyl; $R^2$ is an unsubstituted $C_1$-$C_8$ alkyl or halo; $R^4$ is an unsubstituted $C_1$-$C_4$ alkyl and $R^3$ is acylamino, carbonylalkoxy, acyloxy, aminoacyl or aminocarbonylalkoxy. In a particular variation, compounds of formula (J-6) are provided where $R^1$ is methyl or ethyl, $R^2$ is methyl or chloro; $R^4$ is methyl, ethyl, isopropyl or tert-butyl and $R^3$ is acylamino, carbonylalkoxy, acyloxy, aminoacyl or aminocarbonylalkoxy. In a further variation of formula (J-6), $R^1$ is an unsubstituted $C_1$-$C_4$ alkyl; $R^2$ is an unsubstituted $C_1$-$C_4$ alkyl or halo; $R^4$ is an unsubstituted $C_1$-$C_4$ alkyl; and $R^3$ is acylamino or aminoacyl. In yet a further variation of formula (J-6), $R^1$ is an unsubstituted $C_1$-$C_4$ alkyl; $R^2$ is an unsubstituted $C_1$-$C_4$ alkyl or halo; $R^4$ is an unsubstituted $C_1$-$C_4$ alkyl; and $R^3$ is either an acylamino of the formula —C(O)NR$_a$R$_b$ where R$_a$ and R$_b$ are independently an unsubstituted $C_1$-$C_8$ alkyl or R$_a$ and R$_b$ are taken together with the nitrogen to which they are attached to form a heterocyclic moiety or an aminoacyl.

Compounds of the formula (J-7) are also detailed herein:

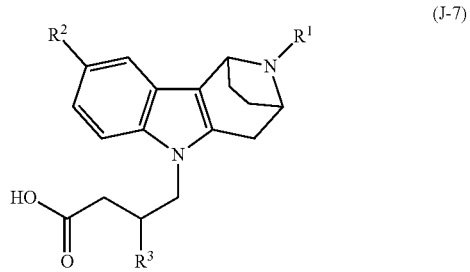

(J-7)

or a salt of solvate thereof, where $R^1$, $R^2$ and $R^3$ are as detailed for formula (J-1). In one variation of formula (J-7), $R^1$ is an unsubstituted $C_1$-$C_8$ alkyl (e.g., methyl). In another variation of formula (J-7), $R^2$ is unsubstituted $C_1$-$C_8$ alkyl (e.g., methyl) or halo (e.g., chloro). In a particular variation of formula (J-7), $R^1$ is an unsubstituted $C_1$-$C_8$ alkyl and $R^2$ is unsubstituted $C_1$-$C_8$ alkyl or halo. In another variation of formula (J-7), $R^1$ and $R^2$ are independently an unsubstituted $C_1$-$C_8$ alkyl (e.g., methyl). In one variation of formula (J-7), $R^1$ is an unsubstituted $C_1$-$C_8$ alkyl, $R^2$ is unsubstituted $C_1$-$C_8$ alkyl or halo and $R^3$ is acylamino, carbonylalkoxy, acyloxy, aminoacyl or aminocarbonylalkoxy. In a particular variation of formula (J-7), $R^1$ and $R^2$ are independently an unsubstituted $C_1$-$C_8$ alkyl and $R^3$ is acylamino, carbonylalkoxy, acyloxy, aminoacyl or aminocarbonylalkoxy. In one variation of formula (J-7), $R^3$ is acylamino.

Compounds of the formula (J-8) are also detailed herein:

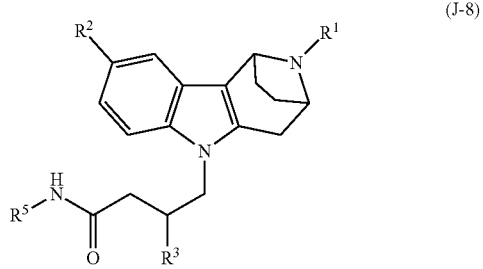

(J-8)

or a salt of solvate thereof, where $R^1$, $R^2$ and $R^3$ are as detailed for formula (J-1) and $R^5$ is an unsubstituted $C_1$-$C_8$ alkyl. In one variation of formula (J-8), $R^1$ is an unsubstituted $C_1$-$C_8$ alkyl (e.g., methyl or ethyl). In another variation of formula (J-8), $R^2$ is unsubstituted $C_1$-$C_8$ alkyl (e.g., methyl) or halo (e.g., chloro). In a particular variation of formula (J-8), $R^1$ is an unsubstituted $C_1$-$C_8$ alkyl and $R^2$ is unsubstituted $C_1$-$C_8$ alkyl or halo. In another variation of formula (J-8), $R^1$ and $R^2$ are independently an unsubstituted $C_1$-$C_8$ alkyl. In a particular variation of formula (J-8), $R^5$ is an unsubstituted $C_1$-$C_4$ alkyl. In a further variation of formula (J-8), $R^5$ is methyl, ethyl, propyl or butyl. In one aspect, $R^5$ is iso-propyl. In another aspect, $R^5$ is tert-butyl. In one variation of formula (J-8), $R^1$ is an unsubstituted $C_1$-$C_8$ alkyl, $R^2$ is unsubstituted $C_1$-$C_8$ alkyl or halo and $R^3$ is acylamino, carbonylalkoxy, acyloxy, aminoacyl or aminocarbonylalkoxy. In a further variation of formula (J-8), $R^1$ is an unsubstituted $C_1$-$C_8$ alkyl, $R^2$ is unsubstituted $C_1$-$C_8$ alkyl or halo and $R^3$ is acylamino, or aminoacyl.

Compounds of the formula (J-9) are also detailed herein:

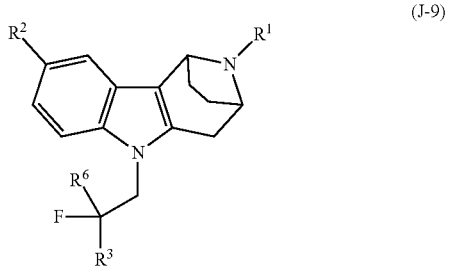

(J-9)

or a salt or solvate thereof, where $R^1$, $R^2$ and $R^3$ are as defined for formula (J-1) and $R^6$ is an unsubstituted $C_1$-$C_8$ alkyl. In one variation of formula (J-9), $R^1$ is an unsubstituted $C_1$-$C_8$ alkyl (e.g., methyl, ethyl or isopropyl). In another variation of formula (J-9), $R^2$ is unsubstituted $C_1$-$C_8$ alkyl (e.g., methyl) or halo (e.g., chloro). In a particular variation of formula (J-9), $R^1$ is an unsubstituted $C_1$-$C_8$ alkyl and $R^2$ is unsubstituted $C_1$-$C_8$ alkyl or halo. In another variation of formula (J-9), $R^1$ and $R^2$ independently an unsubstituted $C_1$-$C_8$ alkyl. In a particular variation of formula (J-9), $R^6$ is an unsubstituted $C_1$-$C_4$ alkyl. In a further variation of formula (J-9), $R^6$ is methyl, ethyl, propyl or butyl. In one aspect, $R^6$ is iso-propyl. In another aspect, $R^6$ is tert-butyl. In one variation of formula (J-9), $R^1$ is an unsubstituted $C_1$-$C_8$ alkyl, $R^2$ is unsubstituted $C_1$-$C_8$ alkyl or halo and $R^3$ is acylamino, carbonylalkoxy, acyloxy, aminoacyl or aminocarbonylalkoxy.

Compounds of the formula (J-10) are also detailed herein:

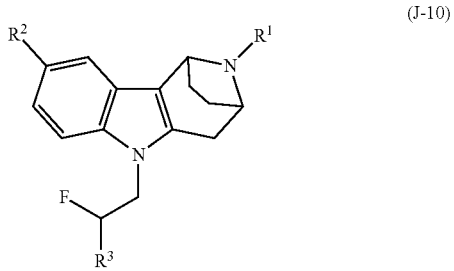

(J-10)

or a salt or solvate thereof, where $R^1$, $R^2$ and $R^3$ are as defined for formula (J-1). In one variation of formula (J-10), $R^1$ and $R^2$ are each an unsubstituted $C_1$-$C_8$ alkyl group. In another variation of formula (J-10), $R^1$ and $R^2$ are each an unsubstituted $C_1$-$C_8$ alkyl group and $R^3$ is acylamino, carbonylalkoxy, acyloxy, aminoacyl or aminocarbonylalkoxy. In another variation of formula (J-10), $R^1$ is an unsubstituted $C_1$-$C_8$ alkyl; $R^2$ is an unsubstituted $C_1$-$C_8$ alkyl or halo and $R^3$ is acylamino or aminoacyl.

Compounds of the formula (J-11) are also detailed herein:

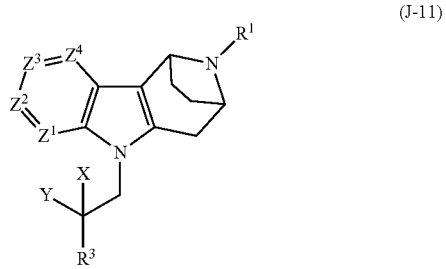

(J-11)

wherein:
each $Z^1$, $Z^2$, $Z^3$ and $Z^4$ is independently N or $CR^2$
each $R^2$ is independently H, halo, unsubstituted $C_1$-$C_8$ alkyl or unsubstituted $C_1$-$C_8$ alkoxy;

$R^1$ is unsubstituted $C_1$-$C_8$ alkyl or a $C_1$-$C_8$ alkyl substituted with a perhaloalkyl moiety;

X is OH, substituted or unsubstituted $C_1$-$C_8$ alkyl or is taken together with Y and the carbon to which they are attached to form a cyclopropyl moiety;

Y is H, substituted or unsubstituted $C_1$-$C_8$ alkyl or is taken together with X and the carbon to which they are attached to form a cyclopropyl moiety; and $R^3$ is acylamino, carbonylalkoxy, acyloxy, aminoacyl or aminocarbonylalkoxy; or a salt or solvate thereof.

In one variation, the salt of formula (J-11) is a pharmaceutically acceptable salt.

In one variation of formula (J-11), each of $Z^1$, $Z^2$, $Z^3$ and $Z^4$ is $CR^2$. In another variation of formula (J-11), at least one of $Z^1$, $Z^2$, $Z^3$ and $Z^4$ is N, which may positioned at any of $Z^1$, $Z^2$, $Z^3$ and $Z^4$. Where more than one of $Z^1$, $Z^2$, $Z^3$ and $Z^4$ is N, the annular nitrogen atoms may be located at any available positions.

In one variation of formula (J-11), $R^1$ and $R^2$ are independently an unsubstituted $C_1$-$C_8$ alkyl. In a particular variation of formula (J-11), $R^1$ and $R^2$ are independently an unsubstituted $C_1$-$C_8$ alkyl and $R^3$ is acylamino, carbonylalkoxy, acyloxy, aminoacyl or aminocarbonylalkoxy. In one variation, $R^1$ and $R^2$ are each methyl and $R^3$ is acylamino, carbonylalkoxy, acyloxy, aminoacyl or aminocarbonylalkoxy. In a particular variation of formula (J-11), $R^1$ and $R^2$ are each methyl and $R^3$ is acylamino, carbonylalkoxy, acyloxy, aminoacyl or aminocarbonylalkoxy.

Examples of compounds according to the invention are depicted in Table 2. The compounds depicted may be present as salts even if salts are not depicted and it is understood that the invention embraces all salts and solvates of the compounds depicted here, as well as the non-salt and non-solvate form of the compound, as is well understood by the skilled artisan.

TABLE 2

| Representative Compounds | |
|---|---|
| Compound | Structure |
| J-1 | |
| J-2 | |

TABLE 2-continued
Representative Compounds
| Compound | Structure |
|---|---|
| J-3 | 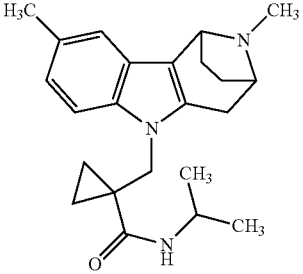 |
| J-4 | 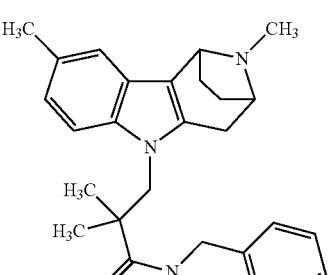 |
| J-5 | 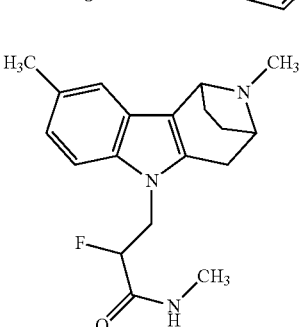 |
| J-6 | 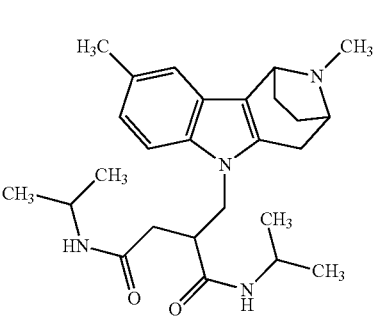 [SMILES: Cc1ccc2c(c1)c1c(n2CC(CC(=O)NC(C)C)C(=O)NC(C)C)CC2CCC1N2C] |
| J-7 | 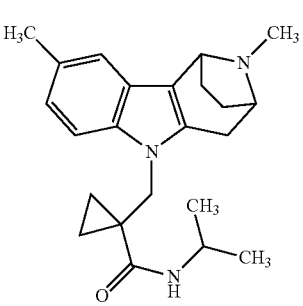 |
| J-8 | 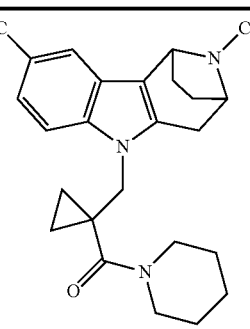 |
| J-9 | 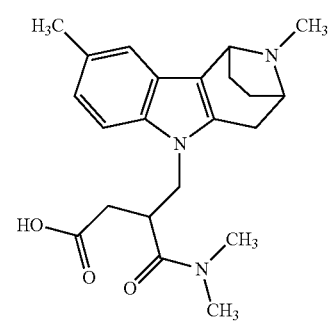 [SMILES: Cc1ccc2c(c1)c1c(n2CC(CC(=O)O)C(=O)N(C)C)CC2CCC1N2C] |
| J-10 | 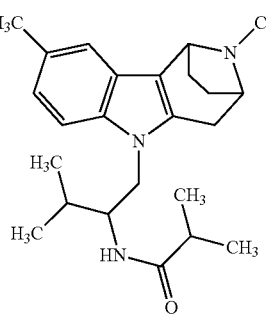 |
| J-11 | 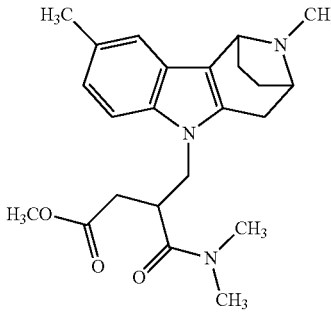 |
| J-12 | 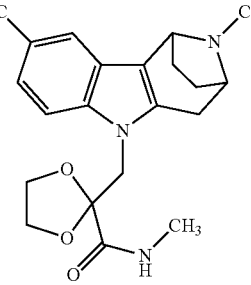 |

TABLE 2-continued

Representative Compounds

| Compound | Structure |
|---|---|
| J-13 | 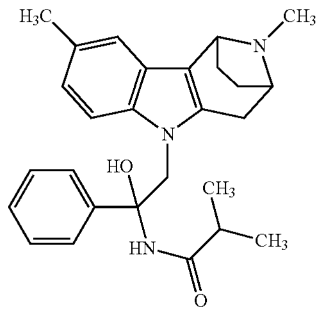 [SMILES: Cc1ccc2c(c1)c1c(n2CC(O)(NC(=O)C(C)C)c2ccccc2)CC2CCC1N2C] |
| J-14 | 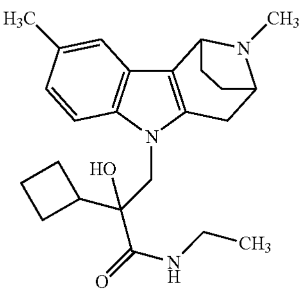 [SMILES: CCNC(=O)C(O)(Cn1c2c(c3cc(C)ccc31)C1CCC(C2)N1C)C1CCC1] |
| J-15 | 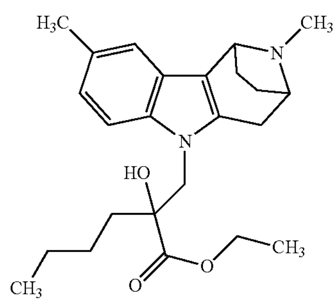 [SMILES: CCCCC(O)(Cn1c2c(c3cc(C)ccc31)C1CCC(C2)N1C)C(=O)OCC] |
| J-16 | 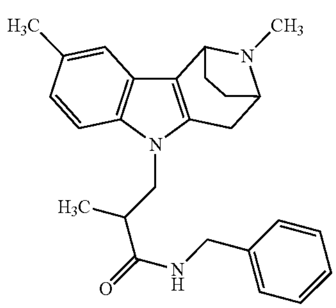 [SMILES: Cc1ccc2c(c1)c1c(n2CC(C)C(=O)NCc2ccccc2)CC2CCC1N2C] |
| J-17 | 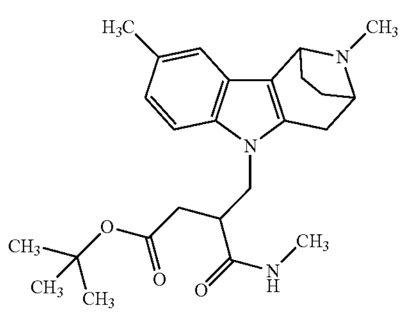 [SMILES: CNC(=O)C(CC(=O)OC(C)(C)C)Cn1c2c(c3cc(C)ccc31)C1CCC(C2)N1C] |
| J-18 | |
| J-19 | |
| J-20 | |
| J-21 | |
| J-22 | |

TABLE 2-continued
Representative Compounds
| Compound | Structure |
|---|---|
| J-23 | 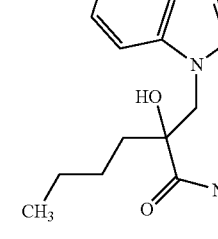 |
| J-24 | 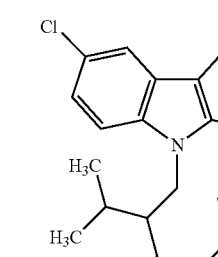 |
| J-25 | 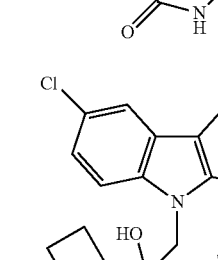 |
| J-26 | 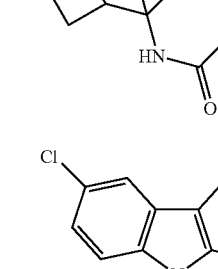 |
| J-27 | 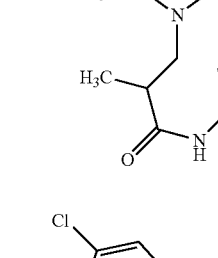 |
| J-28 | |
| J-29 | |
| J-30 | |
Compounds of the formula (K-1) are also detailed herein:
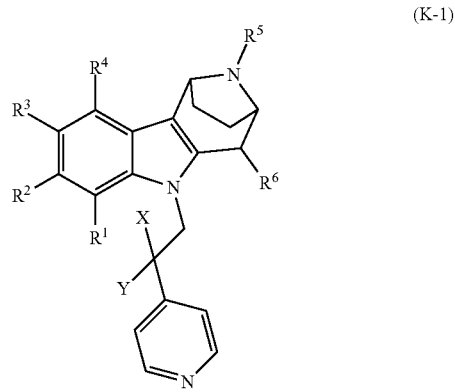
wherein:
$R^1$, $R^2$, $R^3$ and $R^4$ are independently H, halo, $C_1$-$C_8$ unsubstituted alkyl or $C_1$-$C_8$ unsubstituted alkoxy, provided that $R^3$ is other than methyl or chloro when $R^1$, $R^2$ and $R^3$ are each H and X is OH and Y is methyl;

$R^5$ is unsubstituted $C_1$-$C_8$ alkyl or a $C_1$-$C_8$ alkyl substituted with a perhaloalkyl moiety;

$R^6$ is H or an unsubstituted $C_1$-$C_8$ alkyl;

X is OH, $C_1$-$C_8$ alkyl or is taken together with Y to form a cyclopropyl moiety;

Y is H, $C_1$-$C_8$ alkyl or is taken together with X to form a cyclopropyl moiety, or a salt thereof, such as a pharmaceutically acceptable salt thereof, or solvate of the foregoing.

In one variation of formula (K-1), $R^1$ is H, halo or $C_1$-$C_8$ unsubstituted alkoxy; $R^2$ is H; $R^3$ is H, halo, $C_1$-$C_8$ unsubstituted alkyl or $C_1$-$C_8$ unsubstituted alkoxy, provided that $R^3$ is other than methyl or chloro when $R^1$, $R^2$ and $R^3$ are each H and X is OH and Y is methyl; $R^4$ is H or halo; $R^5$ is methyl; $R^6$ is H or methyl; X is OH, $C_1$-$C_8$ alkyl or is taken together with Y to form a cyclopropyl moiety and Y is H, $C_1$-$C_8$ alkyl or is taken together with X to form a cyclopropyl moiety. In another variation of formula (K-1), at least two of $R^1$, $R^2$, $R^3$ and $R^4$ are halo (e.g., when $R^2$ and $R^3$ are chloro). In another variation of formula (K-1), X is OH and Y is H, methyl, ethyl or isopropyl. In a further variation of formula (K-1), $R^1$, $R^2$ and $R^4$ are H. In another variation of formula (K-1), three of $R^1$, $R^2$, $R^3$ and $R^4$ are H and one is methyl, methoxy, isopropyl, chloro or fluoro.

Also provided are compounds of the formula (K-2):

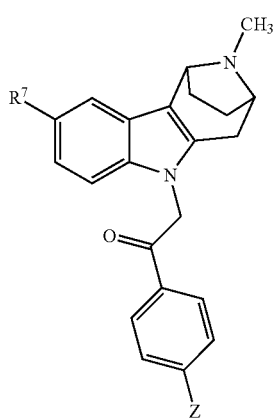

(K-2)

wherein:

$R^7$ is H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl; and Z is H, halo or $C_1$-$C_8$ alkyl, or a salt thereof, such as a pharmaceutically acceptable salt thereof, or solvate of the foregoing.

In one variation of formula (K-2), $R^7$ is unsubstituted $C_1$-$C_8$ alkyl or halo. In another variation of formula (K-2), Z is H or halo. In a further variation of formula (K-2), $R^7$ is an unsubstituted $C_1$-$C_8$ alkyl or halo and Z is H or halo. In a particular variation, $R^7$ is methyl or chloro and Z is H, chloro or fluoro.

Compounds of the formula (K-3) are also embraced:

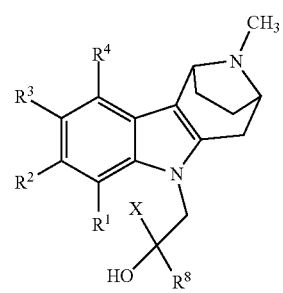

(K-3)

wherein:

$R^1$, $R^2$, $R^3$ and $R^4$ are as defined for formula (K-1);

$R^8$ is a substituted or unsubstituted aryl or a substituted or unsubstituted heteroaryl; and X is a $C_4$-$C_6$ unsubstituted n-alkyl or cycloalkyl or a $C_3$-$C_6$ unsubstituted branched alkyl, or a salt thereof, such as a pharmaceutically acceptable salt thereof, or solvate of the foregoing.

In one variation of formula (K-3), $R^1$, $R^2$ and $R^4$ are each H and $R^3$ is an unsubstituted $C_1$-$C_8$ alkyl (e.g., methyl) or halo (e.g., chloro). In another variation of formula (K-3), X is cyclohexyl, cyclobutyl, n-butyl or iso-propyl. In a particular variation of formula (K-3), $R^1$, $R^2$ and $R^4$ are each H; $R^3$ is an unsubstituted $C_1$-$C_8$ alkyl or halo and X is cyclohexyl, cyclobutyl, n-butyl or iso-propyl. In a further variation of formula (K-3), $R^8$ is a substituted aryl or an unsubstituted heteroaryl. In one aspect, $R^8$ of formula (K-3) is a substituted phenyl or an unsubstituted pyridyl. In a particular aspect, $R^8$ of formula (K-3) is 4-halo-phenyl or 4-pyridyl. In another variation of formula (K-3), $R^1$, $R^2$ and $R^4$ are each H; $R^3$ is an unsubstituted $C_1$-$C_8$ alkyl or halo; X is cyclohexyl, cyclobutyl, n-butyl and $R^8$ is a substituted phenyl. In another variation of formula (K-3), $R^1$, $R^2$ and $R^4$ are each H; $R^3$ is an unsubstituted $C_1$-$C_8$ alkyl or halo; X is isopropyl and $R^8$ is an unsubstituted pyridyl.

Compounds of the formula (K-4) are also provided:

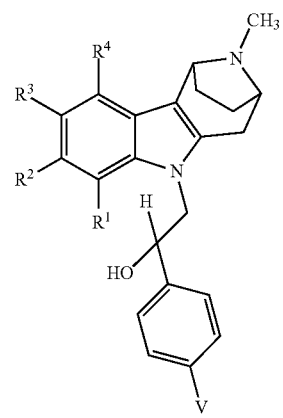

(K-4)

wherein:

$R^1$, $R^2$, $R^3$ and $R^4$ are as defined for formula (K-1); and

V is a halo, or a salt thereof, such as a pharmaceutically acceptable salt thereof, or solvate of the foregoing.

In one variation of formula (K-4), $R^1$, $R^2$ and $R^4$ are H and $R^3$ is unsubstituted $C_1$-$C_8$ alkyl such as methyl. In another variation of formula (K-4), V is fluoro.

Compounds of the formula (K-5) are also detailed herein:

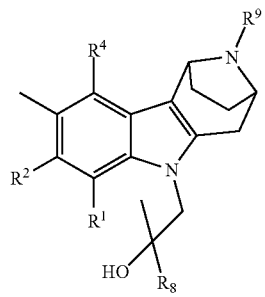

(K-5)

wherein:
$R^1$, $R^2$ and $R^4$ are as defined for formula (K-1); and
$R^8$ is 6-pyrimidyl, 3-methyl-4-pyridyl or a phenyl substituted either: (i) with at least one alkoxy or hydroxyl group or (ii) with at least two halo groups;
$R^9$ is an unsubstituted $C_1$-$C_3$ alkyl;
or a salt thereof, such as a pharmaceutically acceptable salt thereof, or solvate of the foregoing.

In one variation of formula (K-5), $R^1$, $R^2$ and $R^4$ are each H. In another variation of formula (K-5), $R^9$ is methyl. In a further variation of formula (K-5), $R^1$, $R^2$ and $R^4$ are each H and $R^9$ is methyl. In another variation of formula (K-5), $R^8$ is a phenyl substituted with at least one unsubstituted $C_1$-$C_8$ alkoxy group such as methoxy. In one aspect of formula (K-5), $R^1$, $R^2$ and $R^4$ are each H and $R^8$ is a methoxy-substituted phenyl. In another aspect of formula (K-5), $R^9$ is methyl and $R^8$ is a methoxy or hydroxyl-substituted phenyl. In another variation, $R^8$ is a phenyl substituted with at least two halo groups and $R^1$, $R^2$ and $R^4$ are each H.

Also provided are compounds of the formula (K-6):

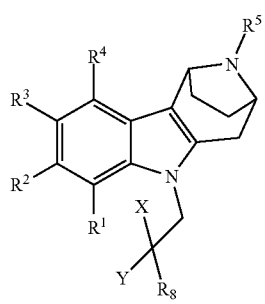

(K-6)

wherein:
$R^1$, $R^2$, $R^3$ and $R^4$ are as defined for formula (K-1);
$R^5$ is

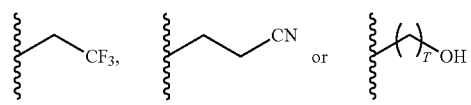

where T is 3 or 4;
X is H or OH;
Y is H or $C_1$-$C_8$ alkyl; and
$R^8$ is a substituted or unsubstituted heteroaryl,
or a salt thereof, such as a pharmaceutically acceptable salt thereof, or solvate of the foregoing.

In one variation of formula (K-6), R1, R2 and R4 are H. In another variation of formula (K-6), R3 is unsubstituted $C_1$-$C_8$ alkyl. In another variation of formula (K-6), $R^1$, $R^2$ and $R^4$ are H and $R^3$ is unsubstituted $C_1$-$C_8$ alkyl. In another variation of formula (K-6), $R^8$ is a substituted or unsubstituted pyridyl. When $R^8$ is an unsubstituted pyridyl, it may be bound to the parent structure at any available position, e.g., 4-pyridyl. When $R^8$ is a substituted pyridyl, in one aspect the pyridyl is substituted with an unsubstituted $C_1$-$C_8$ alkyl such as methyl. When $R^8$ is a substituted pyridyl, it may be bound to the parent structure at any available ring position, e.g., 6-methyl-3-pyridyl. In a particular variation of formula (K-6), $R^1$, $R^2$ and $R^4$ are H; $R^3$ is unsubstituted $C_1$-$C_8$ alkyl and $R^8$ is a substituted or unsubstituted pyridyl. In a further variation of formula (K-6), X and Y are both H. For example, in one aspect a compound is of the formula (K-6) where $R^1$, $R^2$ and $R^4$ are H; $R^3$ is unsubstituted $C_1$-$C_8$ alkyl and $R^8$ is a substituted or unsubstituted pyridyl and X and Y are both H.

Compounds of the formula (K-7) are also detailed herein:

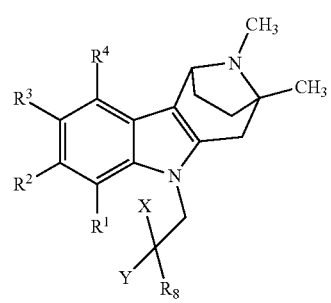

(K-7)

wherein:
$R^1$, $R^2$ and $R^4$ are as defined for formula (K-1);
$R^3$ is methyl or chloro, provided that $R^3$ is methyl when $R^8$ is a substituted heteroaryl;
X is H or OH;
Y is H or $C_1$-$C_8$ alkyl; and
$R^8$ is a substituted or unsubstituted heteroaryl,
or a salt thereof, such as a pharmaceutically acceptable salt thereof, or solvate of the foregoing.

In one aspect of formula (K-7), $R^1$, $R^2$ and $R^4$ are each H. In another aspect of formula (K-7), X is H and Y is an unsubstituted $C_1$-$C_8$ alkyl. In another aspect of formula (K-7), Y and Y are both H. In a particular variation of formula (K-7), $R^1$, $R^2$ and $R^4$ are each H and either (i) X and Y are both H or (ii) X is H and Y is an unsubstituted $C_1$-$C_8$ alkyl such as methyl. In a particular variation, $R^8$ is a substituted or unsubstituted pyridyl. In a specific variation of formula (K-7), $R^8$ is a substituted or unsubstituted pyridyl and either (i) X and Y are both H or (ii) X is H and Y is an unsubstituted $C_1$-$C_8$ alkyl.

Examples of compounds according to the invention are depicted in Table 3. The compounds depicted may be present as salts even if salts are not depicted and it is understood that the invention embraces all salts and solvates of the compounds depicted here, as well as the non-salt and non-solvate form of the compound, as is well understood by the skilled artisan.

TABLE 3
Representative Compounds According to the Invention.
| Comp. # | Compound Structure |
|---|---|
| K-1 | 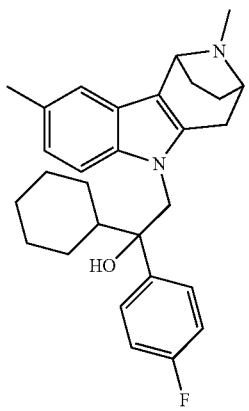 [SMILES: Cc1ccc2c(c1)c1c(n2CC(O)(c2ccc(F)cc2)C2CCCCC2)CC2CCC1N2C] |
| K-2 | 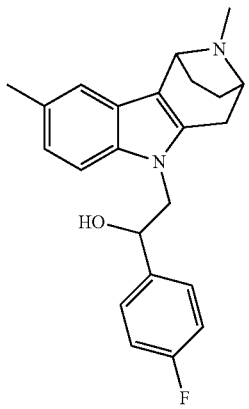 [SMILES: Cc1ccc2c(c1)c1c(n2CC(O)c2ccc(F)cc2)CC2CCC1N2C] |
| K-3 | 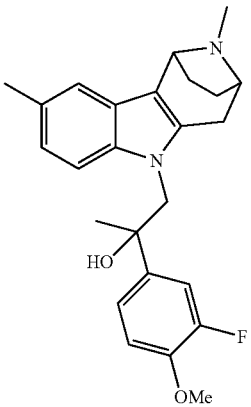 [SMILES: COc1ccc(C(C)(O)Cn2c3c(c4cc(C)ccc42)C2CCC(C3)N2C)cc1F] |
TABLE 3-continued
Representative Compounds According to the Invention.
| Comp. # | Compound Structure |
|---|---|
| K-4 | 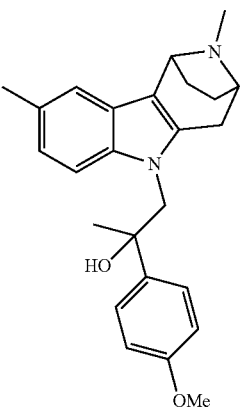 [SMILES: COc1ccc(C(C)(O)Cn2c3c(c4cc(C)ccc42)C2CCC(C3)N2C)cc1] |
| K-5 | 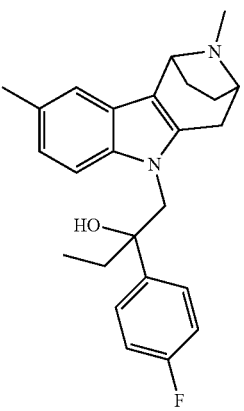 [SMILES: CCC(O)(Cn1c2c(c3cc(C)ccc31)C1CCC(C2)N1C)c1ccc(F)cc1] |
| K-6 | 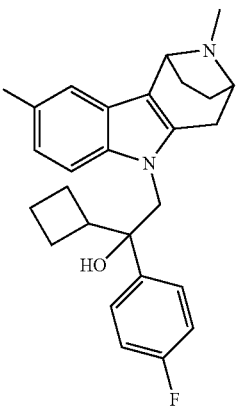 |

TABLE 3-continued

Representative Compounds According to the Invention.

| Comp. # | Compound Structure |
|---|---|
| K-7 | 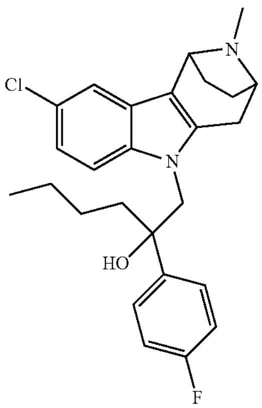 [SMILES: CCCCC(O)(Cn1c2c(c3cc(Cl)ccc31)C1CCC(C2)N1C)c1ccc(F)cc1] |
| K-8 | 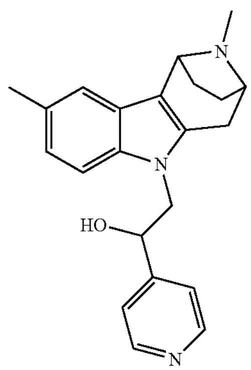 [SMILES: Cc1ccc2c(c1)c1c(n2CC(O)c2ccncc2)CC2CCC1N2C] |
| K-9 | 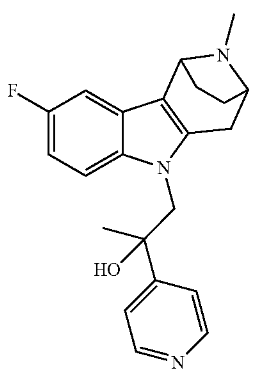 [SMILES: CN1C2CCC1c1c(n(CC(C)(O)c3ccncc3)c3ccc(F)cc13)C2] |
| K-10 | 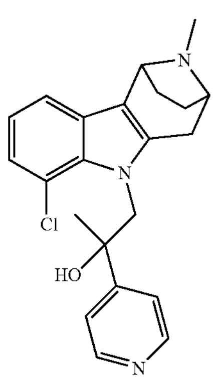 [SMILES: CN1C2CCC1c1c(n(CC(C)(O)c3ccncc3)c3c(Cl)cccc13)C2] |
| K-11 | |
| K-12 | |
| K-13 | |
| K-14 | |

TABLE 3-continued

Representative Compounds According to the Invention.

| Comp. # | Compound Structure |
|---|---|
| K-15 | 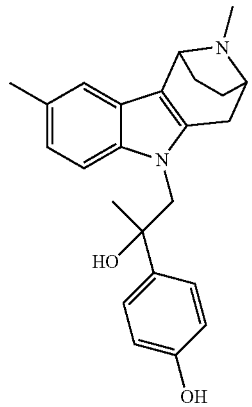 [SMILES: Cc1ccc2c(c1)c1c(n2CC(C)(O)c2ccc(O)cc2)CC2CCC1N2C] |
| K-16 | 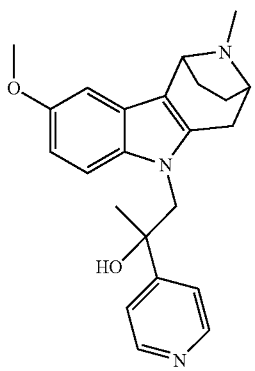 [SMILES: COc1ccc2c(c1)c1c(n2CC(C)(O)c2ccncc2)CC2CCC1N2C] |
| K-17 | 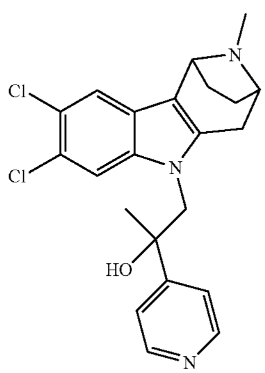 [SMILES: CN1C2CCC1c1c(n(CC(C)(O)c3ccncc3)c3cc(Cl)c(Cl)cc13)C2] |
| K-18 | 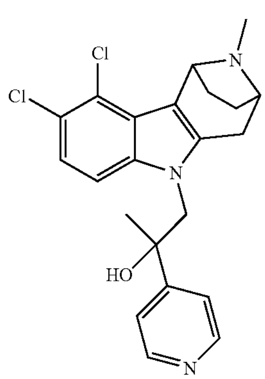 [SMILES: CN1C2CCC1c1c(n(CC(C)(O)c3ccncc3)c3ccc(Cl)c(Cl)c13)C2] |
| K-19 | |
| K-20 | |
| K-21 | |
| K-22 | |

TABLE 3-continued

Representative Compounds According to the Invention.

| Comp. # | Compound Structure |
|---|---|
| K-23 | 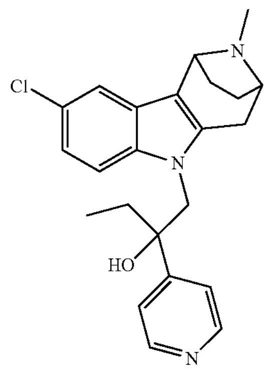 [SMILES: CCC(O)(Cn1c2c(c3cc(Cl)ccc31)C1CCC(C2)N1C)c1ccncc1] |
| K-24 | 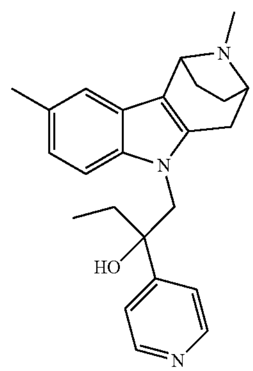 [SMILES: CCC(O)(Cn1c2c(c3cc(C)ccc31)C1CCC(C2)N1C)c1ccncc1] |
| K-25 | 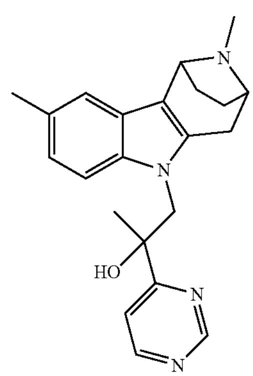 [SMILES: Cc1ccc2c(c1)c1c(n2CC(C)(O)c2ccncn2)CC2CCC1N2C] |
| K-26 | 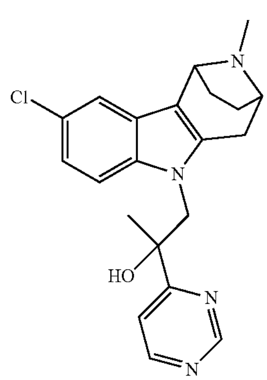 [SMILES: CN1C2CCC1c1c(n(CC(C)(O)c3ccncn3)c3ccc(Cl)cc13)C2] |
| K-27 | 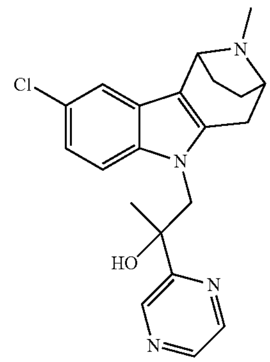 [SMILES: CN1C2CCC1c1c(n(CC(C)(O)c3cnccn3)c3ccc(Cl)cc13)C2] |
| K-28 | 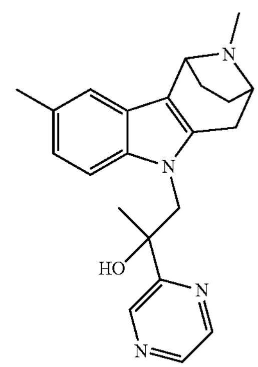 [SMILES: Cc1ccc2c(c1)c1c(n2CC(C)(O)c2cnccn2)CC2CCC1N2C] |
| K-29 | 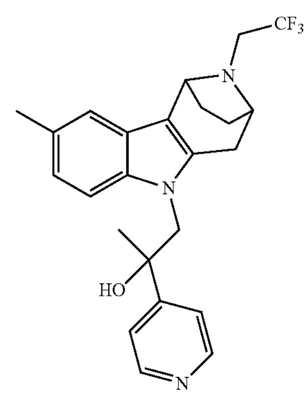 [SMILES: Cc1ccc2c(c1)c1c(n2CC(C)(O)c2ccncc2)CC2CCC1N2CC(F)(F)F] |
| K-30 | 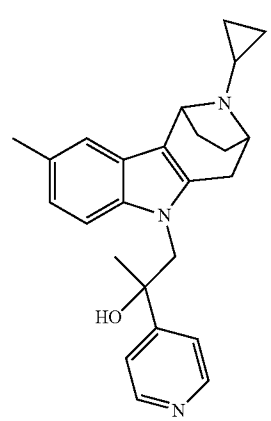 [SMILES: Cc1ccc2c(c1)c1c(n2CC(C)(O)c2ccncc2)CC2CCC1N2C1CC1] |

TABLE 3-continued
Representative Compounds According to the Invention.
| Comp. # | Compound Structure |
|---|---|
| K-31 | 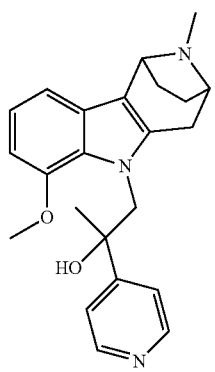 [SMILES: COc1cccc2c3c(n(CC(C)(O)c4ccncc4)c12)CC1CCC3N1C] |
| K-32 | 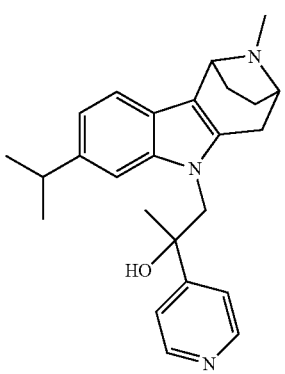 [SMILES: CC(C)c1ccc2c3c(n(CC(C)(O)c4ccncc4)c2c1)CC1CCC3N1C] |
| K-33 | 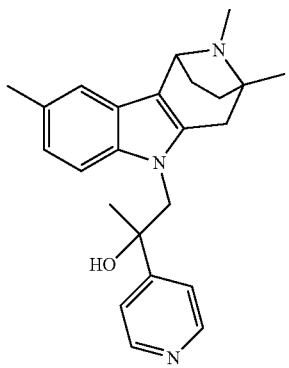 |
TABLE 3-continued
Representative Compounds According to the Invention.
| Comp. # | Compound Structure |
|---|---|
| K-34 | 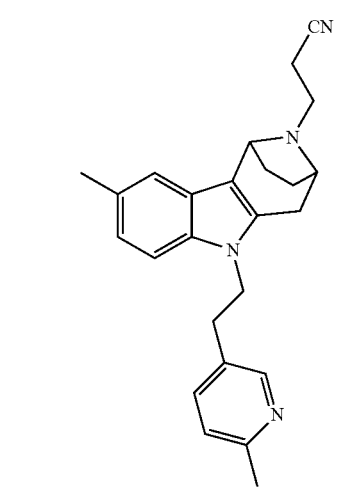 [SMILES: Cc1ccc2c(c1)c1c(n2CCc2ccc(C)nc2)CC2CCC1N2CCC#N] |
| K-35 | 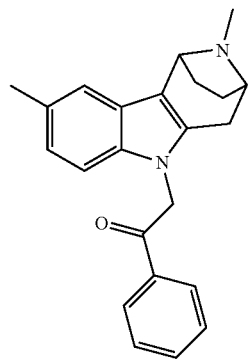 [SMILES: Cc1ccc2c(c1)c1c(n2CC(=O)c2ccccc2)CC2CCC1N2C] |
| K-36 | 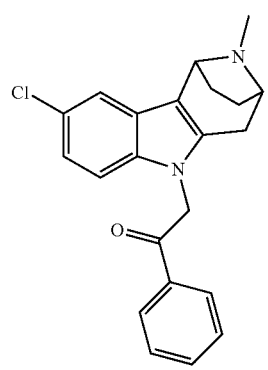 [SMILES: CN1C2CCC1c1c(n(CC(=O)c3ccccc3)c3ccc(Cl)cc13)C2] |

TABLE 3-continued
Representative Compounds According to the Invention.
| Comp. # | Compound Structure |
|---|---|
| K-37 | 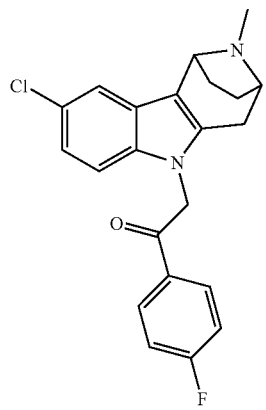 [SMILES: CN1C2CCC1c1c(n(CC(=O)c3ccc(F)cc3)c3ccc(Cl)cc13)C2] |
| K-38 | 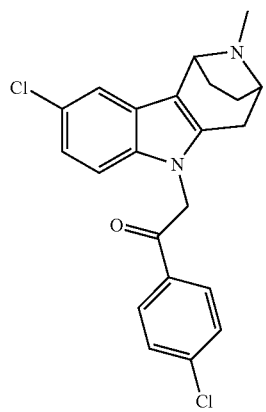 [SMILES: CN1C2CCC1c1c(n(CC(=O)c3ccc(Cl)cc3)c3ccc(Cl)cc13)C2] |
| K-39 | 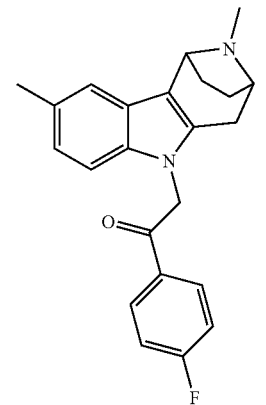 [SMILES: Cc1ccc2c(c1)c1c(n2CC(=O)c2ccc(F)cc2)CC2CCC1N2C] |
| K-40 | 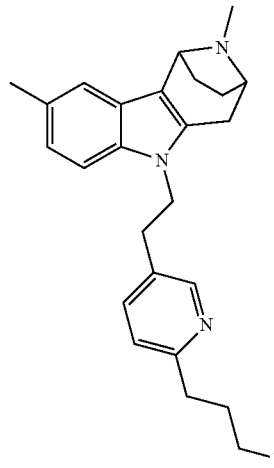 |
| K-41 | 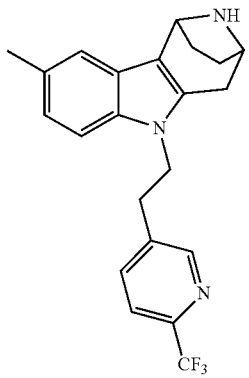 [SMILES: Cc1ccc2c(c1)c1c(n2CCc2ccc(C(F)(F)F)nc2)CC2CCC1N2] |
| K-42 | 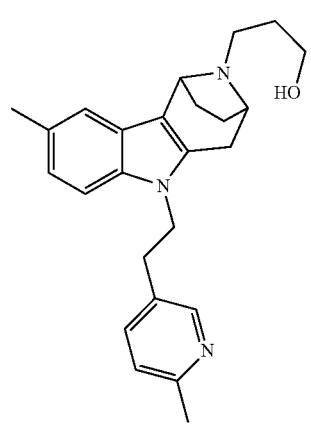 [SMILES: Cc1ccc2c(c1)c1c(n2CCc2ccc(C)nc2)CC2CCC1N2CCCO] |

TABLE 3-continued
Representative Compounds According to the Invention.
| Comp. # | Compound Structure |
|---|---|
| K-43 | 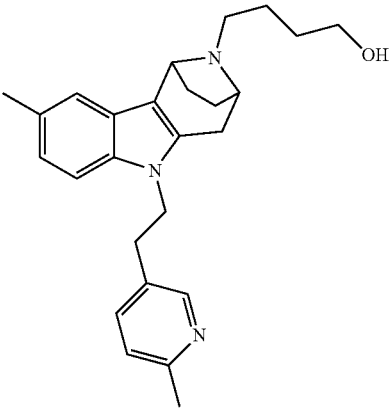 [SMILES: Cc1ccc2c(c1)c1c(n2CCc2ccc(C)nc2)CC2CCC1N2CCCCO] |
| K-44 | 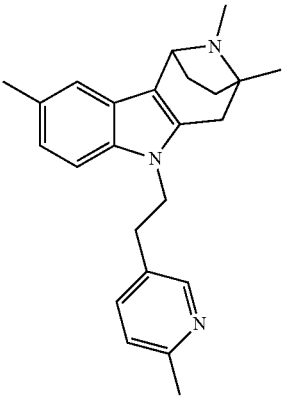 |
| K-45 | 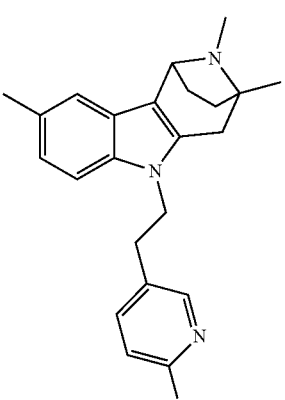 |
| K-46 | 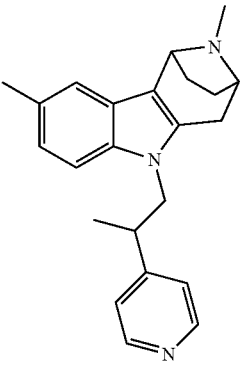 [SMILES: Cc1ccc2c(c1)c1c(n2CC(C)c2ccncc2)CC2CCC1N2C] |
| K-47 | 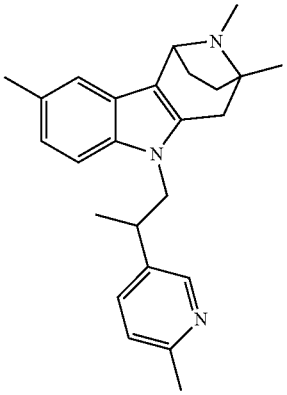 |
| K-48 | 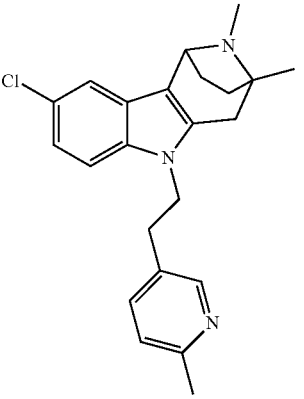 [SMILES: Cc1ccc(CCn2c3c(c4cc(Cl)ccc42)C2CCC(C)(C3)N2C)cn1] |
| K-49 | 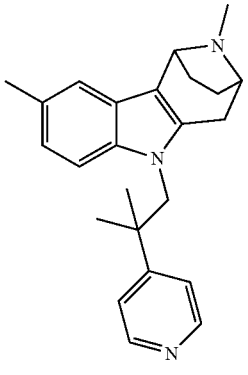 [SMILES: Cc1ccc2c(c1)c1c(n2CC(C)(C)c2ccncc2)CC2CCC1N2C] |

TABLE 3-continued
Representative Compounds According to the Invention.
| Comp. # | Compound Structure |
|---|---|
| K-50 | 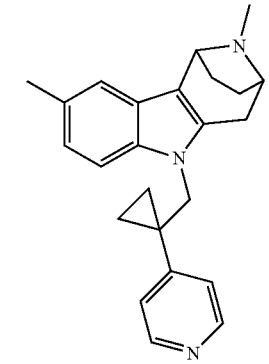 [SMILES: Cc1ccc2c(c1)c1c(n2CC2(c3ccncc3)CC2)CC2CCC1N2C] |
| K-51 | |
| K-52 | |
| K-53 | |
| K-54 | 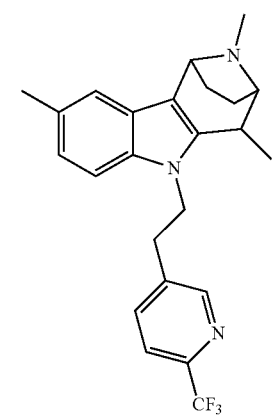 |
| K-55 | 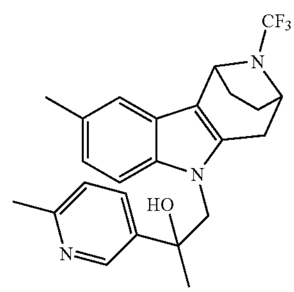 [SMILES: Cc1ccc2c(c1)c1c(n2CC(C)(O)c2ccc(C)nc2)CC2CCC1N2C(F)(F)F] |
| K-56 | 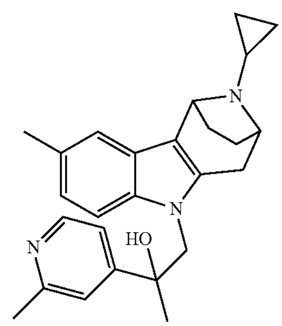 [SMILES: Cc1ccc2c(c1)c1c(n2CC(C)(O)c2ccnc(C)c2)CC2CCC1N2C1CC1] |
| K-57 | 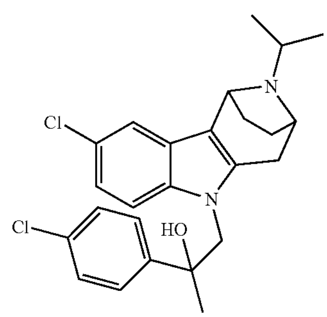 [SMILES: CC(C)N1C2CCC1c1c(n(CC(C)(O)c3ccc(Cl)cc3)c3ccc(Cl)cc13)C2] |
| K-58 | 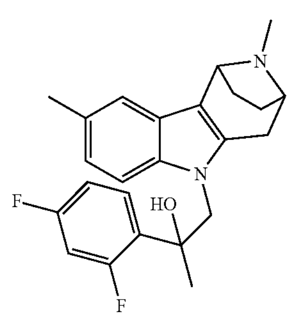 [SMILES: Cc1ccc2c(c1)c1c(n2CC(C)(O)c2ccc(F)cc2F)CC2CCC1N2C] |

TABLE 3-continued

Representative Compounds According to the Invention.

| Comp. # | Compound Structure |
|---|---|
| K-59 | 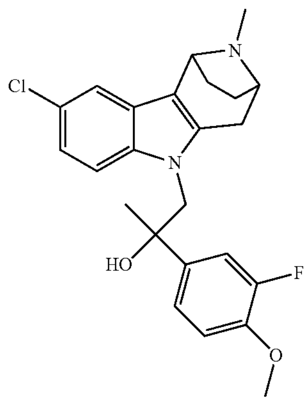 [SMILES: COc1ccc(C(C)(O)Cn2c3c(c4cc(Cl)ccc42)C2CCC(C3)N2C)cc1F] |
| K-60 | 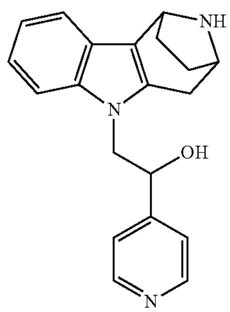 [SMILES: OC(Cn1c2c(c3ccccc31)C1CCC(C2)N1)c1ccncc1] |

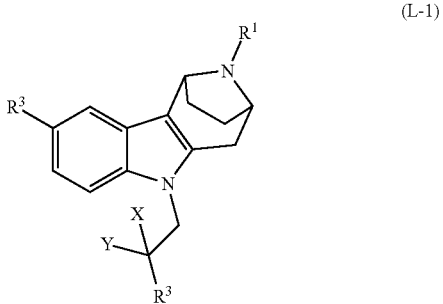

Compounds of the formula (L-1) are also provided:

(L-1)

wherein:

$R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

$R^2$ is H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

X is OH, H, $C_1$-$C_8$ unsubstituted alkyl or is taken together with Y to form a cyclic moiety of the formula —OCH$_2$CH$_2$O—;

Y is halo, substituted or unsubstituted aryl, substituted or unsubstituted heteroaryl, $C_1$-$C_8$ alkyl substituted with a carbonylalkoxy, carboxyl or acylamino moiety or is taken together with X to form a cyclic moiety of the formula —OCH$_2$CH$_2$O—; and $R^3$ is a substituted or unsubstituted aryl, substituted or unsubstituted heteroaryl, substituted or unsubstituted cycloalkyl, substituted or unsubstituted cycloalkenyl or a substituted or unsubstituted heterocyclyl;

or a salt or solvate thereof.

In one variation of formula (L-1), $R^1$ is $C_1$-$C_8$ unsubstituted alkyl; $R^2$ is $C_1$-$C_8$ unsubstituted alkyl, H or halo and $R^3$ is a substituted or unsubstituted aryl or a substituted or unsubstituted heteroaryl. In a particular variation of formula (L-1), $R^1$ is methyl, ethyl or isopropyl; $R^2$ is methyl, H or chloro and $R^3$ is a substituted or unsubstituted aryl or a substituted or unsubstituted heteroaryl. When $R^3$ is an unsubstituted aryl in one variation it is a phenyl moiety. When $R^3$ is a substituted aryl in one aspect it is a substituted phenyl. When $R^3$ is a substituted phenyl, the phenyl may be substituted with one or more than one substituent. For example, on one variation, $R^3$ is a monosubstituted phenyl where the substituent is a halo group. In another variation, $R^3$ is a disubstituted phenyl substituent with two halo groups which may be the same or different. In a particular variation, $R^3$ is 4-fluorophenyl, 2-fluorophenyl, 4-chlorophenyl, 2-chlorophenyl, 4-methoxyphenyl or 2,4-difluorophenyl. When $R^3$ is an unsubstituted heteroaryl in one variation it is a heteroaryl containing an annular nitrogen atom. In one aspect, when $R^3$ is unsubstituted heteroaryl the heteroaryl contains only nitrogen and carbon annular atoms. In a particular variation, $R^3$ is an unsubstituted heteroaryl selected from pyridyl or pyrimidinyl and wherein such groups may be bound to the parent structure at any available ring position. For example, in one variation, $R^3$ is 4-pyridyl, 3-pyridyl or 6-pyrimidyl. When $R^3$ is a substituted heteroaryl in one aspect it is a substituted pyridyl. When $R^3$ is a substituted pyridyl, the pyridyl may be substituted with one or more than one substituent and the substituted pyridyl may be bound to the parent structure at any available ring position. For example, on one variation, $R^3$ is a monosubstituted pyridyl where the substituent is a $C_1$-$C_8$ unsubstituted alkyl (e.g., methyl). In a particular variation, $R^3$ is 2-methyl-4-pyridyl, 6-methyl-3-pyridyl or 3-methyl-4-pyridyl.

In one variation of formula (L-1), X is OH and Y is an unsubstituted aryl. In one aspect, Y is phenyl. In another variation, X is H and Y is a $C_1$-$C_8$ alkyl substituted with a carbonylalkoxy, carboxyl or acylamino moiety. In one aspect, Y is a methylene substituted with a carbonylalkoxy, carboxyl or acylamino moiety. In a particular aspect, Y is a moiety selected from the following structures

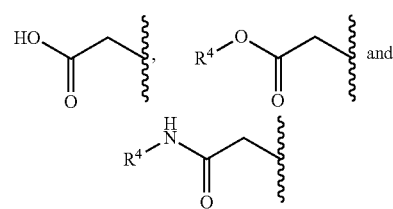

where $R^4$ is a $C_1$-$C_8$ unsubstituted alkyl. In one variation, Y is a moiety selected from the following structures

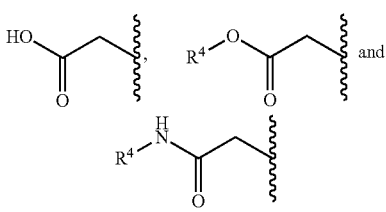

where $R^4$ is a $C_1$-$C_8$ unsubstituted alkyl and X is H. In another variation, X is an unsubstituted $C_1$-$C_8$ alkyl and Y is halo. In a particular aspect, Y is fluoro.

The invention also embraces compounds of the formula (L-2):

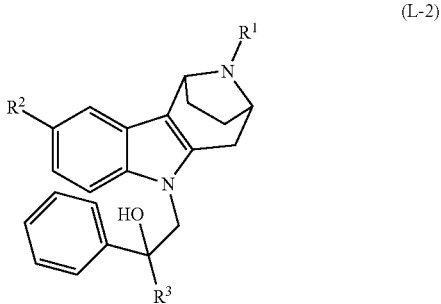

or a salt or solvate thereof, where $R^1$, $R^2$ and $R^3$ are as defined for formula (L-1). In one variation of formula (L-2), $R^1$ and $R^2$ are independently an unsubstituted $C_1$-$C_8$ alkyl. In another variation of formula (L-2), $R^3$ is a substituted aryl, such as a substituted phenyl group, or an unsubstituted heteroaryl, such as pyridyl. In one aspect, $R^3$ is a halo substituted phenyl or pyridyl moiety. When $R^3$ is a halo substituted phenyl, in a particular variation the phenyl is substituted with a fluoro that may be at any position on the phenyl ring. When $R^3$ is a pyridyl group it may be bound to the parent structure at any available ring position. In a particular aspect, $R^3$ is 4-pyridyl. In a particular variation of formula (L-2), $R^1$ and $R^2$ are independently an unsubstituted $C_1$-$C_8$ alkyl and $R^3$ is a substituted aryl or an unsubstituted heteroaryl. In one variation, $R^1$ and $R^2$ are each methyl and $R^3$ is a substituted aryl or unsubstituted heteroaryl. In a particular variation of formula (L-2), $R^1$ and $R^2$ are each methyl and $R^3$ is a fluoro substituted phenyl or pyridyl moiety.

The invention also embraces compounds of the formula (L-3):

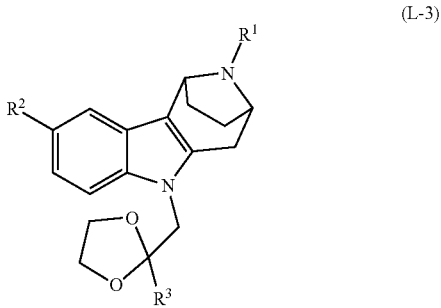

or a salt or solvate thereof, where $R^1$, $R^2$ and $R^3$ are as defined for formula (L-1). In one variation of formula (L-3), $R^1$ is an unsubstituted $C_1$-$C_8$ alkyl (e.g., methyl). In another variation of formula (L-3), $R^2$ is H, an unsubstituted $C_1$-$C_8$ alkyl (e.g., methyl) or halo (e.g., chloro). In one aspect of formula (L-3), $R^1$ is an unsubstituted $C_1$-$C_8$ alkyl and $R^2$ is H, an unsubstituted $C_1$-$C_8$ alkyl or halo. In a particular variation of formula (L-3), $R^1$ is methyl and $R^2$ is H, methyl or chloro. In one variation of formula (L-3), $R^1$ and $R^2$ are independently an unsubstituted $C_1$-$C_8$ alkyl such as methyl. In one variation of formula (L-3), $R^3$ is a substituted or unsubstituted aryl or a substituted or unsubstituted heteroaryl, such as those listed herein for formula (L-1). For example, compounds of the formula (L-3) are intended wherein $R^3$ is an unsubstituted aryl, which in one variation is a phenyl moiety. Compounds of the formula (L-3) are also intended wherein $R^3$ is a substituted aryl, which in one aspect it is a substituted phenyl. When $R^3$ is a substituted phenyl, the phenyl may be substituted with one or more than one substituent. For example, on one variation, $R^3$ is a monosubstituted phenyl where the substituent is a halo group. In another variation, $R^3$ is a disubstituted phenyl substituent with two halo groups which may be the same or different. In a particular variation, $R^3$ is 4-fluorophenyl, 2-fluorophenyl, 4-chlorophenyl, 2-chlorophenyl, 4-methoxyphenyl or 2,4-difluorophenyl. Compounds of formula (L-3) are provided where $R^3$ is an unsubstituted heteroaryl, which in one variation is a heteroaryl containing an annular nitrogen atom. In one aspect, when $R^3$ is unsubstituted heteroaryl the heteroaryl contains only nitrogen and carbon annular atoms. In a particular variation of formula (L-3), $R^3$ is an unsubstituted heteroaryl selected from pyridyl or pyrimidinyl and wherein such groups may be bound to the parent structure at any available ring position. For example, in one variation of formula (L-3), $R^3$ is 4-pyridyl, 3-pyridyl or 6-pyrimidyl. When $R^3$ is a substituted heteroaryl in one aspect it is a substituted pyridyl. When $R^3$ is a substituted pyridyl, the pyridyl may be substituted with one or more than one substituent and the substituted pyridyl may be bound to the parent structure at any available ring position. For example, in one variation of formula (L-3), $R^3$ is a monosubstituted pyridyl where the substituent is a $C_1$-$C_8$ unsubstituted alkyl (e.g., methyl). In a particular variation of formula (L-3), $R^3$ is 2-methyl-4-pyridyl, 6-methyl-3-pyridyl or 3-methyl-4-pyridyl. In another variation of formula (L-3), $R^3$ is a substituted aryl, such as a substituted phenyl group. In one aspect, $R^3$ is a halo substituted phenyl. When $R^3$ is a halo substituted phenyl, in a particular variation the phenyl is substituted with a fluoro or chloro that may be at any position on the phenyl ring. In a further variation of formula (L-3), $R^1$ is an unsubstituted $C_1$-$C_8$ alkyl; $R^2$ is H, an unsubstituted $C_1$-$C_8$ alkyl or halo and $R^3$ is a substituted or unsubstituted phenyl, a substituted or unsubstituted pyridyl or an unsubstituted pyrimidyl. In a particular variation, compounds of formula (L-3) are provided where $R^1$ is methyl, $R^2$ is H, methyl or chloro and $R^3$ is a substituted or unsubstituted phenyl, a substituted or unsubstituted pyridyl or an unsubstituted pyrimidyl.

Compounds of the formula (L-4) are also provided:

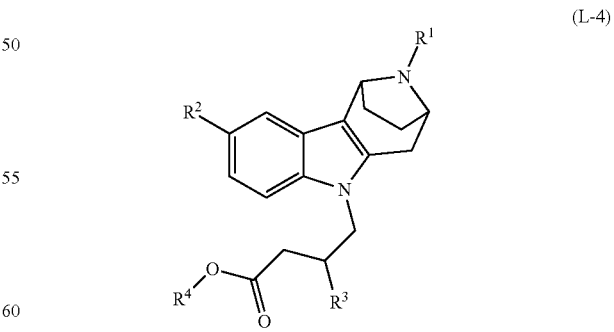

or a salt or solvate thereof, where $R^1$, $R^2$ and $R^3$ are as detailed for formula (L-1) and $R^4$ is an unsubstituted $C_1$-$C_8$ alkyl. In one variation of formula (L-4), $R^1$ is an unsubstituted $C_1$-$C_8$ alkyl. In one variation of formula (L-4), $R_2$ is an unsubstituted $C_1$-$C_8$ alkyl or halo. In one variation of formula (L-4), $R^1$ and $R^2$ are independently an unsubstituted $C_1$-$C_8$ alkyl (e.g., methyl or ethyl). In one variation of formula (L-4), $R^1$ is an unsubstituted $C_1$-$C_8$ alkyl (e.g., methyl or ethyl) and $R^2$ is an unsubstituted $C_1$-$C_8$ alkyl or halo. In a particular variation of formula (L-4), $R^4$ is a $C_1$-$C_4$ unsubstituted alkyl. In a further variation of formula (L-4), $R^4$ is methyl, ethyl, propyl or butyl. In one aspect, $R^4$ is iso-propyl. In another aspect, $R^4$ is tert-butyl. In a particular variation of formula (L-4), $R^1$ is an unsubstituted $C_1$-$C_8$ alkyl; $R^2$ is an unsubstituted $C_1$-$C_8$ alkyl or halo and $R^4$ is a $C_1$-$C_4$ unsubstituted alkyl. In another variation of formula (L-4), $R^3$ is a substituted or unsubstituted aryl or a substituted or unsubstituted heteroaryl, such as those listed herein for formula (L-1). For example, compounds of the formula (L-4) are intended wherein $R^3$ is a substituted aryl, which in one aspect it is a substituted phenyl. When $R^3$ is a substituted phenyl, the phenyl may be substituted with one or more than one substituent. For example, on one variation, $R^3$ is a monosubstituted phenyl where the substituent is a halo group. In another variation, $R^3$ is a dihalosubstituted phenyl wherein the halo moieties may be the same or different. In a particular variation, $R^3$ is 4-fluorophenyl, 4-chlorophenyl, 2,4-difluorophenyl or 4-methoxyphenyl. Compounds of formula (L-4) are also provided where $R^3$ is an unsubstituted heteroaryl, which in one variation is a heteroaryl containing an annular nitrogen atom. In one aspect, when $R^3$ is unsubstituted heteroaryl the heteroaryl contains only nitrogen and carbon annular atoms. In a particular variation of formula (L-4), $R^3$ is an unsubstituted heteroaryl selected from pyridyl or pyrimidinyl and wherein such groups may be bound to the parent structure at any available ring position. For example, in one variation of formula (L-4), $R^3$ is 4-pyridyl, 3-pyridyl or 6-pyrimidyl. When $R^3$ is a substituted heteroaryl in one aspect it is a substituted pyridyl. When $R^3$ is a substituted pyridyl, the pyridyl may be substituted with one or more than one substituent and the substituted pyridyl may be bound to the parent structure at any available ring position. For example, in one variation of formula (L-4), $R^3$ is a monosubstituted pyridyl where the substituent is a $C_1$-$C_8$ unsubstituted alkyl (e.g., methyl). In a particular variation of formula (L-4), $R^3$ is 2-methyl-4-pyridyl, 6-methyl-3-pyridyl or 3-methyl-4-pyridyl. In a further variation of formula (L-4), $R^1$ is an unsubstituted $C_1$-$C_8$ alkyl; $R^2$ is an unsubstituted $C_1$-$C_8$ alkyl or halo; $R^4$ is a $C_1$-$C_4$ unsubstituted alkyl and $R^3$ is a substituted phenyl, a substituted or unsubstituted pyridyl or an unsubstituted pyrimidyl. In a particular variation, compounds of formula (L-4) are provided where $R^1$ is methyl or ethyl, $R^2$ is methyl or chloro; $R^4$ is methyl, ethyl, isopropyl or tert-butyl and $R^3$ is a substituted phenyl, a substituted or unsubstituted pyridyl or an unsubstituted pyrimidyl.

Also provided herein are compounds of the formula (L-5):

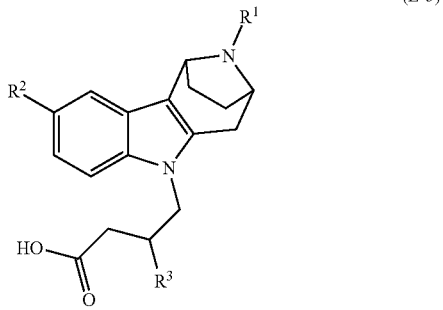

(L-5)

or a salt of solvate thereof, where $R^1$, $R^2$ and $R^3$ are as detailed for formula (L-1). In one variation of formula (L-5), $R^1$ is an unsubstituted $C_1$-$C_8$ alkyl (e.g., methyl). In another variation of formula (L-5), $R^2$ is unsubstituted $C_1$-$C_8$ alkyl (e.g., methyl) or halo (e.g., chloro). In a particular variation of formula (L-5), $R^1$ is an unsubstituted $C_1$-$C_8$ alkyl and $R^2$ is unsubstituted $C_1$-$C_8$ alkyl or halo. In another variation of formula (L-5), $R^1$ and $R^2$ are independently an unsubstituted $C_1$-$C_8$ alkyl (e.g., methyl). In one variation of formula (L-5), $R^3$ is a substituted or unsubstituted aryl or a substituted or unsubstituted heteroaryl, such as those listed herein for formula (L-1). For example, compounds of the formula (L-5) are intended wherein $R^3$ is a substituted aryl, which in one aspect it is a substituted phenyl. When $R^3$ is a substituted phenyl, the phenyl may be substituted with one or more than one substituent. For example, on one variation, $R^3$ is a monosubstituted phenyl where the substituent is a halo group. In another variation, $R^3$ is a disubstituted phenyl substituent with two halo groups which may be the same or different. In a particular variation, $R^3$ is 4-fluorophenyl, 2-fluorophenyl, 4-chlorophenyl, 4-methoxyphenyl or 2,4-difluorophenyl. Compounds of formula (L-5) are also provided where $R^3$ is an unsubstituted heteroaryl, which in one variation is a heteroaryl containing an annular nitrogen atom. In one aspect, when $R^3$ is unsubstituted heteroaryl the heteroaryl contains only nitrogen and carbon annular atoms. In a particular variation of formula (L-5), $R^3$ is an unsubstituted heteroaryl selected from pyridyl or pyrimidinyl and wherein such groups may be bound to the parent structure at any available ring position. For example, in one variation of formula (L-5), $R^3$ is 4-pyridyl, 3-pyridyl or 6-pyrimidyl. When $R^3$ is a substituted heteroaryl in one aspect it is a substituted pyridyl. When $R^3$ is a substituted pyridyl, the pyridyl may be substituted with one or more than one substituent and the substituted pyridyl may be bound to the parent structure at any available ring position. For example, in one variation of formula (L-5), $R^3$ is a monosubstituted pyridyl where the substituent is a $C_1$-$C_8$ unsubstituted alkyl (e.g., methyl). In a particular variation of formula (L-5), $R^3$ is 2-methyl-4-pyridyl, 6-methyl-3-pyridyl or 3-methyl-4-pyridyl. In one variation of formula (L-5), $R^1$ is an unsubstituted $C_1$-$C_8$ alkyl, $R^2$ is unsubstituted $C_1$-$C_8$ alkyl or halo and $R^3$ is a substituted phenyl, a substituted or unsubstituted pyridyl or an unsubstituted pyrimidyl. In a particular variation of formula (L-5), $R^1$ and $R^2$ are independently an unsubstituted $C_1$-$C_8$ alkyl and $R^3$ is a substituted phenyl, a substituted or unsubstituted pyridyl or an unsubstituted pyrimidyl.

Additional compounds detailed herein are of the formula (L-6):

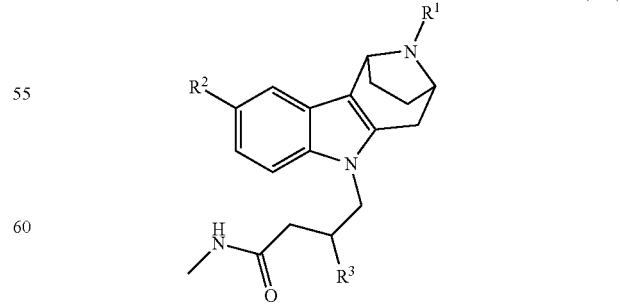

(L-6)

or a salt of solvate thereof, where $R^1$, $R^2$ and $R^3$ are as detailed for formula (L-1). In one variation of formula (L-6), $R^1$ is an unsubstituted $C_1$-$C_8$ alkyl (e.g., methyl or ethyl). In another variation of formula (L-6), $R^2$ is unsubstituted $C_1$-$C_8$ alkyl (e.g., methyl) or halo (e.g., chloro). In a particular variation of formula (L-6), $R^1$ is an unsubstituted $C_1$-$C_8$ alkyl and $R^2$ is unsubstituted $C_1$-$C_8$ alkyl or halo. In another variation of formula (L-6), $R^1$ and $R^2$ are independently an unsubstituted $C_1$-$C_8$ alkyl. In one variation of formula (L-6), $R^3$ is a substituted or unsubstituted aryl or a substituted or unsubstituted heteroaryl, such as those listed herein for formula (L-1). For example, compounds of the formula (L-6) are intended wherein $R^3$ is a substituted aryl, which in one aspect it is a substituted phenyl. When $R^3$ is a substituted phenyl, the phenyl may be substituted with one or more than one substituent. For example, on one variation, $R^3$ is a monosubstituted phenyl where the substituent is a halo group. In another variation, $R^3$ is a disubstituted phenyl substituent with two halo groups which may be the same or different. In a particular variation, $R^3$ is 4-fluorophenyl, 2-fluorophenyl, 4-chlorophenyl, 4-methoxyphenyl or 2,4-difluorophenyl. Compounds of formula (L-6) are also provided where $R^3$ is an unsubstituted heteroaryl, which in one variation is a heteroaryl containing an annular nitrogen atom. In one aspect, when $R^3$ is unsubstituted heteroaryl the heteroaryl contains only nitrogen and carbon annular atoms. In a particular variation of formula (L-6), $R^3$ is an unsubstituted heteroaryl selected from pyridyl or pyrimidinyl and wherein such groups may be bound to the parent structure at any available ring position. For example, in one variation of formula (L-6), $R^3$ is 4-pyridyl, 3-pyridyl or 6-pyrimidyl. When $R^3$ is a substituted heteroaryl in one aspect it is a substituted pyridyl. When $R^3$ is a substituted pyridyl, the pyridyl may be substituted with one or more than one substituent and the substituted pyridyl may be bound to the parent structure at any available ring position. For example, in one variation of formula (L-6), $R^3$ is a monosubstituted pyridyl where the substituent is a $C_1$-$C_8$ unsubstituted alkyl (e.g., methyl). In a particular variation of formula (L-6), $R^3$ is 2-methyl-4-pyridyl, 6-methyl-3-pyridyl or 3-methyl-4-pyridyl. In one variation of formula (L-6), $R^1$ is an unsubstituted $C_1$-$C_8$ alkyl, $R^2$ is unsubstituted $C_1$-$C_8$ alkyl or halo and $R^3$ is a substituted phenyl, a substituted or unsubstituted pyridyl or an unsubstituted pyrimidyl.

Compounds of the formula (L-7) are also detailed herein:

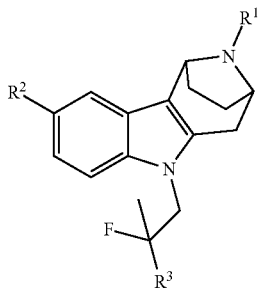

(L-7)

or a salt or solvate thereof, where $R^1$, $R^2$ and $R^3$ are as defined for formula (L-1). In one variation of formula (L-7), $R^1$ is an unsubstituted $C_1$-$C_8$ alkyl (e.g., methyl, ethyl or isopropyl). In another variation of formula (L-7), $R^2$ is unsubstituted $C_1$-$C_8$ alkyl (e.g., methyl) or halo (e.g., chloro). In a particular variation of formula (L-7), $R^1$ is an unsubstituted $C_1$-$C_8$ alkyl and $R^2$ is unsubstituted $C_1$-$C_8$ alkyl or halo. In another variation of formula (L-7), $R^1$ and $R^2$ are independently an unsubstituted $C_1$-$C_8$ alkyl. In one variation of formula (L-7), $R^3$ is a substituted or unsubstituted aryl or a substituted or unsubstituted heteroaryl, such as those listed herein for formula (L-1). For example, compounds of the formula (L-7) are intended wherein $R^3$ is a substituted aryl, which in one aspect it is a substituted phenyl. When $R^3$ is a substituted phenyl, the phenyl may be substituted with one or more than one substituent. For example, on one variation, $R^3$ is a monosubstituted phenyl where the substituent is a halo group. In another variation, $R^3$ is a disubstituted phenyl substituent with two halo groups which may be the same or different. In a particular variation, $R^3$ is 4-fluorophenyl, 4-chlorophenyl, 4-methoxyphenyl or 2,4-difluorophenyl. Compounds of formula (L-7) are also provided where $R^3$ is an unsubstituted heteroaryl, which in one variation is a heteroaryl containing an annular nitrogen atom. In one aspect, when $R^3$ is unsubstituted heteroaryl the heteroaryl contains only nitrogen and carbon annular atoms. In a particular variation of formula (L-7), $R^3$ is an unsubstituted heteroaryl selected from pyridyl or pyrimidinyl and wherein such groups may be bound to the parent structure at any available ring position. For example, in one variation of formula (L-7), $R^3$ is 4-pyridyl, 3-pyridyl or 6-pyrimidyl. When $R^3$ is a substituted heteroaryl in one aspect it is a substituted pyridyl. When $R^3$ is a substituted pyridyl, the pyridyl may be substituted with one or more than one substituent and the substituted pyridyl may be bound to the parent structure at any available ring position. For example, in one variation of formula (L-7), $R^3$ is a monosubstituted pyridyl where the substituent is a $C_1$-$C_8$ unsubstituted alkyl (e.g., methyl). In a particular variation of formula (L-7), $R^3$ is 6-methyl-3-pyridyl or 3-methyl-4-pyridyl. In one variation of formula (L-7), $R^1$ is an unsubstituted $C_1$-$C_8$ alkyl, $R^2$ is unsubstituted $C_1$-$C_8$ alkyl or halo and $R^3$ is a substituted phenyl, a substituted or unsubstituted pyridyl or an unsubstituted pyrimidyl.

Compounds of the formula (L-8) are also provided:

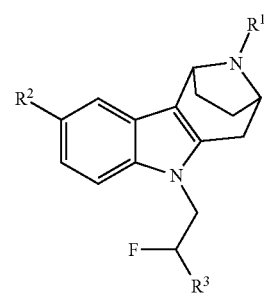

(L-8)

or a salt or solvate thereof, where $R^1$, $R^2$ and $R^3$ are as defined for formula (L-1). In one variation of formula (L-8), $R^1$ and $R^2$ are each a $C_1$-$C_8$ unsubstituted alkyl group. In another variation of formula (L-8), $R^3$ is an unsubstituted heteroaryl such as pyridyl. In a particular variation of formula (L-8), $R^1$ and $R^2$ are each a $C_1$-$C_8$ unsubstituted alkyl group and $R^3$ is an unsubstituted heteroaryl.

Examples of compounds according to the invention are depicted in Table 4. The compounds depicted may be present as salts even if salts are not depicted and it is understood that the invention embraces all salts and solvates of the compounds depicted here, as well as the non-salt and non-solvate form of the compound, as is well understood by the skilled artisan.

TABLE 4
Representative Compounds According to the Invention.
| Comp. # | Compound Structure |
|---|---|
| L-1 | 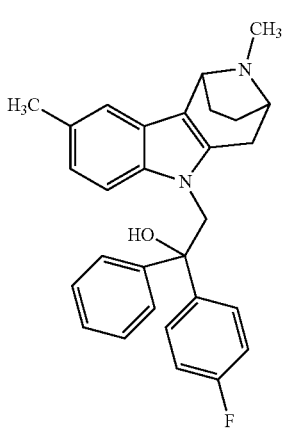 [SMILES: Cc1ccc2c(c1)c1c(n2CC(O)(c2ccccc2)c2ccc(F)cc2)CC2CCC1N2C] |
| L-2 | 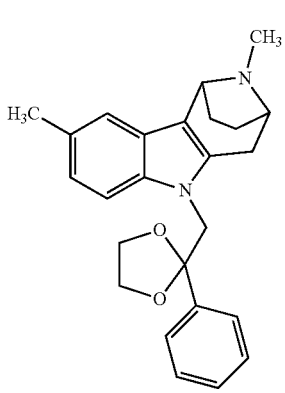 [SMILES: Cc1ccc2c(c1)c1c(n2CC2(c3ccccc3)OCCO2)CC2CCC1N2C] |
| L-3 | 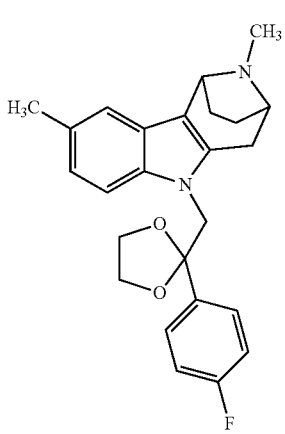 [SMILES: Cc1ccc2c(c1)c1c(n2CC2(c3ccc(F)cc3)OCCO2)CC2CCC1N2C] |
TABLE 4-continued
Representative Compounds According to the Invention.
| Comp. # | Compound Structure |
|---|---|
| L-4 | 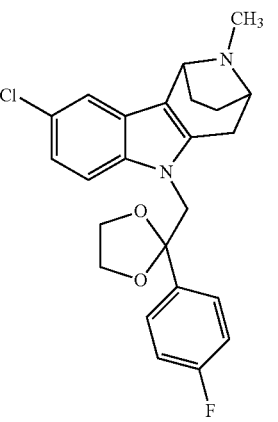 [SMILES: CN1C2CCC1c1c(n(CC3(c4ccc(Cl)cc4)OCCO3)c3ccc(Cl)cc13)C2] |
| L-5 | 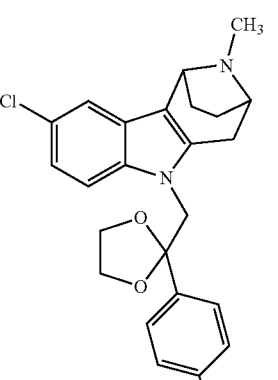 |
| L-6 | 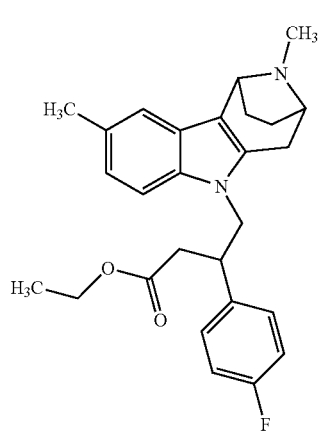 [SMILES: CCOC(=O)CC(Cn1c2c(c3cc(C)ccc31)C1CCC(C2)N1C)c1ccc(F)cc1] |

TABLE 4-continued
Representative Compounds According to the Invention.
| Comp. # | Compound Structure |
|---|---|
| L-7 | 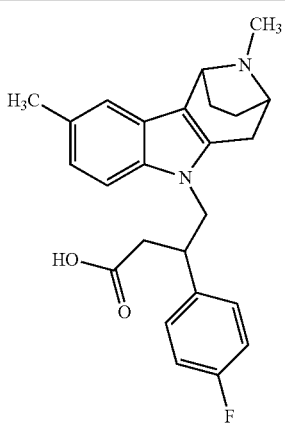 [SMILES: Cc1ccc2c(c1)c1c(n2CC(CC(=O)O)c2ccc(F)cc2)CC2CCC1N2C] |
| L-8 | 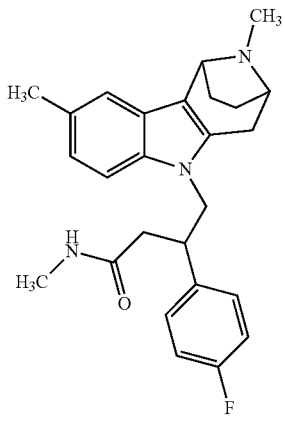 [SMILES: CNC(=O)CC(Cn1c2c(c3cc(C)ccc31)C1CCC(C2)N1C)c1ccc(F)cc1] |
| L-9 | 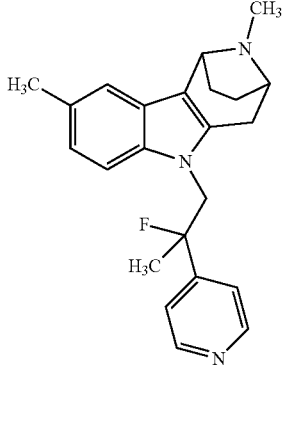 [SMILES: Cc1ccc2c(c1)c1c(n2CC(C)(F)c2ccncc2)CC2CCC1N2C] |
| L-10 | 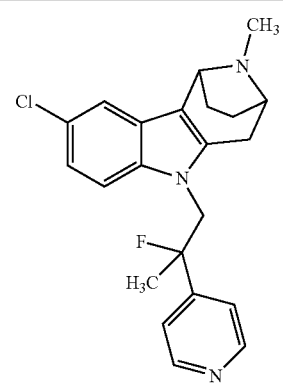 [SMILES: CN1C2CCC1c1c(n(CC(C)(F)c3ccncc3)c3ccc(Cl)cc13)C2] |
| L-11 | 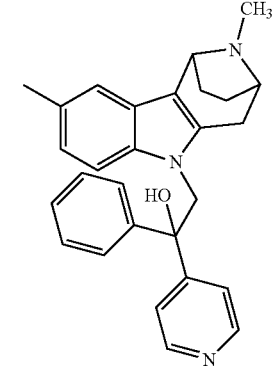 [SMILES: Cc1ccc2c(c1)c1c(n2CC(O)(c2ccccc2)c2ccncc2)CC2CCC1N2C] |
| L-12 | 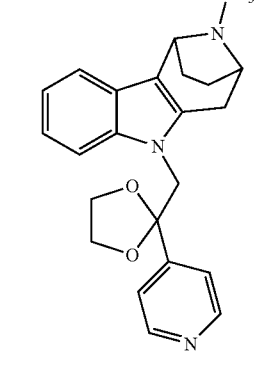 |
| L-13 | 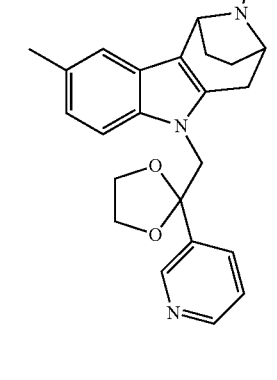 |

TABLE 4-continued
Representative Compounds According to the Invention.
| Comp. # | Compound Structure |
|---|---|
| L-14 | 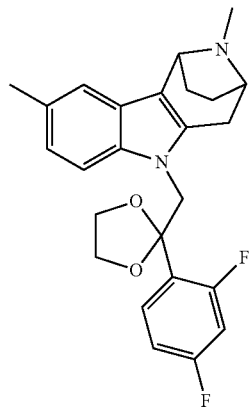 [SMILES: Cc1ccc2c(c1)c1c(n2CC2(c3ccc(F)cc3F)OCCO2)CC2CCC1N2C] |
| L-15 | 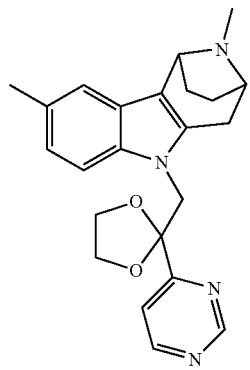 [SMILES: Cc1ccc2c(c1)c1c(n2CC2(c3ccncn3)OCCO2)CC2CCC1N2C] |
| L-16 | 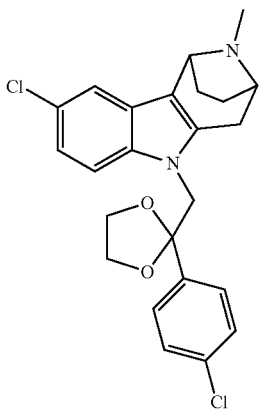 |
| L-17 | 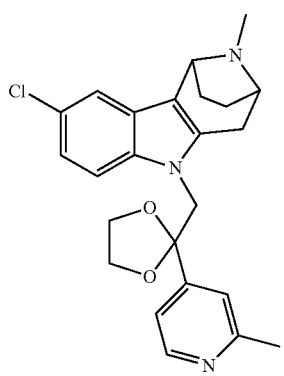 [SMILES: Cc1cc(C2(Cn3c4c(c5cc(Cl)ccc53)C3CCC(C4)N3C)OCCO2)ccn1] |
| L-18 | 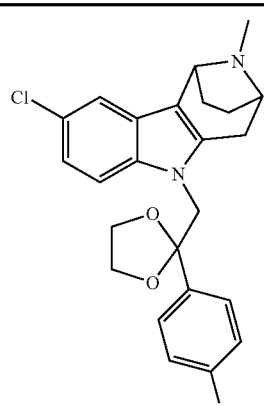 |
| L-19 | 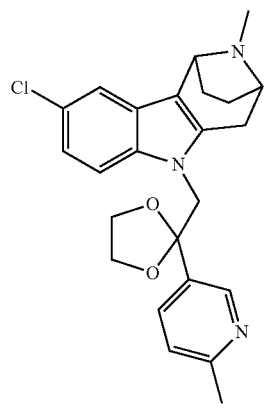 [SMILES: Cc1ccc(C2(Cn3c4c(c5cc(Cl)ccc53)C3CCC(C4)N3C)OCCO2)cn1] |
| L-20 | 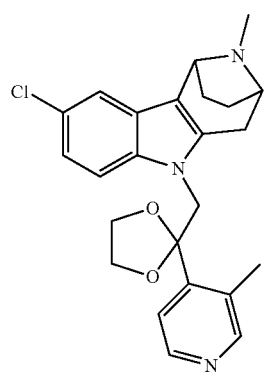 [SMILES: Cc1cnccc1C1(Cn2c3c(c4cc(Cl)ccc42)C2CCC(C3)N2C)OCCO1] |

TABLE 4-continued
Representative Compounds According to the Invention.
| Comp. # | Compound Structure |
|---|---|
| L-21 | 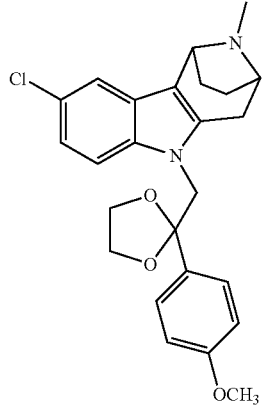 [SMILES: COc1ccc(C2(Cn3c4c(c5cc(Cl)ccc53)C3CCC(C4)N3C)OCCO2)cc1] |
| L-22 | 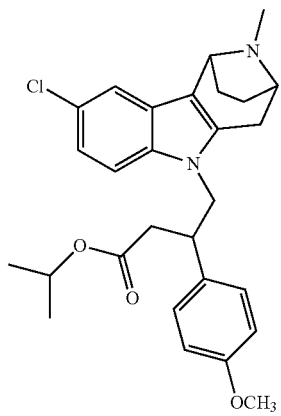 [SMILES: COc1ccc(C(CC(=O)OC(C)C)Cn2c3c(c4cc(Cl)ccc42)C2CCC(C3)N2C)cc1] |
| L-23 | 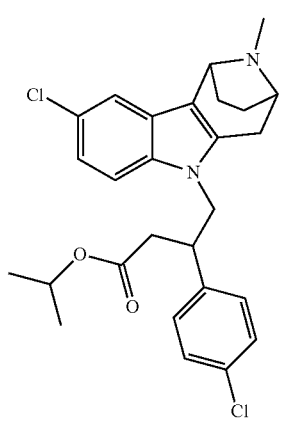 [SMILES: CC(C)OC(=O)CC(Cn1c2c(c3cc(Cl)ccc31)C1CCC(C2)N1C)c1ccc(Cl)cc1] |
| L-24 | 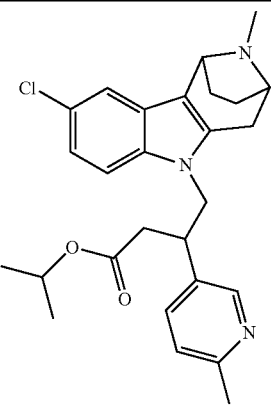 |
| L-25 | 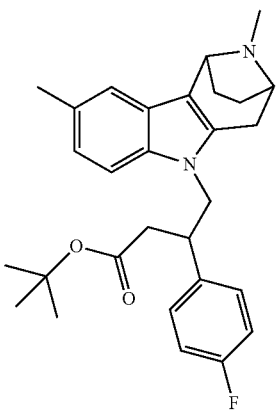 [SMILES: Cc1ccc2c(c1)c1c(n2CC(CC(=O)OC(C)(C)C)c2ccc(F)cc2)CC2CCC1N2C] |
| L-26 | 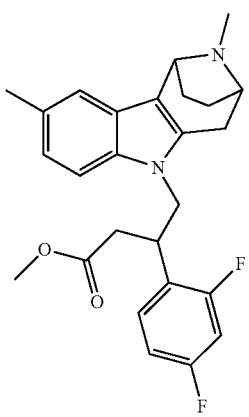 [SMILES: COC(=O)CC(Cn1c2c(c3cc(C)ccc31)C1CCC(C2)N1C)c1ccc(F)cc1F] |

TABLE 4-continued
Representative Compounds According to the Invention.
| Comp. # | Compound Structure |
|---|---|
| L-27 | 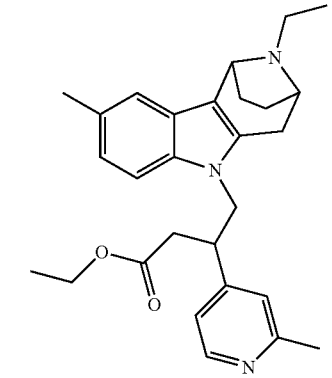 |
| L-28 | 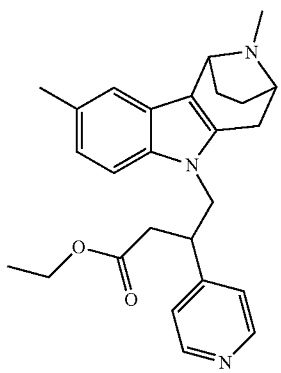 [SMILES: CCOC(=O)CC(Cn1c2c(c3cc(C)ccc31)C1CCC(C2)N1C)c1ccncc1] |
| L-29 | 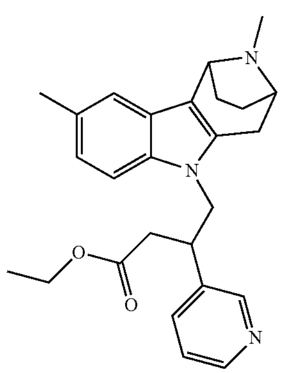 [SMILES: CCOC(=O)CC(Cn1c2c(c3cc(C)ccc31)C1CCC(C2)N1C)c1cccnc1] |
| L-30 | 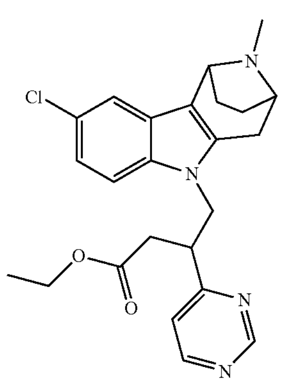 [SMILES: CCOC(=O)CC(Cn1c2c(c3cc(Cl)ccc31)C1CCC(C2)N1C)c1ccncn1] |
| L-31 | 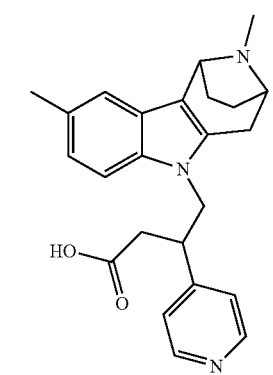 [SMILES: Cc1ccc2c(c1)c1c(n2CC(CC(=O)O)c2ccncc2)CC2CCC1N2C] |
| L-32 | |
| L-33 | |
| L-34 | |

TABLE 4-continued
Representative Compounds According to the Invention.
| Comp. # | Compound Structure |
|---|---|
| L-35 | 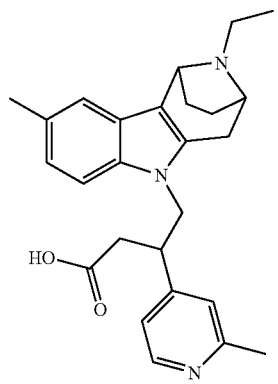 [SMILES: CCN1C2CCC1c1c(n(CC(CC(=O)O)c3ccnc(C)c3)c3ccc(C)cc13)C2] |
| L-36 | 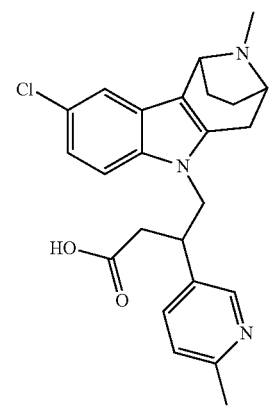 [SMILES: Cc1ccc(C(CC(=O)O)Cn2c3c(c4cc(Cl)ccc42)C2CCC(C3)N2C)cn1] |
| L-37 | 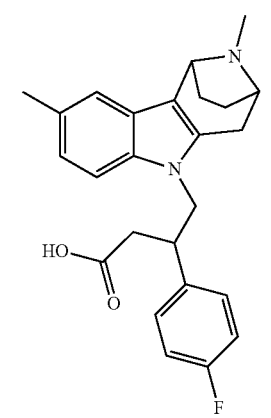 [SMILES: Cc1ccc2c(c1)c1c(n2CC(CC(=O)O)c2ccc(F)cc2)CC2CCC1N2C] |
| L-38 | 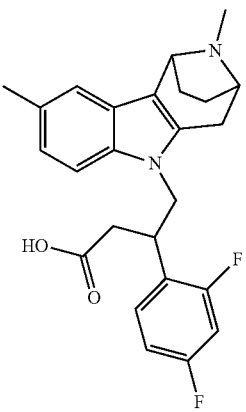 [SMILES: Cc1ccc2c(c1)c1c(n2CC(CC(=O)O)c2ccc(F)cc2F)CC2CCC1N2C] |
| L-39 | 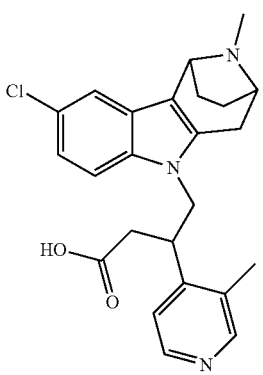 [SMILES: Cc1cnccc1C(CC(=O)O)Cn1c2c(c3cc(Cl)ccc31)C1CCC(C2)N1C] |
| L-40 | 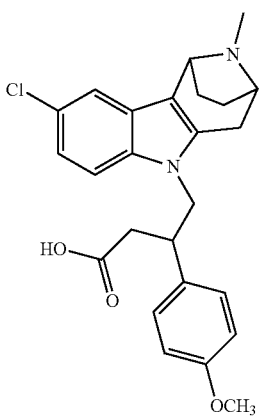 [SMILES: COc1ccc(C(CC(=O)O)Cn2c3c(c4cc(Cl)ccc42)C2CCC(C3)N2C)cc1] |

TABLE 4-continued
Representative Compounds According to the Invention.
| Comp. # | Compound Structure |
|---|---|
| L-41 | 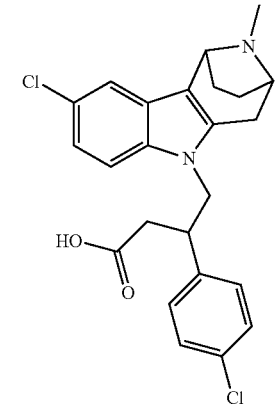 [SMILES: CN1C2CCC1c1c(n(CC(CC(=O)O)c3ccc(Cl)cc3)c3ccc(Cl)cc13)C2] |
| L-42 | 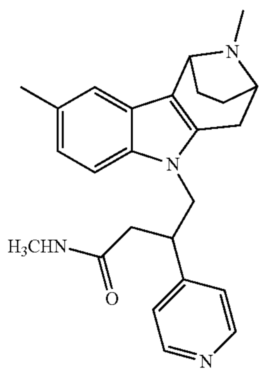 |
| L-43 | 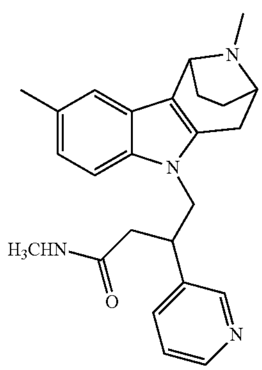 |
| L-44 | 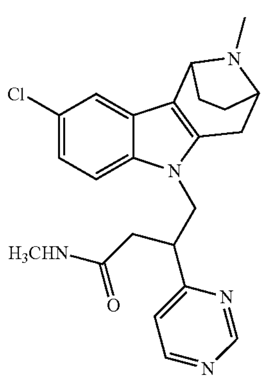 |
| L-45 | 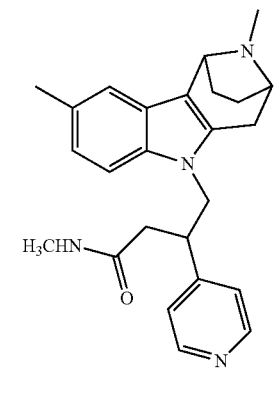 |
| L-46 | 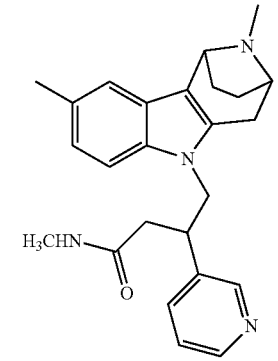 |
| L-47 | 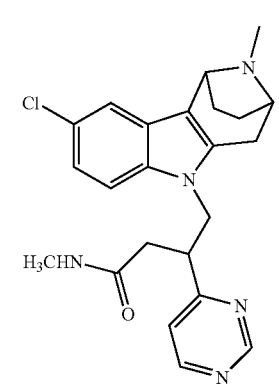 |

TABLE 4-continued
Representative Compounds According to the Invention.
| Comp. # | Compound Structure |
|---|---|
| L-48 | 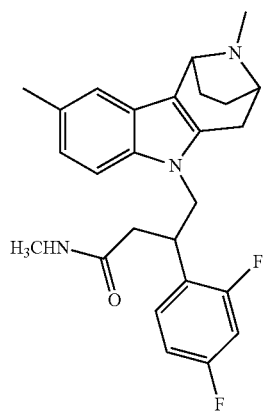 |
| L-49 | 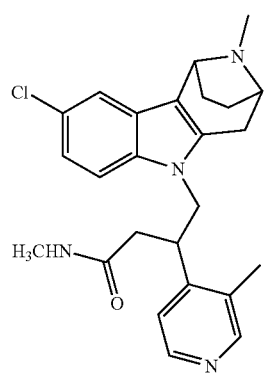 |
| L-50 | 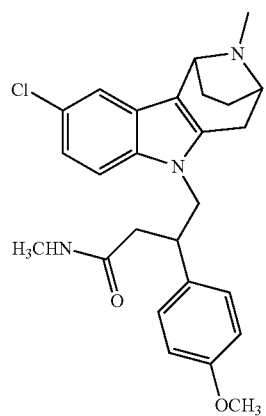 |
| L-51 | 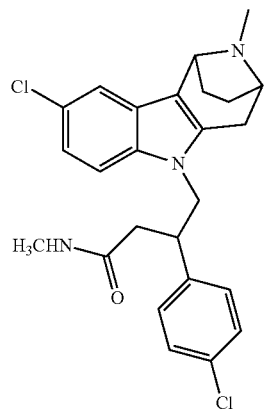 |
| L-52 | 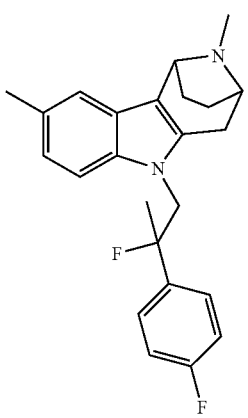 [SMILES: Cc1ccc2c(c1)c1c(n2CC(C)(F)c2ccc(F)cc2)CC2CCC1N2C] |
| L-53 | 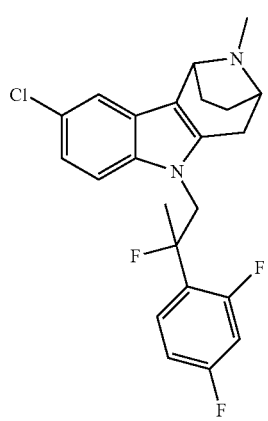 [SMILES: CN1C2CCC1c1c(n(CC(C)(F)c3ccc(F)cc3F)c3ccc(Cl)cc13)C2] |

TABLE 4-continued
Representative Compounds According to the Invention.
| Comp. # | Compound Structure |
|---|---|
| L-54 | 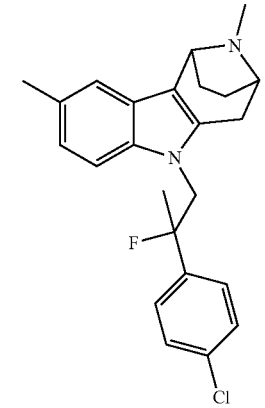 [SMILES: Cc1ccc2c(c1)c1c(n2CC(C)(F)c2ccc(Cl)cc2)CC2CCC1N2C] |
| L-55 | 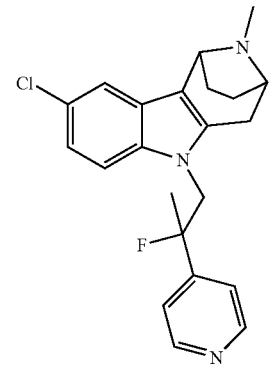 [SMILES: CN1C2CCC1c1c(n(CC(C)(F)c3ccncc3)c3ccc(Cl)cc13)C2] |
| L-56 | 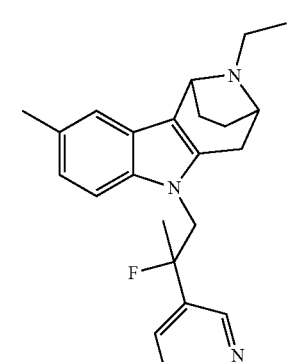 |
| L-57 | 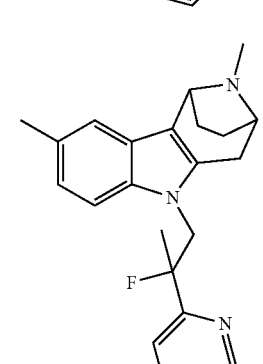 |
| L-58 | 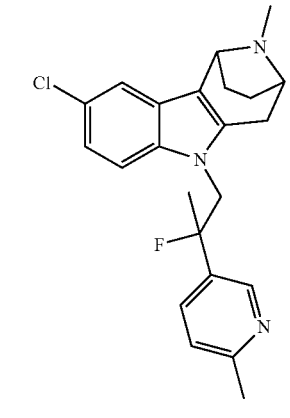 [SMILES: Cc1ccc(C(C)(F)Cn2c3c(c4cc(Cl)ccc42)C2CCC(C3)N2C)cn1] |
| L-59 | 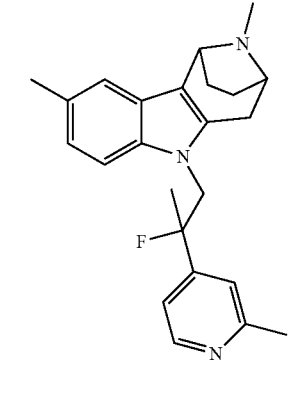 |
| L-60 | 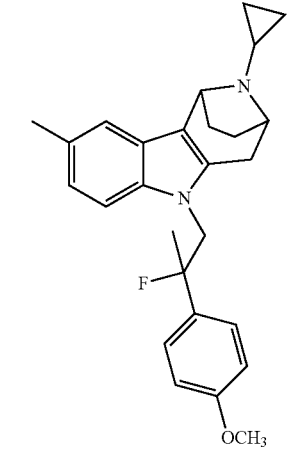 [SMILES: COc1ccc(C(C)(F)Cn2c3c(c4cc(C)ccc42)C2CCC(C3)N2C2CC2)cc1] |

TABLE 4-continued

Representative Compounds According to the Invention.

| Comp. # | Compound Structure |
|---|---|
| L-61 | 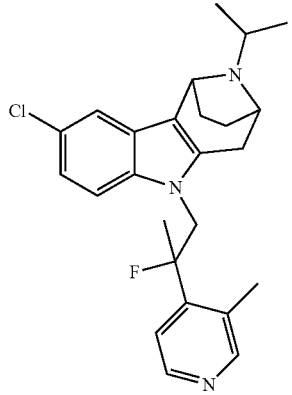 [SMILES: Cc1cnccc1C(C)(F)Cn1c2c(c3cc(Cl)ccc31)C1CCC(C2)N1C(C)C] |

Pharmaceutical compositions of any of the compounds detailed herein are embraced by this invention. Thus, the invention includes pharmaceutical compositions comprising a compound of the invention or a pharmaceutically acceptable salt thereof and a pharmaceutically acceptable carrier or excipient. In one aspect, the pharmaceutically acceptable salt is an acid addition salt, such as a salt formed with an inorganic or organic acid. Pharmaceutical compositions according to the invention may take a form suitable for oral, buccal, parenteral, nasal, topical or rectal administration, or a form suitable for administration by inhalation.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form. Unless otherwise stated, "substantially pure" intends a composition that contains no more than 35% impurity, wherein the impurity denotes a compound other than the compound comprising the majority of the composition or a salt thereof. Taking compound 1 as an example, a composition of substantially pure compound 1 intends a composition that contains no more than 35% impurity, wherein the impurity denotes a compound other than compound 1 or a salt thereof. In one variation, a composition of substantially pure compound or a salt thereof is provided wherein the composition contains no more than 25% impurity. In another variation, a composition of substantially pure compound or a salt thereof is provided wherein the composition contains or no more than 20% impurity. In still another variation, a composition of substantially pure compound or a salt thereof is provided wherein the composition contains or no more than 10% impurity. In a further variation, a composition of substantially pure compound or a salt thereof is provided wherein the composition contains or no more than 5% impurity. In another variation, a composition of substantially pure compound or a salt thereof is provided wherein the composition contains or no more than 3% impurity. In still another variation, a composition of substantially pure compound or a salt thereof is provided wherein the composition contains or no more than 1% impurity. In a further variation, a composition of substantially pure compound or a salt thereof is provided wherein the composition contains or no more than 0.5% impurity.

In one variation, the compounds herein are synthetic compounds prepared for administration to an individual. In another variation, compositions are provided containing a compound in substantially pure form. In another variation, the invention embraces pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein.

Compounds of the invention may be used in a method of modulating a histamine receptor.

General Description of Biological Assays

The binding properties of compounds disclosed herein to a panel of aminergic G protein-coupled receptors including adrenergic receptors, dopamine receptors, serotonin receptors, histamine receptors and an imidazoline receptor may be determined. Binding properties may be assessed by methods known in the art, such as competitive binding assays. In one variation, compounds are assessed by the binding assays detailed herein. Compounds disclosed herein may also be tested in cell-based assays or in in vivo models for further characterization. In one aspect, compounds disclosed herein are of any formula detailed herein and further display one or more of the following characteristics: inhibition of binding of a ligand to an adrenergic receptor (e.g., $\alpha_{1D}$, $\alpha_{2A}$ and $\alpha_{2B}$), inhibition of binding of a ligand to a serotonin receptor (e.g., 5-$HT_{2A}$, 5-$HT_{2C}$, 5-$HT_6$ and 5-$HT_7$), inhibition of binding of a ligand to a dopamine receptor (e.g., $D_{2L}$), and inhibition of binding of a ligand to a histamine receptor (e.g., $H_1$, $H_2$ and $H_3$); agonist/antagonist activity to a serotonin receptor (e.g., 5-$HT_{2A}$, 5-$HT_6$); agonist/antagonist activity to a dopamine receptor (e.g., $D_{2L}$, $D_{2S}$); agonist/antagonist activity to a histamine receptor (e.g., $H_1$); activity in a neurite outgrowth assay; efficacy in a preclinical model of memory dysfunction associated with cholinergic dysfunction/hypofunction; efficacy in a preclinical model of attention/impulsivity and executive function and efficacy in a preclinical model of schizophrenia.

In one variation, inhibition of binding of a ligand to a receptor is measured in the assays described herein. In another variation, inhibition of binding of a ligand is measured in an assay known in the art. In one variation, binding of a ligand to a receptor is inhibited by at least about 80% as determined in a suitable assay known in the art such as the assays described herein. In one variation, binding of a ligand to a receptor is inhibited by greater than about any one of 80%, 85%, 90%, 95%, 100%, or between about 85% and about 95% or between about 90-100% as determined in a suitable assay known in the art such as the assays described herein. In one variation, binding of a ligand to a receptor is inhibited by at least about 80%±20% as determined in an assay known in the art.

In one variation, a compound of the invention inhibits binding of a ligand to at least one receptor and as many as eleven as detailed herein (e.g. $\alpha_{1D}$, $\alpha_{2A}$, $\alpha_{2B}$, 5-$HT_{2A}$, 5-$HT_{2C}$, 5-$HT_6$, 5-$HT_7$, $D_{2L}$, $H_1$, $H_2$, $H_3$). In one variation, a compound of the invention inhibits binding of a ligand to at least one receptor and as many as eleven as detailed herein (e.g., $a_{1D}$, $a_{2A}$, $a_{2B}$, 5-$HT_{2A}$, 5-$HT_{2C}$, 5-$HT_6$, 5-$HT_7$, $D_2$, $H_1$, $H_2$, $H_3$). In one variation, a compound of the invention inhibits binding of a ligand to at least one and as many as eleven receptors detailed herein and further displays agonist or antagonist activity to one or more receptors detailed herein (e.g., serotonin receptor 5-$HT_{2A}$, serotonin receptor 5-$HT_6$, dopamine receptor $D_{2L}$, and dopamine receptor $D_{2S}$, histamine receptor $H_1$) as measured in the assays described herein. In one variation, agonist response of serotonin receptor 5-$HT_{2A}$ is inhibited by compounds of the invention by at least about any one of 50%, 50%, 70%, 80%, 90%, 100%, 110%, 120%, 130%, 140%, 150% as determined in a suitable assay such as the assay described herein.

In one variation, a compound of the invention displays the above described neurotransmitter receptor binding profile i.e. inhibits binding of a ligand to at least one receptor and as many as eleven as detailed herein and further stimulates neurite outgrowth, e.g. as measured by the assays described herein. In one variation, a compound of the invention shows activity in neurite outgrowth assays using primary neurons in culture. In another variation, a compound of the invention has activity comparable in magnitude to that of naturally occurring prototypical neurotrophic proteins such as brain derived neurotrophic factor (BDNF) and nerve growth factor (NGF). Notably, neurite outgrowth plays a critical part of new synaptogenesis, which is beneficial for the treatment of neuronal disorders. In one variation, neuronal disorders include ADHD. In one variation, neurite outgrowth is observed with a potency of about 1 µM as measured in a suitable assay known in the art such as the assays described herein. In another variation, neurite outgrowth is observed with a potency of about 500 nM. In a further variation, neurite outgrowth is observed with a potency of about 50 nM. In another variation, neurite outgrowth is observed with a potency of about 5 nM.

In another variation, a compound of the invention inhibits binding of a ligand to at least one receptor and as many as eleven as detailed herein, further displays agonist or antagonist activity to one or more receptors detailed herein and further stimulates neurite outgrowth.

In a further variation, a compound of the invention inhibits binding of a ligand to at least one and as many as eleven receptors as detailed herein and/or display the above described neurotransmitter receptor binding profile and further shows efficacy in a preclinical model of memory dysfunction associated with cholinergic dysfunction/hypofunction, and in preclinical models of attention/impulsivity and executive function, i.e. shows pro-cognitive effects in a preclinical model of memory dysfunction. In one variation, a compound of the invention is effective in a preclinical model of memory dysfunction associated with cholinergic hypofunction. As $H_1$ antagonism may contribute to sedation, weight gain and reduced cognition, low affinity (less than about 80% inhibition of binding of Pyrilamine at 1 µM in the assay described herein) for this receptor may be associated with pro-cognitive effects and a more desirable side effect profile. Furthermore, compounds of the invention with increased potency as a 5-$HT_6$ antagonist may have cognition-enhancing effects as serotonin acting through this receptor may impair memory.

In another variation, a compound of the invention inhibits binding of a ligand to at least one and as many as eleven receptors as detailed herein, further shows efficacy in a preclinical model of memory dysfunction associated with cholinergic dysfunction/hypofunction i.e. shows pro-cognitive effects in a preclinical model of memory dysfunction, and in preclinical models of attention/impulsivity and executive function, and further displays agonist or antagonist activity to one or more receptors detailed herein.

In a further variation, a compound of the invention inhibits binding of a ligand to at least one and as many as eleven receptors as detailed herein, further shows efficacy in a preclinical model of memory dysfunction associated with cholinergic dysfunction/hypofunction i.e. shows pro-cognitive effects in a preclinical model of memory dysfunction, and in preclinical models of attention/impulsivity and executive function, and in preclinical models of attention/impulsivity and executive function, and further stimulates neurite outgrowth.

In another variation, a compound of the invention inhibits binding of a ligand to at least one and as many as eleven receptors as detailed herein, further shows efficacy in a preclinical model of memory dysfunction associated with cholinergic dysfunction/hypofunction i.e. shows pro-cognitive effects in a preclinical model of memory dysfunction, and in preclinical models of attention/impulsivity and executive function, and in preclinical models of attention/impulsivity and executive function, further displays agonist or antagonist activity to one or more receptor detailed herein and further stimulates neurite outgrowth.

In a further variation, a compound of the invention inhibits binding of a ligand to at least one and as many as eleven receptors and further possesses anti-psychotic effects as measured in a preclinical model of schizophrenia, i.e., shows efficacy in a preclinical model of schizophrenia.

In another variation, a compound of the invention inhibits binding of a ligand to at least one and as many as eleven receptors, further shows efficacy in a preclinical model of schizophrenia and further displays agonist or antagonist activity to one or more receptors detailed herein.

In a further variation, a compound of the invention inhibits binding of a ligand to at least one and as many as eleven receptors, further shows efficacy in a preclinical model of schizophrenia and further stimulates neurite outgrowth.

In a further variation, a compound of the invention inhibits binding of a ligand to at least one and as many as eleven receptors, further shows efficacy in a preclinical model of memory dysfunction associated with cholinergic dysfunction/hypofunction such as enhancement of memory retention and reduction of memory impairment, and in preclinical models of attention/impulsivity and executive function, and further shows efficacy in a preclinical model of schizophrenia.

In another variation, a compound of the invention inhibits binding of a ligand to at least one and as many as eleven receptors, further shows efficacy in a preclinical model of schizophrenia, further displays agonist or antagonist activity to one or more receptors detailed herein and further shows efficacy in a preclinical model of memory dysfunction associated with cholinergic dysfunction/hypofunction such as enhancement of memory retention and reduction of memory impairment and in preclinical models of attention/impulsivity and executive function.

In another variation, a compound of the invention inhibits binding of a ligand to at least one and as many as eleven receptors, further shows efficacy in a preclinical model of schizophrenia, further stimulates neurite outgrowth and further shows efficacy in a preclinical model of memory dysfunction associated with cholinergic dysfunction/hypofunction such as enhancement of memory retention and reduction of memory impairment, and in preclinical models of attention/impulsivity and executive function.

In a further variation, a compound of the invention inhibits binding of a ligand to at least one and as many as eleven receptors detailed herein, further displays agonist or antagonist activity to one or more receptors detailed herein, further stimulates neurite outgrowth and further shows efficacy in a preclinical model of schizophrenia.

In another variation, a compound of the invention inhibits binding of a ligand to at least one and as many as eleven receptors, further shows efficacy in a preclinical model of schizophrenia, further displays agonist or antagonist activity to one or more receptors detailed herein, further stimulates neurite outgrowth and further shows efficacy in a preclinical model of memory dysfunction associated with cholinergic dysfunction/hypofunction such as enhancement of memory retention and reduction of memory impairment, and in preclinical models of attention/impulsivity and executive function.

In another variation, a compound of the invention stimulates neurite outgrowth. In another variation, a compound of the invention shows efficacy in a preclinical model of schizophrenia and further stimulates neurite outgrowth. In another variation, a compound of the invention stimulates neurite outgrowth and further shows efficacy in a preclinical model of memory dysfunction associated with cholinergic dysfunction/hypofunction such as enhancement of memory retention and reduction of memory impairment, and in preclinical models of attention/impulsivity and executive function. In another variation, a compound of the invention shows efficacy in a preclinical model of schizophrenia, further stimulates neurite outgrowth and further shows efficacy in a preclinical model of memory dysfunction associated with cholinergic dysfunction/hypofunction such as enhancement of memory retention and reduction of memory impairment, and in preclinical models of attention/impulsivity and executive function.

In one aspect, compounds of the invention inhibit binding of a ligand to adrenergic receptors $\alpha_{1D}$, $\alpha_{2A}$, $\alpha_{2B}$ and inhibit binding of a ligand to serotonin receptor 5-HT$_6$. In another variation, compounds of the invention inhibit binding of a ligand to adrenergic receptors $\alpha_{1D}$, $\alpha_{2A}$, $\alpha_{2B}$, to serotonin receptor 5-HT$_6$ and to any one or more of the following receptors: serotonin receptor 5-HT$_7$, 5-HT$_{2A}$ and 5-HT$_{2C}$. In another variation, compounds of the invention inhibit binding of a ligand to adrenergic receptors $\alpha_{1D}$, $\alpha_{2A}$, $\alpha_{2B}$, to serotonin receptor 5-HT$_6$ and to any one or more of the following receptors: serotonin receptor 5-HT$_7$, 5-HT$_{2A}$ and 5-HT$_{2C}$ and further show weak inhibition of binding of a ligand to histamine receptor H$_1$ and/or H$_2$. In one variation, compounds of the invention that also display strong inhibition of binding of a ligand to the serotonin receptor 5-HT$_7$ are particularly desired. In another variation, compounds of the invention inhibit binding of a ligand to adrenergic receptors $\alpha_{1D}$, $\alpha_{2A}$, $\alpha_{2B}$, to serotonin receptor 5-HT$_6$ and further show weak inhibition of binding of a ligand to histamine receptor H$_1$ and/or H$_2$. Weak inhibition of binding of a ligand to the histamine H$_1$ receptor is permitted as agonists of this receptor have been implicated in stimulating memory as well as weight gain. In one variation, binding to histamine receptor H1 is inhibited by less than about 80%. In another variation, binding of a ligand to histamine receptor H1 is inhibited by less than about any of 75%, 70%, 65%, 60%, 55%, or 50% as determined by a suitable assay known in the art such as the assays described herein.

In another variation, compounds of the invention inhibit binding of a ligand to a dopamine receptor D$_2$. In another variation, compounds of the invention inhibit binding of a ligand to dopamine receptor D$_{2L}$. In another variation, compounds of the invention inhibit binding of a ligand to dopamine receptor D$_2$ and to serotonin receptor 5-HT$_{2A}$. In another variation, compounds of the invention inhibit binding of a ligand to dopamine receptor D$_{2L}$ and to serotonin receptor 5-HT$_{2A}$. In another variation, compounds of the invention inhibit binding of a ligand to histamine receptor H$_1$. In certain aspects, compounds of the invention further show one or more of the following properties: strong inhibition of binding of a ligand to the serotonin 5-HT$_7$ receptor, strong inhibition of binding of a ligand to the serotonin 5-HT$_{2A}$ receptor, strong inhibition of binding of a ligand to the serotonin 5-HT$_{2C}$ receptor, weak inhibition of binding of a ligand to the histamine H$_1$ receptor, weak inhibition of binding of ligands to the histamine H$_2$ receptor, and antagonist activity to serotonin receptor 5-HT$_{2A}$.

In one variation, compounds of the invention show any of the receptor binding aspects detailed herein and further display agonist/antagonist activity to one or more of the following receptors: serotonin receptor 5-HT$_{2A}$, serotonin receptor 5-HT$_6$, dopamine receptor D$_{2L}$, dopamine receptor D$_{2S}$ and histamine receptor H$_1$. In one variation, compounds of the invention show any of the receptor binding aspects detailed herein and further stimulate neurite outgrowth. In one variation, compounds of the invention show any of the receptor binding aspects detailed herein and further show efficacy in a preclinical model of memory dysfunction associated with cholinergic dysfunction/hypofunction such as enhancement of memory retention and reduction of memory impairment and in preclinical models of attention/impulsivity and executive function. In one variation, compounds of the invention show any of the receptor binding aspects detailed herein and further show efficacy in a preclinical model of schizophrenia. In one variation, compounds of the invention show any of the receptor binding aspects detailed herein and further show efficacy in any one or more of agonist/antagonist assays (e.g., to serotonin receptor 5-HT$_{2A}$, 5-HT$_6$, dopamine receptor D$_{2L}$, dopamine receptor D$_2$ and histamine receptor H$_1$), neurite outgrowth, a preclinical model of memory dysfunction associated with cholinergic dysfunction/hypofunction and a preclinical model of schizophrenia.

In some aspects, compounds of the invention inhibit binding of a ligand to adrenergic receptors a$_{1D}$, a$_{2A}$, a$_{2B}$, serotonin receptor 5-HT$_6$ and a dopamine receptor D$_2$ by at least about 80% as determined in a suitable assay known in the art such as the assays described herein. In some aspects, compounds of the invention inhibit binding of a ligand to adrenergic receptors a$_{1D}$, a$_{2A}$, a$_{2B}$, serotonin receptor 5-HT$_6$ and dopamine receptor D$_{2L}$ by at least about 80% as determined in a suitable assay known in the art such as the assays described herein. In one variation binding is inhibited by at least about 80% as measured in a suitable assay such as the assays described herein. In one variation binding is inhibited by at least about 80% as measured in a suitable assay such as the assays described herein. In one variation, binding of a ligand to a receptor is inhibited by greater than about any one of 80%, 85%, 90%, 95%, 100%, or between about 85% and about 95%, or between about 90% and about 100% as determined in a suitable assay known in the art such as the assays described herein.

In some aspects, compounds of the invention display the above described neurotransmitter receptor binding profile and further show antipsychotic effects. In one variation, a compound of the invention has a binding profile similar to compounds with antipsychotic activity. In another variation, a compound of the invention is effective in a preclinical model of schizophrenia. In addition, compounds of the invention might possess the cognitive enhancing properties of dimebon and thus add to the beneficial pharmacology profile of these antipsychotic molecules. In one variation, compounds of the invention display the above described neurotransmitter receptor binding profile and further show pro-cognitive effects in a preclinical model of memory dysfunction such as enhancement of memory retention and reduction of memory impairment due to cholinergic hypofunction in preclinical animal models. In another variation, compounds of the invention display the above described neurotransmitter receptor binding profile and do not show pro-cognitive effects in a preclinical model of memory dysfunction, learning and memory.

In one variation, compounds of the invention demonstrate pro-cognitive effects in a preclinical model of memory dysfunction, learning and memory. In a further variation, compounds of the invention possess anti-psychotic effects in a preclinical model of schizophrenia. In a further variation, compounds of the invention demonstrate pro-cognitive effects in a preclinical model of memory dysfunction, learning and memory and further possess anti-psychotic effects in a preclinical model of schizophrenia.

Overview of the Methods

The compounds described herein may be used to treat, prevent, delay the onset and/or delay the development of cognitive disorders, psychotic disorders, neurotransmitter-mediated disorders and/or neuronal disorders in individuals, such as humans. In one aspect, the compounds described herein may be used to treat, prevent, delay the onset and/or delay the development of a cognitive disorder. In one variation, cognitive disorder as used herein includes and intends disorders that contain a cognitive component, such as psychotic disorders (e.g., schizophrenia) containing a cognitive component (e.g., CIAS). In one variation, cognitive disorder includes ADHD. In another aspect, the compounds described herein may be used to treat, prevent, delay the onset and/or delay the development of a psychotic disorder. In one variation, psychotic disorder as used herein includes and intends disorders that contain a psychotic component, for example cognitive disorders (e.g., Alzheimer's disease) that contain a psychotic component (e.g., psychosis of Alzheimer's Disease or dementia). In one variation, methods of improving at least one cognitive and/or psychotic symptom associated with schizophrenia are provided. In one aspect, methods of improving cognition in an individual who has or is suspected of having CIAS are provided. In a particular aspect, methods of treating schizophrenia are provided wherein the treatment provides for an improvement in one or more negative symptom and/or one or more positive symptom and/or one or more disorganized symptom of schizophrenia. In yet another aspect, the compounds described herein may be used to treat, prevent, delay the onset and/or delay the development of a neurotransmitter-mediated disorders disorder. In one aspect, a neurotransmitter-mediated disorder includes ADHD. In one embodiment, the neurotransmitter-mediated disorder includes spinal cord injury, diabetic neuropathy, allergic diseases (including food allergies) and diseases involving geroprotective activity such as age-associated hair loss (alopecia), age-associated weight loss and age-associated vision disturbances (cataracts). In another variation, the neurotransmitter-mediated disorder includes spinal cord injury, diabetic neuropathy, fibromyalgia and allergic diseases (including food allergies). In still another embodiment, the neurotransmitter-mediated disorder includes Alzheimer's disease, Parkinson's Disease, ADD, ADHD, autism, Guillain-Barré syndrome, mild cognitive impairment, multiple sclerosis, stroke and traumatic brain injury. In yet another embodiment, the neurotransmitter-mediated disorder includes schizophrenia, anxiety, bipolar disorders, psychosis, depression, and ADHD. In one variation, depression as used herein includes and intends treatment-resistant depression, depression related to a psychotic disorder, or depression related to a bipolar disorder. In another aspect, the compounds described herein may be used to treat, prevent, delay the onset and/or delay the development of a neuronal disorder. In one aspect, the compounds described herein may also be used to treat, prevent, delay the onset and/or delay the development of cognitive disorders, psychotic disorders, neurotransmitter-mediated disorders and/or neuronal disorders for which the modulation of an aminergic G protein-coupled receptor is believed to be or is beneficial.

The invention also provides methods of improving cognitive functions and/or reducing psychotic effects comprising administering to an individual in need thereof an amount of a compound of the invention or a pharmaceutically acceptable salt thereof effective to improve cognitive functions and/or reduce psychotic effects. In a particular variation, a method of treating schizophrenia is provided, wherein the treatment provides an improvement in at least one cognitive function, such as an improvement in a cognitive function in an individual who has or is suspected of having CIAS. In a further variation, a method of treating schizophrenia is provided wherein the method reduces psychotic effects associated with schizophrenia. In one embodiment, a method of treating schizophrenia is provided wherein the method improves the negative symptoms of schizophrenia in an individual in need thereof. In one embodiment, a method of treating schizophrenia is provided wherein the method improves the positive symptoms of schizophrenia in an individual in need thereof. In a further variation, a method of treating schizophrenia is provided wherein the method both improves cognitive function and reduces psychotic effects in an individual in need thereof. A method of improving one or more negative, positive and disorganized symptoms of schizophrenia is also provided, where the method entails administering a compound as detailed herein, or a pharmaceutically acceptable salt thereof, to an individual in need of such improvement. In one variation, a method of improving at least one negative symptom of schizophrenia is provided, where the method entails administering a compound as detailed herein, or a pharmaceutically acceptable salt thereof, to an individual in need of such improvement. In another variation, a method of improving at least one negative and at least one positive symptom of schizophrenia is provided, where the method entails administering a compound as detailed herein, or a pharmaceutically acceptable salt thereof, to an individual in need of such improvement. In yet another variation, a method of improving at least one negative and at least one disorganized symptom of schizophrenia is also provided, where the method entails administering a compound as detailed herein, or a pharmaceutically acceptable salt thereof, to an individual in need of such improvement. In still another variation, a method of improving at least one positive and at least one disorganized symptom of schizophrenia is also provided, where the method entails administering a compound as detailed herein, or a pharmaceutically acceptable salt thereof, to an individual in need of such improvement. In still a further variation, a method of improving at least one negative, at least one positive and at least one disorganized symptom of schizophrenia is provided, where the method entails administering a compound as detailed herein, or a pharmaceutically acceptable salt thereof, to an individual in need of such improvement.

The invention also provides methods of stimulating neurite outgrowth and/or promoting neurogenesis and/or enhancing neurotrophic effects in an individual comprising administering to an individual in need thereof an amount of a compound of the invention or a pharmaceutically acceptable salt thereof effective to stimulate neurite outgrowth and/or to promote neurogenesis and/or to enhance neurotrophic effects.

The invention further encompasses methods of modulating an aminergic G protein-coupled receptor comprising administering to an individual in need thereof an amount of a compound of the invention or a pharmaceutically acceptable salt thereof effective to modulate an aminergic G protein-coupled receptor.

It is to be understood that methods described herein also encompass methods of administering compositions comprising the compounds of the invention.

Methods for Treating, Preventing, Delaying the Onset, and/or Delaying the Development Cognitive Disorders, Psychotic Disorders, Neurotransmitter-Mediated Disorders and/or Neuronal Disorders In one aspect, the invention provides methods for treating, preventing, delaying the onset, and/or delaying the development of cognitive disorders, psychotic disorders, neurotransmitter-mediated disorders and/or neuronal disorders for which the modulation of an aminergic G protein-coupled receptor is believed to be or is beneficial, the method comprising administering to an individual in need thereof a compound of the invention. In some variations, modulation of adrenergic receptor $\alpha_{1D}$, $\alpha_{2A}$, $\alpha_{2B}$, serotonin receptor 5-HT$_{2A}$, 5-HT$_6$, 5-HT$_7$, histamine receptor H$_1$ and/or H$_2$ is expected to be or is beneficial for the cognitive disorders, psychotic disorders, neurotransmitter-mediated disorders and/or neuronal disorders. In some variations, modulation of adrenergic receptor $\alpha_{1D}$, $\alpha_{2A}$, $\alpha_{2B}$ and a serotonin receptor 5-HT$_6$ receptor is expected to be or is beneficial for the cognitive disorders, psychotic disorders, neurotransmitter-mediated disorders and/or neuronal disorders. In some variations, modulation of adrenergic receptor $\alpha_{1D}$, $\alpha_{2A}$, $\alpha_{2B}$, and a serotonin receptor 5-HT$_6$ receptor and modulation of one or more of the following receptors serotonin 5-HT$_7$, 5-HT$_{2A}$, 5-HT$_{2C}$ and histamine H$_1$ and H$_2$ is expected to be or is beneficial for the cognitive disorders, psychotic disorders, neurotransmitter-mediated disorders and/or neuronal disorders. In some variations, modulation of a dopamine receptor D$_2$ is expected to be or is beneficial for the cognitive disorders, psychotic disorders, neurotransmitter-mediated disorders and/or neuronal disorders. In some variations, modulation of dopamine receptor D$_{2L}$ is expected to be or is beneficial for the cognitive disorders, psychotic disorders, neurotransmitter-mediated disorders and/or neuronal disorders. In certain variations, modulation of a dopamine D$_{2L}$ receptor and serotonin receptor 5-HT$_{2A}$ is expected to be or is beneficial for the cognitive disorders, psychotic disorders, neurotransmitter-mediated disorders and/or neuronal disorders. In some variations, the cognitive disorders, psychotic disorders, neurotransmitter-mediated disorders and/or neuronal disorders are treated, prevented and/or their onset or development is delayed by administering a compound of the invention.

Methods to Improve Cognitive Functions and/or Reduce Psychotic Effects

The invention provides methods for improving cognitive functions by administering a compound of the invention to an individual in need thereof. In some variations, modulation of one or more of adrenergic receptor $\alpha_{1D}$, $\alpha_{2A}$, $\alpha_{2B}$, serotonin receptor 5-HT$_{2A}$, 5-HT$_6$, 5-HT$_7$, histamine receptor H$_1$ and/or H$_2$ is desirable or expected to be desirable to improve cognitive functions. In some variations modulation of $\alpha_{1D}$, $\alpha_{2A}$, $\alpha_{2B}$ adrenergic receptors and a serotonin 5-HT$_6$ receptor is desirable or expected to be desirable to improve cognitive functions. In some variations, modulation of $\alpha_{1D}$, $\alpha_{2A}$, $\alpha_{2B}$ adrenergic receptors and serotonin receptor 5-HT$_6$ and modulation of one or more of the following receptors: serotonin receptor 5-HT$_7$, 5-HT$_{2A}$, 5-HT$_{2C}$ and histamine receptor H$_1$ and H$_2$, is desirable or expected to be desirable to improve cognitive functions. In another aspect, the invention encompasses methods to reduce psychotic effects by administering a compound of the invention to an individual in need thereof.

In some embodiments, modulation of a dopamine D$_2$ receptor is expected to be or is desirable to reduce psychotic effects. In some embodiments, modulation of a dopamine D$_2$ receptor and a serotonin 5-HT$_{2A}$ receptor is expected to be or is desirable to reduce psychotic effects. In some embodiments, modulation of a dopamine D$_{2L}$ receptor and a serotonin 5-HT$_{2A}$ receptor is expected to be or is desirable to reduce psychotic effects. In some variations, a compound of the invention is administered to an individual in need thereof.

Methods to Stimulate Neurite Outgrowth, Promote Neurogenesis and/or Enhance Neurotrophic Effects In a further aspect, the invention provides methods of stimulating neurite outgrowth and/or enhancing neurogenesis and/or enhancing neurotrophic effects comprising administering a compound of the invention or pharmaceutically acceptable salt thereof under conditions sufficient to stimulate neurite outgrowth and/or to enhance neurogenesis and/or enhance neurotrophic effects to an individual in need thereof. In some variations, a compound of the invention stimulates neurite outgrowth at a potency of about 1 µM as measured in a suitable assay such as the assays described herein. In some variations, a compound of the invention stimulates neurite outgrowth at a potency of about 500 nM as measured in a suitable assay such as the assays described herein. In some variations, a compound of the invention stimulates neurite outgrowth at a potency of about 50 nM as measured in a suitable assay such as the assays described herein. In some variations, a compound of the invention stimulates neurite outgrowth at a potency of about 5 nM as measured in a suitable assay such as the assays described herein.

Methods to Modulate an Aminergic G Protein-Coupled Receptor

The invention further contemplates methods for modulating the activity of an aminergic G-protein-coupled receptor comprising administering a compound of the invention or pharmaceutically acceptable salt thereof under conditions sufficient to modulate the activity of an aminergic G protein-coupled receptor. In some variations, the aminergic G protein-coupled receptor is a $\alpha_{1D}$, $\alpha_{2A}$, $\alpha_{2B}$ adrenergic receptor and a serotonin 5-HT$_6$ receptor. In some variations, the aminergic G protein-coupled receptor is a $\alpha_{1D}$, $\alpha_{2A}$, $\alpha_{2B}$ adrenergic receptor and a serotonin 5-HT$_6$ and 5-HT$_7$ receptor. In some variations, the aminergic G protein-coupled receptor is a $\alpha_{1D}$, $\alpha_{2A}$, $\alpha_{2B}$ adrenergic receptor, a serotonin 5-HT$_6$ and one or more of the following receptors: serotonin 5-HT$_7$, 5-HT$_{2A}$ and 5-HT$_{2C}$ and histamine H$_1$ and H$_2$ receptor. In some variations, the aminergic G protein-coupled receptor is a dopamine D$_2$ receptor. In some variations, the aminergic G protein-coupled receptor is a dopamine D$_{2L}$ receptor. In some variations, the aminergic G protein-coupled receptor is a dopamine D$_2$ receptor and a serotonin 5-HT$_{2A}$ receptor. In some variations, the aminergic G protein-coupled receptor is a dopamine D$_{2L}$ receptor and a serotonin 5-HT$_{2A}$ receptor. In some variations, the aminergic G protein-coupled receptor is a histamine H$_1$ receptor.

General Synthetic Methods

The compounds of the invention may be prepared by a number of processes as generally described below and more specifically in the Examples hereinafter. In the following process descriptions, the symbols when used in the formulae depicted are to be understood to represent those groups described above in relation to formula (I) or a variation thereof unless otherwise indicated.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g. a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

By way of example only, using suitable methods such as those detailed herein, compounds of the formula (E) may be resolved to provide compounds of the formulae (Ea) and (Eb):

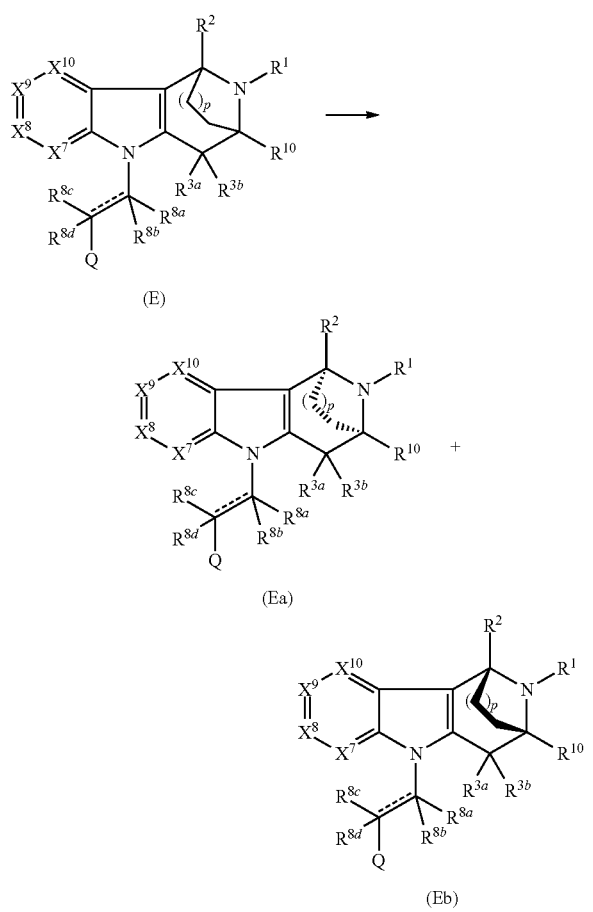

The following abbreviations are used herein: thin layer chromatography (TLC); hour (h); minute (min); second (sec); ethanol (EtOH); ethyl acetate (EtOAc); dimethylsulfoxide (DMSO); N,N-dimethylformamide (DMF); room temperature (RT); trifluoroacetic acid (TFA); tetrahydrofuran (THF); Normal (N); aqueous (aq.); methanol (MeOH); dichloromethane (DCM); Retention factor (Rf).

A method of synthesizing an intermediate used in the synthesis of compounds of the invention is shown as General Method 1-12. Compounds made by General Methods 2 and 12 may also be used as intermediates for the synthesis of other compounds of the invention.

Methods of preparing gamma-carboline compounds may be found in U.S. Provisional Patent Application Nos. 61/181,262, 61/181,259 and 61/229,638, which may be adapted to provide the compounds as detailed herein.

General Synthetic Method 1

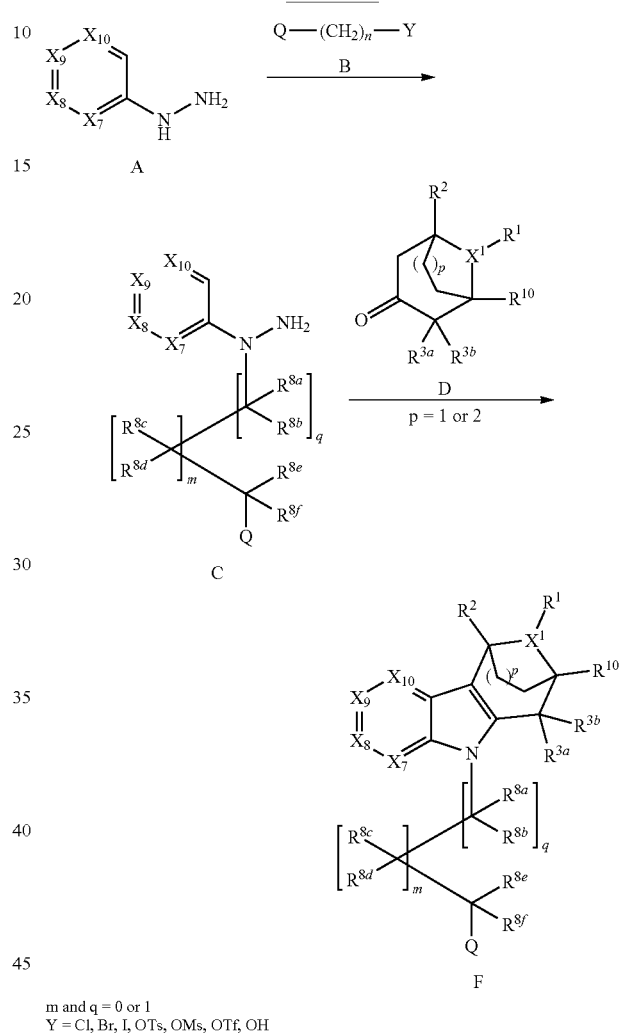

m and q = 0 or 1
Y = Cl, Br, I, OTs, OMs, OTf, OH

In general, a suitably substituted hydrazine A can be reacted with an appropriately substituted reagent B to generate a substituted hydrazine C, where the internal nitrogen on the hydrazine is substituted, as shown above. The reaction of intermediate C with an appropriately substituted 4-dialkylamino cyclohexanone D should provide structures of the type generally described by structure F.

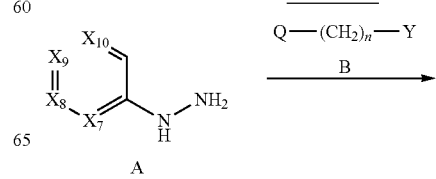

-continued

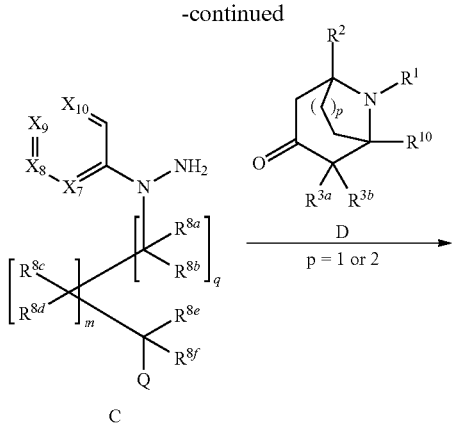

C

F m and q = 0 or 1
Y = Cl, Br, I, OTs, OMs, OTf, OH

Similar synthetic details may be employed for compounds made according to Scheme 1-A.

Scheme 1-C

Similar synthetic details may be employed for compounds made according to Scheme 1-A in general methods for synthesis of structures of the type generally described by structure F, wherein Q is aryl, substituted aryl, heteroaryl (five and six membered) and substituted heteroaryl (five and six membered).

Scheme 1-D

Similar synthetic details may be employed for compounds made according to Scheme 1-A in general methods for synthesis of structures of the type generally described by structure F, wherein Q is alkyl, substituted alkyl, substituted or unsubstituted amino, thio, substituted thio, alkoxy, cycloalkyl and heterocyclic (including 4, 5, 6 and 7-membered rings).

Scheme 1-E

Similar synthetic details may be employed for compounds made according to Scheme 1-A in general methods for synthesis of structures of the type generally described by structure F, wherein q and m=0, and Q is alkyl, substituted alkyl, substituted or unsubstituted amino, thio, substituted thio, alkoxy, cycloalkyl and heterocyclic (including 4, 5, 6 and 7-membered rings).

Scheme 1-F

Similar synthetic details may be employed for compounds made according to Scheme 1-A in general methods for synthesis of structures of the type generally described by structure F, wherein m=0, q=1, $R^{8a}$ and $R^{8b}$ taken together with the carbon to which it is attached form a carbonyl moiety, $R^{8e}$ and $R^{8f}$ is independently H, hydroxyl or $C_1$-$C_8$ alkyl; and Q is alkyl, substituted alkyl, substituted or unsubstituted amino, thio, substituted thio, alkoxy, cycloalkyl and heterocyclic (including 4, 5, 6 and 7-membered rings).

Scheme 1-G

Similar synthetic details may be employed for compounds made according to Scheme 1-A in general methods for synthesis of structures of the type generally described by structure F, wherein m=0, q=1, $R^{8e}$ and $R^{8f}$ taken together with the carbon to which it is attached form a carbonyl moiety, $R^{8a}$ and $R^{8b}$ is independently H, hydroxyl or $C_1$-$C_8$ alkyl; and Q is alkyl, substituted alkyl, substituted or unsubstituted amino, thio, substituted thio, alkoxy, cycloalkyl and heterocyclic (including 4, 5, 6 and 7-membered rings).

Scheme 1-H

Similar synthetic details may be employed for compounds made according to Scheme 1-A in general methods for synthesis of structures of the type generally described by structure F, wherein m and q=1, $R^{8a}$ and $R^{8b}$ taken together with the carbon to which it is attached form a carbonyl moiety, $R^{8c}$, $R^{8d}$, $R^{8e}$ and $R^{8f}$ is independently H, hydroxyl or $C_1$-$C_8$ alkyl; and Q is alkyl, substituted alkyl, substituted or unsubstituted amino, thio, substituted thio, alkoxy, cycloalkyl and heterocyclic (including 4, 5, 6 and 7-membered rings).

Scheme 1-I

Similar synthetic details may be employed for compounds made according to Scheme 1-A in general methods for synthesis of structures of the type generally described by structure F, wherein m and q=1, $R^{8e}$ and $R^{8f}$ taken together with the carbon to which it is attached form a carbonyl moiety, $R^{8a}$, $R^{8b}$, $R^{8c}$ and $R^{8d}$ is independently H, hydroxyl or $C_1$-$C_8$ alkyl; and Q is alkyl, substituted alkyl, substituted or unsubstituted amino, thio, substituted thio, alkoxy, cycloalkyl and heterocyclic (including 4, 5, 6 and 7-membered rings).

Scheme 1-J

Similar synthetic details may be employed for compounds made according to Scheme 1-A in general methods for synthesis of structures of the type generally described by structure F, wherein q and m=0, and Q is COOR.

Scheme 1-K

Similar synthetic details may be employed for compounds made according to Scheme 1-A in general methods for synthesis of structures of the type generally described by structure F, wherein m=0, q=1, and Q is COOR.

Scheme 1-L

Similar synthetic details may be employed for compounds made according to Scheme 1-A in general methods for synthesis of structures of the type generally described by structure F, wherein m and q=1, and Q is COOR.

General Method 2

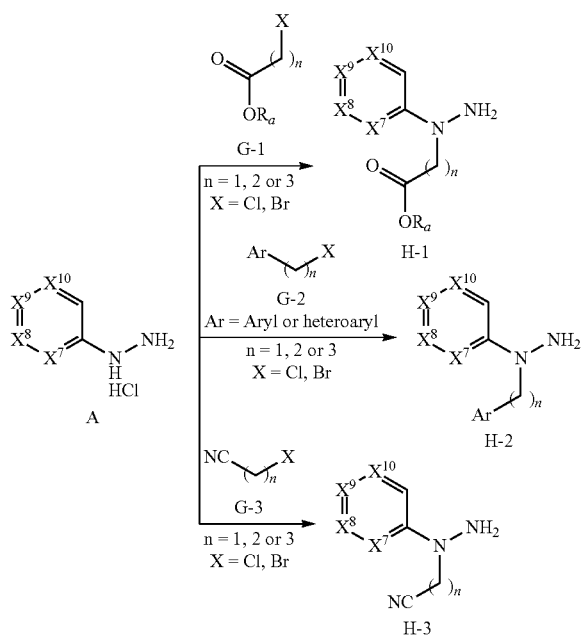

Arylhydrazine hydrochloride (1 equiv) is mixed with triethylamine (3 equiv) and alkyl halide (1 equiv) at 25° C. The reaction mixture is stirred at RT for 1 h and subsequently heated at 90° C. until completion of the reaction as determined by TLC and LC-MS (approx 16 h). The reaction mixture is concentrated under reduced pressure, diluted with water and extracted with ethyl acetate. The combined organic layer is dried ($Na_2SO_4$) and concentrated to obtain crude product that is purified by column chromatography (silica gel, 100-200 mesh, eluent: ethyl acetate-hexanes gradient).

General Method 3

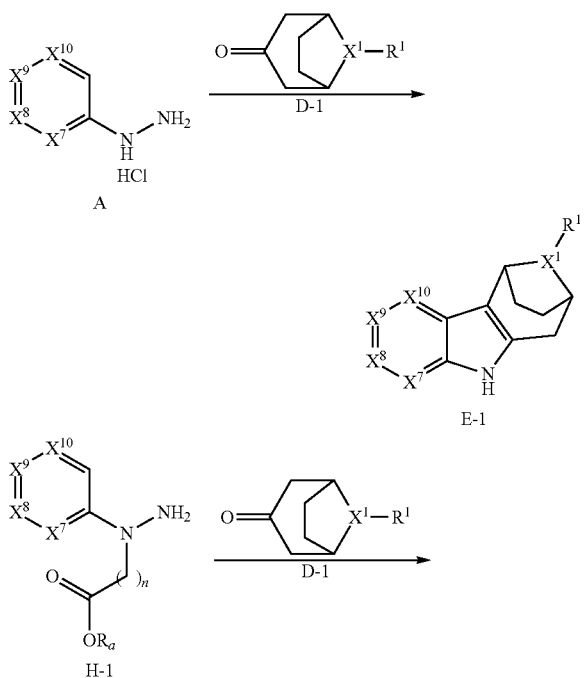

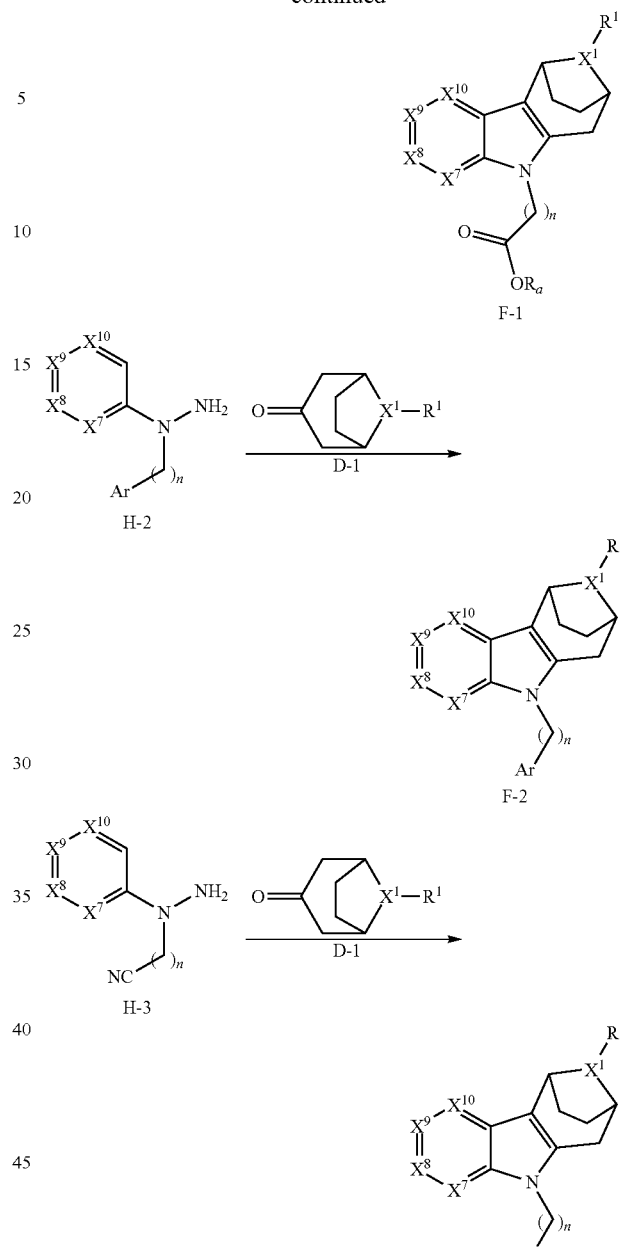

Aryl hydrazine or substituted aryl hydrazine hydrochloride (1 equiv) and appropriate hydrochloride salt of tropinone (1 equiv) are mixed in a suitable solvent such as EtOH and heated at 80-100° C. for 16 h (overnight) after which the solvent is removed in vacuo. The remaining residue is basified, e.g., with saturated aq. $NaHCO_3$. The aqueous layer is extracted with DCM or ethyl acetate and the combined organic layers are dried over $Na_2SO_4$, and concentrated in vacuo. The resulting crude product is purified by silica gel chromatography (100-200 mesh or 230-400 mesh) using MeOH-DCM gradient, by neutral alumina using ethyl acetate-hexane gradient, and/or by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

General Method 4

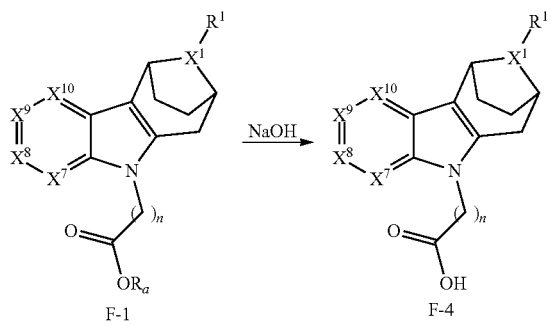

A mixture of appropriate carboline derivative with side chain carboxylate ester (1 equiv) and NaOH (3N, 5 folds w/v) in ethanol (5 folds w/v) is stirred at 50° C. for 3 h after which it is cooled to RT and neutralized with conc. HCl. The solvent is removed under reduced pressure to obtain corresponding crude carboxylic acid. The resulting crude product is purified by silica gel chromatography (100-200 mesh or 230-400 mesh) using MeOH-DCM gradient, by neutral alumina using ethyl acetate-hexane gradient, and/or by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

General Method 5

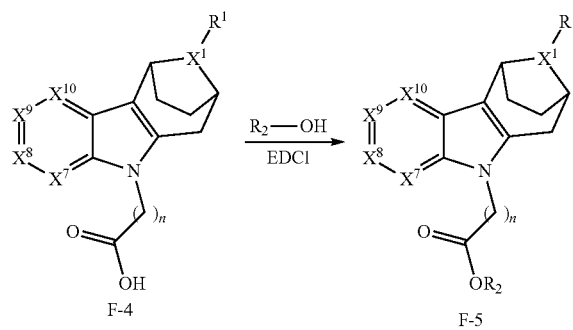

A mixture of appropriate carboline derivative with side chain carboxylic acid (1 equiv) is stirred with appropriate alcohol (1 equiv), EDCI-HCl (1 equiv) and triethylamine (1 equiv) in DCM for 12-16 h. The reaction mixture is evaporated under vacuo to obtain the crude ester that is purified by silica gel chromatography (100-200 mesh or 230-400 mesh) using MeOH-DCM gradient, by neutral alumina using ethyl acetate-hexane gradient, and/or by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

General Method 6A

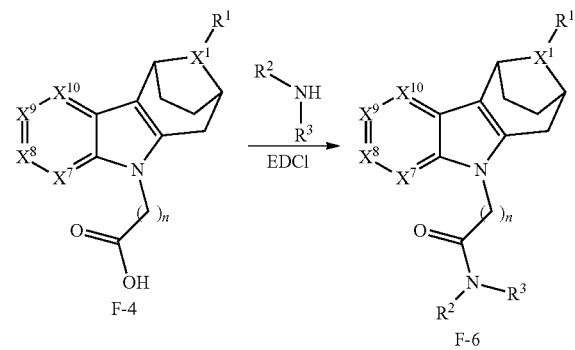

A mixture of appropriate carboline derivative with side chain carboxylic acid (1 equiv) is stirred with appropriate amine (1 equiv), EDCI (1 equiv) and triethylamine (1 equiv) in DCM for 12-16 h. The reaction mixture is evaporated in vacuo to obtain the crude amide that is purified by silica gel chromatography (100-200 mesh or 230-400 mesh) using MeOH-DCM gradient, by neutral alumina using ethyl acetate-hexane gradient, and/or by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

General Method 6B

Appropriate carboxylic acid (1 equiv 0.150 g, 0.472 mmol) is dissolved in DCM and cooled to 0° C. Oxalyl chloride (1.5 equiv) is added drop-wise followed by addition of a catalytic amount of dimethyl-formamide and the reaction mixture is stirred for 1 h at RT. Excess oxalyl chloride is distilled off under reduced pressure; a solution of appropriate amine (1.1 equiv) in DCM and 4-(N,N-dimethylamino)pyridine (1.2 equiv) is added to t his residue under nitrogen at RT and reaction mixture is stirred for 30 min at RT. The reaction mixture is quenched with water and neutralized with 10% NaHCO$_3$, extracted with ethyl acetate (2×10 mL). The combined organic layers are dried over sodium sulfate and concentrated under reduced pressure to provide the crude product that is purified by silica gel chromatography and/or reverse phase HPLC.

General Method 7

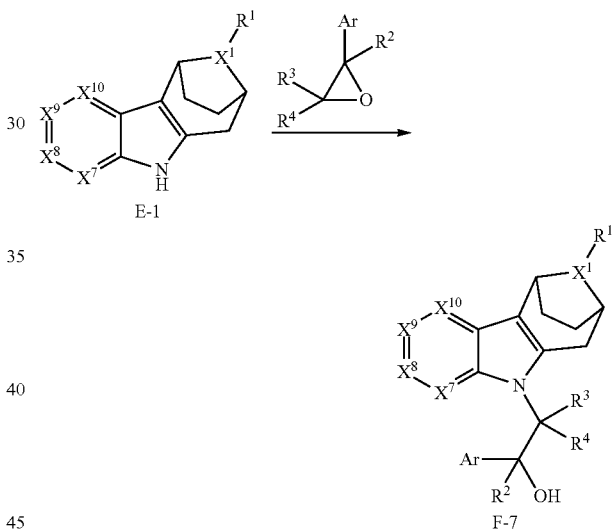

Carboline derivative (1 equiv), epoxide derivative (4-7.5 equiv) and NaH (3 equiv) are heated in DMF (3 mL/mmol) at 120° C. for 16 h. The contents are quenched by MeOH and evaporated to dryness. The resulting crude product is purified by silica gel chromatography (100-200 mesh or 230-400 mesh) using MeOH-DCM gradient, by neutral alumina using ethyl acetate-hexane gradient, and/or by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

General Method 8

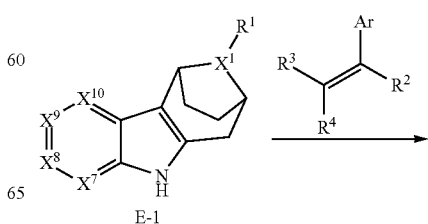

-continued

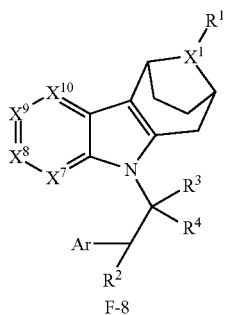

F-8

Appropriate carboline (1 equiv) is dissolved in NMP (0.6 mL/mmol). Powdered KOH (3.5 equiv) is added to this solution, and the reaction mixture is stirred for 10 min at 25° C. Appropriate vinylpyridine derivative (1.1 equiv) is added and the reaction mixture is heated in sealed tube at 45° C. for 30 min. The reaction is monitored by LCMS. After this period, the reaction mixture is cooled to 25° C. and diluted with saturated aqueous NaCl (5 mL). The product is extracted with ethyl acetate. The combined organic layer is dried over anhydrous sodium sulfate and evaporated under reduced pressure. The resulting crude product is purified by silica gel chromatography (100-200 mesh or 230-400 mesh) using MeOH-DCM gradient, by neutral alumina using ethyl acetate-hexane gradient, and/or by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

General Method 9

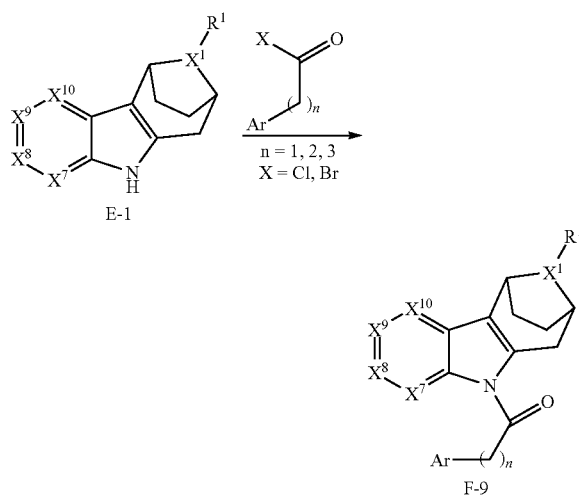

Appropriate carboline (1 equiv) is dissolved in DCM (3 mL/mmol) and cooled to 0° C. Triethylamine (1 equiv) is added followed by appropriate acid chloride. The reaction mixture is slowly allowed to warm to 25° C. and stirred at 25° C. for 24 h. The reaction mixture is quenched by adding saturated aqueous NaHCO₃ and extracted with DCM. The combined organic layer is dried over anhydrous sodium sulfate and evaporated under reduced pressure. The resulting crude product is purified by silica gel chromatography (100-200 mesh or 230-400 mesh) using MeOH-DCM gradient, by neutral alumina using ethyl acetate-hexane gradient, and/or by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

General Method 10

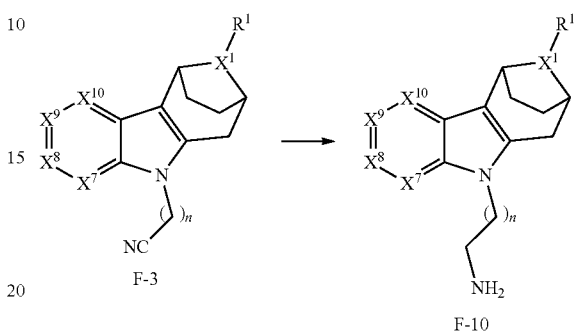

An appropriate carboline derivative with side chain nitrile (1 equiv) is treated with diisobutylaluminum hydride (3 equiv) in toluene (5 ml/mmol) at 80° C. for 1-2 h. The reaction mixture is cooled to 25° C., quenched with water and extracted ethyl acetate. The combined organic layer is dried over anhydrous sodium sulfate and evaporated under reduced pressure. The resulting crude product is purified by silica gel chromatography (100-200 mesh or 230-400 mesh) using MeOH-DCM gradient, by neutral alumina using ethyl acetate-hexane gradient, and/or by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

General Method 11

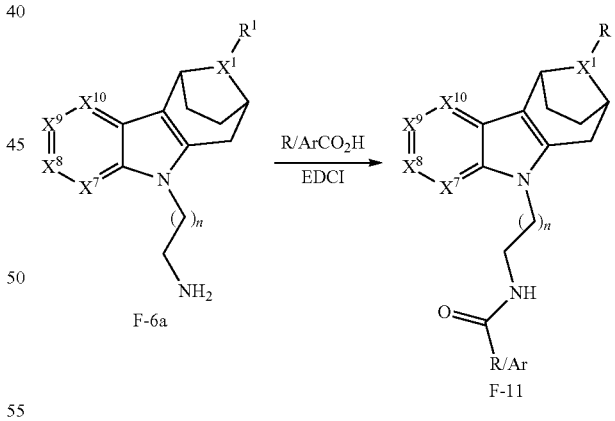

A mixture of appropriate carboline derivative with side chain amine (1 equiv) is stirred with appropriate carboxylic acid (1 equiv), EDCI (1 equiv) and triethylamine (1 equiv) in DCM for 12-16 h. The reaction mixture is evaporated in vacuo to obtain the crude amide that is purified by silica gel chromatography (100-200 mesh or 230-400 mesh) using MeOH-DCM gradient, by neutral alumina using ethyl acetate-hexane gradient, and/or by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

General Method 12

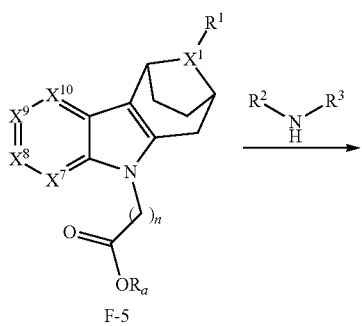

F-5

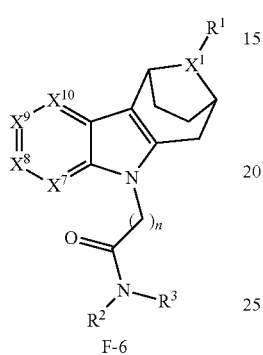

F-6

A mixture of appropriate carboline derivative with side chain carboxylate ester (1 equiv) and appropriate amine (10 fold w/v) is heated at 120° C. for 12-18 h after which the reaction mixture is evaporated to dryness and the resulting crude product was purified by silica gel chromatography (100-200 mesh or 230-400 mesh) using MeOH-DCM gradient, by neutral alumina using ethyl acetate-hexane gradient, and/or by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

General Method 13.

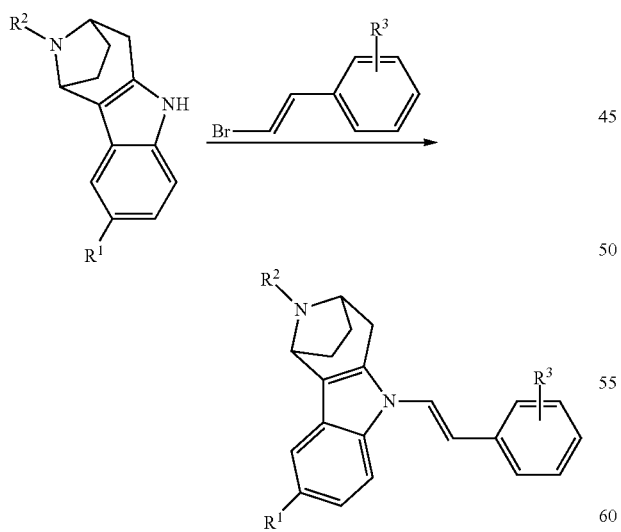

Appropriately substituted 5,6,7,8,9,10-hexahydro-7,10-iminocyclohept[b]indole (0.36 mmol) is dissolved in DMF. To this solution CuI (1 equiv), L-proline (0.02 equiv), $K_3PO_4$ (2 equiv) are added and the reaction mixture is stirred for 10 min at RT. This is followed by drop wise addition of (2-bromovinyl)arene (100 mg, 1.2 equiv). The reaction mixture is heated at 80° C. for overnight. DMF is evaporated under reduced pressure and the product is extracted with ethyl acetate and the organic layer is washed with brine. The organic layer is dried over anhydrous Na2SO4, and concentrated under reduced pressure. The crude compound thus obtained is purified by column chromatography on silica gel to afford the product. The general method may be modified to reach similar products, e.g., by substituting (2-bromovinyl)arene with like compounds.

General Method 14.

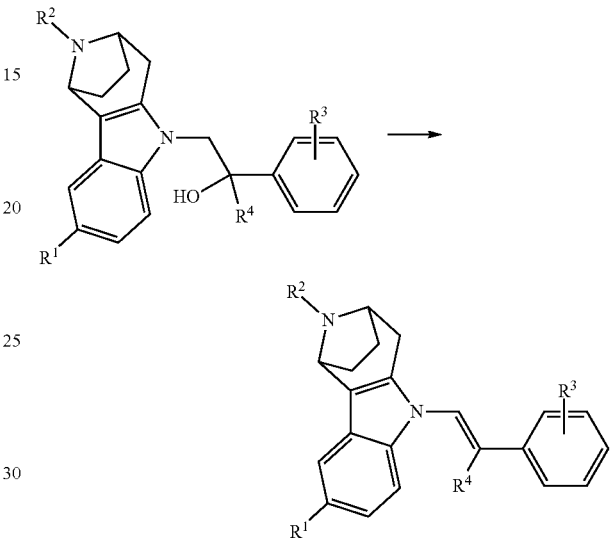

Appropriately substituted (5,6,7,8,9,10-hexahydro-7,10-iminocyclohept[b]indol-5-yl)ethanol derivative (1 equiv) is refluxed with 25% aqueous sulfuric acid for 2 h. The reaction mixture is cooled to 5° C. with an ice-water bath. KOH (15% aq. solution) is added drop wise to the reaction mixture till pH of 9-10. The reaction mixture is extracted with ethyl acetate. The combined organic layer is washed with water (10 ml) followed by brine, dried over sodium sulfate and evaporated under vacuum. The crude product is purified by column chromatography on silica gel (100-200 mesh).

General Method 15A.

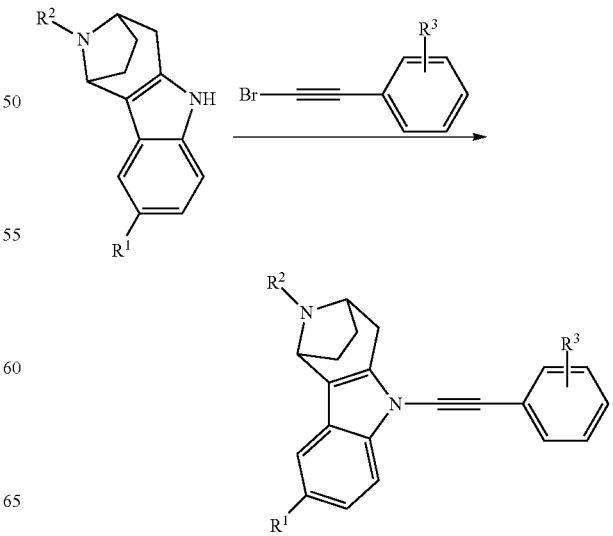

To a stirred solution of appropriately substituted 5,6,7,8,9,10-hexahydro-7,10-iminocyclohept[b]indole (1 equiv) and copper sulfate (0.01 equiv) in toluene is added potassium carbonate (2 equiv) and 1,10 phenanthroline (0.05 equiv), reaction mixture is stirred for 5 min at RT. A solution of 1-Bromoethynylarene (1 equiv) in toluene is added to the reaction mixture. The reaction mixture is stirred for 2 h at 80° C. Solvent is removed under pressure and the resulting crude product is purified by column chromatography on silica gel. The general method may be modified to reach similar products, e.g., by substituting 1-Bromoethynylarene with like compounds.

General Method 15B.

An appropriately substituted 5,6,7,8,9,10-hexahydro-7,10-iminocyclohept[b]indole (1 equiv) is added to a solution of sodium hydride (5 equiv) in THF at 0° C. and the contents are stirred at 0° C. for 30 min. A solution of appropriately substituted alkyl halide (2 equiv.) in THF is added dropwise to the reaction mixture which and stirred at RT for three h. After completion of the reaction, the reaction mixture is quenched with ice cold water and product extracted with ethyl acetate, washed with water, dried over sodium sulfate and concentrated under reduced pressure to obtain crude compound. The crude product is purified to yield the desired product. The general method may be modified to reach similar products, e.g., by substituting chloroacetamide with like compounds.

General Method 15C.

I. Tetrabutylammonium chloride (0.5 equiv.) is dissolved in 50% NaOH followed by addition of appropriately substituted 5,6,7,8,9,10-hexahydro-7,10-iminocyclohept[b]indole (1 equiv.). The reaction mixture is stirred for 5 min at RT, and appropriate alkyl halide (1 equiv.) is added and stirred at 100° C. for 12 h. The reaction is quenched with water and extracted in DCM. The combined organic layers are dried over sodium sulfate and concentrated under vacuum to yield the crude product which is purified by reverse phase chromatography.

II. An appropriately substituted 5,6,7,8,9,10-hexahydro-7,10-iminocyclohept[b]indole (1 equiv.) and appropriate alkyl halide (1 equiv.) is added to vigorously stirred mixture of tetra-n-butyl ammonium chloride (0.5 equiv.) in 50% aq NaOH solution and the resultant mixture is heated to 60° C. for 6 h. Upon completion (the reaction is monitored by LCMS), the reaction is quenched with and extracted with DCM, the combined organic layers are separated, dried over Na$_2$SO$_4$ and concentrated, and the resultant crude is purified by reverse-phase chromatography.

III. An appropriately substituted 5,6,7,8,9,10-hexahydro-7,10-iminocyclohept[b]indole (1 equiv.) is added to a solution of tetra n-butyl ammonium chloride (0.5 equiv.) in 50% aq NaOH and stirred for 30 min. Appropriate alkyl halide (1 equiv.) is added and the reaction mixture is heated at 60° C. for 15 h. The progress of the reaction is monitored by LCMS, TLC. After complete reaction, the reaction mixture is quenched with water and extracted with ethyl acetate. The combined organic layers are dried over sodium sulfate and concentrated under reduced pressure and the resultant crude product is purified by chromatography.

General Method 16

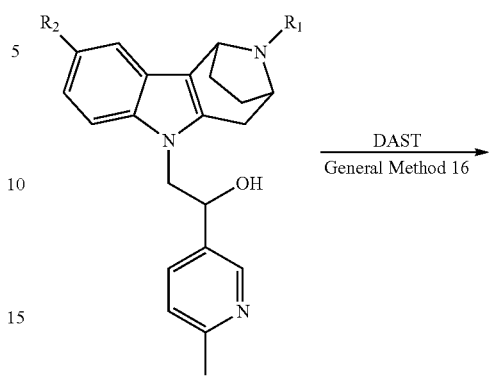

Appropriate carboline (1 equiv.) is dissolved in DCM and the solution is cooled to 0° C. Diethylaminosulfur trifluoride (DAST) (1.5 equiv.) is added dropwise and the reaction mixture is stirred at RT for 2 h. The reaction mixture is diluted with saturated aqueous NaHCO$_3$ solution and the organic layer is separated. The organic layer is dried over anhydrous sodium sulfate and evaporated under reduced pressure. The residue is purified by chromatography on neutral alumina to give pure product.

General Method 17

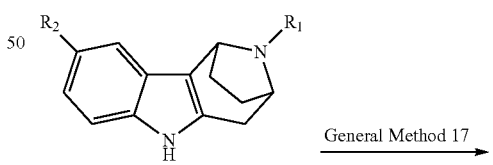

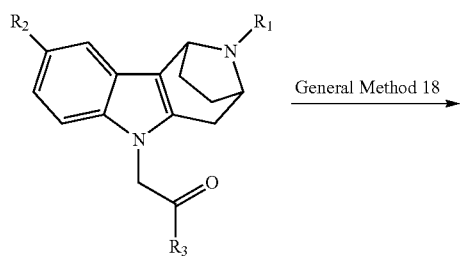

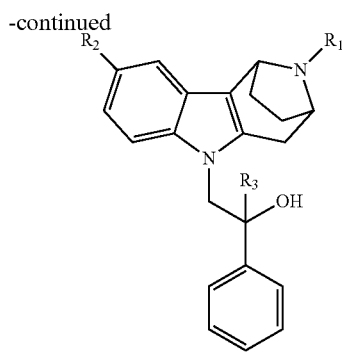

To a solution of appropriate carboline (1 equiv.) in N-methyl-2-pyrrolidone is added KOH (7 equiv.). The reaction mixture is stirred at RT for 20 min. A solution of appropriate 2-bromo-1-(aryl)ethanone (1 equiv.) in N-methyl-2-pyrrolidone is added dropwise and stirring is continued for additional 2-4 h. The reaction is monitored by LCMS and TLC. The reaction mixture is diluted by adding water and extracted with ethyl acetate. The organic layer is washed with water, dried over anhydrous sodium sulfate and concentrated under reduced pressure. The residue is purified by silica gel chromatography to give pure ketone product.

General Method 18

The ketone product of General Method 17 (1 equiv.) is dissolved in anhydrous THF. Grignard reagent (3 equiv) is added to it dropwise at RT under nitrogen atmosphere and reaction mixture is stirred at RT for 1 h. Water is added to the reaction mixture and the product is extracted with ethyl acetate. The organic layer is washed with water, dried over anhydrous sodium sulfate and concentrated under reduced pressure. The residue is purified by HPLC to give pure alcohol product.

General Method 19

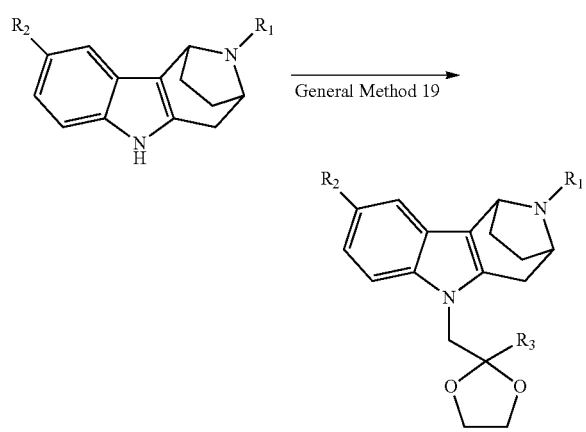

Appropriately substituted carboline (1 equiv.) is dissolved in DMF (2 mL per mmol) and sodium hydride (2 equiv.) is added to it under nitrogen atmosphere. Appropriate 2-(bromomethyl)-1,3-dioxolane (1 equiv.) is added and the reaction mixture is heated at 100° C. overnight. The reaction mixture is diluted by adding water and extracted with ethyl acetate. The organic layer is washed with water, dried over anhydrous sodium sulfate and concentrated under reduced pressure. The residue is purified by silica gel chromatography to give pure product.

General Methods for HPLC Analysis

Method-1
 Column: YMC ODS-A 150 mm×4.6 mm×5μ, ID: E-AC-1/06/COL/013
 Mobile Phase: A: 0.05% TFA in Water/B: 0.05% TFA in Acetonitrile
 Inj. Vol: 10 μL, Col. Temp.: 30° C., Flow rate: 1.2 mL/min
 Gradient: 10% B to 80% B in 5 min, Hold for 2 min, 7.01-10 min 10% B Method-2
 Column: YMC ODS-A 150 mm×4.6 mm×5μ, ID: E-AC-1/06/COL/013
 Mobile Phase: A: 0.05% TFA in Water/B: 0.05% TFA in Acetonitrile
 Inj. Vol: 10 μL, Col. Temp.: 30° C., Flow rate: 1.2 mL/min
 Gradient: 50% B to 100% B in 5 min, Hold for 2 min, 7.01-10 min 50% B Method-3
 Column: YMC ODS-A 150 mm×4.6 mm×5μ, ID: E-AC-1/06/COL/013
 Mobile Phase: A: 0.05% TFA in Water/B: 0.05% TFA in Acetonitrile
 Inj. Vol: 10 μL, Col. Temp.: 30° C., Flow rate: 1.4 mL/min
 Gradient: 5% B to 95% B in 8 min, Hold for 1.5 min, 9.51-12 min 5% B The methods detailed above may be adapted as known by those of skill in the art. Particular examples of each General Method are provided in the Examples below. Additional synthetic methods which may be adapted to arrive at the compounds detailed herein are found in U.S. application Ser. No. 12/259,234 and PCT Application No. PCT/US2008/081390, both filed Oct. 27, 2008.

The following Examples are provided to illustrate but not limit the invention.

All references disclosed herein are incorporated by reference in their entireties.

EXAMPLES

Example 1

Preparation of Compound No. K-8

To a stirred solution of 2-methyl-11-methyl-5,6,7,8,9,10-hexahydro-7,10-epiminocyclohepta[b]indole (1 g, 4.4 mmol) in DMF (10 mL), was added sodium hydride (528 mg, 13.2 mmol) under nitrogen at RT. After stirring for 5 min, a solution of 4-oxiranyl-pyridine (803 mg, 6.6 mmol) in DMF was added dropwise into the reaction mixture, which was stirred at RT for 16 h. The progress of reaction was monitored by LCMS and TLC. The reaction mass was poured into ice-cold water and extracted with EtOAc (3×40 mL). The combined organic layer was washed with water (6×30 mL), dried over anhydrous sodium sulfate and concentrated under reduced pressure. The residue obtained was re-crystallized in ethanol-ether to yield the title compound.

$^1$H NMR (CDCl$_3$, free base) d (ppm): 8.59 (d, 1H), 8.58 (d, 1H), 7.38 (d, 1H), 7.24 (d, 1H), 7.20 (d, 1H), 7.08 (d, 1H), 7.0 (d, 1H), 5.0 (m, 1H), 4.62 (dd, 2H), 4.18 (m, 2H), 4.0 (m, 1H), 2.70 (m, 2H), 2.58 (m, 2H), 2.45 (s, 3H), 2.42 (s, 3H), 2.10 (m, 1H), 1.70 (m, 1H).

Example 2

Preparation of Compound No. K-11

To a stirred solution of 2-chloro-11-methyl-5,6,7,8,9,10-hexahydro-7,10-epiminocyclohepta[b]indole (1.0 g, 4.03 mmol) in DMF (20 mL) was added sodium hydride (483 mg, 12.09 mmol). After stirring the suspension at RT for 10 min, a solution of 4-(oxiran-2-yl) pyridine (1.0 g, 8.0 mmol) in DMF (5 mL) was added slowly into the reaction mixture, which was stirred at RT overnight. The progress of reaction was monitored by TLC and LCMS. The reaction mass was poured into ice cold water (200 mL) and extracted with EtOAc (3×200 mL). The organic layer was washed with water (4×300 mL), dried over anhydrous sodium sulfate and concentrated. The residue obtained was washed with hexane (4×30 mL) and triturated with diethyl ether (200 mL) to yield the title compound.

$^1$H NMR (CDCl$_3$, free base) d (ppm): 8.55 (d, 2H), 7.35 (m, 2H), 7.15-7.10 (m, 3H), 4.70 (m, 1H), 4.10 (m, 1H), 4.0-3.90 (m, 2H), 3.5 (m, 1H), 2.80 (d, 1H), 2.25-2.15 (m, 5H), 1.80 (m, 1H), 1.70-1.50 (m, 2H), 1.40 (m, 1H).

Example 3

Preparation of Compound No. K-60

To a solution of 11-methyl-5,6,7,8,9,10-hexahydro-7,10-epiminocyclohepta[b]indole (1 g, 5.05 mmol) in DMF (10 mL), was added sodium hydride (607 mg, 15.17 mmol) under nitrogen at 0° C. After stirring the solution for 10 min, 4-oxiranyl-pyridine (1.1 g, 9.09 mmol) was added dropwise under nitrogen into the reaction mixture, which was stirred at RT for 12 h. The progress of reaction was monitored by TLC and LCMS. The reaction mass was poured into ice-cold water and extracted with EtOAc (2×100 mL). The combined organic layer was washed with water (5×50 mL), dried over anhydrous sodium sulfate, concentrated and purified by reverse phase chromatography to yield the title compound.

$^1$H NMR (CD$_3$OD, free base) d (ppm): 8.42 (d, 1H), 8.36 (d, 1H), 7.42 (m, 1H), 7.36 (d, 1H), 7.30 (m, 1H), 7.16 (d, 1H), 7.04 (m, 2H), 5.05 (m, 1H), 4.58 (m, 1H), 4.20 (m, 1H), 4.10 (m, 1H), 3.92 (m, 1H), 3.15 (m, 1H), 3.0 (m, 1H), 2.80 (d, 1H), 2.10-2.0 (m, 3H).

Example B1

Determination of the Ability of Compounds of the Invention to Bind a Histamine Receptor Histamine H1

To evaluate in radioligand binding assays the activity of compounds of the invention, human recombinant histamine H1 receptor expressed in Chinese hamster ovary (CHO) cells (De Backer, M. D. et al., Biochem. Biophys. Res. Comm. 197(3):1601, 1993) in a modified Tris-HCl buffer (50 mM Tris-HCl, pH 7.4, 2 mM MgCl$_2$, 100 mM NaCl, 250 mM Sucrose) is used. Compounds of the invention are incubated with 1.2 nM [$^3$H]Pyrilamine for 180 min at 25° C. Non-specific binding is estimated in the presence of 1 µM pyrilamine. Receptor proteins are filtered and washed, the filters are then counted to determine [$^3$H]Pyrilamine specifically bound. Compounds are screened at 1 µM or lower, using 1% DMSO as vehicle. Compounds of the invention are tested in this biochemical assay and percent inhibition of specific binding is determined.

Histamine H2

To evaluate in radioligand binding assays the activity of compounds of the invention, human recombinant histamine H2 receptor expressed in Chinese hamster ovary (CHO) K1 cells (Ruat, M., Proc. Natl. Acad. Sci. USA. 87(5):1658, 1990) in a 50 mM Phosphate buffer, pH 7.4 is used. Compounds of the invention are incubated with 0.1 nM [$^{125}$I] Aminopotentidine for 120 min at 25° C. Non-specific binding is estimated in the presence of 3 µM Tiotidine. Receptor proteins are filtered and washed, the filters are then counted to determine [$^{125}$I]Aminopotentidine specifically bound. Compounds are screened at 1 µM or lower, using 1% DMSO as vehicle. Compounds of the invention are tested in this biochemical assay and percent inhibition of specific binding is determined.

Histamine H3

To evaluate in radioligand binding assays the activity of compounds of the invention, human recombinant histamine H$_3$ receptor expressed in Chinese hamster ovary (CHO-K1) cells (Yanai K et al. Jpn J Pharmacol. 65(2): 107, 1994; Zhu Y et al. Mol Pharmacol. 59(3): 434, 2001) in a modified Tris-HCl buffer (50 mM Tris-HCl, pH 7.4, 5 mM MgCl$_2$, 0.04% BSA) is used. Compounds of invention are incubated with 3 nM [$^3$H]R(−)-α-Methylhistamine for 90 min at 25° C. Non-specific binding is estimated in the presence of 1 µM R(−)-α-Methylhistamine. Receptor proteins are filtered and washed, the filters are counted to determine [$^3$H] R(−)-α-Methylhistamine specifically bound. Compounds are screened at 1 µM or lower, using 1% DMSO as vehicle. Compounds of the invention are tested in this biochemical assay and percent inhibition of specific binding is determined.

Example B2

Determination of the Ability of Compounds of the Invention to Bind a Imidazoline I$_2$ Receptor Central Imidazoline I$_2$ To evaluate in radioligand binding assays the activity of compounds of the invention, rat central imidazoline I$_2$ receptor obtained from Wistar Rat cerebral cortex (Brown, C. M. et al., Br. J. Pharmacol. 99:803, 1990) in a modified Tris-HCl buffer (50 mM Tris-HCl buffer, pH 7.4, 0.5 mM EDTA) is used. Compounds of the invention are incubated with 2 nM [$^3$H]Idazoxan for 30 min at 25° C. Non-specific binding is estimated in the presence of 1 µM Idazoxan. Receptor proteins are filtered and washed, the filters are then counted to determine [$^3$H]Idazoxan specifically bound. Compounds are screened at 1 µM or lower, using 1% DMSO as vehicle. Compounds of the invention are tested in this biochemical assay and percent inhibition of specific binding is determined.

Example B3

Determination of the Ability of Compounds of the Invention to Bind an Adrenergic Receptor Adrenergic α$_{1A}$ To evaluate in radioligand binding assays the activity of compounds of the invention, rat adrenergic α$_{1A}$ receptor obtained from Wistar Rat submaxillary glands (Michel, A. D. et al., Br. J. Pharmacol. 98:883, 1989) in a modified Tris-HCl buffer (50 mM Tris-HCl, pH 7.4, 0.5 mM EDTA) is used. Compounds of the invention are incubated with 0.25 nM [$^3$H]Prozosin for 60 min at 25° C. Non-specific binding is estimated in the presence of 10 µM phentolamine Receptor proteins are filtered and washed, the filters are then counted to determine [$^3$H]Prozosin specifically bound. Compounds of the invention are screened at 1 µM or lower, using 1% DMSO as vehicle. Compounds of the invention are tested in this biochemical assay and percent inhibition of specific binding is determined.

Adrenergic $\alpha_{1B}$

To evaluate in radioligand binding assays the activity of compounds of the invention, rat adrenergic $\alpha_{1B}$ receptor obtained from Wistar Rat liver (Garcia-S'ainz, J. A. et al., Biochem. Biophys. Res. Commun. 186:760, 1992; Michel A. D. et al., Br. J. Pharmacol. 98:883, 1989) in a modified Tris-HCl buffer (50 mM Tris-HCl buffer, pH 7.4, 0.5 mM EDTA) was used. Compounds of the invention were incubated with 0.25 nM [$^3$H]Prozosin for 60 min at 25° C. Non-specific binding was estimated in the presence of 10 µM phentolamine Receptor proteins were filtered and washed, the filters were then counted to determine [$^3$H]Prozosin specifically bound. Compounds were screened at 1 µM or lower, using 1% DMSO as vehicle. Compounds of the invention were tested in this biochemical assay and percent inhibition of specific binding was determined.

Adrenergic $\alpha_{1D}$

To evaluate in radioligand binding assays the activity of compounds of the invention, human recombinant adrenergic $\alpha_{1D}$ receptor expressed in human embryonic kidney (HEK-293) cells (Kenny, B. A. et al. Br. J. Pharmacol. 115(6):981, 1995) in a 50 mM Tris-HCl buffer, pH 7.4, is used. Compounds of invention are incubated with 0.6 nM [$^3$H]Prozosin for 60 min at 25° C. Non-specific binding is estimated in the presence of 10 µM phentolamine. Receptor proteins are filtered and washed, the filters are then counted to determine [$^3$H]Prozosin specifically bound. Compounds are screened at 1 µM or lower, using 1% DMSO as vehicle. Compounds of the invention are tested in this biochemical assay and percent inhibition of specific binding is determined.

Adrenergic $\alpha_{2A}$

To evaluate in radioligand binding assays the activity of compounds of the invention, human recombinant adrenergic $\alpha_{2A}$ receptor expressed in insect Sf9 cells (Uhlen S et al. J Pharmacol Exp Ther. 271:1558, 1994) in a modified Tris-HCl buffer (50 mM Tris-HCl, pH 7.4, 12.5 mM MgCl$_2$, 2 mM EDTA) was used. Compounds of invention were incubated with 1 nM [$^3$H]MK-912 for 60 min at 25° C. MK912 was (2S-trans)-1,3,4,5',6,6',7,12b-octahydro-1',3'-dimethyl-spiro [2H-benzofuro[2,3-a]quinolizine-2,4'(1'H)-pyrimidin]-2' (3'H)-one hydrochloride Non-specific binding was estimated in the presence of 10 µM WB-4101 (2-(2,6-Dimethoxyphenoxyethyl)aminomethyl-1,4-benzodioxane hydrochloride). Receptor proteins were filtered and washed, the filters were then counted to determine [$^3$H]MK-912 specifically bound. Compounds were screened at 1 µM or lower, using 1% DMSO as vehicle. Compounds of the invention were tested in this biochemical assay and percent inhibition of specific binding was determined.

Adrenergic $\alpha_{2B}$

To evaluate in radioligand binding assays the activity of compounds of the invention, human recombinant adrenergic $\alpha_{2B}$ receptor expressed in Chinese hamster ovary (CHO-K1) cells (Uhlen S et al. Eur J Pharmacol. 343(1):93, 1998) in a modified Tris-HCl buffer (50 mM Tris-HCl, pH 7.4, 12.5 mM MgCl$_2$, 1 mM EDTA, 0.2% BSA) was used. Compounds of the invention were incubated with 2.5 nM [$^3$H]Rauwolscine for 60 min at 25° C. Non-specific binding was estimated in the presence of 10 µM Prozosin. Receptor proteins were filtered and washed, the filters were then counted to determine [$^3$H] Rauwolscine specifically bound. Compounds were screened at 1 µM or lower, using 1% DMSO as vehicle. Compounds of the invention were tested in this biochemical assay and percent inhibition of specific binding was determined.

Adrenergic $\alpha_{2C}$

To evaluate in radioligand binding assays the activity of compounds of the invention, human recombinant adrenergic $\alpha_{2C}$ receptor expressed in insect Sf9 cells (Uhlen S et al. J Pharmacol Exp Ther. 271:1558, 1994) in a modified Tris-HCl buffer (50 mM Tris-HCl, pH 7.4, 12.5 mM MgCl$_2$, 2 mM EDTA) is used. Compounds of the invention are incubated with 1 nM [$^3$H]MK-912 for 60 min at 25° C. Non-specific binding is estimated in the presence of 10 µM WB-4101. Receptor proteins are filtered and washed, the filters are then counted to determine [$^3$H]MK-912 specifically bound. Compounds are screened at 1 µM or lower, using 1% DMSO as vehicle. Compounds of the invention are tested in this biochemical assay and percent inhibition of specific binding is determined.

Example B4

Determination of the Ability of Compounds of the Invention to Bind a Dopamine Receptor Dopamine $D_{2L}$ To evaluate in radioligand binding assays the activity of compounds of the invention, human recombinant dopamine $D_{2L}$ receptor expressed in Chinese hamster ovary (CHO) cells (Grandy, D. K. et al. Proc. Natl. Acad. Sci. USA. 86:9762, 1989; Hayes, G. et al., Mol. Endocrinol. 6:920, 1992) in a modified Tris-HCl buffer (50 mM Tris-HCl, pH 7.4, 1.4 mM Ascorbic Acid, 0.001% BSA, 150 mM NaCl) is used. Compounds of the invention are incubated with 0.16 nM [$^3$H] Spiperone for 120 min at 25° C. Non-specific binding is estimated in the presence of 10 µM Haloperidol. Receptor proteins are filtered and washed, the filters are then counted to determine [$^3$H]Spiperone specifically bound. Compounds are screened at 1 µM or lower, using 1% DMSO as vehicle. Compounds of the invention are tested in this biochemical assay and percent inhibition of specific binding is determined.

Example B5

Determination of the Ability of Compounds of the Invention to Bind a Serotonin Receptor Serotonin (5-Hydroxytryptamine) 5-HT$_{1A}$ To evaluate in radioligand binding assays the activity of compounds of the invention, human recombinant serotonin (5-Hydroxytryptamine) 5-HT$_{1A}$ receptor expressed in Chinese hamster ovary (CHO-K1) cells (Martin G R and Humphrey P P A. Neuropharmacol. 33:261, 1994; May J A, et al. J Pharmacol Exp Ther. 306(1): 301, 2003) in a modified Tris-HCl buffer (50 mM Tris-HCl, pH 7.4, 0.1% Ascorbic Acid, 0.5 mM EDTA, 10 mM MgSO$_4$) is used. Compounds of invention are incubated with 1.5 nM [$^3$H] 8-OH-DPAT for 60 min at 25° C. Non-specific binding is estimated in the presence of 10 µM Metergoline. Receptor proteins are filtered and washed, the filters are then counted to determine [$^3$H] 8-OH-DPAT specifically bound. Compounds are screened at 1 µM or lower, using 1% DMSO as vehicle. Compounds of the invention are tested in this biochemical assay and percent inhibition of specific binding is determined.

Serotonin (5-Hydroxytryptamine) 5-HT$_{1B}$

To evaluate in radioligand binding assays the activity of compounds of the invention, serotonin (5-Hydroxytryptamine) 5-HT$_{1B}$ receptor from Wistar Rat cerebral cortex (Hoyer et al. Eur J Pharmaco. 118: 1, 1985; Pazos et al. Eur J Pharmacol. 106: 531, 1985) in a modified Tris-HCl buffer (50 mM Tris-HCl, pH 7.4, 154 mM NaCl, 10 µM Pargyline, 30 µM Isoprenaline) is used. Compounds of invention are incubated with 10 pM [$^{125}$I]Cyanopindolol for 90 min at 37° C. Non-specific binding is estimated in the presence of 10 µM Serotonin (5-HT). Receptor proteins are filtered and washed, the filters are then counted to determine [$^{125}$I]Cyanopindolol specifically bound. Compounds are screened at 1 µM or lower, using 1% DMSO as vehicle. Compounds of the invention are tested in this biochemical assay and percent inhibition of specific binding is determined.

Serotonin (5-Hydroxytryptamine) 5-HT$_{2A}$

To evaluate in radioligand binding assays the activity of compounds of the invention, human recombinant serotonin (5-Hydroxytryptamine) 5-HT$_{2A}$ receptor expressed in Chinese hamster ovary (CHO-K1) cells (Bonhaus, D. W. et al. Br. J. Pharmacol. 115:622, 1995; Saucier, C. and Albert, P. R., J. Neurochem. 68:1998, 1997) in a 50 mM Tris-HCl buffer, pH 7.4, is used. Compounds of the invention are incubated with 0.5 nM [$^3$H]Ketanserin for 60 min at 25° C. Non-specific binding is estimated in the presence of 1 µM Mianserin. Receptor proteins are filtered and washed, the filters are then counted to determine [$^3$H]Ketanserin specifically bound. Compounds are screened at 1 µM or lower, using 1% DMSO as vehicle. Compounds of the invention are tested in this biochemical assay and percent inhibition of specific binding is determined.

Serotonin (5-Hydroxytryptamine) 5-HT$_{2B}$

To evaluate in radioligand binding assays the activity of compounds of the invention, human recombinant serotonin (5-Hydroxytryptamine) 5-HT$_{2B}$ receptor expressed in Chinese hamster ovary (CHO-K1) cells (Bonhaus, D. W. et al., Br. J. Pharmacol. 115:622, 1995) in a modified Tris-HCl buffer (50 mM Tris-HCl, pH 7.4, 4 mM CaCl$_2$, 0.1% Ascorbic Acid) is used. Compounds of invention are incubated with 1.2 nM [$^3$H]Lysergic acid diethylamide (LSD) for 60 min at 37° C. Non-specific binding is estimated in the presence of 10 µM Serotonin (5-HT). Receptor proteins are filtered and washed, the filters are then counted to determine [$^3$H]LSD specifically bound. Compounds are screened at 1 µM or lower, using 1% DMSO as vehicle. Compounds of the invention are tested in this biochemical assay and percent inhibition of specific binding is determined.

Serotonin (5-Hydroxytryptamine) 5-HT$_{2C}$

To evaluate in radioligand binding assays the activity of compounds of the invention, human recombinant serotonin (5-Hydroxytryptamine) 5-HT$_{2C}$ receptor expressed in Chinese hamster ovary (CHO-K1) cells (Wolf, W. A. and Schutz, J. S., J. Neurochem. 69:1449, 1997) in a modified Tris-HCl buffer (50 mM Tris-HCl, pH 7.4, 0.1% Ascorbic Acid, 10 µM Pargyline) is used. Compounds of the invention are incubated with 1 nM [$^3$H]Mesulergine for 60 min at 25° C. Non-specific binding is estimated in the presence of 1 µM Mianserin. Receptor proteins are filtered and washed, the filters are then counted to determine [$^3$H]Mesulergine specifically bound. Compounds are screened at 1 µM or lower, using 1% DMSO as vehicle. Compounds of the invention are tested in this biochemical assay and percent inhibition of specific binding is determined.

Serotonin (5-Hydroxytryptamine) 5-HT$_3$

To evaluate in radioligand binding assays the activity of compounds of the invention, human recombinant serotonin (5-Hydroxytryptamine) 5-HT$_3$ receptor expressed in human embryonic kidney (HEK-293) cells (Miller K et al. Synapse. 11:58, 1992; Boess F G et al. Neuropharmacology. 36:637, 1997) in a modified Tris-HCl buffer (50 mM Tris-HCl, pH 7.4, 1 mM EDTA, 5 mM MgCl$_2$) is used. Compounds of invention are incubated with 0.69 nM [$^3$H]GR-65630 for 60 min at 25° C. Non-specific binding is estimated in the presence of 10 µM MDL-72222. Receptor proteins are filtered and washed, the filters are then counted to determine [$^3$H]GR-65630 specifically bound. Compounds are screened at 1 µM or lower, using 1% DMSO as vehicle. Compounds of the invention are tested in this biochemical assay and percent inhibition of specific binding is determined.

Serotonin (5-Hydroxytryptamine) 5-HT$_4$

To evaluate in radioligand binding assays the activity of compounds of the invention, serotonin (5-Hydroxytryptamine) 5-HT$_4$ receptor from Duncan Hartley derived Guinea pig striatum (Grossman C J et al. Br J Pharmacol. 109:618, 1993) in a 50 mM Tris-HCl, pH 7.4, is used. Compounds of invention are incubated with 0.7 nM [$^3$H]GR-113808 for 30 min at 25° C. Non-specific binding is estimated in the presence of 30 µM Serotonin (5-HT). Receptor proteins are filtered and washed, the filters are then counted to determine [$^3$H]GR-113808 specifically bound. Compounds are screened at 1 µM or lower, using 1% DMSO as vehicle. Compounds of the invention are tested in this biochemical assay and percent inhibition of specific binding is determined.

Serotonin (5-Hydroxytryptamine) 5-HT$_{5A}$

To evaluate in radioligand binding assays the activity of compounds of the invention, human recombinant serotonin (5-Hydroxytryptamine) 5-HT$_{5A}$ receptor expressed in Chinese hamster ovary (CHO-K1) cells (Rees, S. et al., FEBS Lett. 355:242, 1994) in a modified Tris-HCl buffer (50 mM Tris-HCl, pH 7.4, 10 mM MgCl$_2$, 0.5 mM EDTA) is used. Compounds of the invention are incubated with 1.7 nM [$^3$H] Lysergic acid diethylamide (LSD) for 60 min at 37° C. Non-specific binding is estimated in the presence of 100 µM Serotonin (5-HT). Receptor proteins are filtered and washed, the filters are then counted to determine [$^3$H]LSD specifically bound. Compounds are screened at 1 µM or lower, using 1% DMSO as vehicle. Compounds of the invention are tested in this biochemical assay and percent inhibition of specific binding is determined.

Serotonin (5-Hydroxytryptamine) 5-HT$_6$

To evaluate in radioligand binding assays the activity of compounds of the invention, human recombinant serotonin (5-Hydroxytryptamine) 5-HT6 receptor expressed in human HeLa cells (Monsma, F. J. Jr. et al., Mol. Pharmacol. 43:320, 1993) in a modified Tris-HCl buffer (50 mM Tris-HCl, pH 7.4, 150 mM NaCl, 2 mM Ascorbic Acid, 0.001% BSA) is used. Compounds of the invention are incubated with 1.5 nM [3H]Lysergic acid diethylamide (LSD) for 120 min at 37° C. Non-specific binding is estimated in the presence of 5 µM Serotonin (5-HT). Receptor proteins are filtered and washed, the filters are then counted to determine [3H]LSD specifically bound. Compounds are screened at 1 µM or lower, using 1% DMSO as vehicle. Compounds of the invention are tested in this biochemical assay and percent inhibition of specific binding is determined.

Serotonin (5-Hydroxytryptamine) 5-HT$_7$

To evaluate in radioligand binding assays the activity of compounds of the invention, human recombinant serotonin (5-Hydroxytryptamine) 5-HT$_7$ receptor expressed in Chinese hamster ovary (CHO) cells (Roth, B. L. et al., J. Pharmacol. Exp. Ther. 268:1403, 1994; Shen, Y. et al., J. Biol. Chem. 268:18200, 1993) in a modified Tris-HCl buffer (50 mM Tris-HCl, pH 7.4, mM MgCl$_2$, 0.5 mM EDTA) is used. Compounds of invention are incubated with 5.5 nM [$^3$H] Lysergic acid diethylamide (LSD) for 2 h at 25° C. Non-specific binding is estimated in the presence of 10 µM Serotonin (5-HT). Receptor proteins are filtered and washed, the filters are then counted to determine [$^3$H]LSD specifically bound. Compounds are screened at 1 µM or lower, using 1% DMSO as vehicle. Compounds of the invention are tested in this biochemical assay and percent inhibition of specific binding is determined.

Example B6

Determination of Serotonin (5-Hydroxytryptamine) 5-HT$_{2A}$ Agonist/Antagonist Activity of Compounds of the Invention To determine for agonist or antagonist activity of compounds of the invention in functional assays, human recombinant serotonin 5-HT$_{2A}$ receptor expressed in human embryonic kidney (HEK-293) cells (Jerman J C, Brough S J, Gager T, Wood M, Coldwell M C, Smart D and Middlemiss D N. Eur J Pharmacol, 414: 23-30, 2001) is used. Cells are suspended in DMEM buffer, and distributed in microplates. A cytoplasmic calcium fluorescent indicator which varies proportionally to the free cytosolic Ca$^{2+}$ ion concentration is mixed with probenecid in HBSS buffer complemented with 20 mM Hepes (pH 7.4), added into each well and equilibrated with the cells for 30 min at 37° C. followed by 30 min at 22° C.

To measure agonist effects, compounds of the invention, reference agonist or HBSS buffer (basal control) is added to the cells and changes in fluorescence intensity are measured using a microplate reader. For stimulated control measurements, 5-HT at 100 nM is added in separate assay wells.

The results are expressed as a percent of the control response to 100 nM 5-HT. The standard reference agonist is 5-HT, which is tested in each experiment at several concentrations to generate a concentration-response curve from which its EC$_{50}$ value is calculated.

To measure antagonist effects, the addition of the compounds of the invention, reference antagonist or HBSS buffer is followed by the addition of 3 nM 5-HT or HBSS buffer (basal control) prior the fluorescence measurements. The results are expressed as a percent inhibition of the control response to 3 nM 5-HT. The standard reference antagonist is ketanserin, which is tested in each experiment at several concentrations to generate a concentration-response curve from which its IC$_{50}$ value is calculated. Compounds are screened at 3 μM or lower, using DMSO as vehicle.

Example B7

Determination of Serotonin (5-Hydroxytryptamine) 5-HT$_6$ Agonist/Antagonist Activity of Compounds of the Invention To determine for agonist or antagonist activity of compounds of the invention in functional assays, human recombinant 5-HT$_6$ receptor is transfected in CHO cells (Kohen, R., Metcalf, M. A., Khan, N., Druck, T., Huebner, K., Lachowicz, J. E., Meltzer, H. Y., Sibley, D. R., Roth, B. L. And Hamblin, M. W. Cloning, characterisation and chromosomal localization of a human 5-HT6 serotonin receptor, J. Neurochem., 66: 47, 1996) and the activity of compounds of the invention is determined by measuring their effects on cAMP production using the Homogeneous Time Resolved Fluorescence (HTRF) detection method. Cells are suspended in HBSS buffer complemented with HEPES 20 mM (pH 7.4) and 500 μM IBMX, and then distributed in microplates and incubated for 45 min at 37° C. in the absence (control) or presence of compounds of the invention or the reference agonist or antagonist.

For agonist determinations, stimulated control measurement, separate assay wells contain 10 μM 5-HT. Following incubation, the cells are lysed and the fluorescence acceptor (D2-labeled cAMP) and fluorescence donor (anti-cAMP antibody labeled with europium cryptate) are added. After 60 min at RT, the fluorescence transfer is measured at lex=337 nm and lem=620 and 665 nm using a microplate reader. The cAMP concentration is determined by dividing the signal measured at 665 nm by that measured at 620 nm (ratio).

The results are expressed as a percent of the control response to 10 μM 5-HT. The standard reference agonist is 5-HT, which is tested in each experiment at several concentrations to generate a concentration-response curve from which its EC$_{50}$ value is calculated.

For antagonist determinations, the reference agonist 5-HT is added at a final concentration of 100 nM. For basal control measurements, separate assay wells do not contain 5-HT. Following 45 min incubation at 37° C., the cells are lysed and the fluorescence acceptor (D2-labeled cAMP) and fluorescence donor (anti-cAMP antibody labeled with europium cryptate) are added.

After 60 min at RT, the fluorescence transfer is measured as mentioned above. The results are expressed as a percent inhibition of the control response to 100 nM 5-HT. The standard reference antagonist is methiothepin

Example B8

Determination of Dopamine D$_{2L}$ Antagonist Activity of Compounds

To determine for agonist or antagonist activity of compounds of the invention in functional assays, human recombinant dopamine D$_{2L}$ receptor stably expressed in Chinese hamster ovary (CHO) cells (Senogles S E et al. J Biol Chem. 265(8): 4507, 1990) is used. Compounds of invention are pre-incubated with the membranes (0.1 mg/mL) and 10 mM GDP in modified HEPES buffer (20 mM HEPES, pH 7.4, 100 mM NaCl, 10 mM MgCl$_2$, 1 mM DTT, 1 mM EDTA) for 20 min and Scintillation Proximity Assay (SPA) beads are added for another 60 min at 30° C. The reaction is initiated by 0.3 nM [$^{35}$S]GTPγS for an additional 15 min incubation period. Increase of [$^{35}$S]GTPγS binding by 50 percent or more (350%) relative to the 1 mM dopamine response by compounds of the invention indicates possible dopamine D$_{2L}$ receptor agonist activity. Inhibition of a 10 μM dopamine-induced increase of [$^{35}$S]GTPγS binding response by 50 percent or more (350%) by compounds of the invention indicates receptor antagonist activity. Compounds are screened at 3 μM or lower, using 0.4% DMSO as vehicle. Assay results are presented as the percent response of specific binding.

Example B9

Determination of Dopamine D$_2$ Antagonist Activity of Compounds of the Invention To determine for agonist or antagonist activity of compounds of the invention in functional assays, human recombinant dopamine D$_2$ receptor stably expressed in Chinese hamster ovary (CHO) cells (Gilliland S L and Alper R H. Naunyn-Schmiedeberg's Archives of Pharmacology. 361: 498, 2000) is used. Compounds of invention are pre-incubated with the membranes (0.05 mg/mL) and 3 μM GDP in modified HEPES buffer (20 mM HEPES, pH 7.4, 100 mM NaCl, 10 mM MgCl$_2$, 1 mM DTT, 1 mM EDTA) for 20 min and Scintillation Proximity Assay (SPA) beads are then added for another 60 min at 30° C. The reaction is initiated by 0.3 nM [$^{35}$S]GTPγS for an additional 30 min incubation period. Increase of [$^{35}$S]GTPγS binding by 50 percent or more (350%) relative to the 100 μM dopamine response by compounds of the invention indicates possible dopamine D$_{2S}$ receptor agonist activity. Inhibition of a 3 μM dopamine-induced increase of [$^{35}$S]GTPγS binding response by 50 percent or more (350%) by compounds of the invention indicates receptor antagonist activity. Compounds are screened at 3 µM or lower, using 0.4% DMSO as vehicle. Assay results are presented as the percent response of specific binding.

Example B10

Determination for Agonist or Antagonist Activity of Compounds of the Invention in a Histamine H1 Functional Assay To determine for agonist or antagonist activity of compounds of the invention in functional assays, human recombinant Histamine $H_1$ receptor expressed in human embryonic kidney (HEK-293) cells (Miller, T. R., Witte, D. G., Ireland, L. M., Kang, C. H., Roch, J. M., Masters, J. N., Esbenshade, T. A And Hancock, A. A. J. Biomol. Screen., 4: 249-258, 1999) is used. Cells are suspended in DMEM buffer, and then distributed in microplates. A cytoplasmic calcium fluorescent indicator—which varies proportionally to the free cytosolic $Ca^{2+}$ ion concentration—is mixed with probenecid in HBSS buffer complemented with 20 mM Hepes (pH 7.4) and is then added into each well and equilibrated with the cells for 30 min at 37° C. and then for another 30 min at 22° C. To measure agonist effects, compounds of the invention, reference agonist or HBSS buffer (basal control) are added to the cells and changes in fluorescence intensity are measured using a microplate reader. For stimulated control measurements, histamine at 10 µM is added in separate assay wells.

The results are expressed as a percent of the control response to 10 µM histamine. The standard reference agonist is histamine, which is tested in each experiment at several concentrations to generate a concentration-response curve from which its $EC_{50}$ value is calculated.

To measure antagonist effects, the addition of the compounds of the invention, reference antagonist or HBSS buffer is followed by the addition of 300 nM histamine or HBSS buffer (basal control) prior the fluorescence measurements. The results are expressed as percent inhibition of the control response to 300 nM histamine. The standard reference antagonist is ketanserin, which is tested in each experiment at several concentrations to generate a concentration-response curve from which its $IC_{50}$ value is calculated. Compounds are screened at 3 µM or lower, using DMSO as vehicle.

Example B11

Increase of Neurite Outgrowth

Neurite Outgrowth in Cortical Neurons

Compounds are tested to determine their ability to stimulate neurite outgrowth of cortical neurons. Standard methods are used to isolate cortical neurons. For the isolation of primary rat cortical neurons, the fetal brain from a pregnant rat at 17 days of gestation is prepared in Leibovitz's medium (L15; Gibco). The cortex is dissected out, and the meninges are removed. Trypsin (Gibco) is used to dissociate cortical C with DNAse I. The cells are triturated for 30 min with a pipette in Dulbecco's Modified Eagle Media ("DMEM"; Gibco) with 10% Fetal Bovine Serum ("FBS") (Gibco) and centrifuged at 350×g for 10 min at RT. The cells are suspended in Neurobasal medium supplemented with 2% B27 (Gibco) and 0.5 mM L-glutamine (Gibco). The cells are maintained at 30,000 cells per well of poly-L-lysine coated plates at 37° C. in 5% $CO_2$-95% air atmosphere. After adhesion, a vehicle control or compounds of the invention are added at different concentrations to the medium. BDNF (50 ng/mL) is used as a positive control for neurite growth. After treatment, cultures are washed in phosphate-buffered saline ("PBS"; Gibco) and fixed in glutaraldehyde 2.5% in PBS. Cells are fixed after 3 days growth. Several pictures (~80) of cells with neurites are taken per condition with a camera. The length measurements are made by analysis of the pictures using software from Image-Pro Plus (France). The results are expressed as mean (s.e.m.). Statistical analysis of the data is performed using one way analysis of variance (ANOVA).

Neurite Outgrowth in Rat Mixed Cortical Cultures

Cortical mixed cultures are prepared from E18 Wistar rat embryos. The cortices are dissected out and the tissue is cut to small pieces. The cells are separated by 15-min incubation with DNase and papain. The cells are collected by centrifugation (1500 rpm, 5 min). The tissue is triturated with a pipette and the cells are plated using the micro-islet protocol (20 000 cells in 25 µL medium) on poly-L-lysine coated 48 wells, in MEM supplemented with 2 mM glutamine, 0.1 µg/ml gentamicin, 10% heat-inactivated fetal bovine serum (FBS-HI) and 10% heat-inactivated horse serum (HS-HI). After the cells attach to the well, 250 µL medium is added to the wells. Four h after plating the medium is changed to fresh medium (MEM with supplements and 5% HS-HI) containing test compound at 0.5, 5 and 50 nM concentrations. As positive controls BDNF (50, 100 and/or 150 ng/mL), and/or NGF (50 ng/mL and/or 100 ng/mL) are used. After 2 days in vitro, the cell's conditioned media are collected from plates before fixing the cells. The media samples are centrifuged 13 000 rpm 3 min to get rid of cell debris. The samples are stored at −20° C. for later analysis. Cells are formaldehyde-fixed and processed for immunocytochemistry. BDNF levels in the conditioned media are determined with a BDNF ELISA using the manufacturers (Promega, BDNF Emax® ImmunoAssay System, catalog number: G7610) instructions.

The cultures are fixed with 4% formaldehyde in 0.01 M PBS for 30 min and washed once with PBS. The fixed cells are first permeabilized and non-specific binding is blocked by a 30-min incubation with blocking buffer containing 1% bovine serum albumin and 0.3% Triton X-100 in PBS. Rabbit anti-MAP-2 (dilution 1:1000, AB5622, Chemicon, in blocking buffer) is used as a primary antibody. The cells are incubated with the primary antibody for 48 h at +4° C., washed with PBS and incubated with secondary antibody goat anti-rabbit IgG conjugated to Alexa Fluor568 (1:200, A11036, Molecular Probes) for 2 h at RT. The immunopositive cells are visualized by a fluorescence microscope equipped with appropriate filter set, and documented by a high resolution image capturing. The number of cells per field (4 field per well) are counted, and the neurite outgrowth is quantified using Image Pro Plus software.

The number of wells per compound concentration used is 6 (n=6). All data are presented as mean±standard deviation (SD) or standard error of mean (SEM), and differences are considered to be statistically significant at the p<0.05 level. Statistical analysis is performed using StatsDirect statistical software. Differences between group means are analyzed by using 1-way-ANOVA followed by Dunnet's test (comparison to the vehicle treated group).

Example B12

Use of an In Vivo Model to Evaluate the Ability of Compounds to Enhance Cognition, Learning and Memory in Scopolamine Treated Rats The two-trial object recognition paradigm developed by Ennaceur and Delacour in the rat is used as a model of episodic/short-term memory. Ennaceur, A., and Delacour, J. (1988), *Behav. Brain Res.* 31:47-59. The paradigm is based on spontaneous exploratory activity of rodents and does not involve rule learning or reinforcement. The novel object recognition paradigm is sensitive to the effects of ageing and cholinergic dysfunction. See, e.g., Scali, C., et al., (1994), *Neurosci. Letts.* 170:117-120; and Bartolini, L., et al., (1996), *Biochem. Behav.* 53:277-283.

Male Sprague-Dawley rats between six and seven weeks old, weighing between 220-300 grams are obtained, e.g., from Centre d'Elevage (Rue Janvier, B. P. 55, Le Genest-Saint-Isle 53940, France). The animals are housed in groups of 2 to 4 in polypropylene cages (with a floor area of 1032 cm$^2$) under standard conditions: at RT (22±2° C.), under a 12 hour light/12 hour dark cycle, with food and water provided ad libitum. Animals are permitted to acclimate to environmental conditions for at least 5 days before the experiment begins, and are numbered on their tails with indelible marker.

The experimental arena is a square wooden box (60 cm×60 cm×40 cm) painted dark blue, with 15 cm×15 cm black squares under a clear plexiglass floor. The arena and objects placed inside the arena are cleaned with water between each trial to eliminate any odor trails left by rats. The arena is placed in a dark room illuminated only by halogen lamps directed towards the ceiling in order to produce a uniformly dim light in the box of approximately 60 lux. The day before testing, animals are allowed to freely explore the experimental arena for three min in the presence of two objects (habituation). Animals to be tested are placed in the experimental room at least 30 min before testing.

Novel object recognition test is comprised of two trials separated by an interval of 120 min or 24 h. When agents that disrupt memory such as the cholinergic antagonist scopolamine are used an inter-trial interval of 120 min is preferred. Alternatively a 24 h inter-trial interval is used when studying effect of natural forgetting on novel object recognition task. During the first, or acquisition, trial ($T_1$), rats are placed in the arena, where two identical objects have been previously placed. The time required for each animal to complete 15 sec of object exploration is determined, with a cut-off time of four min. Exploration is considered to be directing the nose at a distance less than 2 centimeters ("cm") from the object and/or touching the object. During the second, or testing, trial ($T_2$), one of the objects presented in the first trial is replaced with an unknown or novel object, while the second, familiar object is left in place. Rats are placed back in the arena for three min, and exploration of both objects is determined. Locomotor activity of rats (number of times rats cross grid lines visible under the clear plexiglass floor) is scored for during $T_1$ and $T_2$. At the conclusion of the experiments, the rats are sacrificed by an overdose of pentobarbital given intraperitoneally.

The following parameters are measured as part of the novel object recognition task: (1) time required to achieve 15 sec of object exploration during $T_1$; (2) locomotor activity during $T_1$ (number of crossed lines); (3) time spent in active exploration of the familiar object during $T_2$ ($T_{Familiar}$); (4) time spent in active exploration of the novel object during $T_2$ ($T_{Novel}$); and (5) locomotor activity during $T_2$ (number of crossed lines). The difference between time spent in active exploration of the novel object during $T_2$ and time spent in active exploration of the familiar object during $T_2$ ($\Delta T_{Novel} - T_{Familiar}$) is evaluated. The % of animals in each group with $T_{Novel} - T_{Familiar}$ greater than or equal to 5 sec is also derived; described as % of good learners.

Animals not meeting a minimal level of object exploration are excluded from the study as having naturally low levels of spontaneous exploration. Thus, only rats exploring the objects for at least five sec ($T_{Novel} + T_{Familiar} > 5$ sec) are included in the study.

Animals are randomly assigned to groups of 14. Compounds of the invention and controls are administered to animals the groups as follows: Solutions of compounds are prepared freshly each day at a concentration of 0.25 mg/mL using purified water or saline as vehicle. Donepezil, used as a positive control, and scopolamine are administered simultaneously in a single solution of saline (5 mL/kg) prepared freshly each day. Scopolamine is purchased from Sigma Chemical Co. (Catalog No. S-1875; St. Quentin Fallavier, France) is dissolved in saline to a concentration of 0.06 mg/mL.

Donepezil or its vehicle and scopolamine are administered intraperitoneally forty min before the acquisition trial ($T_1$). Compounds or their vehicle are administered by gavage twenty-five min before the acquisition trial ($T_1$), i.e., five min after administration of scopolamine. The volume of administration is 5 mL/kg body weight for compounds administered intraperitoneally, and 10 mL/kg for compounds administered orally. Recognition scores and % of good learners for compounds are determined.

Example B13

Use of an In Vivo Model to Determine the Ability of Compounds to Treat, Prevent and/or Delay the Onset and/or the Development of Schizophrenia in PCP Treated Animals In vivo models of schizophrenia can be used to determine the ability of the compounds described herein to treat and/or prevent and/or delay the onset and/or the development of schizophrenia.

One exemplary model for testing the activity of one or more compounds described herein to treat and/or prevent and/or delay the onset and/or development of schizophrenia employs phencyclidine (PCP), which is administered to the animal (e.g., non-primate (rat) or primate (monkey)), resulting in dysfunctions similar to those seen in schizophrenic humans. See Jentsch et al., 1997, Science 277:953-955 and Piercey et al., 1988, Life Sci. 43(4):375-385). Standard experimental protocols may be employed in this or in other animal models. One protocol involves PCP-induced hyperactivity.

Male mice (various strains, e.g., C57Bl/6J) from appropriate vendor (for example, Jackson Laboratories (Bar Harbor, Me.) are used. Mice are received at 6-weeks of age. Upon receipt, mice are assigned unique identification numbers (tail marked) and are group housed with 4 mice/cage in OPTI mouse ventilated cages. All animals remain housed in groups of four during the remainder of the study. All mice are acclimated to the colony room for at least two weeks prior to testing and are subsequently tested at an average age of 8 weeks. During the period of acclimation, mice are examined on a regular basis, handled, and weighed to assure adequate health and suitability. Animals are maintained on a 12/12 light/dark cycle. The RT is maintained between 20 and 23° C. with a relative humidity maintained between 30% and 70%. Food and water are provided ad libitum for the duration of the study. In each test, animals are randomly assigned across treatment groups.

The open filed (OF) test assesses locomotor behavior, i.e. to measure mouse locomotor activity at baseline and in response to pharmacological agents. The open field chambers are Plexiglas square chambers (27.3×27.3×20.3 cm; Med Associates Inc., St Albans, Vt.) surrounded by infrared photobeams (16×16×16) to measure horizontal and vertical activity. The analysis is configured to divide the open field into a center and periphery zone such that the infrared photobeams allow measurement of activity in the center and periphery of the field. Distance traveled is measured from horizontal beam breaks as the mouse moved whereas rearing activity is measured from vertical beam breaks.

Mice (10 to 12 animals per treatment group) are brought to the activity experimental room for at least 1 h acclimation to the experimental room conditions prior to testing. Eight animals are tested in each run. Mice are administered vehicle (e.g. 10% DMSO or 5% PEG200 and 1% Tween 80), compound of the invention, clozapine (positive control, 1 mg/kg ip) and placed in the OF chambers for 30 min following which they are injected with either water or PCP and placed back in the OF chambers for a 60-min session. At the end of each OF test session the OF chambers are thoroughly cleaned.

PCP Hyperactivity Mouse Model of Schizophrenia

The test compound at the desired dose is dissolved in appropriate vehicle, e.g., 5% PEG200, 1% Tween80 and administered orally 30 min prior to PCP injection. Clozapine (1 mg/kg) is dissolved in 10% DMSO and administered i.p. 30 min prior to PCP injection. PCP (5 mg/kg) is dissolved in sterile injectable saline solution and administered i.p.

Data are analyzed by analysis of variance (ANOVA) followed by post-hoc comparisons with Fisher Tests when appropriate. Baseline activity is measured during the first 30 min of the test prior to PCP injection. PCP-induced activity is measured during the 60 min following PCP injection. Statistical outliers that fell above or below 2 standard deviations from the mean are removed from the final analyses. An effect is considered significant if $p<0.05$. Total distances traveled and total rearing following PCP administration are compared between groups treated with compounds and groups treated with vehicle and positive control clozapine.

PCP Hyperactivity Mouse Model of Schizophrenia

Protocol is as described above with the exception of the treatment groups which are as follows: All injections are at a dose volume of 10 mL/kg. The test compound at the desired dose is dissolved in Phosphate Buffered Saline (PBS) and administered orally 30 min prior to PCP injection. Clozapine (0.5 and 1.0 mg/kg) is dissolved in 10% DMSO and administered i.p. 30 min prior to Phencyclidine (PCP) injection. PCP (5.0 mg/kg) is dissolved in sterile injectable saline and administered i.p. Total distances traveled for is determined.

Example B14

Use of an In Vivo Model to Determine the Ability of Compounds to Treat, Prevent and/or Delay the Onset and/or the Development of Schizophrenia in Amphetamine Treated Animals Male mice (various strains e.g., C57Bl/6J) from appropriate supplier (for example Jackson Laboratories, Bar Harbor, Me.) are used. Mice typically are received at 6-weeks of age. Mice are acclimated to the colony room for at least two weeks prior to testing. During the period of acclimation, mice are examined on a regular basis, handled, and weighed to assure adequate health and suitability and maintained on a 12/12 light/dark cycle. The RT is maintained between 20 and 23° C. with a relative humidity maintained between 30% and 70%. Food and water are provided ad libitum for the duration of the study. In each test, animals are randomly assigned between treatment groups.

The open field test (OF) is used to assess motor activity. The open field chambers are plexiglass square chambers (e.g., 27.3×27.3×20.3 cm; Med Associates Inc., St Albans, Vt.) surrounded by infrared photobeam sources (16×16×16). The enclosure is configured to split the open field into a center and periphery zone and the photocell beams are set to measure activity in the center and in the periphery of the OF chambers. Horizontal activity (distance traveled) and vertical activity (rearing) are measured from consecutive beam breaks.

On the day of testing, animals are brought to the experimental room for at least 1 h acclimation prior to start of treatment. Animals are administered with vehicle, haloperidol (positive control, 0.1 mg/kg ip) or test compound and placed in the OF. The time of administration of client compound to each animal is recorded. Baseline activity is recorded for 30 min following which mice receive amphetamine (4 mg/kg) or water and are placed back in the OF chambers for a 60-min session. At the end of each open field test session the OF chambers are thoroughly cleaned. Typically ten to twelve mice are tested in each group. Test compound doses typically range from 0.01 mg/kg to 60 mg/kg.

Data are analyzed by analysis of variance (ANOVA) followed by post-hoc comparisons with Fisher Tests when appropriate. Baseline activity is measured during the first 30 min of the test prior to amphetamine injection. Amphetamine-induced activity is measured during the 60 min following amphetamine injection. Statistical outliers that fall above or below 2 standard deviations from the mean are removed from the final analyses. An effect is considered significant if $p<0.05$. Total distance traveled and total rearing following amphetamine administration are compared between groups treated with compound and groups treated with vehicle and positive control haloperidol.

Example B15

Use of the In Vivo Conditioned Avoidance Response (CAR) Model to Determine the Ability of Compounds to Treat, Prevent and/or Delay the Onset and/or the Development of Schizophrenia All currently approved antipsychotic agents (typical and atypical) are known to have the ability to selectively suppress conditioned avoidance response (CAR) behavior in the rat. This evidence makes CAR one of the primary tests to assess antipsychotic activity of novel compounds.

Rats (various strains, 2 months of age) are trained and tested in a computer-assisted, two-way active avoidance apparatus (shuttle box). This box consists of two compartments of equal size divided by a stainless steel partition containing an opening of 7×7 cm. Each compartment is equipped with an electrified grid floor made of stainless steel rods spaced 1 cm apart. Rats trained to avoid the foot shock are placed each day in the shuttle box for a 4 min habituation period followed by 30 trials spaced by inter-trial interval varying at random between 20 and 30 sec. Each trial consists of a 10-sec stimulus light (conditioned stimulus, CS) followed by a 10-sec foot shock (unconditioned stimulus, US) in presence of the light presented in the compartment where the rat is located. If the animal leaves the compartment prior to the delivery of the foot shock, the response is considered an avoidance response. If the rat does not change compartment during the 10-sec light period and during the 10-sec shock+ light period, an escape failure is recorded. This test requires animals to be trained 5 days/week. On each training day, rats are submitted to one training session of 30-trials. Treatment with test compound is initiated only when rats reach an avoidance performance of at least 80% on at least two consecutive training sessions. The test compound is administered orally at various doses and various pre-treatment times (depending upon specific pharmacokinetic properties).

Compounds with antipsychotic profile inhibit conditioned avoidance responses with or without increases in escape failures. Statistical analysis is performed using a Friedman two-way ANOVA by ranks followed by the Wilcoxon matched-pairs signed-ranks test to test each dose of the test compound administered versus vehicle control treated rats. The ability of compounds of the invention to bind receptors detailed hereinabove is evaluated in multiple concentrations.

Example B16

Use of the 5-Choice Serial Reaction Task to Determine the Ability of Compounds to Enhance Attention/Vigilance and Reduce Impulsivity Attention and impulsivity are characteristic of several disease states. The continuous performance test (CPT), used in humans, is capable of detecting attention deficits in a number of disorders, including attention deficit hyperactivity disorder [Riccio et al., *J. Neuropsychiatry Clin. Neurosci* (2001), 13(3):326-335], schizophrenia [Lee et al., *Schizophr. Res.* (2006), 81(2-3):191-197], and mild cognitive impairment [Levinoff et al., *Neuropsychology* (2006), 20(1):123-132]. The pre-clinical analogue of the CPT is the 5-choice serial reaction time task ["5-CSRTT"; Robbins, T., *Psychopharmacology* (2002), 3-4:362-380]. In this operant-based test, rats are required to be attentive and withhold responding while they monitor 5 apertures for the appearance of a brief stimulus light in one of the apertures. The brief illumination of the stimulus light in the 5-CSRTT is analogous to the appearance of the "correct" letters in the CPT in humans. Upon observing the stimulus light, the rat must nose-poke in the corresponding aperture to receive a food reward. The 5-CSRTT allows the measurement of similar behavioral responses as the CPT, including accuracy, speed of responding, impulsive and compulsive responding. In the present studies, drug tests are performed under altered test parameters which results in increased premature responding. This premature responding is hypothesized to indicate impulsivity, i.e., a failure to withhold an inappropriate response, and has been shown to be sensitive to atomoxetine [Navarra et al., Prog. Neuropsychopharmacol. Biol. Psychiatry (2008), 32(1):34-41].

A minimum of 12 male Long-Evans rats (275-300 g) are obtained from Harlan Laboratories, Indianapolis, Ind. At the time of testing, rats are approximately 16-18 months old. Upon arrival, the rats are assigned unique identification numbers (tail marked). Rats are single-housed in OptiRAT cages and acclimated for 7 days prior to commencing a food-restriction regimen: rats are held at 85% of age-matched free-feeding control body-weights, receiving approximately 10-20 g of rat chow daily. Water is provided ad libitum, except during testing. Animals are maintained in a 12/12 h light/dark cycle (lights on at 0700 EST) with RT maintained at 22±2° C. and the relative humidity maintained at approximately 50%. All animals are examined, handled and weighed prior to initiation of the study to assure adequate health and suitability and to minimize non-specific stress associated with testing. The 5-CSRTT sessions are performed during the animal's light cycle phase. All experiments and procedures are approved by the Institutional Animal Care and Use Committee of PsychoGenics, Inc.

Apparatus: The apparatus consists of aluminum and Plexiglas chambers with grid floors (width 31.5 cm, depth 25.0 cm, height 33.0 cm), housed in sound-attenuating cabinets. Each cabinet is fitted with a low-level noise extractor fan which also helps to mask external noise. The left wall of each chamber is concavely curved with 5 apertures evenly spaced, located approximately 2.5 cm from the floor. Each aperture contains a standard 3 W LED to serve as stimulus lights. The opposite wall contains a food magazine, located approximately 3.0 cm from the floor. Each chamber is illuminated with a 3 W house-light located in the center of the ceiling panel. After each test session the apparatus is cleaned with 70% EtOH.

Experimental procedure: Training: Animals are trained to monitor the five apertures for stimulus light illumination. Each session is initiated by the illumination of the house light, and the delivery of a food reward into the magazine. The first trial begins when the rat opens the magazine to obtain the food pellet. After the inter-trial interval (ITI) one of the stimulus lights is illuminated for 500 msec. The rat must nose-poke in the illuminated aperture either during or within 5 sec of stimulus light illumination. Such a response is defined as a correct response, and is rewarded with delivery of a food pellet. Collection of the pellet initiates the next trial. A nose-poke response in a non-illuminated aperture (incorrect response) or a nose-poke after the 5 sec limited hold (missed trial) results in termination of the trial with extinction of the house-light and imposition of a time-out period. Testing: After acquisition of the 5-CSRTT with a high level of accuracy (at least 75% correct, at least 50 trials completed per session), drug testing begins. Animals are treated with test compound (various doses, appropriate vehicle), vehicle and positive control (atomoxetine 1 mg/kg ip). During drug test sessions, the ITI is varied between 10, 7, 5 or 4 sec in duration, presented in groups of 4 trials (each of which contains 1 trial at each ITI duration in a randomized order). The session ends when 60 min have elapsed. All rats receive all drug treatments, according to a randomized-order within-subjects design. Drug tests are performed on Wednesdays and Fridays of each week, only when rats have performed at least 75% correct trials for a minimum of 50 trials in the previous test session.

Measures obtained during the test sessions are: (1) percent correct, defined as the number of correct trials×100, divided by the total number of correct and incorrect trials, (2) missed trials, defined as responding beyond the 5 sec limited hold or failing to respond, (3) correct latency, defined as the time taken to make a correct response after the illumination of the stimulus, (4) magazine latency, defined as the time taken to enter the magazine to collect the food pellet after making a correct response, (5) premature responding, defined as the total number of nose-poke responses made during the ITI, and (6) preservative responding, defined as the total number of additional responses emitted after the initial nose-poke.

Statistical Analysis

Data are expressed as percent correct; the numbers of missed trials, preliminary and preservative responses; and latencies (in sec) to make correct responses and to collect food pellets after a correct response. Data are analyzed by analyses of variance (ANOVA). In all cases, values of $p<0.05$ are considered to be significant. Post-hoc comparisons are made using Fisher LSD post-hoc tests where appropriate.

Example B17

An Animal Model of the Negative Symptoms of Schizophrenia: Subchronic PCP-Induced Social Interaction Deficits Phencyclidine (PCP) administered to humans as well to experimental animals induces full-spectrum of schizophrenia symptoms, including negative symptoms and cognitive deficits. A major symptom of schizophrenia is considered to be social isolation/withdrawal as part of the cluster of negative symptoms. Subchronic treatment with PCP in rats leads to the development of clear signs of social withdrawal as measured by deficits in the interaction time with a cage intruder rat. Male Sprague Dawley rats (about 150 g, obtained from different vendors, for example Harlan, Ind.) are used in this study. Upon receipt, rats are group housed in OPTI rat ventilated cages. Rats are housed in groups of 2-3 per cage for the remainder of the study. During the period of acclimation, rats are examined on a regular basis, handled, and weighed to assure adequate health and suitability. Rats are maintained on a 12/12 light/dark cycle with the light on at 7:00 a.m. The room temperature is maintained between 20-23° C. with a relative humidity maintained between 30-70%. Food and water are provided ad libitum for the duration of the study. Animals are randomly assigned across treatment groups and balanced by age.

For five days prior to test, rats are injected twice daily with either PCP (2 mg/kg; s.c) or saline (s.c). On day 6 and following a 30 min pretreatment with vehicle, clozapine (2.5 mg/kg ip dissolved in 5% PEG:5% Tween 80) as positive control and test compound at desired dose dissolved in appropriate vehicle, a pair of rats, unfamiliar to each other, receiving the same treatment are placed in a white plexiglas open field arena (24"×17"×8") and allowed to interact with each other for 6 min. Social interactions ('SI') include: sniffing the other rat; grooming the other rat; climbing over or under or around the other rat; following the other rat; or exploring the ano-genital area of the other rat. Passive contact and aggressive contact are not considered a measure of social interaction. The time the rats spent interacting with each other during the 6 min test is recorded by a trained observer. The social interaction chambers are thoroughly cleaned between the different rats. Data are analyzed by analysis of variance (ANOVA) followed by post-hoc analysis (e.g., Fischer, Dunnett) when appropriate. An effect is considered significant if $p<0.05$.

Example B18

An Animal Model of Extrapyramidal Syndrome (EPS): Measurement of Catalepsy in the Mouse Bar Test Antipsychotic drugs are known to induce extrapyramidal syndrome (EPS) in animals and in humans. An animal model considered to be predictive of EPS is the mouse bar test, which measures cataleptic responses to pharmacological agents. Male mice (various strains) from appropriate vendor (for example, Jackson Laboratories (Bar Harbor, Me.) are used. Mice are received at 6-weeks of age. Upon receipt, mice are assigned unique identification numbers (tail marked) and are group housed with 4 mice per cage in OPTI mouse ventilated cages. All animals remain housed in groups of four during the remainder of the study. All mice are acclimated to the colony room for at least two weeks prior to testing and are subsequently tested at an average age of 8 weeks. During the period of acclimation, mice are examined on a regular basis, handled, and weighed to assure adequate health and suitability. Animals are maintained on a 12/12 light/dark cycle. The room temperature is maintained between 20-23° C. with a relative humidity maintained between 30-70%. Food and water are provided ad libitum for the duration of the study. In each test, animals are randomly assigned across treatment groups.

In the mouse bar test, the front paws of a mouse are placed on a horizontal bar raised 2" above a Plexiglas platform and time is recorded for up to 30 sec per trial. The test ends when the animal's front paws return to the platform or after 30 sec. The test is repeated 3 times and the average of 3 trials is recorded as index of catalepsy. In these studies the typical antipsychotic agent haloperidol (2 mg/kg ip dissolved in 10% DMSO) is used as positive control and induces rigidity and catalepsy as measured by time spent holding on the bar. 30 min prior to the trial, test compound at desired dose and dissolved in appropriate vehicle is administered PO, vehicle and positive control haloperidol (2 mg/kg ip) are administered to separate groups of mice. Catalepsy responses are measure 30 min, 1 h and 3 h following treatments. A trained observer is measuring time spent holding onto the bar during the 30 sec trial. Data are analyzed by analysis of variance (ANOVA) followed by post-hoc analysis (e.g., Fischer, Dunnett) when appropriate. An effect is considered significant if $p<0.05$.

Example B19

An Animal Model to Test the Anxiolytic Effects of Compounds Using the Elevated Plus Maze (EPM) Test This study may be used to test the anxiolytic properties of compounds detailed herein using the elevated plus maze (EPM) test in C57Bl/6J mice.

Male C57Bl/6J mice from Jackson Laboratories (Bar Harbor, Me.) are used for the open field study. Mice are received at 6-weeks of age. Upon receipt, mice are assigned unique identification numbers (tail marked) and are group housed with 4 mice/cage in OPTI mouse ventilated cages. All animals remain housed in groups of four during the remainder of the study. All mice are acclimated to the colony room for approximately 2 week prior to testing and are subsequently tested at an average age of 8 weeks of age. During the period of acclimation, mice and rats are examined on a regular basis, handled, and weighed to assure adequate health and suitability. Animals are maintained on a 12 h/12 h light/dark cycle. The room temperature is maintained between 20 and 23° C. with a relative humidity maintained between 30% and 70%. Chow and water are provided ad libitum for the duration of the study. In each test, animals are randomly assigned across treatment groups. All animals are euthanized after the completion of the study.

Compounds may be dissolved in 5% PEG200/$H_2O$ and administered orally at a dose volume of 10 mL/kg 30 min prior to test; 2) Diazepam (2.5 mg/kg) is dissolved in 45% hydroxypropyl-β-cyclodextrin and administered orally at a dose volume of 10 mL/kg 30 min prior to test.

The elevated plus maze test assesses anxiety. The maze (Hamilton Kinder) consists of two closed arms (14.5 h×5 w×35 cm length) and two open arms (6 w×35 1 cm) forming a cross, with a square center platform (6×6 cm). All visible surfaces are made of black acrylic. Each arm of the maze is placed on a support column 56 cm above the floor. Antistatic black vinyl curtains (7' tall) surround the EPM to make a 5'×5" enclosure. Animals are brought to acclimate to the experimental room at least 1 h before the test. Mice are placed in the center of the elevated plus maze facing the closed arm for a 5-min run. All animals are tested once. The time spent, distance traveled and entries in each arm are automatically recorded by a computer. The EPM is thoroughly cleaned after each mouse.

Data are analyzed using analysis of variance (ANOVA) followed by Fisher's LSD post hoc analysis when appropriate. An effect is considered significant if p<0.05.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

All references throughout, such as publications, patents, patent applications and published patent applications, are incorporated herein by reference in their entireties.

The invention claimed is:

1. A compound of the formula (E):

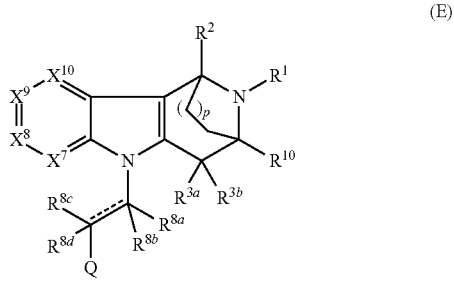

(E)

where:
- $R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;
- $R^2$ is H, hydroxyl, alkoxy or substituted or unsubstituted $C_1$-$C_8$ alkyl;
- each $R^{3a}$ and $R^{3b}$ is independently H, substituted or unsubstituted $C_1$-$C_8$ alkyl, halo, cyano, nitro, hydroxyl, alkoxy, substituted or unsubstituted amino, cycloalkyl, aryl, heteroaryl, heterocyclyl, acylamino or acyloxy or $R^{3a}$ and $R^{3b}$ are taken together to form a cycloalkyl moiety or a carbonyl moiety;
- each $X^7$, $X^8$, $X^9$ and $X^{10}$ is independently N or $CR^4$;
- p is 1 or 2;
- each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, carbonylalkoxy, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;
- each $R^{8a}$, $R^{8b}$, $R^{8c}$ and $R^{8d}$ is independently H, hydroxyl, alkoxy, halo, substituted or unsubstituted $C_1$-$C_8$ alkyl, substituted or unsubstituted $C_3$-$C_8$ cycloalkyl, substituted or unsubstituted $C_2$-$C_8$ alkenyl, $C_1$-$C_8$ perhaloalkyl, carboxyl, carbonylalkoxy, substituted or unsubstituted aryl, substituted or unsubstituted heteroaryl, or is taken together with a geminal $R^{8(a-d)}$ to form a substituted or unsubstituted methylene moiety or a moiety of the formula —$OCH_2CH_2O$—, or is taken together with a geminal $R^{8(a-d)}$ and the carbon to which they are attached to form a carbonyl moiety or a cycloalkyl moiety, or is taken together with a vicinal $R^{8(a-d)}$ and the carbon atoms to which they are attached to form a substituted or unsubstituted $C_3$-$C_8$ cycloalkyl, substituted or unsubstituted $C_3$-$C_8$ cycloalkenyl, or substituted or unsubstituted heterocyclyl moiety, or is taken together with a vicinal $R^{8(a-d)}$ to form a bond provided when an $R^8$ taken together with a vicinal $R^{8(a-d)}$ to form a bond, the geminal $R^{8(a-d)}$ is other than hydroxyl;
- wherein at least one of $R^{8a}$, $R^{8b}$, $R^{8c}$ and $R^{8d}$ is alkoxy, halo, $C_1$-$C_8$ alkyl substituted with an acylamino, carbonylalkoxy or carboxyl moiety, substituted or unsubstituted $C_3$-$C_8$ cycloalkyl, substituted or unsubstituted $C_2$-$C_8$ alkenyl, substituted or unsubstituted aryl, substituted or unsubstituted heteroaryl, or is taken together with a geminal $R^{8(a-d)}$ to form a moiety of the formula —$OCH_2CH_2O$—;
- ══ represents a single or double bond, provided that when ══ is a double bond, $R^{8a}$ and $R^{8c}$ are absent and $R^{8b}$ and $R^{8d}$ are other than OH;
- $R^{10}$ is H, hydroxyl, alkoxy or a substituted or unsubstituted $C_1$-$C_8$ alkyl;
- Q is substituted or unsubstituted aryl, substituted or unsubstituted heteroaryl, substituted or unsubstituted $C_3$-$C_8$ cycloalkyl, substituted or unsubstituted $C_3$-$C_8$ cycloalkenyl, substituted or unsubstituted heterocyclyl, substituted or unsubstituted amino, alkoxy, aminoacyl, acyloxy, carboxyl, carbonylalkoxy, cyano, alkynyl, aminocarbonylalkoxy or acylamino;

or a salt or solvate thereof.

2. A compound selected from the group consisting of compounds L-1 to L-61, or a pharmaceutically acceptable salt thereof.

3. The compound of claim 1 or 2, wherein the compound modulates at least one of the following receptors: adrenergic receptor, serotonin receptor, dopamine receptor and histamine receptor.

4. A method of treating a cognitive disorder, psychotic disorder, neurotransmitter-mediated disorder or a neuronal disorder in an individual comprising administering to an individual in need thereof an effective amount of compound of claim 1 or 2.

5. A pharmaceutical composition comprising a compound of claim 1 or 2 and a pharmaceutically acceptable carrier.

6. A kit comprising a compound of claim 1 or 2 and instructions for use in the treatment of a cognitive disorder, psychotic disorder, neurotransmitter-mediated disorder or a neuronal disorder.

7. A compound of the formula (L-1):

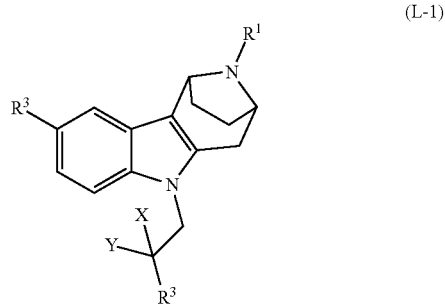

(L-1)

wherein:
- $R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

$R^2$ is H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

X is OH, H, $C_1$-$C_8$ unsubstituted alkyl or is taken together with Y to form a cyclic moiety of the formula —OCH$_2$CH$_2$O—;

Y is halo; substituted or unsubstituted aryl; substituted or unsubstituted heteroaryl; $C_1$-$C_8$ alkyl substituted with a carbonylalkoxy, carboxyl or acylamino moiety; or is taken together with X to form a cyclic moiety of the formula —OCH$_2$CH$_2$O—; and $R^3$ is a substituted or unsubstituted aryl, substituted or unsubstituted heteroaryl, substituted or unsubstituted cycloalkyl, substituted or unsubstituted cycloalkenyl, or substituted or unsubstituted heterocyclyl;

or a salt or solvate thereof.

8. The compound of claim 7, wherein the compound is of the formula (L-2):

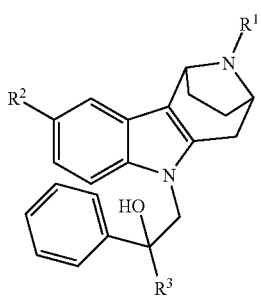

(L-2)

or a salt or solvate thereof.

9. The compound of claim 7, wherein the compound is of the formula (L-3):

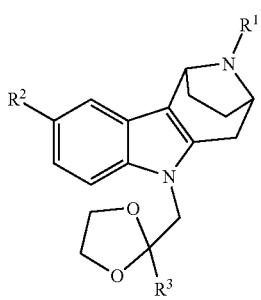

(L-3)

or a salt or solvate thereof.

10. The compound of claim 7, wherein the compound is of the formula (L-4):

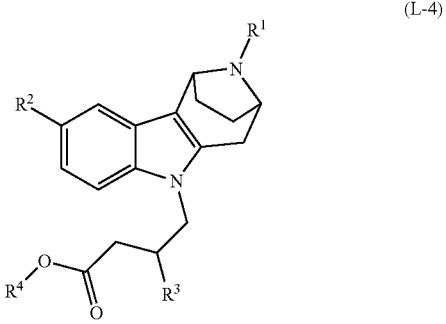

(L-4)

wherein $R^4$ is an unsubstituted $C_1$-$C_8$ alkyl; or a salt or solvate thereof.

11. The compound of claim 7, wherein the compound is of the formula (L-5):

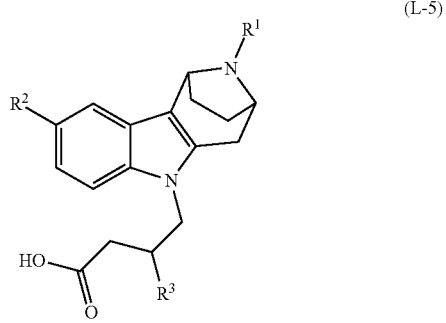

(L-5)

or a salt or solvate thereof.

12. The compound of claim 7, wherein the compound is of the formula (L-6):

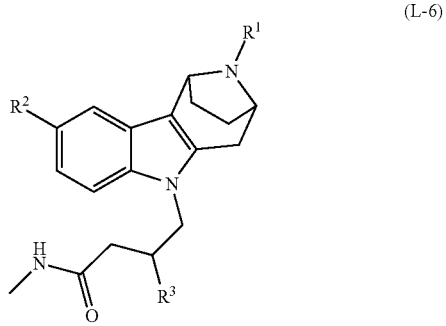

(L-6)

or a salt or solvate thereof.

13. The compound of claim 7, wherein the compound is of the formula (L-7):

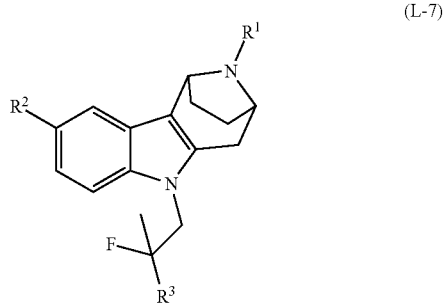

(L-7)

or a salt or solvate thereof.

14. The compound of claim 7, wherein the compound is of the formula (L-8):

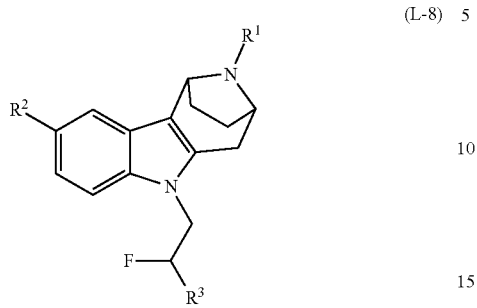

(L-8)

or a salt or solvate thereof.

15. A pharmaceutical composition comprising a compound of claim 7 and a pharmaceutically acceptable carrier.

16. A kit comprising a compound claim 7 and instructions for use in the treatment of a cognitive disorder, psychotic disorder, neurotransmitter-mediated disorder or a neuronal disorder.

* * * * *